(12) United States Patent
Knudsen et al.

(10) Patent No.: US 9,834,760 B2
(45) Date of Patent: Dec. 5, 2017

(54) BARLEY AND MALT-DERIVED BEVERAGES WITH LOW DMS LEVEL

(75) Inventors: Søren Knudsen, Måløv (DK); Gustav Hambraeus, Malmö (SE); Lene Molskov Bech, Smørum (DK); Steen Bech Sørensen, Solrød Strand (DK); Birgitte Skadhauge, Birkerød (DK); Klaus Breddam, Osted (DK); Ole Olsen, Copenhagen S. (DK)

(73) Assignees: CARLSBERG BREWERIES A/S, Copenhagen V (DK); HEINEKEN SUPPLY CHAIN B.V., Amsterdam (NL)

( * ) Notice: Subject to any disclaimer, the term of this patent is extended or adjusted under 35 U.S.C. 154(b) by 1152 days.

(21) Appl. No.: 13/132,765

(22) PCT Filed: Dec. 1, 2009

(86) PCT No.: PCT/DK2009/050315
§ 371 (c)(1),
(2), (4) Date: Aug. 23, 2011

(87) PCT Pub. No.: WO2010/063288
PCT Pub. Date: Jun. 10, 2010

(65) Prior Publication Data
US 2011/0293779 A1    Dec. 1, 2011

(30) Foreign Application Priority Data
Dec. 3, 2008  (DK) .................................. 2008 01708

(51) Int. Cl.
*A01H 5/00* (2006.01)
*C12N 9/10* (2006.01)
*C12C 1/18* (2006.01)
*C12C 12/00* (2006.01)
*C12N 15/82* (2006.01)

(52) U.S. Cl.
CPC ............ *C12N 9/1007* (2013.01); *C12C 1/18* (2013.01); *C12C 12/00* (2013.01); *C12N 15/8243* (2013.01); *C12C 2200/01* (2013.01)

(58) Field of Classification Search
None
See application file for complete search history.

(56) References Cited

U.S. PATENT DOCUMENTS

| | | | |
|---|---|---|---|
| 5,242,694 A | 9/1993 | Reuther | |
| 6,660,915 B2 * | 12/2003 | Douma et al. ................ | 800/320 |
| 7,420,105 B2 | 9/2008 | Breddam et al. | |
| 2005/0204437 A1 | 9/2005 | Breddam et al. | |
| 2006/0057684 A1 * | 3/2006 | Bisgaard-Frantzen et al. ................ | 435/93 |
| 2008/0193593 A1 | 8/2008 | Hirota et al. | |

FOREIGN PATENT DOCUMENTS

| | | |
|---|---|---|
| AU | 38578/93 | 11/1993 |
| DE | 20 2007 005 281 | 8/2007 |
| GB | 2 220 955 | 1/1990 |
| WO | 9920795 | 4/1999 |
| WO | WO 00/15757 | 3/2000 |
| WO | WO 00/49157 | 8/2000 |
| WO | WO 02/053721 | 7/2002 |
| WO | WO 02/088301 | 11/2002 |
| WO | WO 2004/011591 | 2/2004 |
| WO | WO 2005/087934 | 9/2005 |

OTHER PUBLICATIONS

Kocsis et al, 2003, Plant Physiol., 131:1808-1815.*
McElroy et al, 1995, Bio/Technology, 13:245-249.*
Pimenta et al, 1998, Plant Physiol., 118:431-438.*
International Search Report from International Application No. PCT/DK2009/050315 dated May 25, 2011.
Written Opinion from International Application No. PCT/DK2009/050315, dated Jun. 16, 2011.
Anness et al: "Dimethyl sulphide—a review". *J. Inst. Brew*, vol. 88, pp. 244-252, Jul.-Aug. 1982.
Bourgis, F. et al., "S-Methylmethionine plays a major role in pholem sulfur transport and is synthesized by a novel type of methyltransferase" *Plant Cell* 11:pp. 1485-1497, 1999.
Dethier et al: "In Vivo and in Vitro Investigations of the synthesis of S-Methylmethionine During Barley Germination". American Society of Brewing Chemists, 1991.
Dickenson et al: "The relative importance of 5-methylmethionine and dimethyl sulphoxide as precursors of dimethyl sulphide in beer". EBC Congress, 1981.
Dickenson: "Identification of the dimethyl sulphide precursor in malt". *J. Inst. Brew*, vol. 85, pp. 329-333 Nov.-Dec. 1979.
Dufour et al: "Role of the methyltransferase activity in the synthesis of S-methylmethionine (DMS precursor) during germination and kilning". Proceedings of the Congress—European Brewery Convention, 1987.
Dufour, J.P., "Direct assay of S-methylmethionine using high-performance liquid chromatography and flourescence techniques." *J. Am. Soc. brew. Chem.* 44: pp. 1-6, 1986.
Durai, S. et al., "Zinc finger nucleases: custom-designed molecular scissors for genome engineering of plant and mammalian cells." *Nucleic Acids Res.*33: pp. 5978-5990, 2005.

(Continued)

*Primary Examiner* — Jason Deveau Rosen
(74) *Attorney, Agent, or Firm* — McNeill Baur PLLC

(57) ABSTRACT

According to the invention, there is provided barley-derived beverages characterized by notably reduced levels of both dimethyl sulfide (DMS) and/or its precursor S-methyl-L-methionine (SMM), or lacking said compounds. In addition, the invention relates to methods for producing the above-mentioned beverages—and also to barley plants useful in the preparation of such beverages, as well as other plant products prepared from said plants. Utilization of the invention clears the way for making improved production procedures of beverages with improved taste profiles, and promises also for notable reductions in the thermal energy input for production of beer.

26 Claims, 34 Drawing Sheets

(56) References Cited

OTHER PUBLICATIONS

Hansen, M. et al., "Antisense-mediated suppression of C-hordein biosynthesis in the barley grain results in correlated changes in the transcriptome, protein profile, and amino acid composition." *J. Exp. Bot.* 58:pp. 3987-3995, 2007.
Hirota et al: "Characterization of lipoxygenase-1 null mutants in barley".*Theor Appl Genet* , vol. 111. pp. 1580-1584, 2005.
Hirota N et al "Brewing performance of malted lipoxygenase-1 null barley and effect on the flavor stability of beer" *Cereal Chem.* 83(3), p. 250-254, 2006.
Hotzel et al. "Recovery and characterization of residual DNA from beer as a prerequisite for the detection of genetically modified ingredients", *Eur Food Res Technol.* 209, p. 192-196, 1999.
Hysert, D.W. et al., "The origin and control of dimethyl sulfide and its precursor in malt." *Tech. Q. MBAA* 17:34-43, 1980.
Iida, S. et al., "Modification of endogenous natural genes by gene targeting in rice and other higher plants." *Plant Mol. Biol.* 59:205-219, 2005.
Imashuku, H., "Two new technologies for efficient and flexible wort boiling: 1. Rest before wort boiling to convert SMM to DMS; 2. Hop boiling separately from wort." 3rd World Brewing Congress, Presentation O-52, Program Book, p. 91 and attached presentation slides, 2008.
Kleinhofs, A. et al., "Induction and selection of specific gene mutations in Hordeum and Pisum." *Mutat. Res.* 51:29-35, 1978.
Ko, S. et al., "S-Methylmethionine is both a substrate and an inactivator of 1-aminocyclopropane-1-carboxylate synthase." *Arch. Biochem. Biophys.* 421:85-90, 2004.
Kocsic, M.G. et al., "Insertional inactivation of the methionine S-methyltransferase gene eliminates the 5-methylmethionine cycle and increases the methylation ratio." *Plant Physiol.* 131:1808-1815, 2003.
Kumar, S. et al., "Gene targeting in plants: fingers on the move." *Trends Plant Sci.* 11:159-161, 2006.
Lal et al: "A Splice Site Mutant of Maize Activates Cryptic Splice Sites, Elicits Intron Inclusion and Exon Exclusion, and Permits Branch Point Elucidation". *Plant Physiology*, vol. 121, pp. 411-418, Oct. 1999.
Lillo et al: "Biosynthesis of the Methyl Donors S Adenosyl methionine and S Methyl Methionine in Barley Seedlings Hordeum-Vulgare Cultivar Ingrid". *BPP*, vol. 175 No. 2 pp. 104-122, 1980.
Maquat, L.E. et al., "Quality control of mRNA function." *Cell* 104:pp. 173-176, 2001.
McElroy, D. et al., "What's brewing in barley biotechnology?" *Bio/Technology* 13: pp. 245-249, 1995.
Meilgaard, M.C., "Prediction of flavor differences between beers from their chemical composition." *J. Agric. Food Chem.* 30:pp. 1009-1017, 1982.
Mendell, J.T. and Dietz, H.C., "When the message goes awry: Disease-producing mutations that influence mRNA content and performance." *Cell* 107: pp. 411-414, 2001.
Mudd, S.H. et al., "The S-methylmethionine cycle in Lemna paucicostata." *Plant Physiol.* 93:623-630, 1990.

Nevo, E., "Origin, evolution, population genetics and resources for breeding of wild barley, Hordeum spontaneum, in the Fertile Crescent." In Shewry, P. R. (ed.): Barley: Genetics, Biochemistry, Molecular Biology and Biotechnology. CAB International, Wallingford, UK, pp. 19-43. 1992.
Pimenta et al: "S-Adenosyl—L—Methionine: L—Methionine S-Methyltransferase from Germinating Barley". *Plant Physiol*, vol. 118. pp. 431-438, 1998.
Pimenta, M.J. et al., "Determination of S-adenosyl-L-methionine:L-methionine S-methyltransferase activity by selective adsorption of [methyl-3H]S-adenosylmethionine onto activated charcoal." *Anal. Biochem.* 225: pp. 167-169, 1995.
Ranocha, P. et al., "The S-methylmethionine cycle in angiosperms: ubiquity, antiquity and activity." *Plant J.* 25:pp. 575-584, 2001.
Rasmussen, S.K. et al., "Identification of two low-phytate barley (*Hordeum vulgare* L.) grain mutants by TLC and genetic analysis." *Hereditas* 129: pp. 107-112, 1998.
Robbins M.P. et al., "Genetic manipulation of condensed tannins in higher plants." *Plant Physiol.* 116: pp. 1133-1144, 1998.
Tagmount et al: "An Essential Role of S-Adenosyl—L—Methionine: L—Mrthionine S-Methyltransferase in selenium Volatilization by Plants. Methylation of Selenomethionine to Selenium-Methyl-L-Selenium-Methionine, the Prescursor of Volatile Selenium". *Plant Physiology*, vol. 130: pp. 847-856. Oct. 2002.
Thanbichler et al. "S-Methylmethione Metabolism in *Escherichia coli.*" *J. of Bacteriology*. vol. 181. No. 2. pp. 662-665. 1999.
Tzfira, T. et al., "Towards targeted mutagenesis and gene replacement in plants." *Trends Biotechnol.* 23:pp. 567-569, 2005.
von Bothmer, R., "The wild species of Hordeum: Relationships and potential use for Improvement of cultivated barley." In Shewry, P. R. (ed.): "Barley: Genetics, Biochemistry, Molecular Biology and Biotechnology." pp. 3-18. CAB International, Wallingford, UK, 1992.
Wu, J. et al., "Nonsense-mediated mRNA decay (NMD) silences the accumulation of aberrant trypsin proteinase inhibitor mRNA in Nicotiana attenuata." Plant J. 51:693-706, 2007.
Yang et al: "Factors Involved in the Formation of Two Precursors of Dimethylsulfide During Malting". American Society of Brewing Chemists, 1998.
Scheuren, H. and Sommer, K., "Vaporescence versus boiling—Expulsion of aromatic compounds during the whole wort production." 3$^{rd}$ World Brewing Congress, Presentation O-55, Program Book, p. 92 and attached presentation slides, 2008.
Sinibaldi, R.M. ad Mettler I.J., "Intron splicing and intron-mediated enhanced expression in monocots." *Prog. Nucleic Acid Res. Mol. Biol.*, vol. 42, 1992, pp. 229-257.
Nucleotide Sequence, Access No. EBI AB028870, Apr. 21, 2000.
B. Khursheed & J.C. Rogers, J. Biol. Chem. 263(35): 18953-60 (1988).
M.J. Hawkesford, Physiologia Plantarum 117: 155-163, 2003.
G Yang & PB Schwarz, J. Am. Brew. Chem. 53(2): 45-49 (1995).
R. Willaert, Chapter 20 (pp. 441-503) in the Handbook of Food Products Manufacturing, Y.H. Hui, Ed., John Wiley & Sons, Inc. (2007).
USPTO PAIR prosecution history of U.S. Appl. No. 13/701,604.
USPTO PAIR prosecution history of U.S. Appl. No. 13/141,579.

* cited by examiner

```
   1 ATGGCTGCGGCGGCGGGGGACGTGGAGGCGTTCCTGGCGGCGTGCCAGGCGTCGGGCGAC   60
   1  M  A  A  A  A  G  D  V  E  A  F  L  A  A  C  Q  A  S  G  D    20

61 GCGGCGTACGGCGCCGCCAAGGCCGTGCTGGAGCGGCTCGAGGCGCCGGCCACGCGCGCC  120
  21  A  A  Y  G  A  A  K  A  V  L  E  R  L  E  A  P  A  T  R  A    40

121 GAGGCCAGGCGGCTCCTCGGCGCCGTGCGACGGCGCTTCGCCGCCGGCGGCCCGGCCGCG  180
  41  E  A  R  R  L  L  G  A  V  R  R  R  F  A  A  G  G  P  A  A    60

181 GGGCTCGAGTGCTTCCGCACCTTCCACTTCCGCATCCACGACGTCGTCCTCGACCCCCAC  240
  61  G  L  E  C  F  R  T  F  H  F  R  I  H  D  V  V  L  D  P  H    80

241 CTCCAAGGATTCCAGCAAAGAAAGAAGCTAACAATGATGGAGATACCCAGCATTTTCATT  300
  81  L  Q  G  F  Q  Q  R  K  K  L  T  M  M  E  I  P  S  I  F  I   100

301 CCAGAAGACTGGTCATTCACTTTCTACGAGGGTCTCAACCGGCATCCAGATTCCATCTTC  360
 101  P  E  D  W  S  F  T  F  Y  E  G  L  N  R  H  P  D  S  I  F   120

361 AGGGATAAGACAGTAGCAGAGCTGGGATGTGGCAATGGTTGGATATCCATTGCACTTGCA  420
 121  R  D  K  T  V  A  E  L  G  C  G  N  G  W  I  S  I  A  L  A   140

421 GAAAAGTGGTGCCCTTCGAAGGTTTATGGTCTGGATATAAACCCAAGAGCTATCAAGATT  480
 141  E  K  W  C  P  S  K  V  Y  G  L  D  I  N  P  R  A  I  K  I   160

481 GCATGGATAAACCTTTACTTGAATGCACTAGACGACGATGGTCTCCCAATCTATGATGCG  540
 161  A  W  I  N  L  Y  L  N  A  L  D  D  D  G  L  P  I  Y  D  A   180

541 GAGGGGAAAACATTGCTTGACAGAGTCGAATTCTATGAATCTGATCTTCTTTCTTACTGT  600
 181  E  G  K  T  L  L  D  R  V  E  F  Y  E  S  D  L  L  S  Y  C   200

601 AGAGATAACAAGATAGAACTTGATCGCATTGTTGGATGCATACCACAGATTCTTAACCCC  660
 201  R  D  N  K  I  E  L  D  R  I  V  G  C  I  P  Q  I  L  N  P   220

661 AATCCAGAGGCAATGTCAAAGATTGTAACTGAAAATTCAAGTGAGGAGTTCTTGTACTCC  720
 221  N  P  E  A  M  S  K  I  V  T  E  N  S  S  E  E  F  L  Y  S   240

721 TTGAGCAACTACTGTGCTCTCCAGGGTTTTGTTGAGGACCAATTTGGCCTCGGGTTGATT  780
 241  L  S  N  Y  C  A  L  Q  G  F  V  E  D  Q  F  G  L  G  L  I   260

781 GCTCGGGCTGTTGAAGAAGGGATATCTGTGATAAAGCCTAGTGGTCTTATGGTATTCAAC  840
 261  A  R  A  V  E  E  G  I  S  V  I  K  P  S  G  L  M  V  F  N   280

841 ATGGGAGGCCGGCCAGGACAAGGTGTCTGTGAGCGCCTATTTCTACGCCGTGGATTTCGC  900
 281  M  G  G  R  P  G  Q  G  V  C  E  R  L  F  L  R  R  G  F  R   300

901 ATCAATAAGCTCTGGCAAACAAAAATTATGCAGGCTGCTGACACAGACATCTCCGCTTTA  960
 301  I  N  K  L  W  Q  T  K  I  M  Q  A  A  D  T  D  I  S  A  L   320

961 GTTGAAATTGAGAAAAATAGCCGACATCGCTTCGAGTTCTTTATGGATCTTGTTGGGGAT 1020
 321  V  E  I  E  K  N  S  R  H  R  F  E  F  F  M  D  L  V  G  D   340

1021 CAGCCTGTGTGTGCGCGCACAGCATGGGCATACATGAAATCTGGTGGCCGCATTTCACAT 1080
 341  Q  P  V  C  A  R  T  A  W  A  Y  M  K  S  G  G  R  I  S  H   360
```

FIG. 10

```
1081  GCTTTGTCTGTGTATAGCTGTCAACTTCGCCAGCCCAACCAGGTGAAGAAAATATTTGAG  1140
 361   A  L  S  V  Y  S  C  Q  L  R  Q  P  N  Q  V  K  K  I  F  E   380

1141  TTCCTTAAAGACGGATTCCATGAAGTCAGCAGCTCCCTCGATTTGTCCTTTGATGATGAT  1200
 381   F  L  K  D  G  F  H  E  V  S  S  S  L  D  L  S  F  D  D  D   400

1201  TCTGTTGCTGATGAAAAAATTCCTTTCCTAGCATACCTAGCTAGTTTCTTGCAAGAGAAT  1260
 401   S  V  A  D  E  K  I  P  F  L  A  Y  L  A  S  F  L  Q  E  N   420

1261  AAGTCTAATCCTTGTGAGCCTCCAGCTGGATGTTTAAATTTCCGGAATCTTGTTGCTGGA  1320
 421   K  S  N  P  C  E  P  P  A  G  C  L  N  F  R  N  L  V  A  G   440

1321  TTTATGAAGAGTTACCACCACATCCCATTAACTCCTGATAATGTTGTTGTGTTCCCATCC  1380
 441   F  M  K  S  Y  H  H  I  P  L  T  P  D  N  V  V  V  F  P  S   460

1381  CGTGCTGTTGCAATCGAAAATGCTCTTCGGTTGTTCTCACCTGGACTTGCAATTGTTGAC  1440
 461   R  A  V  A  I  E  N  A  L  R  L  F  S  P  G  L  A  I  V  D   480

1441  GAACACCTAACCAGACACTTGCCCAAGCAATGGTTAACATCTTTAGCAATTGAGGAAAGT  1500
 481   E  H  L  T  R  H  L  P  K  Q  W  L  T  S  L  A  I  E  E  S   500

1501  AACCATGCTAAAGATACAGTAACTGTAATCGAAGCACCACGCCAATCAGATTTGCTGATT  1560
 501   N  H  A  K  D  T  V  T  V  I  E  A  P  R  Q  S  D  L  L  I   520

1561  GAGTTGATCAGGAAACTGAAGCCTCAGGTTGTTGTTACTGGCATGGCTCAGTTTGAGGCT  1620
 521   E  L  I  R  K  L  K  P  Q  V  V  V  T  G  M  A  Q  F  E  A   540

1621  ATCACCAGTGCTGCTTTCGTGAACTTATTAAGTGTAACGAAAGATGTTGGTTCCCGATTA  1680
 541   I  T  S  A  A  F  V  N  L  L  S  V  T  K  D  V  G  S  R  L   560

1681  TTACTAGATATTTCAGAACATCTGGAATTGTCTAGTCTGCCAAGCTCAAATGGTGTATTG  1740
 561   L  L  D  I  S  E  H  L  E  L  S  S  L  P  S  S  N  G  V  L   580

1741  AAATATCTTGCTGGGAAGACCCTGCCTTCACATGCGGCTATATTGTGTGGCTTAGTTAAG  1800
 581   K  Y  L  A  G  K  T  L  P  S  H  A  A  I  L  C  G  L  V  K   600

1801  AATCAGGTTTATTCTGATCTGGAAGTTGCTTTTGCTATCTCTGAAGATCCAACTGTTTAT  1860
 601   N  Q  V  Y  S  D  L  E  V  A  F  A  I  S  E  D  P  T  V  Y   620

1861  AAGGCATTGTCACAAACTATTGAGCTATTGGAAGGACATACTTCTGTGATCAGCCAGCAC  1920
 621   K  A  L  S  Q  T  I  E  L  L  E  G  H  T  S  V  I  S  Q  H   640

1921  TATTATGGTTGTCTTTTCCATGAGCTGCTGGCATTTCAAATTGGTGACCGGCATCCACAA  1980
 641   Y  Y  G  C  L  F  H  E  L  L  A  F  Q  I  G  D  R  H  P  Q   660

1981  CAAGAGAGAGAACCTGCAGAAGTGATATCTAAGGAGATGATAGGGTTTTCAAGTTCAGCT  2040
 661   Q  E  R  E  P  A  E  V  I  S  K  E  M  I  G  F  S  S  S  A   680

2041  ATGTCCACCCTAGAAGGAGCTGAGTTTTTCGTTCCTGGTTCCATGGAATCCGGTGTCATA  2100
 681   M  S  T  L  E  G  A  E  F  F  V  P  G  S  M  E  S  G  V  I   700

2101  CATATGGATCTGGACCGCAGCTTCTTGCCAGTACCTTCTGCAGTAAACGCCTCCATTTTC  2160
 701   H  M  D  L  D  R  S  F  L  P  V  P  S  A  V  N  A  S  I  F   720

2161  GAAAGTTTTGTTCGTCAGAACATCACTGATTCTGAAACCGATGTCCGTTCCAGCATTCAG  2220
 721   E  S  F  V  R  Q  N  I  T  D  S  E  T  D  V  R  S  S  I  Q   740
```

FIG. 10 - continued

```
2221  CAGCTGGTGAAAGATAGCTATGGTTTCTCAGCAGGCGGTGCTTCTGAAATTATATACGGG  2280
 741   Q  L  V  K  D  S  Y  G  F  S  A  G  G  A  S  E  I  I  Y  G   760
2281  AACACCTGTCTCGCGCTCTTCAACAAGCTTGTTCTTTGCTGCATGCAAGAACAGGGCACC  2340
 761   N  T  C  L  A  L  F  N  K  L  V  L  C  C  M  Q  E  Q  G  T   780
2341  TTGCTTTTCCCCTTGGGAACCAACGGGCATTACGTCAACGCAGCAAAGTTTGTGAATGCA  2400
 781   L  L  F  P  L  G  T  N  G  H  Y  V  N  A  A  K  F  V  N  A   800
2401  ACCACCTTGACTATTCCAACGAAGGCAGATTCAGGCTTCAAGATCGAACCAAGTGCTCTA  2460
 801   T  T  L  T  I  P  T  K  A  D  S  G  F  K  I  E  P  S  A  L   820
2461  GCCGACACACTAGAGAAGGTGTCTCAGCCGTGGGTCTATATTTCTGGCCCCACAATCAAC  2520
 821   A  D  T  L  E  K  V  S  Q  P  W  V  Y  I  S  G  P  T  I  N   840
2521  CCTACTGGCTTCCTGTACAGTGACGACGATATAGCAGAGCTGCTTTCTGTCTGTGCGACA  2580
 841   P  T  G  F  L  Y  S  D  D  D  I  A  E  L  L  S  V  C  A  T   860
2581  TACGGAGCCAGGGTGGTGATAGATACCTCCTCCTCTGGTCTGGAGTTCCAAGCCACCGGC  2640
 861   Y  G  A  R  V  V  I  D  T  S  S  S  G  L  E  F  Q  A  T  G   880
2641  TGCAGCCAGTGGAATTTGGAAAGATGTCTTTCTAATGTCAAGTCTTCAAAGCCCTCGTTC  2700
 881   C  S  Q  W  N  L  E  R  C  L  S  N  V  K  S  S  K  P  S  F   900
2701  TCCGTTGTCCTGCTCGGAGAGCTGTCCTTTGAGCTGACCACGGCTGGGCTTGATTTCGGG  2760
 901   S  V  V  L  L  G  E  L  S  F  E  L  T  T  A  G  L  D  F  G   920
2761  TTTCTGATTATGAGCGACTCGTCCTTGGTTGACACATTTTACAGTTTCCCAAGCTTGAGT  2820
 921   F  L  I  M  S  D  S  S  L  V  D  T  F  Y  S  F  P  S  L  S   940
2821  CGGCCACACAGCACGTTGAAGTACACGTTCAGGAAGCTGTTGGGTCTTAAGAACCAGAAG  2880
 941   R  P  H  S  T  L  K  Y  T  F  R  K  L  L  G  L  K  N  Q  K   960
2881  GATCAGCATTTCTCTGATCTCATCCTTGAGCAGAAGGAGACGTTGAAGAATCGTGCCGAC  2940
 961   D  Q  H  F  S  D  L  I  L  E  Q  K  E  T  L  K  N  R  A  D   980
2941  CAGTTGATCAAGACGCTTGAGAGCTGCGGCTGGGACGCTGTGGGCTGCCATGGCGGCATC  3000
 981   Q  L  I  K  T  L  E  S  C  G  W  D  A  V  G  C  H  G  G  I  1000
3001  TCGATGCTTGCAAAACCGACCGCCTACATTGGCAAATCGCTCAAGGTGGACGGCTTTGAG  3060
1001   S  M  L  A  K  P  T  A  Y  I  G  K  S  L  K  V  D  G  F  E  1020
3061  GGCAAGCTGGACAGCCACAACATGAGGGAAGCCCTCCTGAGGTCCACCGGGCTGTGCATT  3120
1021   G  K  L  D  S  H  N  M  R  E  A  L  L  R  S  T  G  L  C  I  1040
3121  AGCAGCAGCGGGTGGACAGGGGTGCCGGACTACTGCCGCTTCAGCTTTGCTCTGGAGAGC  3180
1041   S  S  S  G  W  T  G  V  P  D  Y  C  R  F  S  F  A  L  E  S  1060
3181  GGCGACTTCGACCGGGCCATGGAGTGCATCGCCCGGTTCAGGGAGCTGGTCCTTGGTGGC  3240
1061   G  D  F  D  R  A  M  E  C  I  A  R  F  R  E  L  V  L  G  G  1080
3241  GGTGCTAAGGTGAATGGTAGCAACTAG
1081   G  A  K  V  N  G  S  N  *
```

FIG. 10 - continued

```
                  1                                                           60
cv. Haruna Nijo   MAAAAGDVEAFLAACQASGDAAYGAAKAVLERLEAPATRAEARRLLGAVRRRFAAGGPAA
cv. Prestige      MAAAAGDVEAFLAACQASGDAAYGAAKAVLERLEAPATRAEARRLLGAVRRRFAAGGPAA 61                                                          120
cv. Haruna Nijo   GLECFRTFHFRIHDVVLDPHLQGFQQRKKLTMMEIPSIFIPEDWSFTFYEGLNRHPDSIF
cv. Prestige      GLECFRTFHFRIHDVVLDPHLQGFQQRKKLTMMEIPSIFIPEDWSFTFYEGLNRHPDSIF 121                                                         180
cv. Haruna Nijo   RDKTVAELGCGNGWISIALAEKWCPSKVYGLDINPREIKIAWINLYLNALDDDGLPIYDA
cv. Prestige      RDKTVAELGCGNGWISIALAEKWCPSKVYGLDINPRAIKIAWINLYLNALDDDGLPIYDA 181                                                         240
cv. Haruna Nijo   EGKTLLDRVEFYESDLLSYCRDNKIELDRIVGCIPQILNPNPEAMSKIVTENSSEEFLYS
cv. Prestige      EGKTLLDRVEFYESDLLSYCRDNKIELDRIVGCIPQILNPNPEAMSKIVTENSSEEFLYS 241                                                         300
cv. Haruna Nijo   LSNYCALQGFVEDQFGLGLIARAVEEGISVIKPSGLMVFNMGGRPGQGVCERLFLRRGFR
cv. Prestige      LSNYCALQGFVEDQFGLGLIARAVEEGISVIKPSGLMVFNMGGRPGQGVCERLFLRRGFR 301                                                         360
cv. Haruna Nijo   INKLWQTKIMQAADTDISALVEIEKNSRHRFEFFMDLVGDQPVCARTAWAYMKSGGRISH
cv. Prestige      INKLWQTKIMQAADTDISALVEIEKNSRHRFEFFMDLVGDQPVCARTAWAYMKSGGRISH 361                                                         420
cv. Haruna Nijo   ALSVYSCQLRQPNQVKKIFEFLKDGFHEVSSSLDLSFDDDSVADEKIPFLAYLASFLQEN
cv. Prestige      ALSVYSCQLRQPNQVKKIFEFLKDGFHEVSSSLDLSFDDDSVADEKIPFLAYLASFLQEN 421                                                         480
cv. Haruna Nijo   KSNPCEPPAGCLNFRNLVAGFMKSYHHIPLTPDNVVVFPSRAVAIENALRLFSPGLAIVD
cv. Prestige      KSNPCEPPAGCLNFRNLVAGFMKSYHHIPLTPDNVVVFPSRAVAIENALRLFSPGLAIVD 481                                                         540
cv. Haruna Nijo   EHLTRHLPKQWLTSLAIEESNHAKDTVTVIEAPRQSDLLIELIRKLKPQVVVTGMAQFEA
cv. Prestige      EHLTRHLPKQWLTSLAIEESNHAKDTVTVIEAPRQSDLLIELIRKLKPQVVVTGMAQFEA
```

FIG. 11

```
                541                                                          600
cv. Haruna Nijo ITSAAFVNLLSVTKDVGSRLLLDISEHLELSSLPSSNGVLKYLAGKTLPSHAAILCGLVK
cv. Prestige    ITSAAFVNLLSVTKDVGSRLLLDISEHLELSSLPSSNGVLKYLAGKTLPSHAAILCGLVK 601                                                          660
cv. Haruna Nijo NQVYSDLEVAFAISEDPTVYKALSQTIELLEGHTSVISQHYYGCLFHELLAFQIGDRHPQ
cv. Prestige    NQVYSDLEVAFAISEDPTVYKALSQTIELLEGHTSVISQHYYGCLFHELLAFQIGDRHPQ 661                                                          720
cv. Haruna Nijo QEREPAEVISKEMIGFSSSAMSTLEGAEFFVPGSMESGVIHMDLDRSFLPVPSAVNASIF
cv. Prestige    QEREPAEVISKEMIGFSSSAMSTLEGAEFFVPGSMESGVIHMDLDRSFLPVPSAVNASIF 721                                                          780
cv. Haruna Nijo ESFVRQNITDSETDVRSSIQQLVKDSYGFSAGGASEIIYGNTCLALFNKLVLCCMQEQGT
cv. Prestige    ESFVRQNITDSETDVRSSIQQLVKDSYGFSAGGASEIIYGNTCLALFNKLVLCCMQEQGT 781                                                          840
cv. Haruna Nijo LLFPLGTNGHYVNAAKFVNATTLTIPTKADSGFKIEPSALADTLEKVSQPWVYISGPTIN
cv. Prestige    LLFPLGTNGHYVNAAKFVNATTLTIPTKADSGFKIEPSALADTLEKVSQPWVYISGPTIN 841                                                          900
cv. Haruna Nijo PTGFLYSDDDIAELLSVCATYGARVVIDTSSSGLEFQATGCSQWNLERCLSNVKSSKPSF
cv. Prestige    PTGFLYSDDDIAELLSVCATYGARVVIDTSSSGLEFQATGCSQWNLERCLSNVKSSKPSF 901                                                          960
cv. Haruna Nijo SVVLLGELSFELTTAGLDFGFLIMSDSSLVDTFYSFPSLSRPHSTLKYTFRKLLGLKNQK
cv. Prestige    SVVLLGELSFELTTAGLDFGFLIMSDSSLVDTFYSFPSLSRPHSTLKYTFRKLLGLKNQK 961                                                         1020
cv. Haruna Nijo DQHFSDLILEQKETLKNRADQLIKMLESCGWDAVGCHGGISMLAKPTAYIGKSLKVDGFE
cv. Prestige    DQHFSDLILEQKETLKNRADQLIKTLESCGWDAVGCHGGISMLAKPTAYIGKSLKVDGFE 1021                                                        1080
cv. Haruna Nijo GKLDSHNMREALLRSTGLCISSSGWTGVPDYCRFSFALESGDFDRAMECIARFRELVLGG
cv. Prestige    GKLDSHNMREALLRSTGLCISSSGWTGVPDYCRFSFALESGDFDRAMECIARFRELVLGG 1081
cv. Haruna Nijo GAKVNGSN
cv. Prestige    GAKVNGSN
```

```
                              1                                                            60
cv. Prestige         (  1) MAAAAGDVEAFLAACQASGDAAYGAAKAVLERLEAPATRAEARRLLGAVRRRFAAGGPAA
Line 8063, Product 2 (  1) MAAAAGDVEAFLAACQASGDAAYGAAKAVLERLEAPATRAEARRLLGAVRRRFAAGGPAA
Line 8063, Product 3 (  1) MAAAAGDVEAFLAACQASGDAAYGAAKAVLERLEAPATRAEARRLLGAVRRRFAAGGPAA
Line 8063, Product 4 (  1) MAAAAGDVEAFLAACQASGDAAYGAAKAVLERLEAPATRAEARRLLGAVRRRFAAGGPAA 61                                                          120
cv. Prestige         ( 61) GLECFRTFHFRIHDVVLDPHLQGFQQRKKLTMMEIPSIFIPEDWSFTFYEGLNRHPDSIF
Line 8063, Product 2 ( 61) GLECFRTFHFRIHDVVLDPHLQGFQQRKKLTMMEIPSIFIPEDWSFTFYEGLNRHPDSIF
Line 8063, Product 3 ( 61) GLECFRTFHFRIHDVVLDPHLQGFQQRKKLTMMEIPSIFIPEDWSFTFYEGLNRHPDSIF
Line 8063, Product 4 ( 61) GLECFRTFHFRIHDVVLDPHLQGFQQRKKLTMMEIPSIFIPEDWSFTFYEGLNRHPDSIF 121                                                         180
cv. Prestige         (121) RDKTVAELGCGNGWISIALAEKWCPSKVYGLDINPRAIKIAWINLYLNALDDDGLPIYDA
Line 8063, Product 2 (121) RDKTVAELGCGNGWISIALAEKWCPSKVYGLDINPRAIKIAWINLYLNALDDDGLPIYDA
Line 8063, Product 3 (121) RDKTVAELGCGNGWISIALAEKWCPSKVYGLDINPRAIKIAWINLYLNALDDDGLPIYDA
Line 8063, Product 4 (121) RDKTVAELGCGNGWISIALAEKWCPSKVYGLDINPRAIKIAWINLYLNALDDDGLPIYDA
                                                                             ***********
                              181                                                         240
cv. Prestige         (181) EGKTLLDRVEFYESDLLSYCRDNKIELDRIVGCIPQILNPNPEAMSKIVTENSSEEFLYS
Line 8063, Product 2 (181) EGKTLLDRVEFYESDLLSYCRDNKIELDRIVGCIPQILNPNPEAMSKIVTENSSEEFLYS
Line 8063, Product 3 (181) EGKTLLDRVEFYESDLLSYCRDNKIELDRIVGCIPQILNPNPEAMSKIVTENSSEEFLYS
Line 8063, Product 4 (181) EGKTLLDRVEFYESDLLSYCRDNKIELDRIVGCIPQILNPNPEAMSKIVTENSSEEFLYS
                           ***
                              241                                                         300
cv. Prestige         (241) LSNYCALQGFVEDQFGLGLIARAVEEGISVIKPSGLMVFNMGGRPGQGVCERLFLRRGFR
Line 8063, Product 2 (241) LSNYCALQGFVEDQFGLGLIARAVEEGISVIKPSGLMVFNMGGRPGQGVCERLFLRRGFR
Line 8063, Product 3 (241) LSNYCALQGFVEDQFGLGLIARAVEEGISVIKPSGLMVFNMGGRPGQGVCERLFLRRGFR
Line 8063, Product 4 (241) LSNYCALQGFVEDQFGLGLIARAVEEGISVIKPSGLMVFNMGGRPGQGC 301                                                        1088
cv. Prestige         (301) INKLWQTKIMQAADTDISALVEIEKNSRMDLV-------->>>>>>>>>--------NGSN
Line 8063, Product 2 (301) INKLWQTKIMQIAIL
Line 8063, Product 3 (301) INKLWQTKIMQIAIL
Line 8063, Product 4 (290)
```

Mutant 14018
G1462→A

Exon 2 — Intron 2 — Exon 3

WT  GAT ··· 145 nt ··· TGGT ··· 40 nt ··· AGgt ··· 79 nt ··· aggt ··· 275 nt ··· agGT ··· 202 nt ··· CAG
Mut. GAT ··· 145 nt ··· TGGT ··· 40 nt ··· AGat ··· 79 nt ··· aggt ··· 275 nt ··· agGT ··· 202 nt ··· CAG 8    6*   7

E

|  | 5' Splice site | | | | 3' Splice site | | | |
| --- | --- | --- | --- | --- | --- | --- | --- | --- |
|  | -2 | -1 : | 1 | 2 | -2 | -1 : | 1 | 2 |
|  | Base composition in percent | | | | | | | |
| G | 9 | 79 | 100 | 0 | 0 | 100 | 62 | 24 |
| A | 64 | 7 | 0 | 0 | 100 | 0 | 14 | 18 |
| C | 14 | 8 | 0 | 0 | 0 | 0 | 15 | 18 |
| T | 12 | 6 | 0 | 100 | 0 | 0 | 9 | 39 |
| Consensus | A | G : | G | T | A | G : | G | T |
| Intron 2, Mutant 14018 | A | G : | G | T | A | G : | G | C |

E

```
                              1                                                            60
cv. Prestige          (  1)  MAAAAGDVEAFLAACQASGDAAYGAAKAVLERLEAPATRAEARRLLGAVRRRFAAGGPAA
Line 14018, Product 6 (  1)  MAAAAGDVEAFLAACQASGDAAYGAAKAVLERLEAPATRAEARRLLGAVRRRFAAGGPAA
Line 14018, Product 7 (  1)  MAAAAGDVEAFLAACQASGDAAYGAAKAVLERLEAPATRAEARRLLGAVRRRFAAGGPAA
Line 14018, Product 8 (  1)  MAAAAGDVEAFLAACQASGDAAYGAAKAVLERLEAPATRAEARRLLGAVRRRFAAGGPAA 61                                                          120
cv. Prestige          ( 61)  GLECFRTFHFRIHDVVLDPHLQGFQQRKKLTMMEIPSIFIPEDWSFTFYEGLNRHPDSIF
Line 14018, Product 6 ( 61)  GLECFRTFHFRIHDVVLDPHLQGFQQRKKLTMMEIPSIFIPEDWSFTFYEGLNRHPDSIF
Line 14018, Product 7 ( 61)  GLECFRTFHFRIHDVVLDPHLQGFQQRKKLTMMEIPSIFIPEDWSFTFYEGLNRHPDSIF
Line 14018, Product 8 ( 61)  GLECFRTFHFRIHDVVLDPHLQGFQQRKKLTMMEIPSIFIPEDWSFTFYEGLNRHPDSIF 121                                                         180
cv. Prestige          (121)  RDKTVAELGCGNGWISIALAEKWCPSKVYGLDINPRAIKIAWINLYLNALDDDGLPIYDA
Line 14018, Product 6 (121)  RDKTVAELGCGNGWISIALAEKWCPSKIGTSCSVDIYLISFVANMGPAEVRHLLRLLYMK
Line 14018, Product 7 (121)  RDKTVAELGCGNGWISIALAEKWCPSKIGTSCSVDIYLISFVANMGPAEVRHLLRFMVWI
Line 14018, Product 8 (121)  RDKTVAELGCGNGLWSGYKPKSYQDCMDKPLLECTRRRWSPNL 181                                                        1088
cv. Prestige          (181)  EGKTLLDRVEFYESDLLSYCRDNKIELDRIVG-------->>>>>>>>--------NGSN
Line 14018, Product 6 (181)  LLGVCQ
Line 14018, Product 7 (181)
Line 14018, Product 8 (164)
```

BARLEY AND MALT-DERIVED BEVERAGES WITH LOW DMS LEVEL

This application is a National Stage Application of PCT/DK2009/050315, filed 1 Dec. 2009, which claims benefit of Serial No. 200801708, filed 3 Dec. 2008 in Denmark and which applications are incorporated herein by reference. To the extent appropriate, a claim of priority is made to each of the above disclosed applications.

All patent and non-patent references cited in the application are hereby incorporated by reference in their entirety.

FIELD OF THE INVENTION

The present invention relates to barley-derived beverages characterized by notably reduced levels of both dimethyl sulfide (DMS) and/or its precursor S-methyl-L-methionine (SMM), or lacking one or preferably both of said compounds. In addition, the invention relates to methods for producing the above-mentioned beverages—and also to barley plants useful in the preparation of such beverages, as well as other plant products prepared from said plants. While the invention enables production of beverages characterized by improved taste profiles, it also facilitates a new paradigm for production methods with notable reductions in the thermal energy input—particularly with respect to boiling of wort.

BACKGROUND OF THE INVENTION

Beverages, notably beer, may be produced on the basis of barley—*Hordeum vulgare*, L.—which is a monocotyledonous crop plant cultivated in many parts of the world. Barley is economically important, both as a raw material for industrial products, including beer, and also as a source of animal feed.

In beer, as well as in many vegetables and foodstuffs—including tea, cocoa, milk, wines, spirits (such as rum), sweet corn, and numerous cooked vegetables—DMS adds prominent, generally beneficial odor and flavor notes to the product. However, a high level of DMS imparts a flavor that may be undesirable, usually described as "cooked sweet corn" or sometimes as "blackcurrant-like".

Depending on beer type, DMS levels typically may be up to 144 µg/L and sometimes can reach as much as 150 ppb (150 µg/L), with said compound often contributing to undesirable "cooked vegetable" or "cabbage-like" flavors. However, a low level of the compound is sometimes desirable in lager beer as it may contribute to palate fullness and overall beer aroma; the sensory threshold is ~25-50 ppb, for example around 30-45 µg/L (Meilgaard, 1982). The DMS flavour is generally not noticed when DMS levels are <10 ppb.

SMM, herein also denoted DMS precursor (DMSP), is synthesized in germinating barley kernels by the action of functional components of the SMM cycle (FIG. 1A). Here, the methionine (Met)-S-methyltransferase (MMT) enzyme catalyzes the transfer of a methyl group from S-adenosylmethionine (AdoMet) to Met, forming SMM. The latter compound can in turn serve as methyl donor for Met synthesis from homocysteine (Hcy), a reaction catalyzed by the enzyme Hcy-S-methyltransferase (HMT). Although there is debate on the definitive role of MMT, it was initially proposed to prevent Met pools for protein synthesis from being depleted by an overshoot in AdoMet synthesis (Mudd and Datko, 1990). The SMM cycle also has been suggested to function in the long-distance sulfur transport in plants, with a major flux from Met to SMM in leaves, phloem transport of SMM, and reconversion of SMM to Met in developing kernels or other sink tissues (Bourgis et al., 1999). But later radiotracer experiments revealed that said cycle manages control of AdoMet levels rather than preventing depletion of Met (Ranocha et al., 2001). An alternative explanation on the physiological role of SMM in plants relates to the regulation of ethylene synthesis (Ko et al., 2004), principally with the ideas manifested through studies with recombinant 1-aminocyclopropane-1-carboxylate synthase from yeast of the genus *Pichia*.

McElroy and Jacobsen (1995) have speculated that it may be possible to regulate SMM synthesis by using, for example, antisense technology. However, no guidance was provided on relevant target genes to antisense, but it was expected that the likelihood of a positive outcome was questionable as large reductions in SMM levels could be harmful to barley growth and development. Alternative solutions for obtaining lower level of SMM were not discussed by McElroy and Jacobsen (supra). In addition, as discussed in detail below, antisense technologies have not been successfully applied in barley to completely abolish gene expression.

Unfortunately, no methods are available for preparing transgenic barley plants that completely lack expression of a given protein. In general for barley, application of antisense techniques lead to transgenic plants still expressing some of the protein in question (see for example Robbins et al. 1998; Stahl et al., 2004; Hansen et al., 2007).

Also, effective methods for preparing specific mutations using chimeric RNA/DNA or site directed mutagenesis have not been developed for use in barley plants. In line with this, and despite intensive efforts, inventors of the present publication are not aware of any published example on successful oligonucleotide-directed gene targeting in barley. Although not pursued in barley, Iida and Terada (2005) note that oligonucleotide-directed gene targeting has been tested in maize, tobacco and rice—but in all cases with the herbicide-resistant gene acetolactate synthase (ALS) as a target. According to the conclusion by Iida and Terada (supra), it remains to be established whether the above-mentioned strategy, with appropriate modifications, is applicable to genes other than those directly selectable, such as the ALS genes. Targeted mutagenesis using zinc-finger nucleases represents another tool that potentially could allow future investigations in basic plant biology or modifications in crop plants (Durai et al., 2005; Tzfira and White, 2005; Kumar et al., 2006). Also in this case, mutagenesis has not been pursued or successfully applied in barley.

Nonetheless, barley mutants may be prepared by random mutagenesis using irradiation or chemical treatment, such as by treatment with sodium azide ($NaN_3$). An example concerns barley kernels mutagenized through the use of $NaN_3$, and subsequently screened for high levels of free phosphate in an effort to screen for low-phytate mutants (Rasmussen and Hatzack, 1998); a total of 10 mutants out of 2,000 screened kernels were identified. Although far from always possible, finding a particular mutant after $NaN_3$ treatment is dependent on persistence and an effective screening method, and thus far from always successful.

A difficult part related to identification of promising molecular targets in traditional plant breeding concerns difficulties to ascertain which component(s) of a given biochemical pathway should be perturbed in order to produce the desired alteration of the system read out, and thus the ability to establish a useful screening method.

Beer production-related incubations at elevated temperatures—such as kiln drying of malt, or heating and boiling of wort—may induce chemical conversion of SMM to DMS. Due to inherent properties of DMS, particularly its boiling point of only 37° C.-38° C., a major part of the DMS formed during kilning and wort boiling may be lost to the atmosphere. At temperatures above ~70° C., the volatility of DMS decreases to very low levels (Scheuren and Sommer, 2008), while manifesting conditions for further oxidation to dimethyl sulfoxide (DMSO). When hold time or vigor of wort boiling is inadequate to convert residual SMM, DMS may continue to form as the wort cools—with subsequent transfer into the beer.

Technological methods for reducing the level of DMS in beer have been developed. Thus, AU 38578/93 described a method of reducing DMS levels in malt, comprising steam treatment of said malt. In patent application US 2006/0057684 to Bisgaard-Frantzen, H. et al. was described brewing methods comprising heat treatment of mash at temperatures of 70° C. and above. And in U.S. Pat. No. 5,242,694 to Reuther, H. was described methods for preparing low carbohydrate beer, wherein the methods comprise extensive boiling of wort followed by carbon dioxide washing of said wort. However, all of the aforementioned treatments consume high levels of energy, and further they may alter the characteristics of malt or wort.

SUMMARY OF THE INVENTION

The present invention discloses beverages prepared from barley, or parts thereof, in particular beer with improved flavor. The beverages disclosed herein exhibit very low levels of DMS, or even no DMS at all—particularly beverages with DMS levels below taste threshold, and thus characterized by the absence of DMS taste.

Moreover, the beverages of the invention have superior taste properties. Accordingly, the beverages of the invention are characterized as particularly balanced and drinkable, with a high degree of freshness, aromatic and floral flavor.

Thus, the invention provides beverages with remarkable flavor properties based on the absence of DMS or low DMS levels. It is herein found that DMS strikingly influences the human perception of estery compounds in beer (cf. FIG. 1B), consistent with a model provided by the inventors in which DMS masks the taste of said compounds.

It is considered of profound importance that the present invention provides barley or malt kernels with defects that specifically block formation of the DMS precursor. In this way, the above-described masking of estery taste by DMS may be avoided, which enables new opportunities in the industrial utilization of barley and malt. In addition, barley or malt kernels with defects that specifically block formation of the DMS precursor also have taste properties caused by the absence of DMS per se. Notably, said barley or malt type might be exploited as a raw material in effective industrial applications to help establish tailored production settings far beyond contemporary capabilities. In particular, improvements relate to issues of beer quality and environmental sustainability in beer production, specifically for:

(i) Beer having a low level of DMS-specific taste;
(ii) Beer having an improved estery taste profile;
(iii) Reduced energy input for beer production; and
(iv) Reduced energy consumption in wort production.

Barley plants and kernels fulfilling said improvements are provided by the instant invention.

So, without being bound by theoretical considerations on how the metabolism of SMM could be interwined with other biological processes, the instant application offers not-yet provided opportunities to exploit and explore the breeding and industrial use of barley plants defective in SMM synthesis.

The present invention discloses that beverages characterized by low levels of DMS-specific taste and an improved estery taste profile, and/or beverages that are particularly balanced and drinkable—i.e. with high degrees of freshness, aromatic, and floral flavor—may be prepared from barley plants, or parts thereof, carrying a mutation in the gene encoding MMT, which causes a total loss of MMT activity. Such plants are herein denoted "null-MMT" barley.

Thus, the invention relates in one aspect to beverages prepared from a barley plant, or a part thereof, wherein said beverage contains a level of DMS below 30 bbp (such as less than 30 ppb DMS), and wherein said barley plant carries a mutation in the gene encoding MMT, causing a total loss of MMT activity.

In another aspect, the invention offers barley plants useful for preparing said beverages. Accordingly, it is also an object of the invention to provide a barley plant, or part thereof, wherein the barley plant carries a mutation in the gene encoding MMT that causes a total loss of functional MMT enzyme.

In addition, the invention relates to plant products produced from said null-MMT barley plant, including, for example, malt and wort compositions, or barley-based syrups or extracts, or malt-based syrups or extracts, or adjuncts. Adjuncts in the present context may be unmalted barley, which may be used either alone or in combination with malted barley for preparing wort. Also, methods of preparing said barley plants, as well as methods of preparing the beverages and other plant products, are provided by the invention.

Further, in a world with climate disruption on the international agenda, society and industry should contribute to global greenhouse-gas emission reductions and environmental benefits. An objective of the invention is therefore to provide barley plants useful for production of beer using low-energy consuming methods. Accordingly, barley plants of the invention are useful for production of beer using methods wherein time spans of heating steps are reduced, or the temperature in heating steps are reduced, compared to standard brewing methods. Of fundamental importance are benefits in the steps of kiln drying and wort boiling procedures, which may be significantly shortened or performed at lower temperatures compared to standard brewing and beer production regimes, reducing energy consumption to provide a more sustainable method for beer production.

SEQUENCE LISTING

The invention can be more fully understood from the following detailed description and the accompanying sequence listing (summarized in Table 10), which forms a part of this application. Said table lists the nucleic acids and polypeptides that are described herein, the designation of the oligonucleotide primers as well as the cDNA and gDNA clones that comprise the nucleic acid fragments encoding polypeptides representing all or a substantial portion of these polypeptides, and the corresponding identifier (SEQ ID NO:). The sequence descriptions and sequence listing attached hereto comply with the rules governing nucleotide and/or amino acid sequence disclosures in patent applications.

DESCRIPTION OF DRAWINGS

FIG. 14B,C).

FIG. 10 shows the cDNA sequence for barley MMT of cv. Prestige, spanning the translational start and stop codons, i.e. the coding region (SEQ ID NO:4), aligned with the translated sequence (SEQ ID NO:6), using the one letter code for amino acids.

FIG. 11 shows a sequence alignment of the almost identical MMT enzymes of barley cvs. Haruna Nijo (SEQ ID NO:2) and Prestige (SEQ ID NO:6). Two separate amino acid residue differences are highlighted as black boxes with white lettering.

DETAILED DESCRIPTION OF THE INVENTION

Definitions

Figure 1:
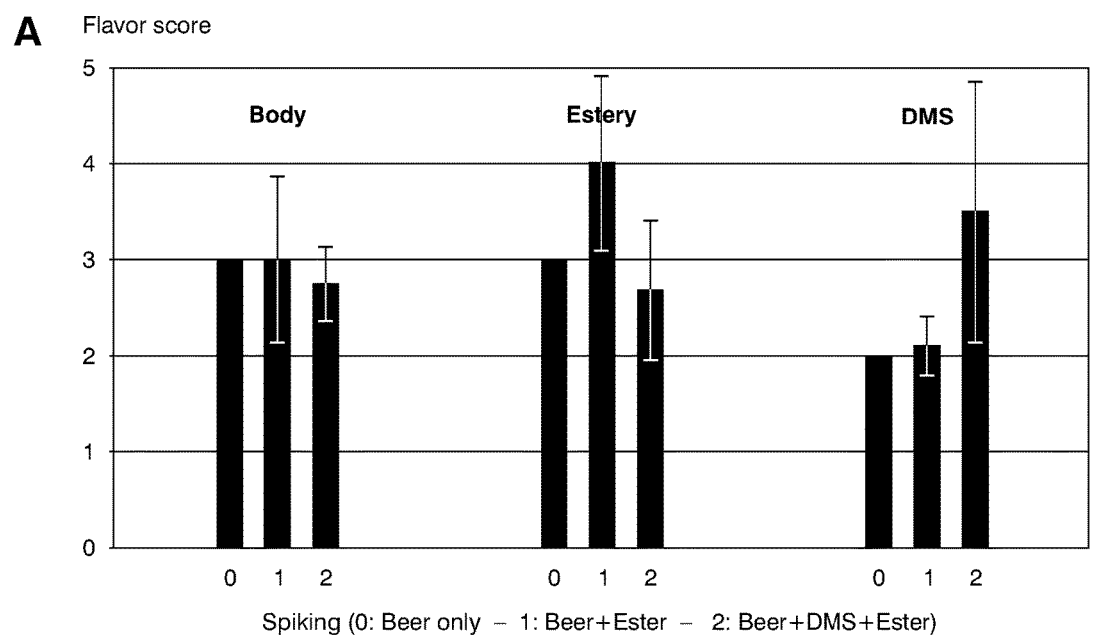
FIG. 1 shows selected components of the SMM cycle and average flavor scores. (A) Selected components of the SMM cycle in which SMM is synthesized by methyl transfer from S-adenosylmethionine (SAM) to methionine (Met), catalyzed by the enzyme Met-S-methyltransferase (MMT). SMM can in turn serve as methyl donor for Met synthesis from homocysteine (Hcy), in a reaction catalyzed by the enzyme Hcy-S-methyltransferase (HMT). The illustration shows how the essentially irreversible reactions are connected. Each turn of the cycle is futile as it consumes and then regenerates two Mets while converting ATP to adenosine, PPi and Pi (not shown). (B) Illustrated are the average flavor scores, ±standard deviation, given by a specialist beer taste panel on the listed properties—body, estery, and DMS—of beer samples. Control samples of standard beer were spiked with beer only (columns marked with "0"), or spiked with a mixture of esters giving the following concentrations in beer: 5 ppm ethyl acetate, 1.5 ppm isoamylacetate, 0.05 ppm ethyl hexanoate, 0.13 ppm ethyl octanoate (columns marked "1"), and the aforementioned ester mix including 100 ppb DMS (columns marked "2").
Figure 1:
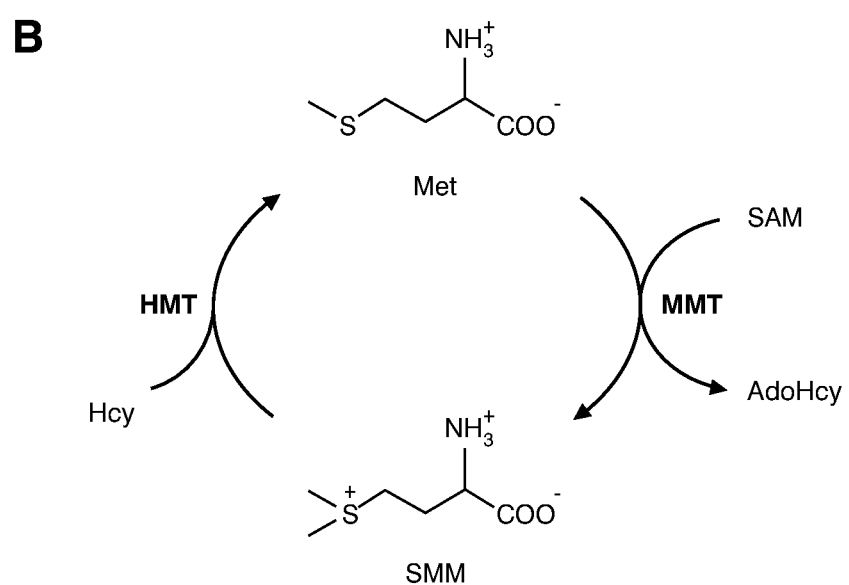

In the description, figures, and tables which follow, a number of terms are used. To provide the specifications and claims, including the scope to be given such terms, the following definitions are provided:

As used herein, "a" can mean one or more, depending on the context in which it is used.

The term "agronomic trait" describes a phenotypic or genetic trait of a plant that contributes to the performance or economic value of said plant. Such traits include disease resistance, insect resistance, virus resistance, nematode resistance, drought tolerance, high salinity tolerance, yield, plant height, days to maturity, kernel grading (i.e. kernel size fractionation), kernel nitrogen content and the like.

The term "barley" in reference to the process of making beer, particularly when used to describe the malting process, means barley kernels. In all other cases, unless otherwise specified, "barley" means the barley plant (*Hordeum vulgare*, L.), including any variety, whereas part of a barley plant may be any part of a barley plant, for example any tissue or cells.

A "cereal" plant as defined herein is a member of the Graminae plant family, cultivated primarily for their starch-containing seeds. Cereal plants include, but are not limited to barley (*Hordeum*), wheat (*Triticum*), rice (*Oryza*), maize (*Zea*), rye (*Secale*), oat (*Avena*), sorghum (*Sorghum*), and Triticale, a rye-wheat hybrid.

"DMSP" as used herein is an abbreviation for DMS precursor or DMS potential, i.e. the molecules that can be converted to DMS during the production of beverages. SMM represents the major part of, if not all, DMSP. The level of DMSP is defined herein as the quantity of DMS that can be generated from DMSP in the specified plant material, or product thereof, by boiling at alkaline conditions for 1 hour. As defined herein, 1 ppb DMSP can be converted to 1 ppb DMS.

By "encoding" or "encoded" in the context of a specified nucleic acid is meant comprising the information for translation into the specified protein. A nucleic acid which encodes a protein may comprise non-translated sequences (e.g. introns) within translated regions of the nucleic acid, or may lack such intervening non-translated sequences (e.g. in cDNA). The information by which a protein is encoded is specified by the use of codons.

As used herein, "expression" in the context of nucleic acids is to be understood as the transcription and accumulation of sense mRNA or antisense RNA derived from a nucleic acid fragment. "Expression" used in the context of proteins refers to translation of mRNA into a polypeptide.

The term "gene" means the segment of DNA involved in producing a polypeptide chain; it includes regions preceding and following the coding region (promoter and terminator). Furthermore, plant genes are discontinuous with proteins encoded by them, consisting of exons interrupted by introns. After transcription into RNA, the introns are removed by splicing to generate a mature messenger RNA (mRNA). The "splice sites" between exons are typically determined by consensus sequences acting as splice signals for the splicing process, consisting of a deletion of the intron from the primary RNA transcript and a joining or fusion of the ends of the remaining RNA on either side of the excised intron.

The term "germination" as used herein means the beginning or resumption of growth by a barley kernel in various compositions, such as normal soil as found in nature. Germination can also take place in the soil of pots placed in growth chambers an the like, or for example take place on wet filter paper placed in standard laboratory Petri dishes or during malting (for example in steep tanks or germination boxes of the malting factory). Germination is generally understood to include hydration of the kernels, swelling of the kernels and inducing growth of the embryo. Environmental factors affecting germination include moisture, temperature and oxygen level. Root and shoot development is observed.

As used herein, the term "isolated" means that the material is removed from its original environment. For example, a naturally-occurring polynucleotide or polypeptide present in a living organism is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated because such vector or composition is not part of its natural environment.

The term "kernel" is defined to comprise the cereal caryopsis, also denoted internal seed, the lemma and palea. In most barley varieties the lemma and palea adhere to the caryopsis and are a part of the kernel following threshing. However, naked barley varieties also occur. In these, the caryopsis is free of the lemma and palea and threshes out free as in wheat. The terms "kernel" and "grain" are used interchangeably herein.

"Grain development" refers to the period in barley's life cyclus that begins with fertilization in which metabolic reserves, e.g. sugars, oligosaccharides, starch, phenolics, amino acids, and proteins are deposited, with and without vacuole targeting, to various tissues in the kernel, e.g. endosperm, testa, aleurone, and scutellum, leading to kernel enlargement, kernel filling, and ending with kernel maturation and desiccation.

The terms "total loss of functional MMT" and "total loss of MMT activity" refer to the lack of the MMT enzymatic activity, i.e. a barley plant with no detectable MMT activity when using the assay described in Example 2 herein below. Alternatively, MMT activity of a barley plant is determined by isolating MMT cDNA of said barley and determining whether the protein encoding by said cDNA is capable of catalyzing transfer of a methyl group from SAM to Met, thereby forming SMM.

The term "malt beverage" refers to beverages prepared using malt, optionally in admixture with other ingredients, such as mixtures of malted and unmalted barley, preferably beverages prepared by a method including a step of incubating malt with hot water. Malt beverage may, for example, be beers or maltinas.

The term "fermented malt beverage" refers to malt beverage which have been fermented, e.g. incubated with yeast.

The term "MMT activity" refers to the enzymatic activity of the barley methionine S-methyltransferase enzyme. In the context of the present invention, "MMT activity" is the MMT-catalyzed methylation at the sulfur atom of Met to yield SMM. Even though the MMT enzyme may be capable of catalyzing other reactions, for the purpose of determining the activity of MMT according to the present invention, only the SMM-forming activity should be considered. FIG. 1B outlines the biochemical reactions wherein Met is converted to SMM by methylation.

"Malting" is a special form of germination of barley kernels taking place under controlled environmental conditions in, but not limited to, steep tanks and germination boxes of the malting factory. In accordance with the process of the present invention, malting begins to occur during and/or after the barley kernels have been steeped. The malting process may be stopped by drying of the barley kernels, for example, in a kiln drying process. In case the malt has not been kiln dried, it is denoted "green malt". A malt composition prepared from null-MMT barley is understood to comprise null-MMT malt, such as pure null-MMT malt or any blend of malt comprising null-MMT malt. Malt may be processed, for example by milling, in which case it may also be referred to as "milled malt" or "flour".

"Mashing" is the incubation of milled malt in water. Mashing is preferably performed at a specific temperature and in a specific volume of water to allow the desired enzymatic depolymerization of substrates. The temperature and volume of water is of importance as this affects the rate of decrease of enzyme activity derived from the malt, and hence the amount of especially starch hydrolysis that can occur. Protease action may also be of importance. Mashing can occur in the presence of adjuncts, which is understood to comprise any carbohydrate source other than malt, such as, but not limited to, barley (including null-MMT barley), or maize, or rice either as whole kernels or processed products like grits or starch, all used principally as an additional source of extract (syrups are typically dosed during wort boiling). The requirements for processing of the adjunct in the brewery depend on the state and type of adjunct used and in particular the starch gelatinization or liquefaction temperatures. If the gelatinization temperature is above that for normal malt saccharification temperature, then the starch is gelatinized and liquefied before adding to the mash.

When a given mutation is fixed as a homozygous genetic characteristic, for example in generation ≥M3, the corresponding barley plant is, interchangeably herein, denoted as "Mutant", or as "mutated line", or as "Line".

Figure 7:
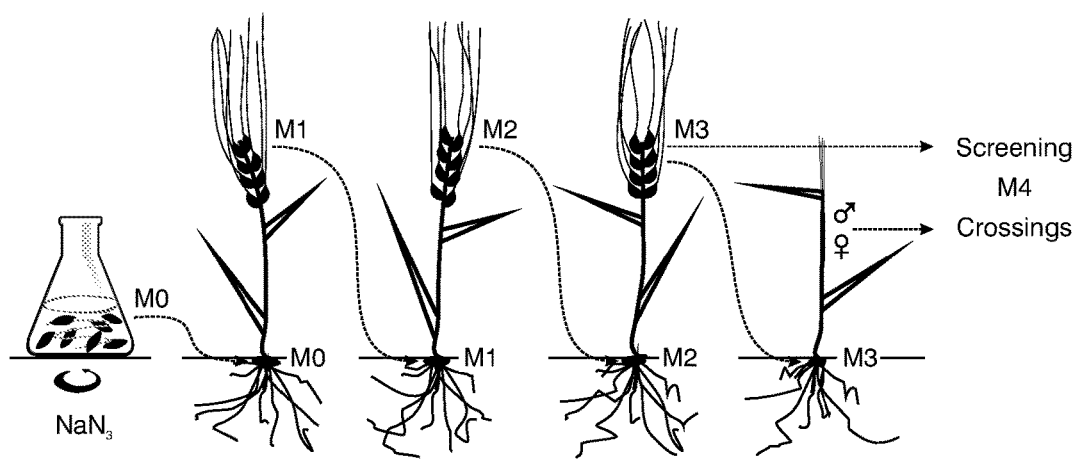
FIG. 7 shows an illustration on a way to propagate NaN$_3$-mutagenized barley kernels. Kernels of generation M0 develop into plants that set kernels of generation M1. These may be sown and develop into M1 plants, which produce new kernels of generation M2. Next, M2 plants grow and set kernels of generation M3. Kernels of generation M3 may be allowed to germinate, and samples thereof, e.g. coleoptiles, may be used for analysis. M3 seeds may also be sown and the flowers of the corresponding plants used for crossings to obtain plants of generation M4.

"Mutations" include deletions, insertions, substitutions, transversions and point mutations in the coding and noncoding regions of a gene, wherein the noncoding region preferably is promoter region or introns. Deletions may be of the entire gene or of only a portion of the gene. Point mutations concern changes of one base or one base pair and may result in stop codons, frameshift mutations or amino acid substitutions. Somatic mutations are those which occur only in certain cells or tissues of the plant and are not inherited to the next generation. Germline mutations can be found in any cell of the plant and are inherited. With reference to FIG. 7 herein—which presents an overview on how grains of mutated barley may be propagated in a breeding program—grains of generation M3, and directly propagated grains thereof, or of any subsequent generation, including the plants thereof, may be termed "raw mutants". Further, still with reference to FIG. 7 herein, the term "breeding line" refers to grains of generation M4, and any subsequent generation, including the plants thereof, which may be the result of a cross to a cultivar plant, or the result of a cross to another breeding line with a separate, specific trait.

As used herein, the term "null-MMT" refers to a total loss of functional methionine S-methyl transferase enzyme. Thus, a "null-MMT barley plant" is a barley plant comprising a mutation in the gene encoding MMT that results in a total loss of functional MMT. Similarly, "null-MMT kernels" are kernels comprising a mutation in the gene encoding MMT, resulting in a total loss of functional MMT, and so forth.

The term "parts of barley plant", for instance comprised within the meaning of the phrase "barley plant or a part thereof", includes barley plant cells, barley plant protoplasts, plant cell tissue cultures from which barley plants can be regenerated, barley plant calli, and barley plant cells that are intact in plants or larger parts of barley plants, such as embryos, pollen, ovules, flowers, kernels, leaves, roots, root tips, anthers, or any part of a plant.

"PCR" or "polymerase chain reaction" is well known by those skilled in the art as a technique used for the amplification of specific DNA segments (U.S. Pat. Nos. 4,683,195 and 4,800,159 to Mullis, K. B. et al.). Also reverse transcription (RT)-PCR is well known by those skilled in the art. Performing a RT-PCR on a biological sample aims at detecting expressed mRNAs for a particular gene. In relation to MMT, RT-PCR in general includes obtaining a sample that is suspected of containing mRNA for MMT, performing a RT-PCR on the sample with a reverse transcriptase, a polymerase, and a pair of specific primers, to amplify the RNA, if present, and detecting the amplification product as an indication of the presence of MMT encoding RNA in the sample. Primers work in pairs—"forward primer" (or "upper strand primer" or "direct primer"), and "reverse primer" (or "lower strand primer"). Primer sequences are herein given in the 5'-to-3' direction.

By the term "plant product" is meant a product resulting from the processing of a plant or plant portion. For example, said plant product may be malt, wort, a fermented or non-fermented beverage, a food, or a feed product.

A "specialist beer taste panel" within the meaning of the present application is a panel of specialists extensively trained in tasting and describing beer flavors, with special focus on esters, higher alcohols, fatty acids, sulfur components and body. Although a number of analytical tools exist for evaluating flavor components, the relative significance of flavor-active components are difficult to assess analytically. However, such complex properties can be evaluated by taste specialists. Their continuous training includes tasting and evaluation of standard beer samples that have been spiked with specified concentrations of beer components—for example isoamylacetate, ethyl acetate, ethyl hexanote and isoamylalcohol.

By the term "splice site" is meant the boundaries between exons and introns of a gene. Thus, a splice site may be the border going from exon to intron—also called a "donor site"—or the border separating intron from exon also denoted "acceptor site." A splice site in plants typically comprises consensus sequences. The 5' end of an intron in general consist of a conserved GT dinucleotide (GU in the mRNA), and the 3' end of an intron usually consists of a conserved dinucleotide AG. The 5' splice site of an intron thus comprises the 5' end of an intron, and the 3' splice site comprises the 3' end of an intron. Preferably, within the context of the present invention, the splice site of an intron is either:
 (i) The 5' splice site consisting of the most 5' dinucleotide of the intron, which in general is GT; or
 (ii) The 3' splice site consisting of the most 3' dinucleotide of the intron, which in general is AG.

"Cryptic splice sites" are not recognized under normal conditions and thus do not normally cause splicing. However, in transcripts bearing point mutations within natural elements, such sites can be activated for splicing events.

"Tissue culture" indicates a composition comprising isolated cells of the same or different types or a collection of such cells organized into parts of a plant, for example protoplasts, calli, embryos, pollen, anthers, and the like.

"Wild barley", Hordeum vulgare ssp. spontaneum, is considered the progenitor of today's cultivated forms of barley. The transition of barley from a wild to a cultivated state is thought to have coincided with domestication of the plant into "barley landraces". These are genetically more closely related to modern cultivars than wild barley.

The term "wild-type" barley refers to a conventionally generated barley plant; preferably the term refers to the barley plant from which the barley plants of the instant invention have been derived, i.e. the parental plants. Wild-type barley kernels are generally available from, for example, seed companies as "cultivars" (often abbreviated "cvs."), i.e. those genetically similar kernels that are listed by national plant breeding organizations. The terms "cultivar" and "variety" are used interchangeably herein.

By the term "wort" is meant a liquid extract of malt, for example milled malt or green malt or milled green malt. In addition to said malt, the liquid extract may be prepared from malt and additional components, such as additional starch-containing material partly converted into fermentable sugars. The wort is in general obtained by mashing, optionally followed by "sparging", i.e. the process of extracting residual sugars and other compounds from spent grain after mashing with hot water. Sparging is typically conducted in a lauter tun, a mash filter, or another apparatus allowing separation of the extracted liquid from spent grain. The wort obtained after mashing is generally referred to as "first wort", while the wort obtained after sparging is generally referred to as the "second wort". If not specified, the term wort may be first wort, second wort or a combination of both. During beer production, wort is generally boiled together with hops. Wort prepared without boiling with hops may also be referred to as "sweet wort", whereas wort which has been boiled with or without hops may be referred to as "boiled wort".

Barley Plant

Barley is a family of plants. Wild barley, Hordeum vulgare ssp. spontaneum, is considered the progenitor of today's cultivated forms of barley. The transition of barley from a wild to a cultivated state is thought to have coincided with a radical change of allele frequencies at numerous loci. Rare alleles and new mutational events were positively selected for by the farmers who quickly established the new traits in the domesticated plant populations, denoted "barley landraces". These are genetically more closely related to modern cultivars than wild barley. Until the late nineteenth century, barley landraces existed as highly heterogeneous mixtures of inbred lines and hybrid segregates, including few plants derived from random crossings in earlier generations. Most of the landraces have been displaced in advanced agricultures by pure line cultivars. Intermediate or high levels of genetic diversity characterize the remaining landraces. Initially, "modern barley" cultivars represented selections from landraces. These were later derived from successive cycles of crosses between established pure lines, such as those of diverse geographical origins. Eventually, the result was a marked narrowing of the genetic base in many, probably all, advanced agricultures. Compared with landraces, modern barley cultivars have numerous improved properties (Nevo, 1992; von Bothmer, 1992), for example, but not limited to:

(i) Covered and naked kernels;
(ii) Seed dormancy;
(iii) Disease resistance;
(iv) Environmental tolerance (for example to drought or soil pH);
(v) Proportions of lysine and other amino acids;
(vi) Protein content;
(vii) Nitrogen content;
(viii) Carbohydrate composition;
(ix) Hordein composition.

Within the present invention, the term "barley" comprises any barley plant. Thus, the invention relates to any barley plant carrying a mutation in the gene encoding MMT, resulting in a total loss of functional MMT.

However, preferred barley plants for use with the present invention are modern barley cultivars or pure lines. The barley cultivar to be used with the present invention may, for example, be selected from the group consisting of Sebastian, Celeste, Tangent, Lux, Prestige, Saloon, Neruda, Harrington, Klages, Manley, Schooner, Stirling, Clipper, Franklin, Alexis, Blenheim, Ariel, Lenka, Maresi, Steffi, Gimpel, Chem, Krona, Camargue, Chariot, Derkado, Prisma, Union, Beka, Kym, Asahi 5, KOU A, Swan Hals, Kanto Nakate Gold, Hakata No. 2, Kirin—choku No. 1, Kanto late Variety Gold, Fuji Nijo, New Golden, Satukio Nijo, Seijo No. 17, Akagi Nijo, Azuma Golden, Amagi Nijpo, Nishino Gold, Misato golden, Haruna Nijo, Scarlett, Quench, NFC Tipple and Jersey preferably from the group consisting of Haruna Nijo, Sebastian, Tangent, Lux, Prestige, Saloon, Neruda, Power, Quench and NFC Tipple.

Accordingly, in one embodiment of the invention, said plant is a modern barley cultivar that carries a mutation in the gene encoding MMT, resulting in a total loss of functional MMT, preferably one a cultivar selected from the group of barley cultivars described herein above. In this embodiment, it is accordingly preferred that the barley plant is not a barley landrace.

The barley plant may be in any suitable form. For example, the barley plant according to the invention may be a viable barley plant, a dried plant, a homogenized plant, or a milled barley kernel. The plant may be a mature plant, an embryo, a germinated kernel, a malted kernel, a milled malted kernel or the like.

Parts of barley plants may be any suitable part of the plant, such as kernels, embryos, leaves, stems, roots, flowers or fractions thereof. A fraction may, for example, be a section of a kernel, embryo, leaf, stem, root or flower. A part of a barley plants may also be a fraction of a homogenate, a fraction of an extract, or a fraction of a milled barley plant or kernel.

In one embodiment of the invention, parts of barley plants may be cells of said barley plant, preferably viable cells that may be propagated in vitro, for example in cell or tissue cultures. In particular, in one embodiment said cells may be cells that are not capable of maturing into an entire barley plant, i.e. cells that are not a reproductive material.

Loss of Functional MMT Enzyme

The present invention relates to plant products, such as beverages prepared from barley plants, or parts thereof, said barley plants carrying a mutation in the gene for MMT, resulting in loss of functional MMT enzyme, for example loss of at least 90% of MMT activity, preferably at least 97%, more preferably at least 99%, yet more preferably at least 99.5% of MMT activity compared to the corresponding level in wild-type barley, preferably compared to any of the wild-type barley cultivars described herein above, more preferably compared to wild-type barley cv. Prestige. Most preferably said barley plant carries a mutation in the gene encoding MMT, resulting in a total loss of MMT function.

The total loss of a functional MMT enzyme may be based on different mechanisms. For example, the total loss of functional MMT enzyme may result from a malfunctioning protein in said plant, i.e. a malfunctioning MMT enzyme, such as a mutant MMT protein with no detectable activity. For instance, the MMT protein of the mutant may be a truncated protein. The loss of MMT activity may similarly be based on different mechanisms, for example malfunctioning MMT protein.

Preferably, the activity of a mutated MMT protein is determined by its capacity to catalyze transfer of a methyl group from SAM to Met, thereby forming SMM. This may, for example, be undertaken as described in Example 4 hereinafter. Preferably, the amino acid sequence of a mutated MMT is obtained by determining the translated sequence of the corresponding, isolated barley cDNA. This may be done essentially as described in Example 8 hereinafter. Alternatively, the mutated MMT of a barley plant of the invention is obtained by heterologous expression in a bacterial cell culture as described in Example 11 and Example 12 hereinafter, followed by verifying that the recombinant protein is inactive as an MMT enzyme.

The total loss of functional MMT may be realized by the lack of MMT protein. Lack of MMT protein will lead to loss of MMT function. Thus, the barley plant may comprise no, or only very little, preferably no detectable MMT protein. The presence or absence of MMT protein may be detected by any suitable means known to the person skilled in the art. However, the protein(s) is preferably analyzed by techniques wherein MMT protein is detected by specific antibodies that recognize MMT. Said techniques may, for example, be western blotting or enzyme-linked immunosorbent assay, and said specific antibodies may be monoclonal or polyclonal. Preferably, however, said antibodies are polyclonals that recognize several different epitopes within the MMT protein. This may also be detected indirectly, for example, by methods for MMT activity determination. Thus, in one preferred embodiment, a barley plant is said to carry a mutation in the gene encoding MMT, thus causing a total loss of MMT activity, when no MMT protein is detectable in said plant. In particular, this is the case when no MMT protein with an approximate mass of 120 kD, ±10%, is detectable in said barley plant—preferably in kernels of said barley plant, as analyzed by western blotting.

The total loss of functional MMT may also be a result of no or very little, preferably no, transcription of an MMT mRNA. The skilled person will acknowledge that the absence of an MMT transcript also will result in the absence of MMT protein.

Preferably, however, the total loss of functional MMT is a result of expression of an aberrant MMT transcript. Said transcript may preferably be caused by an aberrant splicing event of the primary transcript, for example, due to a mutation in a splice site. Expression of transcripts encoding MMT may, for instance, be detected by Northern blotting, or by RT-PCR methods.

The total loss of functional MMT in the barley plants of the present invention is caused by one or more mutations. Thus, the barley plants of the present invention, in general, carry at least one mutation in the MMT gene. Said mutation(s) may be in regulatory regions, for instance within the promoter, or introns, or said mutation(s) may be in the protein coding region. Thus, the loss of functional MMT may also be detected by analyzing for mutations in the gene encoding MMT. Mutations in the MMT-encoding gene may, for example, be detected by sequencing said gene, followed by comparing it to the wild-type sequence, preferably the wild-type sequence of cv. Prestige given herein as SEQ ID NO:3, or that of cv. Sebastian (SEQ ID NO:16). Preferably, after identifying a mutation, the loss of function is confirmed by testing for MMT activity, for instance as described in Example 2 or Example 4.

The term MMT protein is meant to cover the full length MMT protein of barley as set forth in SEQ ID NO:6, or a functional homolog thereof. In this context, a functional homolog is an MMT protein with the same level of MMT activity, ±25%, as that of the MMT protein of barley as set forth in SEQ ID NO:6, wherein the MMT activity is determined as described in Example 2 or Example 4 hereinbelow.

The barley plant with loss of at least 90%, such as 95%, for example 99%, such as 99.5% MMT activity or with total loss of MMT activity may comprise a partly functional or preferably a non-functional, truncated form of MMT, such as an N-terminal or a C-terminal truncated form. A barley plant may comprise more than one truncated form of MMT, such as 2, or for example 3, or such as more than 3 different truncated forms of MMT, which may result from aberrantly spliced transcripts. Said truncated forms comprise only an N-terminal fragment of MMT. In addition to the N-terminal fragment of wild-type MMT, said truncated forms of MMT may comprise additional C-terminal sequences not found in wild-type MMT. Said additional C-terminal sequences may, for instance, be translated intron sequences, such as those comprised in the mutant mRNA due to aberrant splicing. Preferably, said truncated MMT forms comprise at the most the 500, more preferably at the most the 450, even more preferably at the most the 400, yet more preferably at the most the 350, even more preferably at the most the 320, yet more preferably at the most 311, or at the most 288 N-terminal amino acid residues of SEQ ID NO:6. This is in particular the case when said barley plant has a total loss of MMT activity. However, the MMT may also comprise less, such as no more than 300, for example no more than 250, such as no more than 200, for example at the most the 150, for example no more than 147, or no more than 133 N-terminal amino acids of SEQ ID NO:6.

In one very preferred embodiment, the truncated MMT form may consist of amino acids 1-311 or amino acids 1-288 of SEQ ID NO:6 and optionally additional C-terminal sequences not present in wild-type MMT. Preferably, said additional C-terminal sequences consist of at the most 50, more preferably at the most 30, even more preferably at the most 10, yet more preferably of at the most 4, or at the most 1 amino acid. In a very preferred embodiment, the truncated form of MMT may be the protein according to SEQ ID NO:11, or SEQ ID NO:13, or SEQ ID NO:15. None of the proteins of SEQ ID NO:11, or SEQ ID NO:13, or SEQ ID NO:15 are functional MMT enzymes.

In another very preferred embodiment, the truncated MMT form may consist of amino acids 1-147, or of amino acids 1-133, of SEQ ID NO:18, and optionally additional C-terminal sequences not present in wild-type MMT. Preferably, said additional C-terminal sequences consist of at the most 50, more preferably at the most 40, even more preferably at the most 39, or at the most 33, or at the most 30 amino acids. In a very preferred embodiment, the truncated form of MMT may be the protein according to SEQ ID NO:22, or SEQ ID NO:24, or SEQ ID NO:26. None of the proteins of SEQ ID NO:22, or SEQ ID NO:24, or SEQ ID NO:26 are functional MMT enzymes.

Abovementioned truncated forms of MMT may for example be present in a barley plant carrying a mutation in the gene encoding MMT, wherein said mutation introduces a premature stop codon resulting in a gene encoding abovementioned truncated forms of MMT.

Figure 9:
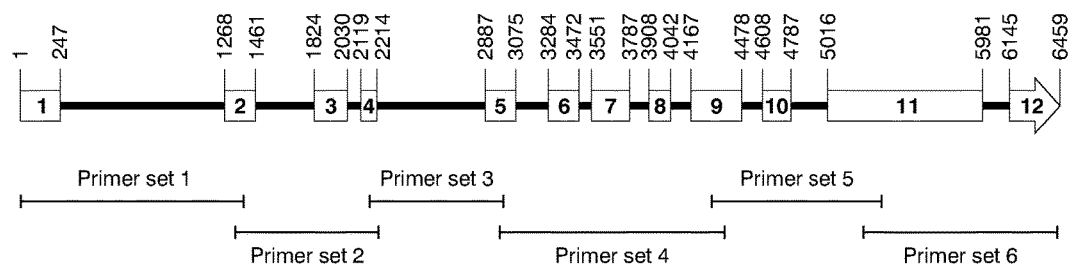
FIG. 9 shows, in a schematic form, the organization of the barley gene encoding MMT. Illustrated is the 6368-bp-long genomic sequence (SEQ ID NO:3), which spans the translational start and stop codons. Exons and introns are shown as numbered boxes and unnumbered lines, respectively. Exon 12 is illustrated as an arrowhead to indicate the overall direction of transcription and translation. Nucleotide numbers refer to the 5' and 3' end of indicated exons relative to the first base of the translational start codon. Also illustrated are the approximate locations of PCR stretches that correspond to the amplifications using the primer sets listed in Table 2.
Figure 12:
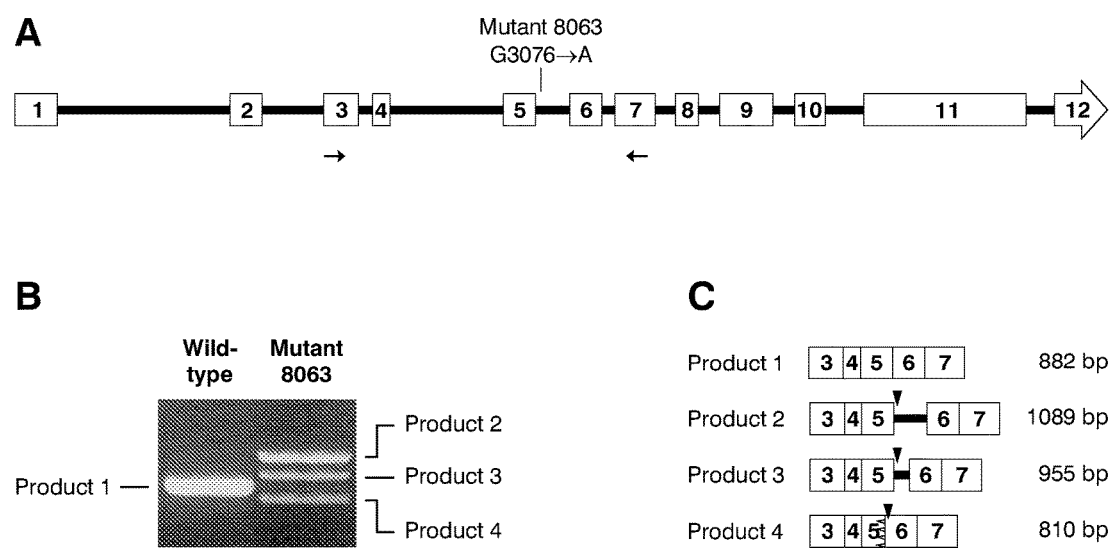
FIG. 12 shows how barley Mutant 8063 activates cryptic splice sites in the gene for MMT. (A) Small horizontal arrows below the illustration of the genomic structure of the gene for MMT indicate the approximate annealing position of primer set 15, cf. Table 4. (B) Visualization of DNA bands following agarose gel electrophoresis of reverse transcription polymerase chain reaction (RT-PCR) analysis of products using RNA template from either wild-type cv. Prestige or Mutant 8063. (C) Illustration to show the intron-exon structure of PCR products in panel B, using the same graphical elements as in A. Exon 5 of Product 4 is shorter in comparison with that of the wild-type. Vertical arrowheads point to the approximate positions of premature translational stop codons. Due to choice of primers, the products do not comprise exons 1 and 2. It is, however, predicted that the imRNA also comprises exons 1 and 2. (D) Detailed illustration of the transcripts resulting from the mutated (Mut; nucleotides 2887 to 3471 of SEQ ID NO 8) and wild-type (WT; nucleotides 2887 to 3471 of SEQ ID NO 16) 5' splice site in intron 5, with the mutation site indicated by the underlined base. Arrows joined by solid lines, labeled 3 and 4, mark the donor and acceptor sites utilized during splicing of Product 3 and Product 4, respectively (cf. Panel C). The broken line, marked 2*, points to splicing of the wild-type transcript (Product 1 in panel C) and to non-spliced Product 2 (cf. Panel C). Bases of exons and intron 5 are in lower and upper case letters, respectively, nt: nucleotide. (E) Overview of the composition of 5' and 3' splice sites in monocots (Sinibaldi and Mettler, 1992), compared with the sequence of intron 5 in the gene for MMT of Mutant 8063.
Figure 12:
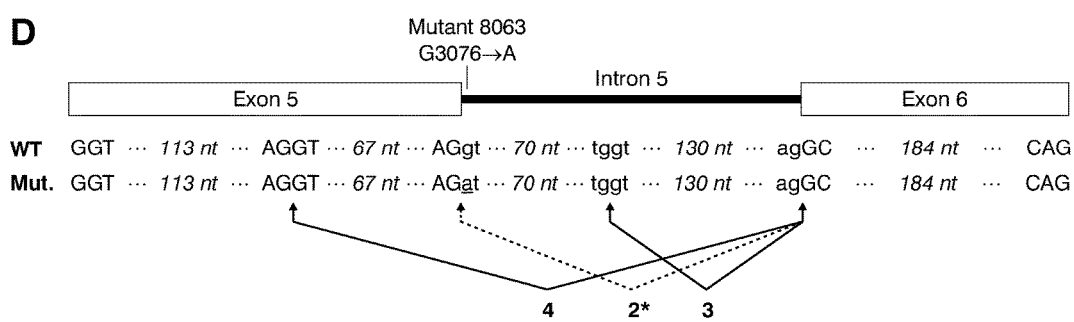
Figure 16:
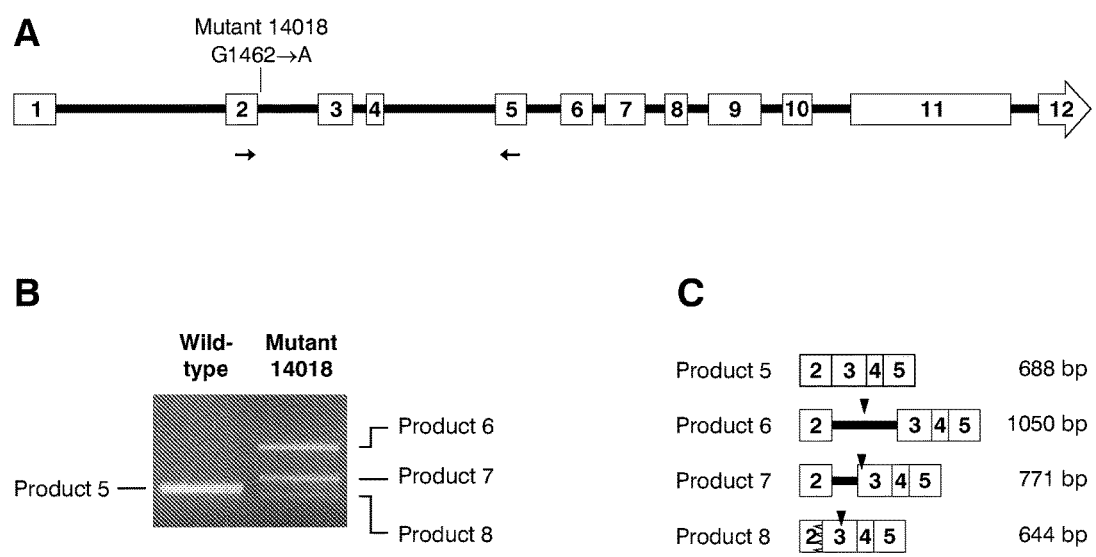
FIG. 16 shows how barley Mutant 14018 activates cryptic splice sites in the gene for MMT. (A) Small horizontal arrows—below the illustration of the genomic structure of the gene for MMT-indicate the approximate annealing position of primer set 16, cf. Table 4. (B) Visualization of DNA bands following agarose gel electrophoresis of RT-PCR products using RNA template from either wild-type (cv. Sebastian) or Mutant 14018. (C) Depiction to illustrate the intron-exon structure of PCR products in panel B, using the same graphical elements as in A. Exon 2 of Product 8 is truncated in comparison with that of the wild-type. Vertical arrowheads point to the approximate positions of premature translational stop codons. Due to the choice of primers, the products do not comprise exon 1. It is, however, predictable that the mRNA also comprises exon 1. (D) Detailed illustration on the transcripts resulting from the mutated (Mut; nucleotide 1268 to 2039 of SEQ ID NO 19) and wild-type (WT; nucleotides 1268 to 2039 of SEQ ID NO 16) 5' splice site in intron 2, with the mutation site indicated by the underlined base. Arrows joined by solid lines labeled 7 and 8 mark the donor and acceptor sites utilized during splicing of Product 7 and Product 8, respectively (cf. panel C). The broken line marked 6* points to splicing of the wild-type transcript (Product 5 in panel C) and to non-spliced Product 6 (cf. Panel C). Bases of exons and intron 2 are in lower and upper case letters, respectively, nt: nucleotide. (E) Overview of the composition of 5' and 3' splice sites in monocots (Sinibaldi and Mettler, supra), compared with the sequence of intron 2 for the gene for MMT, Mutant 14018.
Figure 16:
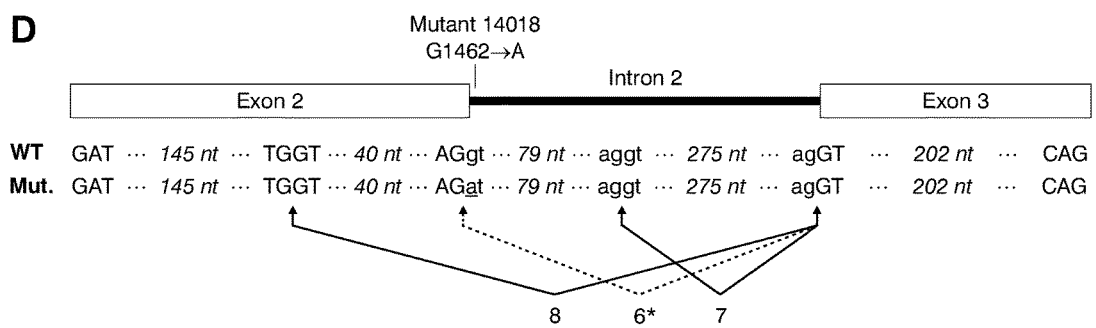

In a preferred embodiment of the invention, the barley plant comprises a gene that is transcribed into mRNA, which comprises some, but not all, of the wild-type MMT gene spliced together without intervention (the intron-exon structure of the wild-type MMT gene of barley is shown in FIG. 9). In one embodiment, it is accordingly preferred that the MMT mRNA of the barley plant according to the invention comprises at the most exons 1, 2, 3, 4, and 5 spliced together without intervention, or for example at the most exons 1 and 2 spliced together without intervention. In addition to said spliced-together exons, the MMT mRNAs of the barley plant according to the invention may comprise additional 3' terminal sequences derived from wild-type introns and/or exons, wherein introns separate exons sequences. Preferred examples of aberrant MMT mRNA of barley plants according to the invention—as determined by RT-PCR and accordingly with fragment lengths in bp—are illustrated in FIG. 12 and FIG. 16. More preferably, the aberrant mRNAs of barley plants according to the invention are those illustrated in FIG. 12, further comprising exons 1 and 2 at the 5' end, or the mRNAs illustrated in FIG. 16, further comprising exon 1 at the 5' end.

In a very preferred embodiment of the present invention, the barley plant carrying a mutation in the gene for MMT comprises a mutation in a splice site within the MMT gene, which results in aberrantly spliced mRNA. More preferably, said mutation is positioned in an intron of the MMT gene, even more preferably in the 5' splice site of an intron, such as in the 5' splice site on intron 1 (the intron separating exons 1 and 2), such as in the 5' splice site on intron 2 (the intron separating exons 2 and 3), such as in the 5' splice site on intron 3 (the intron separating exons 3 and 4), such as in the 5' splice site on intron 4 (the intron separating exons 4 and 5), such as in the 5' splice site on intron 5 (the intron separating exons 5 and 6), such as in the 5' splice site on intron 6 (the intron separating exons 6 and 7), most preferably in the 5' splice site on intron 2 or intron 5.

It is preferred that said mutation is a G→A mutation of the terminal 5' base of the aforementioned introns. Thus, a very preferred mutation is a G→A mutation of the terminal 5' base of intron 2, or a G→A mutation of the most 5' base of intron 5.

The barley plant according to the invention may be prepared by any suitable method known to the person skilled in the art, preferably by the method outlined herein below in the section "Preparing barley plants with a total loss of functional MMT".

In one embodiment of the invention, it is preferred that the barley plants with total loss of MMT activity, according to the present invention, have physiological and developmental grain and plant characteristics comparable to wild-type barley. Here, it is hence preferred that the null-MMT barley plant is similar to wild-type barley with respect to agriculturally important characteristics, such as plant height, number of tillers per plant, onset of flowering and/or number of grains per spike.

In a very preferred embodiment, the gene encoding MMT of the barley plant according to the invention has the sequence as set out in SEQ ID NO:8. Thus, it is preferred that the barley plant according to the invention carries a G→A mutation of base no. 3076 of SEQ ID NO:3 (wherein SEQ ID NO:3 is the wild-type genomic sequence for MMT of barley, cv. Prestige).

One preferred example of a barley plant having total loss of MMT activity is the barley plant deposited on 13 Oct. 2008 with American Type Culture Collection (ATCC), Patent Depository, 10801 University Blvd., Manassas, Va. 20110, United States and referred to as "Barley, *Hordeum vulgare*; Line 8063". Thus, the barley plant of the invention may be barley Line 8063 deposited with ATCC 13 Oct. 2008 (ATCC Patent Deposit Designation: PTA-9543), or any progeny barley plant thereof, wherein the gene encoding MMT of the barley plant according to the invention has the sequence as set out in SEQ ID NO:8.

In a very preferred embodiment, the gene encoding MMT of the barley plant according to the invention has the sequence as set out in SEQ ID NO:19. Thus, it is preferred that the barley plant according to the invention carries a G→A mutation at base no. 1462 of SEQ ID NO:16 (wherein SEQ ID NO:16 is the wild-type genomic sequence for MMT of barley, cv. Sebastian).

Preparing Barley Plants with a Total Loss of Functional MMT

According to the invention, the barley plant with total loss of functional MMT may be prepared by any suitable method known to the person skilled in the art. Preferably, the barley plant of the invention is prepared by a method comprising the steps of mutagenizing barley plants—or parts thereof, for example, barley kernels—followed by screening and selecting barley plants for individuals with total loss of MMT activity. Interestingly, the present invention relates, in one aspect, to a new and very efficient screening method to allow for identification of said barley plants.

Accordingly, it is an objective of the present invention to provide methods of preparing a barley plant that carries a mutation in the gene for MMT, which causes a total loss of MMT activity. Said methods comprise the steps of:

(i) Mutagenizing barley plants, and/or barley cells, and/or barley tissue, and/or barley kernels, and/or barley embryos, thereby obtaining generation M0 barley; and (ii) Propagating (e.g. breeding) said mutagenized barley plants, kernels, and/or embryos for ≥2 generations, thereby obtaining barley plants of generation Mx, wherein x is an integer ≥2; and (iii) Obtaining a sample of said Mx barley plants; and (iv) Determining the level of SMM in said sample; and (v) Selecting plants wherein the sample comprises less than 10 ppb SMM, preferably less than 5 ppb SMM, more preferably no detectable SMM; and (vi) Sequencing at least part of the MMT gene; and (vii) Selecting plants carrying a mutation in the MMT gene;

thereby obtaining a barley plant, which carries a mutation in the MMT gene that causes a total loss of functional MMT.

Step (i) in the above list may involve mutagenizing living barley material selected from the group consisting of barley plants, barley cells, barley tissue, barley kernels and barley embryos, preferably selected from the group consisting of barley plants, barley kernels and barley embryos, more preferably barley kernels. Mutagenesis may be performed by any suitable method. In one embodiment, mutagenesis is performed by incubating a barley plant or a part thereof—for instance barley kernels or individual cells from barley—with a mutagenizing agent. Such agents are known to the person skilled in the art, and may, for example, be selected from the group consisting of sodium azide ($NaN_3$), ethyl methanesulfonate (EMS), azidoglycerol (AG), methyl nitrosourea (MNU), and maleic hydrazide (MH).

In another embodiment, mutagenesis is performed by irradiating, for example by ultraviolet light, a barley plant, or a part thereof, such as the kernel. In preferred embodiments of the invention, the mutagenesis is performed according to any of the methods outlined herein below in the section "Chemical mutagenesis". A non-limiting example of a suitable mutagenesis protocol is given in Example 1 of U.S. Pat. No. 7,420,105 to Breddam, K. et al., as well as in Example 2 herein below.

It is preferred that mutagenesis is performed in a manner such that the expected frequency of desired mutants is at least 0.5, such as in the range of 0.5 to 5, for example in the range of 0.9 to 2.3 per 10,000 grains, when screening barley of generation M3.

In a preferred embodiment, barley kernels are mutagenized. These are designated generation M0 (see also FIG. 7).

Subsequent to mutagenesis, barley plants, or parts thereof, with no detectable MMT activity are selected. Preferably, selection comprises obtaining a sample from a barley plant, preferably from a germinating barley plant, even more preferably from a barley plant, which has germinated for 4 d. It is preferred that the sample is from a coleoptile and/or a primary leaf, preferably from a leaf. Thus, the sample may, for example, be in the range of 1 cm to 3 cm leaf tissue.

The sample may be extracted and analyzed following a newly developed multistep protocol, as described herein, involving the successive use of different solvents and binding materials. In general, the sample may be extracted, for example with a solvent or a mixture of solvents, preferably water and/or organic solvents. The organic solvent may, for example, be an alcohol, preferably methanol—or the organic solvent may for example be an alkyl-halide, preferably chloroform. In one preferred embodiment, the solvent is a mixture of water, methanol, and chloroform. Said extraction may advantageously be performed while mixing, for example, using a shaker or a mixer. A solid support may be added to the solvent/sample mixture—for instance a bead, such as a glass bead.

In a preferred embodiment, the aforementioned leaf sample is taken from generation Mx kernels, wherein x is an integer $\geq 2$, preferably in the range of 2 to 10, more preferably in the range of 3 to 8. In a very preferred embodiment, the level of SMM is determined in M3-germinated plants, or in samples thereof (such as leaves). In said embodiment, it is preferred that mutagenized barley kernels of generation M0 are grown to obtain barley plants, which subsequently are crossed to obtain kernels of generation M1. The procedure is repeated until kernels of generation M3 are available (cf. FIG. 7).

Determination of the SMM level is preferably based on the novel procedure described below. Interestingly, this method allows for high-throughput screenings, rendering it feasible to identify barley plants characterized by a total loss of functional MMT.

Figure 2:
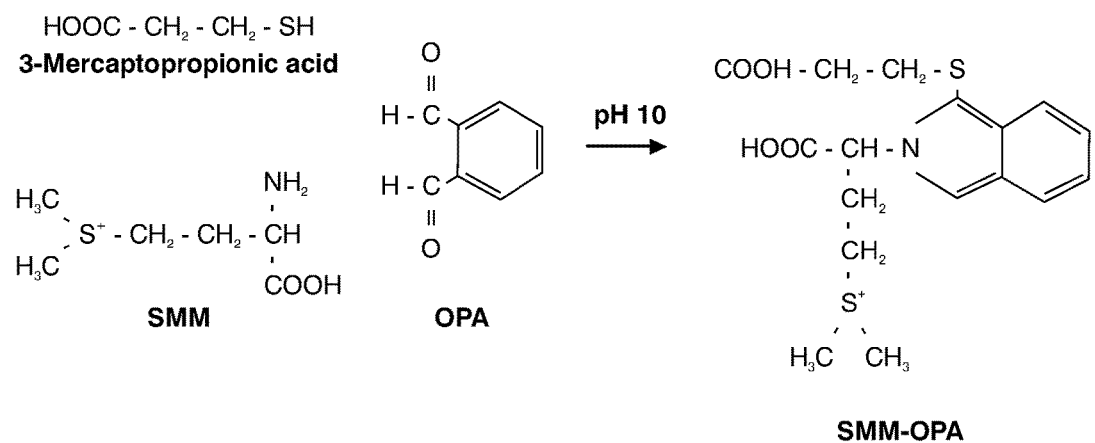
FIG. 2 shows the molecules involved in the alkaline formation of the fluorescent compound SMM-OPA.

In general terms, the method preferably involves reacting the sample, or preferably an extract of said sample, prepared as described above, with a compound capable of binding SMM. It was found that the OPA reagent (Sigma, cat. no. P7914; cf. FIG. 2), hereinafter just referred to as OPA, is particularly useful for determining SMM levels. OPA reacts, amongst others, with SMM to form the molecule referred to as SMM-OPA (cf. FIG. 2). The reaction preferably involves incubating OPA with an extract of the sample prepared as described above. In addition, it is preferred that 3-mercaptopropionic acid is added to the reaction mixture. The mixture is preferably kept at alkaline pH, preferably in the range pH 8 to pH 11, more preferably in the range pH 9 to pH 11, even more preferably in the range pH 9.5 to pH 10.5, such as at pH 10. Incubation is preferably performed at a temperature in the range of 0° C. to 10° C., preferably in the range of 1° C. to 8° C., even more preferably in the range of 2° C. to 6° C., yet more preferably in the range of 3° C. to 5° C., such as at 4° C. Incubation time is preferably $\geq 10$ min.

Figure 3:
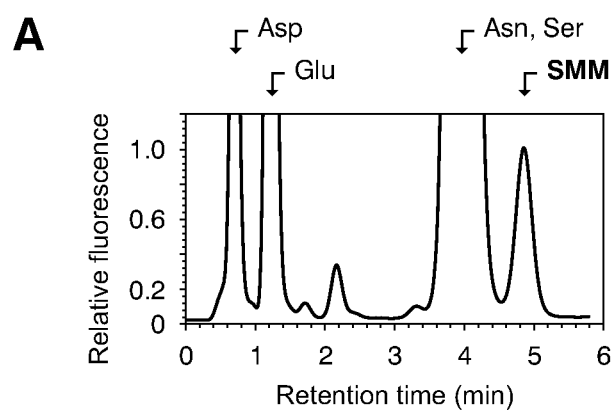
FIG. 3 shows results of HPLC and western blot experiments to verify the null-MMT phenotype of Mutant 8063 and Mutant 14018. (A) An example on HPLC-based separation of an extract from shoots of cv. Prestige, showing elution of aspartic acid (Asp), glutamic acid (Glu), asparagine (Asn), serine (Ser) and SMM. Fluorescence of OPA-derivatized extracts of barley shoots were excited at 340 nm and emission measured at 450 nm. (B) HPLC-based separation of extracts from the indicated mutants and wild-type cv. Sebastian. Separation of components in a mutant extract provided a chromatogram without SMM-specific peaks. (C) Western blot results of size-separated proteins from shoot extracts of wild-type Prestige (lane 2), Mutant 8063 (lane 3), wild-type Sebastian (lane 5), and Mutant 14018 (lane 6). Reference proteins with the indicated masses in kDa were separated in lanes 1, 4, and 7, while recombinant MMT from *E. coli* cells was used as a control and separated in lane 8. As detailed in Example 12, the 120-kDa stained protein bands represent MMT, while the 80-kDa band in the *E. coli* extract is not MMT-derived as it also appears in extracts of negative control cells transformed with vector pET19b (cf.
Figure 3:
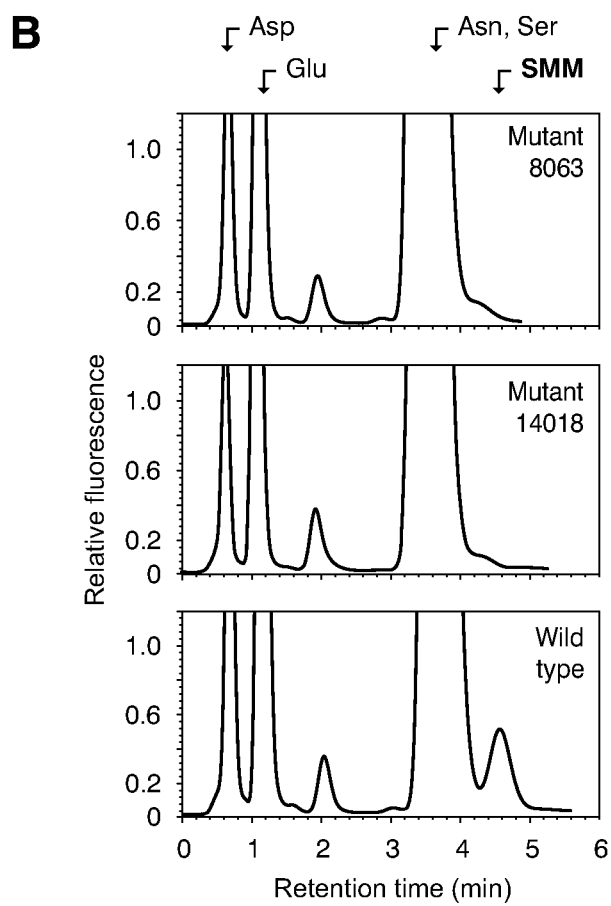
Figure 3:
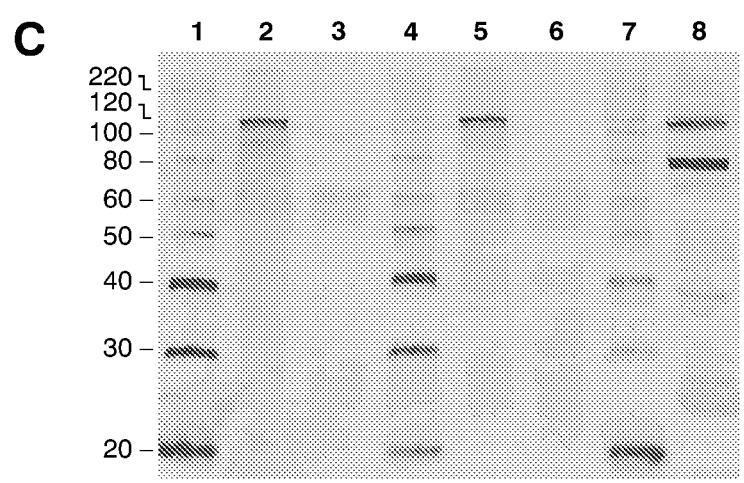

Based on the observation that SMM-OPA absorbs and emits light of 340 nm and 450 nm, respectively, its detection was possible by using fluorescence spectroscopy. The initial process of detection preferably involves extract separation over a column, preferably on a 30×2 mm Gemini 3μ C18 column (Phenomenex, cat. no. 00A-4439-80; Phenomenex, 2006), followed by fluorescence detection using a high-throughput liquid chromatography system, preferably an Ultra Performance Liquid Chromatography (UPLC system, Waters), designed to identify and measure the fluorescent level of molecules having excitation at 340 nm and emission at 450 nm. When using this method, "no detectable SMM" means the absence of detectable compounds that co-elute with SMM. In this context, a small "shoulder" on a chromatogram peak is considered an artifact peak. A small shoulder on the right hand side of the Asn/Ser peak, cf. FIG. 3, is accordingly not considered to represent a SMM peak. Thus, by way of example, the upper two chromatograms as shown in FIG. 3B are considered to depict "no detectable SMM", whereas the lower chromatogram in said figure represents the separation of a sample comprising SMM.

Detection of SMM may preferably be done as described in Example 2. A preferred method for selecting barley plants according to the invention is described hereinafter in Example 2. germinating barley plant, even more preferably from a barley plant, which has germinated for 4 d It is notable that the above-mentioned screening method is particularly useful. First of all the analytical method is novel. Furthermore, it is a significant advantage of the above method that it is established for determination of SMM levels in germinating barley plants, such as leaves of germinating barley plants. The timing of sampling from the germinating barley makes an unexpectedly clean preparation for UPLC-based detection of SMM. Other samples, for example, wort samples of similar grains as described above are too complex in composition, and can generally not be utilized in the mentioned chromatography method for determination of SMM levels.

Subsequent to the identification of a barley plant having less than 10 ppb SMM, preferably no detectable SMM, the corresponding MMT gene, or part thereof, is typically sequenced to determine whether the barley plant in question can be classified as having a mutation in the MMT gene. Barley plants characterized by having no detectable SMM, and wherein one or more bases of the MMT-encoding gene are different as compared with the wild-type sequence, are then selected. In this context, the wild-type sequence is preferably the sequence found in the corresponding wild-type barley cultivar, preferably the sequence given herein as SEQ ID NO:3. Preferred mutations are described hereinabove.

Selected barley mutants may be further propagated, and plants of subsequent generations re-screened for SMM content. After selection of useful barley plants, these may be included in breeding programs utilizing those conventional methods that are described hereinbelow in the section "Plant breeding".

Plant Products

The present invention in one aspect relates to beverages or other plant products with low levels of DMS, prepared from barley plants, or part thereof, carrying a mutation in the gene for MMT, causing a total loss of MMT function. Interestingly, such plant products, in general, comprise very low levels of DMS. Furthermore, such plant products in general also comprise very low levels of SMM, and preferably also very low levels of DMSO. Without being bound by theory, applicants recognize that the absence of barley and malt-derived SMM results in very low levels of DMS in beverages, and also in other plant products prepared from said barley characterized by loss of a functional MMT enzyme. Examples of useful plant products, such as beverages, prepared from barley plants having total loss of MMT activity, are described hereinafter.

It is preferred that said beverages, or said plant products, contain:
(i) Less than 30%, preferably less than 20%, more preferably less than 15%, even more preferably less than 10% DMS; and/or
(ii) Less than 30%, preferably less than 20%, more preferably less than 15%, even more preferably less than 10%, such as less than 5%, for example less than 2% SMM;
of the DMS and SMM content, respectively, of a similar beverage or plant product prepared from wild-type barley plants.

It is even more preferred that said beverages, or said plant products, contain:
(i) Less than 30 ppb, preferably less than 25 ppb, more preferably less than 20 ppb, even more preferably less than 15 ppb, yet more preferably less than 10 ppb, even more preferably less than 5 ppb, yet more preferably no detectable DMS; and/or
(ii) Less than 50 ppb, preferably less than 40 ppb, more preferably less than 30 ppb, even more preferably less than 20 ppb, yet more preferably less than 10 ppb, even more preferably less than 5 ppb, even more preferably no detectable SMM.

In addition, it is preferred that the plant product comprises less than 30%, preferably less than 20%, more preferably less than 15%, even more preferably less than 10% of the DMSO content of a similar beverage or plant product prepared from wild-type barley plants.

The plant product according to the present invention may, in one aspect, be barley kernels carrying a mutation resulting in a total loss of functional MMT. The plant product may also be compositions comprising said kernels and compositions prepared from said kernels, as well as other plant products prepared from said kernels.

Figure 8:
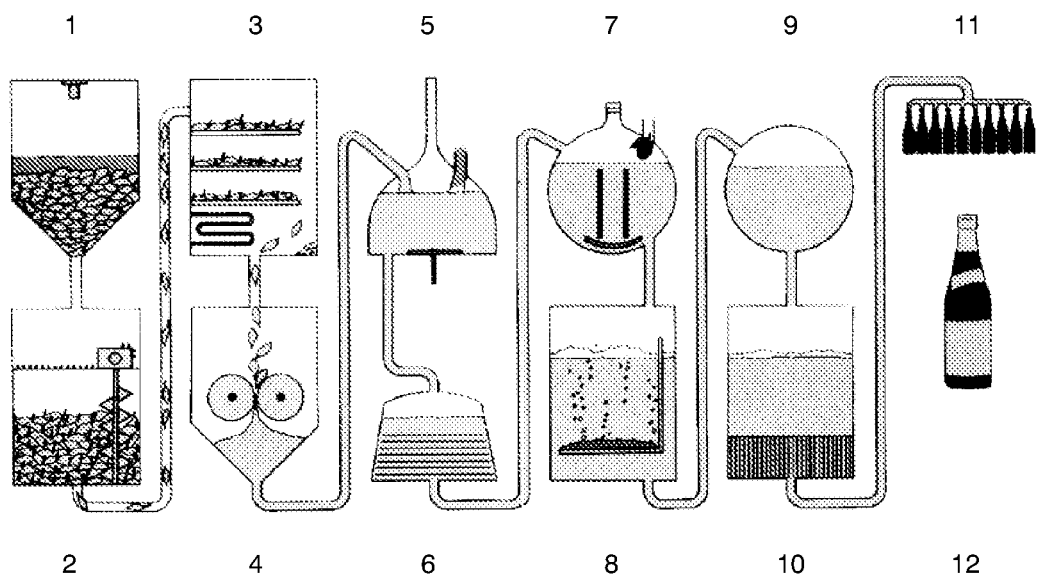
FIG. 8 shows a simplified, schematic overview of a preferred beer production process, including steeping of barley grain (1), germination (2), kiln drying (3), milling of the dried malt (4), mashing (5), filtration (6), wort boiling in the presence of added hops (7), fermentation in the presence of yeast (8), beer maturation (9), beer filtration (10), packaging into, for example, bottles, cans, or the like (11), and labeling (12). The individual processes can be grouped into sections comprising malt production (1-3), wort production (4-7), fermentation (8-9) and the preparation of the finished beer (10-12). Although a preferred method is illustrated, alternative ways may be envisaged that omit some of the depicted steps (filtration, for example, may be omitted or hops may not be added), or additional steps may be added (e.g. addition of adjuncts or carbonate). Beer may also be produced using mixtures of malted and unmalted barley, or only unmalted barley, in which case external enzymes are frequently added during the mashing process.

In one aspect, the plant product according to the invention is a malt composition prepared by malting kernels of barley plants that carry a mutation in the gene encoding MMT, causing total loss of MMT activity. By the term "malting" is to be understood germination of steeped barley kernels, taking place under controlled environmental conditions (for example as illustrated in FIG. 8).

Malting is a process of controlled steeping and germination, followed by drying (preferably kiln drying) of the barley grain. Prior to drying, the steeped and germinated barley grains are referred to as "green malt", which may also be a plant product according to the present invention. This sequence of events is important for the synthesis of numerous enzymes that cause grain modification in processes that principally serve to depolymerize the dead endosperm cell walls and mobilize grain nutrients. In the drying process, flavor and color (for example brown color) are produced as a consequence of chemical reactions. Although the primary use of malt is for beverage production, it can also be utilized in other industrial processes, for example as an enzyme source in the baking industry, or as a flavoring and coloring agent in the food industry, such as malt or as a malt flour, or indirectly as a malt syrup, etc.

In one aspect, the present invention relates to methods of producing said malt composition. The methods preferably comprise the steps of:
(i) Providing barley kernels from a barley plant carrying a mutation in the gene encoding MMT, causing total loss of MMT activity;
(ii) Steeping said kernels;
(iii) Germinating the steeped kernels under predetermined conditions;
(iv) Drying said germinated kernels;
thereby producing a malt composition with a low level of SMM and/or DMS. For example, the malt may be produced by any of the methods described by Briggs et al. (1981) and Hough et al. (1982).

However, any other suitable method for producing malt may also be used with the present invention, such as methods for production of specialty malts, including, but not limited to, methods of roasting the malt.

Figure 5:
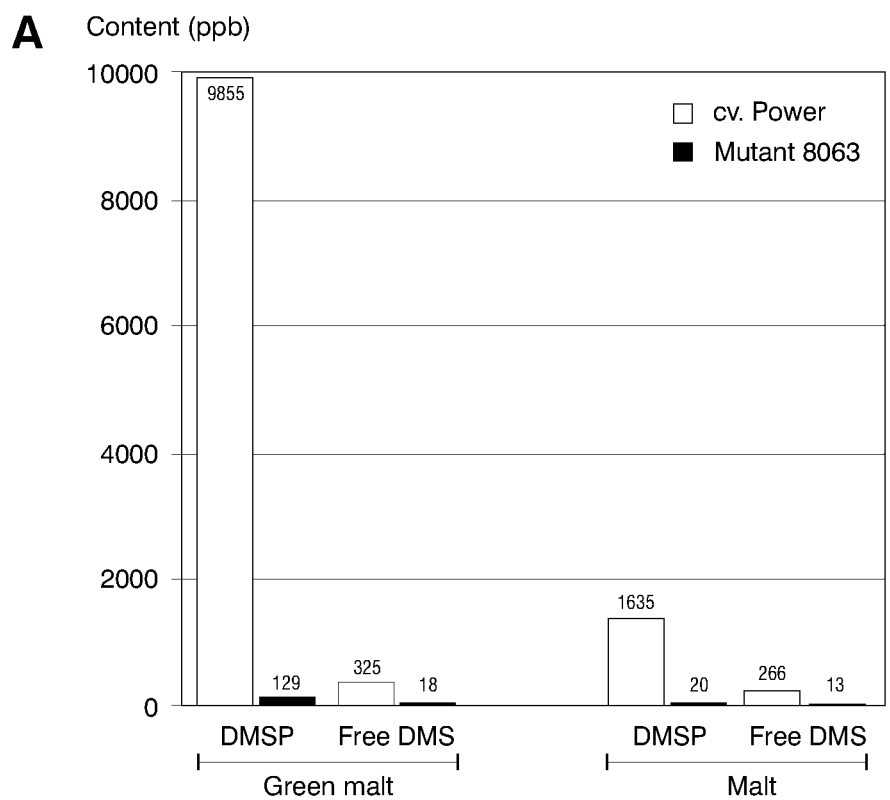
FIG. 5 shows a comparison of free DMSP and free DMS contents in wild-type and null-MMT malt, wort, and beer. (A) Both green and kilned malt of Mutant 8063 had notably reduced in levels of DMSP and free DMS. (B) Sweet and boiled worts of Mutant 8063 almost lacked DMSP and free DMS, and also beer made using Mutant 8063 malt was extremely low in free DMS.
Figure 5:
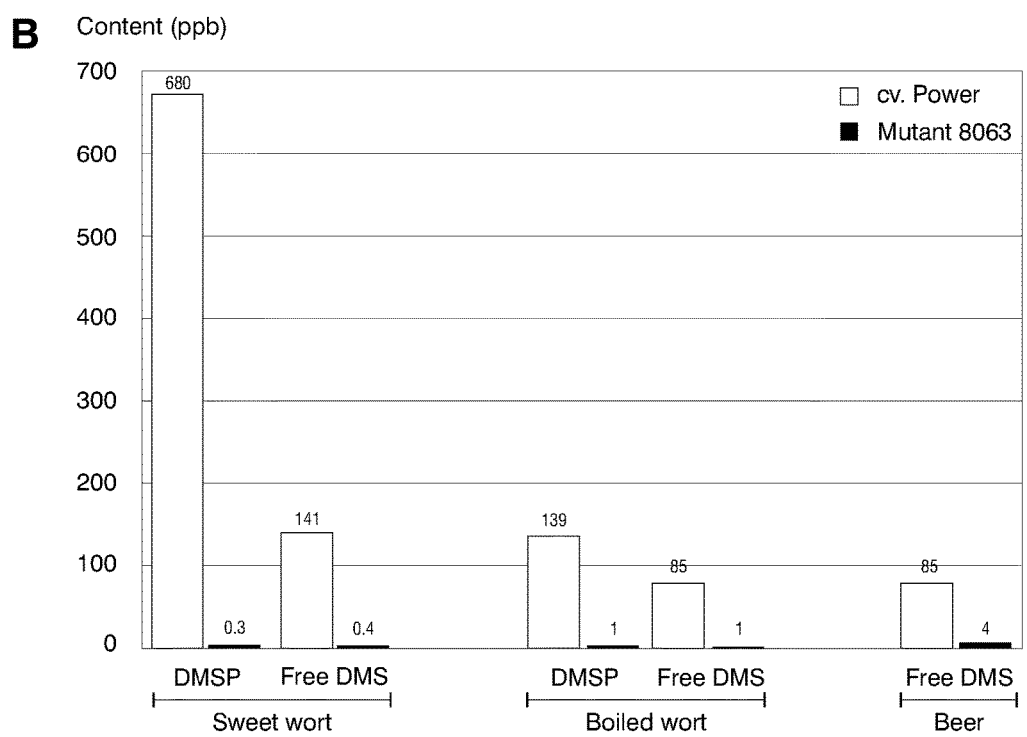

Interestingly, DMS is a rather volatile compound with a boiling point of 37° C.-38° C. (Imashuku, supra), and during malt production, for example during kiln drying, the composition is generally subjected to heat, such that substantial amounts of DMS evaporate away. However, during cooling of a normal malt composition, more DMS may be generated from DMS precursors (DMSP). One major advantage of the present invention is that no, or only very little, DMS is generated in the malt composition (cf. Example 6; FIG. 5A).

Methods for reducing DMS concentration in malt have been described. Many of these methods rely on heat treatment of malt. Said heat treatment may simply be heating of malt, for example during kiln drying to volatize free DMS by application of steam. Thus, steam treatment of malt may reduce the levels of free DMS in malt. However, these methods mainly reduce the level of free DMS in malt, but only affect the level of SMM to a lesser degree. As noted above, it is preferred that the plant products of the invention, such as malt compositions comprise low levels of both DMS and SMM. In one embodiment of the invention, the malt compositions of the invention have only been subjected to limited treatment involving volatizing and removing free DMS by steam, or alternatively have not been subjected to treatment involving volatizing and removing free DMS using steam during kiln drying.

In one embodiment of the invention it is preferred that the malt according to the invention has not been treated with a bromate salt, such as potassium bromate or calcium bromate.

Malt may be further processed, for example, by milling thereby obtaining milled malt. Thus, the plant product according to the invention may be any kind of malt, such as unprocessed malt, or milled malt, or flour thereof. Milled malt, and flour thereof, comprise chemical components of the malt, including dead cells that lack the capacity to re-germinate.

The malt compositions of the invention preferably comprise at the most 3, preferably at the most 2, more preferably at the most 1, even more preferably at the most 0.5, such as at the most 0.2 µg/g free DMS. In addition, it is preferred that the malt compositions of the invention preferably comprises at the most 2, preferably at the most 1, more preferably at the most 0.5 µg/g SMM.

In a preferred aspect the invention provides malt compositions that comprise at the most 200, preferably at the most 150, more preferably at the most 100, even more preferably at the most 50, such as at the most 25 ppb free DMS. In addition, it is preferred that the malt compositions of the invention preferably comprise at the most 1000, preferably at the most 500, more preferably at the most 250, even more preferably at the most 100 ppb, yet more preferably at the most 50 ppb SMM. It is also preferred that the malt compositions of the invention comprise at the most 1000, preferably at the most 500, more preferably at the most 100 ppb, yet more preferably at the most 50 ppb DMSP.

In another aspect the invention relates to green malt compositions comprising at the most 5000, more preferably at the most 2500, yet more preferably at the most 1000, even more preferably at the most 500, yet more preferably at the most 250, for example at the most 150 ppb DMSP. It is also preferred that said green malt compositions comprises at the most 200, preferably at the most 150, more preferably at the most 100, even more preferably at the most 50, such as at the most 25 ppb free DMS.

In another aspect, the plant products according to the invention are syrups, such as a barley syrup or a barley malt syrup. The plant product may also be an extract of barley or malt.

In another aspect, the plant products according to the invention are wort compositions prepared from malt compositions derived from barley kernels that carry a mutation in the gene for MMT, causing total loss of MMT activity (cf. Example 6; FIG. 5B). Said worts may be prepared from null-MMT kernels only, or mixtures comprising other kernels as well. The invention also relates to wort compositions prepared using null-MMT barley, or parts thereof, alone or mixed with other components. Said wort compositions may be first, and/or second, and/or further worts. The wort compositions may be sweet wort, boiled wort, or a mixture thereof. In general, a wort composition contains a high level of amino nitrogen and fermentable carbohydrates, the latter mainly being maltose. In FIG. 8 is illustrated the common method for preparation of wort from malt. In general, wort is prepared by incubating malt with water in a mashing process. During mashing, the malt/water composition may be supplemented with additional carbohydrate-rich compositions, for example barley, maize, or rice adjuncts. Unmalted cereal adjuncts are generally known to contain very low levels of enzymes, making supplementation with malt or exogenous enzymes necessary for sugar conversion and/or extract generation, including generation of free amino nitrogen.

In one embodiment of the invention, the plant product may be unmalted barley, which for example, may be useful as adjunct during mashing.

In general, the first step in the wort production process is the milling of malt such that water may gain access to grain particles in the mashing phase—which may be considered an extension of the malting process with enzymatic depolymerization of substrates. During mashing, milled malt is incubated with liquid, such as water. The incubation temperature is either kept constant (isothermal mashing), or gradually increased. In a preferred embodiment, the initial mashing temperature does not exceed 70° C., preferably does not exceed 69° C., thus for example the initial mashing temperature may be in the range of 50° C. to 69° C., such as in the range of 55° C. to 69° C., for example in the range of 55° C. to 65° C. If the initial mashing temperature is to high, it will affect the enzymatic activity in the mash and may reduce, or even abolish, desirable enzymatic activities, which will result in an altered quality of the wort. In either case, soluble substances produced in malting and mashing are liberated into said liquid fraction. A subsequent filtration confers separation of the wort liquid and residual solid particles, the latter denoted spent grains. Said wort may also be denoted "first wort" After filtration, a "second wort" may be obtained by sparging with hot water. Non-limiting examples of suitable procedures for preparation of wort are described by Briggs et al. (1981) and Hough et al. (1982).

First, second, and further worts may be combined, and subsequently subjected to boiling. The non-boiled wort, either a pure first wort or a combined wort, is also referred to as "sweet wort", while after boiling it may be referred to as "boiled wort". If the wort is to be used in production of beer, hops are frequently added prior to boiling.

The wort composition may also be prepared by incubating null-MMT barley plants, or parts thereof, such as unmalted null-MMT plants, or parts thereof, with one or more suitable enzymes, such as enzyme compositions, or enzyme mixture compositions, for example Ultraflo or Cereflo (Novozymes). The wort composition may also be prepared using a mixture of malt and unmalted barley plants, or parts thereof, or unmalted barley only, optionally adding one or more suitable enzymes during said preparation, in particular amylases, glucanases (preferably (1-4)- and/or (1-3, 1-4)-β-glucanase), and/or xylanase (such as arabinoxylanase), and/or proteases, or enzyme mixtures comprising one or more of the aforementioned enzymes, e.g. adding the enzyme mixture Ondea Pro (Novozymes).

Barley of the instant invention can be added to a malt mash and used as an adjunct. More specifically, barley of the invention can be used together with malt in any combination for mashing, with or without external brewing enzymes, such as, but not limited to the proportions of barley:malt=100:0, or 75:25, or 50:50, or 25:75.

In traditional brewing methods, the wort is boiled for a long time, in general in the range of 60 min to 120 min, one reason being that extended boiling reduces the amount of DMS, which is volatile. However, extended boiling is undesirable for a number of other reasons, for example because extended boiling requires pronounced energy supply. In addition, said boiling may lead to the generation of undesired Strecker aldehyde off-flavors. According to the present invention, wort with low levels of DMS can be produced from null-MMT barley even without extended boiling. Thus, the wort according to a preferred embodiment of the invention is boiled for at the most 45 min, even more preferably for at the most 30 min, for example for at the most 15 min. It is notable that even if a wort is extensively boiled, DMS may still be generated from DMSP over time. Interestingly, the wort according to the present invention maintains a low level of DMS, which is substantially lower than that obtained after boiling a normal wort.

In an additional embodiment of the invention, it is preferred that the wort is not subjected to carbon dioxide washing subsequent to boiling of wort and prior to fermentation.

Preferably, the wort compositions of the invention comprise less than 30 ppb, preferably less than 25 ppb, more preferably less than 20 ppb, even more preferably less than 15 ppb, yet more preferably less than 10 ppb, even more preferably less than 5 ppb, yet more preferably no detectable DMS—and/or less than 50 ppb, preferably less than 40 ppb, more preferably less than 30 ppb, even more preferably less than 20 ppb, yet more preferably less than 10 ppb, even more preferably less than 5 ppb, even more preferably no detectable SMM.

The plant products, or parts thereof, of the present invention may also be food compositions, feed compositions, and fragrance raw material compositions that comprise barley plants carrying a mutation in the gene encoding MMT, causing total loss of MMT activity. Food compositions, for example, may be, but are not limited to, malted and unmalted barley kernels, barley flours, bread, porridge, cereal mixes comprising barley, health products, such as beverages comprising barley, barley syrups, and flaked, milled or extruded barley compositions. Feed compositions, for example, include compositions comprising barley kernels, and/or flours. Fragrance raw material compositions are described herein below.

The invention also relates to mixtures of the plant products described herein. For example, the invention in one aspect relates to a composition prepared by a mixture of:
  (i) A composition comprising a barley plant, or a part thereof, carrying a mutation in the gene encoding MMT, causing total loss of MMT activity; and
  (ii) A malt composition prepared from null-MMT kernels.

In a preferred aspect, the present invention relates to beverages, more preferred to malt-derived beverages, even more preferred to alcoholic beverages, such as beer containing low levels of DMS, wherein said beverages are prepared using null-MMT barley or parts thereof.

Thus, in a preferred embodiment, the invention relates to beverages, more preferred to malt-derived beverages, even more preferred to alcoholic beverages, such as beer, said beverages or beer containing:
  (i) Less than 30 ppb, preferably less than 25 ppb, more preferably less than 20 ppb, even more preferably less than 15 ppb, yet more preferably less than 10 ppb, even more preferably less than 5 ppb, yet more preferably no detectable DSM; and/or
  (ii) Less than 50 ppb, preferably less than 40 ppb, more preferably less than 30 ppb, even more preferably less than 20 ppb, yet more preferably less than 10 ppb, even more preferably less than 5 ppb, even more preferably no detectable SMM.

It is preferred that the beverage is prepared by fermentation of null-MMT barley—or parts thereof, or extracts thereof—for example by fermentation of wort produced using malt produced from null-MMT barley, alone or in combination with other ingredients.

However, in other embodiments of the invention, the beverage is a non-fermented beverage, for example wort, preferably wort prepared from null-MMT malt. It is also comprised within the present invention that said beverage may be prepared from unmalted barley plants or parts thereof, preferably from unmalted null-MMT barley plants or parts thereof.

The beverage may be a non-alcoholic beverage, such as non-alcoholic beer or others kinds of non-alcoholic beverages, such as non-alcoholic malt beverages, such as maltina.

Preferably, however, said beverage is prepared from a malt composition comprising null-MMT barley kernels. More preferably, said beverage is beer. This may be any kind of beer known to the person skilled in the art. In one embodiment, the beer is, for example, a lager beer. The beer is preferably brewed using a malt composition comprising germinated null-MMT barley. The malt composition may, however, also comprise other components, for example other germinated or ungerminated cereals, such as wild-type barley, wheat, and/or rye, or non-germinated raw materials that comprise sugars or compositions derived from malted or unmalted raw materials, including syrup compositions.

It is generally thought that DMS over time may be generated from DMSP including SMM. Thus, even if no or very little DMS initially is present in a beverage, then DMS may accumulate over time. However, it is an objective of the present invention to provide beverages that contain little, or no, DMS—even after storage.

Accordingly, an object of the present invention is to provide barley plant-derived beverages, such as beer containing less than 30 ppb, preferably less than 25 ppb, more preferably less than 20 ppb, even more preferably less than 15 ppb, yet more preferably less than 10 ppb, even more preferably less than 5 ppb, yet more preferably no detectable DSM after storage for at least 1 week, preferably at least 2 weeks, more preferably at least 3 weeks, even more preferably for at least 4 weeks, such as in the range of 1 month to 3 months, for example in the range of 3 months to 6 months, such as in the range of 6 months to 12 months, for example for more than one year. Storage is performed at a temperature in the range of 5° C. to 40° C., such as in the range of 15° C. to 40° C.

Figure 6:
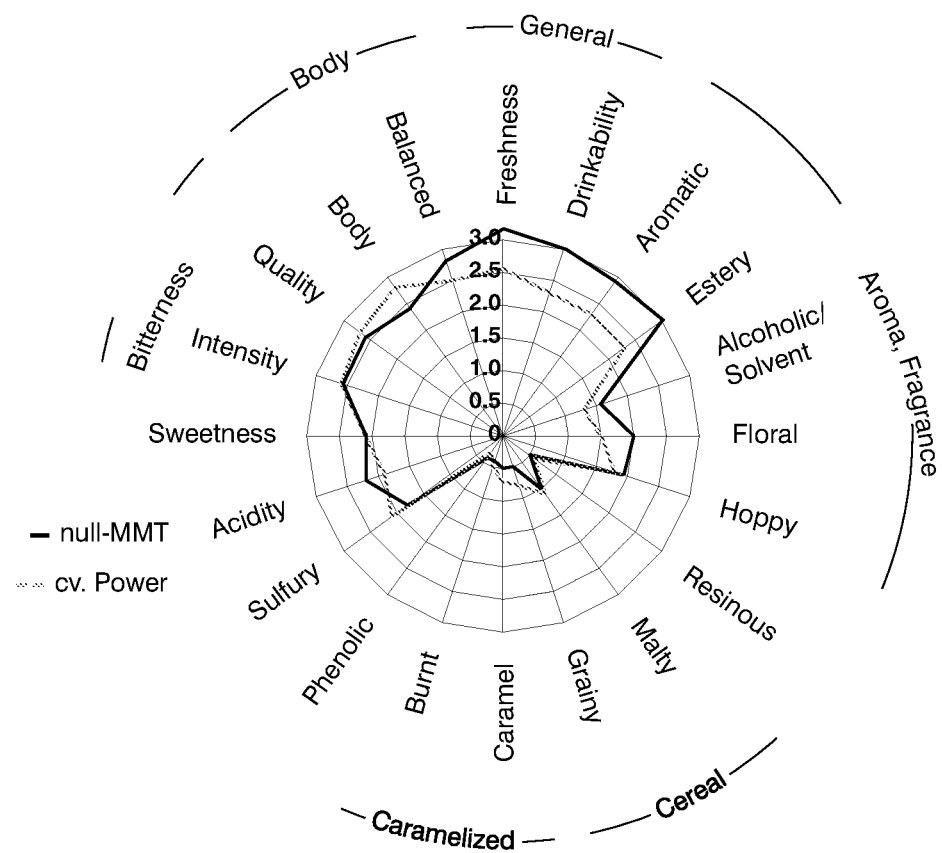
FIG. 6 shows flavor profile comparisons established by a 10-person-large beer taste panel; tests comprised beers brewed with malt of wild-type cv. Power and Mutant 8063 (null-MMT). This type of analysis makes use of a number of pre-defined flavor attributes as shown in the graphics, quantifiable on a scale from 0-5. A flavor is judged as "extremely", corresponding to score 5, only if its property is considered maximal for the beer type being analyzed. (A) Summary of the beer taste panel's evaluation of the beer spiked with esters and alcohols is listed in Table 1. (B) Summary detailing the taste panel's evaluation of an unspiked beer.
Figure 6:
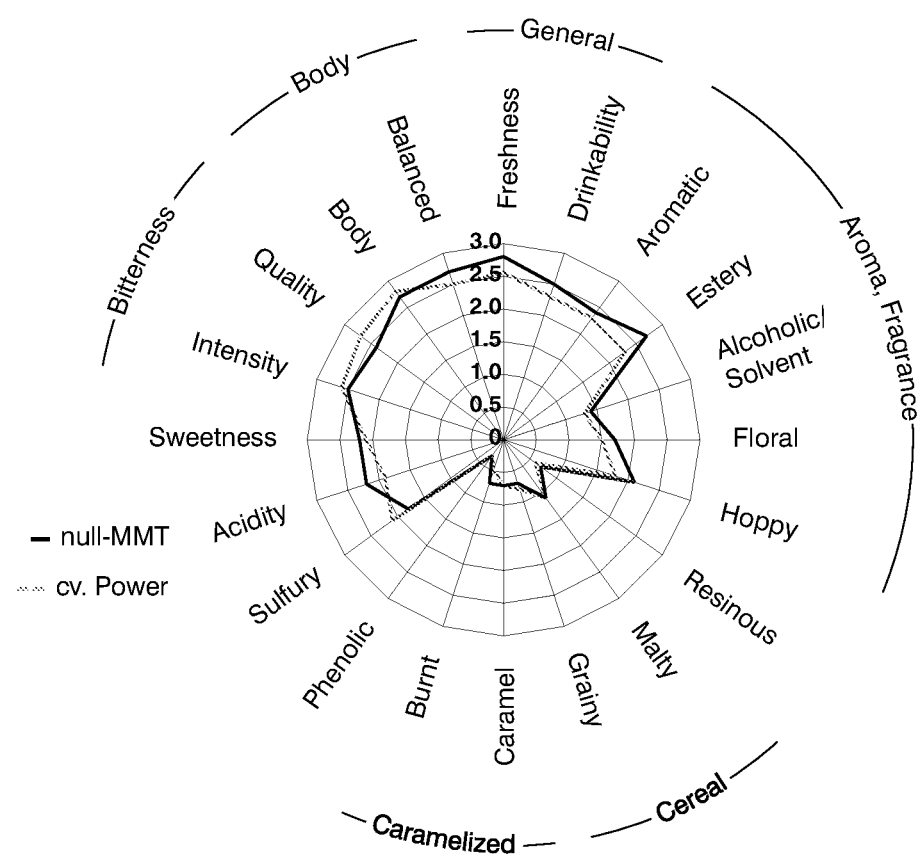

Furthermore, it is preferred that the beverages according to the invention are characterized by superior taste properties. In particular, it is preferred that the beverages according to the invention are characterized as being more aromatic and fragrant than a corresponding "normal" beer (cf. Example 7; FIG. 6). Without being bound by theory, the present invention provides the theory that the low levels, or even absence, of DMS and SMM cause the enhanced perception of aromatic and fragrant flavors.

Preferably, aromatic and fragrant flavors are determined by a professional taste panel. In embodiments where the beverage is beer, then the test panel preferably consists of professional beer tasters. Herein a "professional beer taste panel" is also referred to as a "trained taste panel", or a "specialist beer taste panel". Although there is good knowledge that DMS per se has a profound effect on the taste properties of beer, some taste panels may exhibit a tendency to generate inaccurate evaluations of multifaceted, sulfur-like flavors. The reason is simply that panelists remain inappropriately 'calibrated' as a consequence of differences in their flavor perception. This complex obstacle was solved, as described herein, by establishment of an extensively trained specialist panel of at least 9 beer tasters, who are skilled to critically evaluate the taste properties of esters, higher alcohols, sulfur components, and body of beer.

The taste panel should thus consist of at least 9 persons, preferably in the range of 9 to 20 persons, such as 9 to 12 persons, for example of 10 persons. Each taste panel member should preferably be extensively trained, in particular each member should be skilled to evaluate the taste properties of esters, higher alcohols, sulfur components and body of beer. Each taste panel member may then evaluate different flavor notes on a scale from 0 to 5. The flavor attributes are preferably selected from the group consisting of bitter intensity, bitter quality, body, balanced, freshness, drinkability, aromatic, estery, alcoholic/solvent, floral, hoppy, resinous, malty, grainy, caramel, burnt, phenolic, sulfury, acidity, and sweetness.

In using the above-mentioned approach, it is preferred that the beverages of the invention give a higher score for at least one, preferably at least two, even more preferably for at least 3, yet more preferably for at least 4, even more preferably for all aromatic/fragrant properties selected from the group consisting of aromatic, estery, alcoholic/solvent, floral, and hoppy as compared to a beverage with similar ethanol content, and prepared from a wild-type barley, preferably from cv. Power, when the ester/alcohol profiles of both beverages are adjusted to be similar, and the beverages are prepared in the same manner.

Furthermore, using the above-mentioned approach, it is preferred that the beverages of the invention have a higher score for at least one, preferably at least two, even more preferably for all of the three general properties selected from the group consisting of balanced, freshness, and drinkability as compared to a beverage with similar ethanol content, and prepared from a wild-type barley, preferably from cv. Power, when the ester/alcohol profiles of both beverages are adjusted to be similar.

Using the above-mentioned approach, it is preferred that the beverages of the invention have a score value of at least 0.1, more preferably at least 0.2 higher for freshness and/or estery as compared to a beverage with similar ethanol content, and prepared from a wild-type barley, preferably from cv. Power, when the ester profiles of both beverages are adjusted to be similar.

In the context of the instant application, the ester/alcohol profile is considered to be similar when the 12 compounds mentioned in Table 1 are adjusted to similar levels (see also Example 7), i.e. the beverages contain the same of amount, ±20%, of the 12 compound mentioned in Table 1. The ethanol content is considered similar if it is the same, ±20%, preferably the same, ±10%.

Thus, it is preferred that the beverages of the invention, if adjusted to a content of the following 12 compounds of (cf. listing in Table 1 and Example 7):

| (i)    | Acetaldehyde   | 1.20 ppm ± 20%;  |
|--------|----------------|------------------|
| (ii)   | Ethylformiate  | 0.24 ppm ± 20%;  |
| (iii)  | Ethylacetate   | 23.40 ppm ± 20%; |
| (iv)   | Isobutylacetate| 0.05 ppm ± 20%;  |
| (v)    | 1-Propanol     | 13.80 ppm ± 20%; |
| (vi)   | Isobutanol     | 9.60 ppm ± 20%;  |
| (vii)  | Isoamylacetate | 3.43 ppm ± 20%;  |
| (viii) | 1-Butanol      | 0.23 ppm ± 20%;  |
| (ix)   | Isoamylalcohol | 52.00 ppm ± 20%; |
| (x)    | Ethylhexanoate | 0.13 ppm ± 20%;  |
| (xi)   | n-Hexylacetate | 0.01 ppm ± 20%;  |
| (xii)  | Ethyloctanoate | 0.33 ppm ± 20%.  | are characterized by having a score value of at least 1, preferably at least 2, more preferably at least 3, even more preferably at least 4, yet more preferably at least 5, even more preferably all of the following properties (when determined as described in Example 7):
  (i) "Balanced" (score of at least 2.5, preferably at least 2.7);
  (ii) "Freshness" (score of at least 2.5, preferably at least 2.7, more preferably at least 2.9, yet more preferably at least 3.1);
  (iii) "Drinkability" (score of at least 2.5, preferably at least 2.7, more preferably at least 2.9, yet more preferably at least 3.0);
  (iv) "Aromatic" (score of at least 2.5, preferably at least 2.7, more preferably at least 2.9);
  (v) "Estery" (score of at least 2.5, preferably at least 2.7, more preferably at least 2.9, yet more preferably at least 3.0);
  (vi) "Alcoholic/solvent" (score of at least 1.5);
  (vii) "Floral" (score of at least 1.7, preferably at least 1.9);
  (viii) "Hoppy" (score of at least 1.8);
more preferably the following properties (when determined as described in Example 7):
  (i) "Freshness" (score of at least 2.5, preferably at least 2.7, more preferably at least 2.9, yet more preferably at least 3.1);
  (ii) "Drinkability" (score of at least 2.5, preferably at least 2.7, more preferably at least 2.9, yet more preferably at least 3.0);
  (iii) "Aromatic" (score of at least 2.5, preferably at least 2.7, more preferably at least 2.9);
  (iv) "Estery" (score of at least 2.5, preferably at least 2.7, more preferably at least 2.9, yet more preferably at least 3.0).

Thus, it is preferred that the beverage according to invention has:
  (i) A "freshness" score of at least 2.5 on a scale of 0 to 5 when evaluated by a professional taste panel; and/or
  (ii) A "drinkability" score of at least 2.5 on a scale of 0 to 5 when evaluated by a professional taste panel; and/or
  (iii) An "aromatic flavor" score of at least 2.5 on a scale of 0 to 5 when evaluated by a professional taste panel; and/or
  (iv) An "estery flavor" score of at least 2.5 on a scale of 0 to 5 when evaluated by a professional taste panel; provided that the ester/alcohol profile of the beverage is as indicated in Example 7, Table 1 in the column "null MMT" to which Mix 1 and Mix 2 are added.

In particular, the present invention discloses that the presence of DMS in a beverage may mask an estery taste. Accordingly, it is an objective of the present invention to provide beverages that have a higher score for estery taste, wherein said taste is evaluated by a trained taste panel—preferably a trained taste panel of at least 9 members—in a comparison with a beverage prepared in the same manner, but comprising at least 100 ppb DMS, such as in the range of 100 to 200 ppb DMS, or in comparison with a beverage prepared in the same manner, but comprising at least 50 ppb DMS, such as in the range of 50 to 100 ppb. Said higher score for estery taste is preferably at least 0.5 points, preferably at least 0.7 points, for example at least 0.9 point higher, when the estery taste is determined on a scale from 0 to 5 as described above.

The invention also relates to methods of producing the above-mentioned beverages, preferably comprising the steps of:
  (i) Providing a malt composition comprising germinated null-MMT kernels;
  (ii) Processing said malt composition into a beverage;
thereby obtaining a beverage containing less than 30 ppb, preferably less than 25 ppb, more preferably less than 20 ppb, even more preferably less than 15 ppb, yet more preferably less than 10 ppb, even more preferably less than 5 ppb, yet more preferably no detectable DMS.

In one preferred embodiment, the beverage is beer. In this case, the processing step preferably comprises preparing wort from said malt composition, for example, by any of the methods described hereinabove, and fermenting said wort.

In general terms, alcoholic beverages—such as beer—may be manufactured from malted and/or unmalted barley grains. Malt, in addition to hops and yeast, contributes to beer flavor and color. Furthermore, malt functions as a source of fermentable sugar, and also as a source of enzymes. A schematic representation of a general process of beer production is shown in FIG. 8, while detailed descriptions on methods for malting and brewing can be found, for example, in publications by Briggs et al. (1981) and Hough et al. (1982). Numerous, regularly updated methods for analyses of barley, malt, and beer products are available. These include, for example, but are not limited to American Association of Cereal Chemists (1995), American Society of Brewing Chemists (1992), European Brewery Convention (1998), and Institute of Brewing (1997). It is recognized that many specific procedures are employed for a given brewery, with the most significant variations relating to local consumer preferences. Any such method of producing beer may be used with the present invention.

The malt composition of the aforementioned beverages—including for example beer, malt drinks, or non-fermented wort—may, for example, be obtained by any of the methods described hereinabove. Wort may be prepared from said malt composition.

The first step of producing beer from wort preferably involves boiling said wort. During boiling, other ingredients may be added, such as cereal syrups or hops, wherein the latter component may provide the typical bitter and aromatic beer characteristics. Boiling of wort also causes aggregation between polyphenols and denatured proteins, which may precipitate during the subsequent phases of beer production. Also, boiling of wort may cause evaporation of volatile compounds, including DMS. However, as noted above, wort prepared from null-MMT barley contains little, or no, DMS, thus making it possible to reduce substantially the boiling time of such worts. After being cooled, the wort is transferred to fermentation tanks containing yeast, preferably brewer's yeast of the species Saccharomyces carlsbergensis. The wort will be fermented for any suitable time period, generally in the range of 1 to 100 d. During the several-day-long fermentation process, sugar is converted to alcohol and $CO_2$, concomitantly with the development of some flavor substances.

Subsequently, the beer may be further processed, for instance chilled. It may also be filtered and/or lagered—a process that develops a pleasant aroma and a less-yeasty flavor. Also additives may be added. Furthermore, $CO_2$ may be added. Finally, the beer may be pasteurized and filtered, before it is bottled or canned.

Various methods are available to determine whether a barley plant or a plant product is prepared from a barley plant carrying a mutation in the gene for MMT, causing a total loss of MMT function. Plant products will in general comprise at least some genomic DNA from the plant utilized for its production. Thus, malt will contain large amounts of genomic DNA, but even barley or malt extracts, such as wort, may comprise genomic DNA from said barley or malt. Also barley-based beverages, such as beer, may comprise genomic DNA from said plant. By analysis of DNA in a plant product, it may be established whether the plant from which the plant product is prepared carries a mutation in the gene for MMT, causing a total loss of MMT function. Said mutation could, for example, be any of the mutations in the MMT gene described hereinabove in the section "Loss of functional MMT enzyme". The genomic DNA may be analyzed by any useful method, such as sequencing or by amplication-based methods, including PCR-based methods. If a particular mutation in the gene for MMT is assumed, then polymorphism analysis may be employed, for example SNP analysis. Such analysis may be performed as described hereinafter in Examples 13 and 17. The skilled person will be able to adapt the specific SNP analysis described in these examples for use with other mutations or other starting material.

If the above-mentioned plant products only are prepared from barley plants carrying a mutation in the gene for MMT, causing a total loss of MMT function, then presence vs. absence of barley MMT mRNA and/or MMT protein may also be indicative of whether said plant product is prepared from null-MMT barley. Accordingly, examination of the plant product by western blot analysis, or other protein analysis, or by RT-PCR, or by Northern blot analysis, or by other mRNA analyses may be performed. Such analyses are in particular useful when the plant product is malt.

SMM and DMS

The amount of SMM and DMS in a plant product may be determined by any suitable method. SMM may be determined essentially as described hereinabove in the section "Preparing barley plants with a total loss of functional MMT", wherein is described determination of SMM levels in a barley sample. Thus, SMM may be determined by coupling it to a compound, such as OPA, and determining fluorescence, for example, by using a HPLC system. For a quantitative measurement, the chromatogram area corresponding to a SMM peak may be determined.

For a more precise measure, the amounts of both DMS and DMSP (such as SMM), the latter compound measured as DMS after activation, are preferably determined using high resolution capillary gas chromatography. Total DMS in samples of wort or beer are defined herein as the quantitative sum of free DMS and its precursor forms, denoted DMSP. Using this definition, the quantity of DMSP in a wort or beer sample can be determined as the difference between total DMS (measured in the boiled sample, preferably in a sample boiled at alkaline conditions for 1 hour), and free DMS (measured in the non-boiled sample). Example 6 details preferable ways to measure levels of total and free DMS.

Chemical Mutagenesis

In order to generate barley plants carrying a mutation in the gene encoding MMT, causing total loss of MMT activity according to the present invention, a very large number of barley mutants can be prepared by any suitable mutagenesis method, for example by the use of chemical mutagenesis of barley kernels—a method that is known to induce mutations at random. Mutagenesis of barley may be performed using any mutagenizing chemical. Preferably, however, it is performed by treating kernels with $NaN_3$ (cf. FIG. 7), letting the surviving kernels germinate, followed by analysis of offspring plants. The plant generation growing from the mutagenized kernels, referred to as M0, contains heterozygote chimeras for any given mutation. Progeny plants collected after self-pollination are referred to as the M1 generation, in which a given mutation segregates into the corresponding heterozygotes and homozygotes.

Treating barley kernels with $NaN_3$ is not equivalent to treating a single barley cell, because the kernels after the treatment will contain some non-mutant cells and a variety of cells having DNA mutations. Mutations will be lost in cell lineages that do not lead to the germ line, meaning that the goal is to target the mutagen to the few cells that develop into reproductive tissues, which contribute to development of generation M1.

To assess the overall mutation efficiency, albino chimeras and albino plants may be counted in generations M0 and M1, respectively. Scoring mutant number as a function of surviving plants gives an estimate for the mutation efficiency, while scoring mutant number as a function of treated seeds provides the combined measure of both mutation efficiency and kernel kill.

It is notable that cells have quality assurance mechanisms at virtually every step of gene expression, possibly to moderate the effects of damaging mutations. One well-studied example in eukaryotes is nonsense-mediated mRNA decay, denoted NMD, which prevents the synthesis of potentially deleterious, prematurely truncated proteins (Maquat and Carmichael, 2001; Wu et al., 2007). In NMD, a termination codon is identified as premature by its position relative to downstream destabilizing elements. Mutations that generate premature termination (nonsense) codons, denoted PTCs, sometimes increase the levels of alternatively spliced transcripts that skip the offending mutations, thereby potentially saving protein function (Mendell and Dietz, 2001).

Plant Breeding

Crop development can be seen as a lengthy process that begins with the introduction of a new trait. From the perspective of a plant breeder, this step often may result in a plant that has a less desirable overall profile of agronomic traits than do current commercial varieties. In one preferred embodiment of the instant invention, the objective is accordingly to provide agronomically useful barley plants that carry a mutation in the gene for MMT, causing total loss of functional MMT.

In addition to the null-MMT trait, there are other factors which also may be considered in the art of generating a commercial malting barley variety, including, but not limited to kernel yield, kernel size, and parameters that relate to malting performance or brewing performance. Since many—if not all—of such traits are under genetic control, the present invention also provides modern, homozygous, high-yielding barley cultivars which may be prepared from crosses with the null-MMT barley plants. Kernels of such barley plants provide a new raw material without functional MMT enzyme. The skilled barley breeder will be able to cross the null-MMT barley plant of the invention with other barley plants, and subsequently select and develop off-springs having traits which result in superior cultivars. Such off-springs are also considered part of the present invention. Alternatively, the barley breeder may utilize plants of the present invention for further mutagenesis to generate new cultivars derived from null-MMT barley.

The barley plants according to the present invention may be utilized in breeding efforts according to any suitable scheme.

Another objective of the present invention is to provide agronomically elite barley plants that comprise the null-MMT trait. Accordingly, the instant invention also is directed to methods for producing a new null-MMT barley plant by crossing a first parental barley plant with a second parental barley plant, wherein the first or second plant is a null-MMT barley. Additionally, both first and second parental barley plants represent a null-MMT barley variety. Thus, any such of the following methods using the null-MMT barley variety are part of this invention: selfing, backcrossing, crossing to populations, and the like. All plants produced using a null-MMT barley variety as a parental generation, are within the scope of this invention, including those plants developed from varieties derived from a null-MMT barley variety. The null-MMT barley can also be used for genetic transformation in such cases where exogenous DNA is introduced and expressed in the null-MMT plant or plant tissue.

Backcrossing methods can be used with the present invention to introduce the null-MMT trait of a mutated barley plant into another variety, for example, into another cultivar, such as into cv. Scarlett or cv. Jersey—both of which are contemporary, high-yielding malting barley cultivars. In a standard backcross protocol, the original variety of interest, i.e. the recurrent parental plant of interest, is crossed to a second variety (i.e. non-recurrent parental plant), carrying the single gene of interest to be transferred. The resulting null-MMT progeny plants from this cross are subsequently crossed to the recurrent parent, with the process being repeated until a barley plant is obtained wherein essentially all of the characteristics specified by the recurrent parental plant are recovered in the generated plant, in addition to the transferred genetic set-up for the null-MMT trait of the non-recurrent parental plant. Eventually, the last-generated backcrossed plant is selfed to give pure, null-MMT breeding progeny plants.

Having a suitable recurrent parent is preferable in a successful backcrossing procedure, the goal of which includes introduction of the null-MMT trait into the original variety. To accomplish this, the genetic set-up of the recurrent variety is modified with that of the null-MMT trait from the non-recurrent parental plant, while retaining essentially all of the genetic properties from the original variety. Although backcrossing methods are simplified when the genetic property being transferred is specified by a dominant allele, it is possible to backcross that of the recessive null-MMT trait.

A way to accelerate the process of plant breeding comprises initial multiplication of generated mutants by application of tissue culture and regeneration techniques. Thus, another aspect of the present invention is to provide cells, which—upon growth and differentiation—produce barley plants having the null-MMT trait. For example, breeding may involve traditional crossings, preparing fertile anther-derived plants or using microspore-culturing methods.

It is also an embodiment of the present invention to provide barley plants that not only carry a mutation in the gene encoding MMT, causing a total loss of MMT activity, but also one or more additional useful mutation(s). Such additional mutations may, for example, include mutations in the barley gene encoding lipoxygenase-1 (LOX-1), such as a mutation causing a lower level of LOX-1 activity (for example the mutant described in U.S. Pat. No. 6,660,915 to Douma, A. C. et al.), or a mutation causing a complete loss of LOX-1 function, such as any of the mutants disclosed in U.S. Pat. No. 7,420,105 or PCT patent application WO 2005/087934 to Breddam, K. et al., in particular mutants comprising a genomic sequence of the gene encoding LOX-1 according to SEQ ID NO:2 or SEQ ID NO:6 of U.S. Pat. No. 7,420,105 to Breddam. K. et al.

null-LOX-1 malt, as described in the abovementioned patents and patent applications, could provide, by itself, a raw material for low-temperature kiln drying in the malting process of barley. A combined null-LOX-1-null-MMT double mutant would, however, be superior and highly useful in the brewing industry because both of the LOX-1 and MMT activities would be inactivated. Such barley plants may be obtained by crossing barley plants according to the present invention with those described in U.S. Pat. No. 7,420,105 or PCT patent application WO 2005/087934 to Breddam, K. et al.

EXAMPLES

The examples herein illustrate preferred embodiments of the invention, and should not be considered as limiting for the invention.

Unless otherwise indicated, basic molecular biological techniques were performed for manipulating nucleic acids, proteins, and bacteria as described in Sambrook and Russel (2001).

Example 1

DMS Masks the Estery Taste of Beer

Characterization of sulfur-like flavor notes is generally considered difficult, even among general beer panel tasters. Often, the beer taste panelist uses the generic term "sulfury" rather than the more specialized sulfury notes—e.g. "mercaptan", "hydrogen sulfide" and "DMS"—to characterize a sulfury note.

Following establishment of a 9-taster-large panel, members were extensively trained in tracing the aroma of sulfur-containing components, surprisingly revealing that the addition of sulfur components strongly affect the perception of other aroma components, a property leading to lower scores for e.g. estery taste and body of beer.

In another set of experiments, DMS was chosen for training the panel. Beer samples, spiked with high concentrations of said sulfur-containing components, were presented to the panel, who were asked to taste and rank the characteristics "body", "estery", and "DMS", on a scale from 0 (absent) to 5 (extreme). Each series of tests included a standard, commercially available beer and two, for the panelists, unknown samples.

In FIG. 1B is illustrated the results of the average scores from a test series comprising beer samples spiked with ester and ester/DMS, respectively. The unexpected result was that addition of DMS, when combined with ester, affected negatively the perceived estery score compared to that obtained by spiking with ester only. Likewise, the beer body note was reduced. Not surprisingly, spiking with DMS enhanced the score for that property.

The above-mentioned results demonstrate that the specialized taste panel's ability to taste a single flavor component appears to be highly dependent on the 'flavor background' as determined by other aroma components.

The surprising finding from the taste tests, summarized in FIG. 1B, also provided basis for the present invention by providing beverages with low levels of DMS, and barley mutants useful for preparing such beverages, i.e. barley mutants lacking the capacity to synthesize SMM—such that utilization of the corresponding raw material in beverage production not only could enable for generation of products with less or no DMS, but also with promises in improvements for the estery note.

Example 2

Screening Set-Up, Approach 1

Kernels collected from barley plants of cv. Prestige and cv. Sebastian were incubated separately with the mutagen $NaN_3$, following the experimental details provided by Kleinhofs et al. (1978). This procedure was chosen because of its known potential for inducing point mutations in the barley genomic DNA.

In the experiments, mutated grains of generation M1 were propagated in field plots through two subsequent generations, eventually yielding a high proportion of homozygous plants of generation M3 for screening purposes. Mutated grains of generation M3 were expected to contain gene mutations at a frequency of 0.9-2.3 per 10,000 grains (Kleinhofs et al., supra). It is notable that M2 grains were not screened.

Interestingly, the present invention describes a rapid high-throughput screening procedure for detection of M3 mutant barley grains lacking MMT activity, providing lack of detectable SMM synthesis during malting. Thus, applicants found that SMM mainly accumulated in the coleoptile and primary leaf of germinating barley, and that detection of SMM can be performed by extracting amino acids from crushed leaf tissue of 4-d-old germinated grains, followed by reacting the extracted amino acids with OPA to form highly fluorescent products (cf. FIG. 2).

In practical terms, each assay was performed by germinating—in a closed plastic box with one piece of Whatman #1 filter paper (296×20.9 mm)—two grains from each of 94 potential mutants and two wild-type plants. The assay was repeated for multiple, potential mutant grains (see below). At the beginning of germination, 25 mL of tap water was added to said plastic box, followed by additional 15 mL of tap water at 2 d of germination. After 4 d of germination, 1-3 cm of leaf tissues were transferred to storage plates (ABgene), in which each of the 96 1.2-mL wells contained a 5-mm-diameter glass bead and 500 µL of a 12:5:6 (v/v/v) mixture of water:methanol:chloroform. The plate was then shaken for 45 sec at a frequency of 30 Hz in an MM 300 laboratory mill (Retsch). Subsequently, the plate was transferred to a centrifuge (Rotanta 460R, Hettich), and spun at 4,000 rpm for 15 min at room temperature to precipitate insoluble material. 10 µL of the supernantant was transferred to a 96-well storage plate (Waters, cat no. 186002481), and mixed with 200 µL $H_2O$ and 60 µL of a reaction solution containing a 15,000:45 (v/v) mixture of OPA reagent (Sigma, cat. no. P7914):3-mercaptopropionic acid (Aldrich, cat. no. M5801). The mixture was incubated at 4° C. for at least 10 min to obtain a quantitative derivatization of sample amino acids with OPA. Using a Waters-based HPLC system equipped with a fluorescence detector, 2 µL of the derivatized mixture was separated on a 2.1×30-mm C18 Gemini column of 3-µm particles (Phenomenex, cat. no. 00A-4439-80), using gradient elusion by mixing mobile phase A (a 40-mM $NaH_2PO_4$ buffer, adjusted to pH 7.8) and mobile phase B [a 45:45:10 (v:v:v) solution of acetonitrile:methanol:water as described (Phenomenex, 2006)]. Excitation of eluted OPA derivatives was at 340 nm, while light emission was measured at 450 nm. An example of a chromatogram is shown in FIG. 3A to illustrate the elution profile of aspartic acid (Asp), glutamic acid (Glu), asparagine (Asn), serine (Ser) and SMM. The latter compound was included, as the overall project aim was to identify a barley plant that lacked the capacity to synthesize SMM, i.e. a plant for which the corresponding chromatogram peak was very small or preferably absent.

Screening Set-Up, Approach 2

In parallel with the above-described experiments in the instant example, attempts were carried out to establish a very fast screening method for the identification of barley seedlings lacking active MMT enzyme. Based on the fact that said seedlings can grow in the presence of 250 µM Na-selenite, provided that the plants contain active MMT to convert Na-selenite, a screen was designed to visually score for seedlings with reduced growth in the presence of said Na-selenite concentration. In practical terms, 22,704 spikes—each consisting of 20-30 kernels—of $NaN_3$-mutagenized barley cv. Prestige, generation M3, were placed in plastic trays filled with standard Vermeculite growth medium supplemented with 250 µM Na-selenite. Kernels of the spikes were allowed to germinate and develop into ~15-cm-long seedlings. A total of 812 plants characterized by reduced growth, i.e. seedlings ~15 cm in length, were transferred to fresh soil and allowed to develop further. However, none of said plants were found to have reduced MMT activity, as determined by comparison with wild-type levels of SMM. Accordingly, the above-described screening approach yielded no mutants, and was therefore terminated.

Example 3

Potential Mutants

A total of 10,248 and 3,858 $NaN_3$-mutated kernels of barley cv. Prestige and cv. Sebastian, respectively, were screened for SMM content (cf. approach 1 in Example 2), with the aim to identify those highly reduced in said content when compared with wild-type grains. Only 2 potential mutants of the M3 generation were identified, namely grains of sample no. 8,063 (derived from cv. Prestige, and hereinafter denoted Mutant 8063, a designation also used for grains of subsequent generations; FIG. 3B), and grains of sample no. 14,018 (derived from cv. Sebastian, and hereinafter denoted Mutant 14018, a designation also used for grains of subsequent generations; illustrated in FIG. 3B). Grains of each mutant were propagated to the M4 generation, then harvested, and eventually re-analyzed. The result verified that grains of Mutant 8063 and Mutant 14018 had extremely low SMM contents, possibly totally lacking SMM.

In a separate experiment, western blot analysis was used to verify that Mutant 8063 and Mutant 14018 lacked MMT enzyme. Grains of the mutants and the corresponding wild-type plants were germinated in the dark for 4 d on filter papers soaked in water. One grain of each sample was transferred to an Eppendorf tube containing 250 µL $H_2O$, and homogenized by using a pistil. Following a 10-min-long centrifugation at 13,000 rpm, 15 µL of the liquid extract was mixed with 5 µL of a standard 4-fold concentrated SDS sample buffer. By using the same immuno-methodology as described in Example 12, and an aliquot of the same anti-MMT antibody detailed in said example, proteins of sample extracts of the aforementioned, germinated kernels were electrophoretically separated by size and applied to western blot analysis. The absence of a stained 120-kDa protein band, corresponding to MMT, was noted for the size-separated extracts of Mutant 8063 and Mutant 14018. However, a 120-kDa protein band was clearly visible in extracts of germinated wild-type kernels (FIG. 3C). Combining the results of the western analysis with the absence of SMM in extracts of Mutant 8063 and Mutant 14018, but presence of SMM in extracts of wild-type kernels (cf. FIG. 3B), substantiate that Mutant 8063 and Mutant 14018 represent null mutants with respect to the MMT trait.

Example 4

MMT Activity Measurements of Mutant 8063

Figure 4:
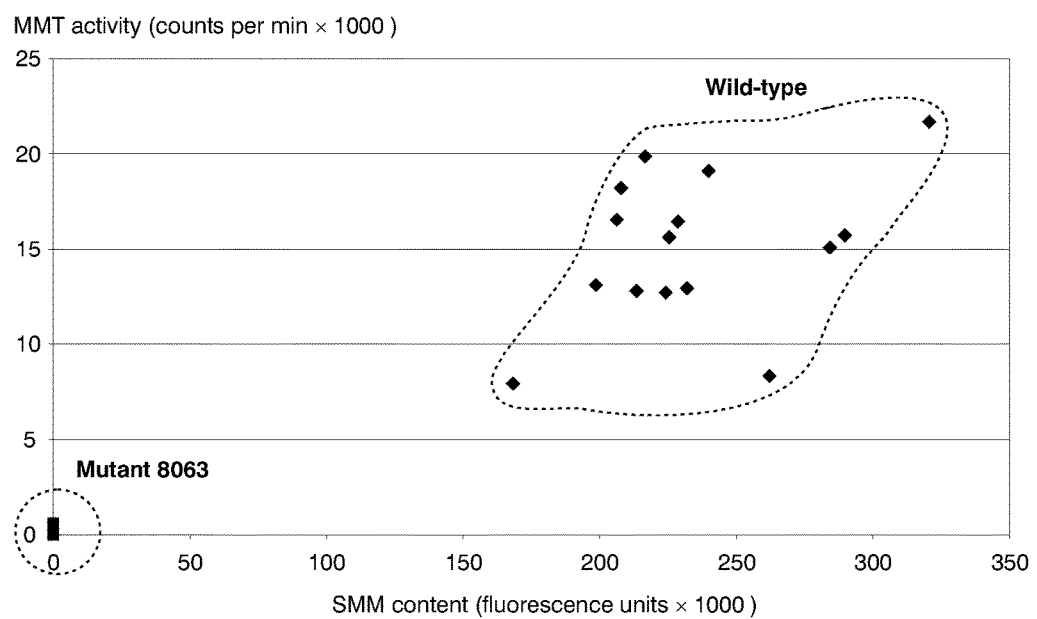
FIG. 4 shows the absence of MMT activity in 4-d-old shoots of Mutant 8063, but pronounced activities in wild-type shoots of similar germination length. MMT activity was determined using [$^3$H]SAM as a substrate. The MMT-catalyzed transfer of a methyl group from [$^3$H]SAM to Met, forming SMM, was monitored by scintillation counting after removal of the remaining [$^3$H]SAM by activated charcoal. This binds the substrate—but not the newly synthesized, labeled product SMM. The illustration also shows that SMM was absent in mutant shoots, but present in those of wild-type. A total of 30 shoots of both mutant and wild-type plants were analyzed, 15 from each of mutant and wild-type plants.

The MMT enzyme catalyzes the transfer of a methyl group from SAM to Met, forming SMM (cf. FIG. 1B). Using [$^3$H]SAM as a substrate, in which the methyl group is labeled with tritium, transfer of said methyl group can be monitored by scintillation counting after removal of the remaining [$^3$H]SAM by activated charcoal. The latter compound binds the substrate, but not the newly synthesized, labeled product SMM (Pimenta et al., 1995). This allowed for determination of MMT activities and SMM contents, the latter determined as described in Example 2, in extracts of 15 shoots of each of Mutant 8063 and cv. Prestige (FIG. 4). Data examination verified that MMT catalyzed the formation of SMM in wild-type kernels, a property that was absent in grains of Mutant 8063.

Example 5

Pilot-Scale Malting and Brewing of Null-MMT Kernels of Mutant 8063

Malting and brewing analyses with malt of Mutant 8063 and reference malt of cv. Power involved the following steps:
(i) Germination, including steeping, to generate green malt, sometimes followed by kiln drying to obtain kilned malt;
(ii) Wort preparation;
(iii) Wort separation;
(iv) Wort boiling;
(v) Fermentation of wort with the yeast *Saccharomyces carlsbergensis*;
(vi) Lagering of beer;
(vii) Bright beer filtration; and
(viii) Bottling of beer.

For both Mutant 8063 and cv. Power (reference sample), 30 kg malt was used for brewing. Malt samples were milled, and then tap water was added to 150 L for each sample. Mashing-in was performed at 60° C. for 20 min, followed by a 5-min ramp to 65° C., at which temperature the incubation was continued for 55 min. The mash was then applied to a 15-min ramp to 78° C., concluding the mashing after a 5-min incubation.

Subsequent brewing operations included wort filtration, a 1-h-long boiling step, and separation in a whirlpool. A 7-d-long fermentation, lagering, and filling of the finished beer in green glass bottles were according to specifications for standard brewing practice, for instance as described by Briggs et al. (1981), and Hough et al. (1982). In total, 100 33-cL bottles were made with beer derived from malt of wild-type and mutant malt.

Example 6

DMS and DMSP Levels in Beer Made of Null-MMT Malt

Beer was brewed from malts of null-MMT and cv. Power as described in Example 5. During the malting and brewing processes, levels of free DMS and DMSP were determined in green and kilned malt (FIG. 5A), as well as in the corresponding sweet and boiled worts, and also in the finished beers (FIG. 5B).

DMS and DMSP levels were determined essentially as described by Hysert et al. (1980), with sulfur-specific detection using static headspace gas chromatography on a 350B Sulfur Chemiluminescence Detector (Sievers). Sampling was performed using an automated apparatus (HS-40 Automated Headspace Sampler, Perkin Elmer). Total levels of DMS, i.e. the sum of free DMS and DMSP in wort and extracts of green and kilned malt, were obtained by boiling the respective samples under alkaline conditions for 1 h. Samples were then subjected to headspace analysis for determination of DMS levels. As described previously, the difference between total DMS levels in the boiled samples, and free DMS in the corresponding un-boiled samples was defined to equal the amount of sample DMSP. The quantity of free DMS in beer was determined essentially as that in wort (Hysert et al., supra).

Example 7

Tasting Beer Brewed with Null-MMT Malt

Seeking to establish how a professional beer taste panel evaluates pilot-scale produced beer brewed with null-MMT malt, a profile tasting was performed on beers measured to contain 4 ppb DMS. As reference was utilized a normal beer of 76 ppb DMS, said beer produced using malt of cv. Power.

Prior to the taste analysis, the profiles of beer esters and higher alcohols were obtained by gas chromatography analysis. The beer of null-MMT malt had lower levels in 3 out of 12 analyzed compounds (Table 1). In the first taste test, Mix 1—consisting of ethylacetate, isoamylacetate, and ethyloctanoate—was spiked into the beer brewed with null-MMT malt, to assure that the two lager beers had similar levels of those flavor-active compounds that contribute to a standard ester profile (cf. Table 1). The aim of the second test was to make a high-ester beer with enhanced flavor notes. Therefore, Mix 2—consisting of isoamylacetate, ethylhexanote, and ethyloctanoate—was spiked into beer of cv. Power malt (Table 1), while the beer of null-MMT malt was spiked with both Mix 1 and Mix 2.

The above-described beers were then tested by a 10-person-large trained beer taste panel, which evaluated 20 specific flavor attributes—each on a scale, or score, from 0 to 5 (FIG. 6).

As detailed in FIG. 6A for the high-ester beers, there was a notable effect on the perception of aromatic-fragrant flavors in the "very-low-DMS-beer" brewed on null-MMT malt, as compared to a standard beer spiked to the same level. Higher scores were noted for all of the aromatic-fragrant flavors assessed. Even in the beer of null-MMT malt, which was spiked to a normal ester profile (FIG. 6B), there was noted an enhanced perception of the aromatic-fragrant flavors, again showing that a low level of DMS confers a positive effect with respect to perception of aromatic beer compounds. An explanation on that phenomenon is simply that DMS in beer masks the taste of pleasant aromatic-fragrant flavors, which represent important factors when beverage freshness is assessed.

TABLE 1

Ester and alcohol analyses of beer.

| | Concentration of flavor compound | | | |
|---|---|---|---|---|
| | Malt type | | Added flavors | |
| Flavor compound | cv. Power | null-MMT Ppm | Mix 1 | Mix 2 |
| Acetaldehyde | 1.00 | 1.20 | | |
| Ethylformiate | 0.26 | 0.24 | | |
| Ethylacetate | 23.40 | 19.40 | 4.00 | |
| Isobutylacetate | 0.06 | 0.05 | | |
| 1-Propanol | 13.80 | 13.80 | | |
| Isobutanol | 9.00 | 9.60 | | |
| Isoamylacetate* | 2.05 | 1.43 | 0.50 | 1.50 |
| 1-Butanol | 0.21 | 0.23 | | |
| Isoamylalcohol** | 59.00 | 52.00 | | |
| Ethylhexanoate | 0.09 | 0.08 | | 0.05 |
| n-Hexylacetate | 0.01 | 0.01 | | |
| Ethyloctanoate | 0.20 | 0.13 | 0.07 | 0.13 |

*Sum of 2-methyl-butyl acetate and isoamylacetate concentrations.
**Sum of 2-methyl-1-butanol and isoamylalcohol concentrations.

Example 8

Sequence Determination of the Gene Encoding MMT in Barley, Cv. Prestige

With the aim to establish the genomic diversity that underlies the difference in MMT activity between wild-type and mutant barley plants, a primary effort was to determine the DNA sequence that spans the start and stop codons of the corresponding barley gene. To establish the previously unknown genomic sequence of the barley MMT gene, a first step was to purify genomic DNA (gDNA) from leaves of 6-d-old barley seedlings, cv. Prestige, following the instructions provided by the supplier of the Plant DNA Isolation Kit (Roche, cat. no. 1667319).

Next, oligonucleotide primers were designed to bind to the cDNA sequence encoding MMT (GenBank accession no. AB028870; SEQ ID NO:1). Using barley gDNA as template, standard PCR amplifications were carried out with 6 different primer sets, the DNA sequences of which are listed in Table 2. Pairwise, the primers were found to anneal in exons 1 (including and downstream of the translational start codon) and 2, exons 2 and 4, exons 4 and 5, exons 5 and 9, exons 9 and 11, and exons 11 and 12 (including and upstream of the translational stop codon). Five of the aforementioned six reactions generated DNA fragments spanning exons 2-4, exons 4-5, exons 5-9, exons 9-11, and exons 11-12 (cf. FIG. 9). One reaction also was assumed to generate a DNA fragment spanning the translational start codon and exon 2 (i.e. the reaction with primer set no. 1 as listed in Table 2 and FIG. 9), but only reaction artifacts were observed. Although the reason for this difficulty remains elusive, a remarkably high content of G and C bases in the gene segment of interest might be the cause for failure in correct sequence amplification. Consequently, numerous commercially available PCR reaction supplements—claimed to facilitate amplification of G-C rich gene regions—were employed in attempts to amplify a DNA fragment downstream of, but still containing, the start codon of the MMT-encoding barley gene. Despite numerous attempts, all efforts utilizing gDNA template failed with respect to amplification of the fragment specified by the primers in reaction 1 as listed in Table 2.

Alongside the experiments with amplification of gDNA, it also was studied if RNA-derived cDNA of barley seedling leaves might constitute a functional template for amplification of the troublesome exon 1 sequence of the gene for MMT. Accordingly, total RNA was extracted and purified from leaflets of 4-d-old barley seedlings, cv. Prestige, employing the components and instructions of the FastRNA ProGreen Kit (Q-BIOgene, cat. no. 6045-050). Aliquots hereof were used in 8×2 standard RT-PCR reactions [i.e. 8 combinations of primer pairs (Table 3), each with 2 reaction buffers], as detailed in the instructions for the OneStep RT-PCR kit (Qiagen, cat. no. 210212). Fragments were separated on 1% agarose gels, with the subsequent analysis revealing that reaction products could only be obtained by using Buffer 1 of said kit. DNA bands of interest were then purified using the QiaexII gel extraction kit (Qiagen, cat. no. 20051). Separate RT-PCR amplifications with primer set nos. 7, 10, and 11 (cf. Table 3), in the presence of Q-solution of the aforementioned RT-PCR kit. DNA fragments of interest were also in this case purified. Following insertion of the individual DNA fragments into vector pCR2.1-TOPO (Invitrogen, cat. no. K4500-01), and transfection of E. coli cells with the construct, the corresponding DNA sequences of plasmid inserts were determined.

Taken together, the combined, above-described efforts crystallized in the assembly of a genomic sequence spanning the translational start and stop codons of the gene for barley MMT of cv. Prestige (SEQ ID NO:3). Through alignment of the cDNA and genomic sequences, i.e. alignment of SEQ ID NO:3 with SEQ ID NO:1, it was determined that the barley gene for MMT, as illustrated in FIG. 9, includes 12 exons (in total 3267 bp) separated by 11 introns (in total 3192 bp). The derived amino acid sequence for MMT of cv. Prestige is shown in FIG. 10, and listed as SEQ ID NO:6. Except for Pro157→Ala and Met985→Tyr in the aforementioned, derived amino acid sequence for MMT of cv. Prestige, a comparison with that of cv. Haruna Nijo (GenBank accession no. AB028870; SEQ ID NO:2) revealed complete identity (FIG. 11).

TABLE 2

Primers for amplification of the genomic sequence encoding barley MMT.

| Primer set no. | PCR product ends * | Forward primer (5'→3' DNA sequence) ** | Reverse primer (5'→3' DNA sequence) *** |
|---|---|---|---|
| 1 | 1-1462 | ATGGCTGCGGCGGCGGGGGACGTGG (SEQ ID NO: 37) | CCTTCGAAGGGCACCACTTTTCTGC (SEQ ID NO: 43) |
| 2 | 1268-2214 | AGGATTCCAGCAAAGAAAGAAGC (SEQ ID NO:38) | CTGGAGAGCACAGTAGTTGCTCAAG (SEQ ID NO: 44) |
| 3 | 2118-3075 | GATTCTTAACCCCAATCCAGAGGC (SEQ ID NO: 39) | CTGCATAATTTTTGTTTGCCAGAGC (SEQ ID NO :45) |
| 4 | 2886-4409 | GGGTTTTGTTGAGGACCAATTTGGC (SEQ ID NO: 40) | TACACCATTTGAGCTTGGCAGACT (SEQ ID NO: 46) |
| 5 | 4301-5188 | TGCTGCTTTCGTGAACTTATT (SEQ ID NO: 41) | AAAATGGAGGCGTTTACTGCAGAA (SEQ ID NO: 47) |
| 6 | 5130-6459 | CATATGGATCTGGACCGCAGCTTCTT (SEQ ID NO: 42) | CTAGTTGCTACCATTCACCTTAGCACC (SEQ ID NO: 48) |

*) Base pair numbering as that of the genomic sequence for MMT (SEQ ID NO: 3; see also FIG. 9).
**) Sequence at the 5' end of the fragment listed in the column labeled "PCR product ends".
***) Complementary sequence at the 3' end of the fragment noted in the column labeled "PCR product ends".

TABLE 3

Primers for amplification of the cDNA sequence encoding barley MMT.

| Primer set no. | RT-PCR product ends * | Forward primer (5'→3' DNA sequence) ** | Reverse primer (5'→3' DNA sequence) *** |
|---|---|---|---|
| 7 | 1-69 | ATGGCTGCGGCGGCGGGGGACGTGG (SEQ ID NO: 49) | GTACGCCGCGTCGCCCGACG (SEQ ID NO: 57) |
| 8 | 1-170 | ATGGCTGCGGCGGCGGGGGACGTGG (SEQ ID NO: 50) | CCGCCGGCGGCGAAGCGCCG (SEQ ID NO: 58) |
| 9 | 1-200 | ATGGCTGCGGCGGCGGGGGACGTGG (SEQ ID NO: 51) | GTGCGGAAGCACTCGAGCCC (SEQ ID NO: 59) |
| 10 | 1-221 | ATGGCTGCGGCGGCGGGGGACGTGG (SEQ ID NO: 52) | CGTGGATGCGGAAGTGGAAG (SEQ ID NO: 60) |
| 11 | 1-247 | ATGGCTGCGGCGGCGGGGGACGTGG (SEQ ID NO. 53) | CTTGGAGGTGGGGGTCGAGGACGACG (SEQ ID NO: 61) |
| 12 | 131-200 | GGCTCCTCGGCGCCGTGCGACGGCG (SEQ ID NO: 54) | GTGCGGAAGCACTCGAGCCC (SEQ ID NO: 62) |
| 13 | 131-221 | GGCTCCTCGGCGCCGTGCGACGGCG (SEQ ID NO. 55) | CGTGGATGCGGAAGTGGAAG (SEQ ID NO: 63) |
| 14 | 131-247 | GGCTCCTCGGCGCCGTGCGACGGCG (SEQ ID NO: 56) | CTTGGAGGTGGGGGTCGAGGACGACG (SEQ ID NO: 64) |

*) Base pair numbering as that of genomic sequence for MMT (SEQ ID NO: 3).
**) Sequence at the 5' end of the fragment noted in the column labeled "PCR product ends".
***) Complementary sequence at the 3' end of the fragment noted in the column labeled "RT-PCR product ends".

Example 9

The Gene Encoding MMT of Barley Mutant 8063 is Mutated in the 5' Splice Site of Intron 5

The content of SMM in barley seedlings of Mutant 8063 is extremely low or absent (Example 3), in line with the absence of MMT activity (Example 4). Based on this finding, it was investigated whether base substitutions in the MMT-encoding gene were caused by the original NaN₃ mutagen treatment of the barley kernels. Consequently, attempts were made to amplify, clone and sequence said gene of Mutant 8063 in order to establish the molecular basis for its null-MMT phenotype.

Having amplified with 6 primer sets the nucleotide sequence of the wild-type gene for MMT of cv. Prestige (Table 2; detailed in Example 8), a similar approach was followed for barley Mutant 8063. In brief, genomic DNA was extracted from the mutant, and MMT gene-specific, amplified fragments thereof were inserted into vector pCR2.1-TOPO (Invitrogen, cat. no. K4500-01), cloned, sequenced, joined (SEQ ID NO:8), and finally compared with that of wild-type barley. No mutation was identified in the protein coding part of the gene for MMT. However, comparing intron sequences of mutant and wild-type genes revealed a G→A base transition at the first base of intron 5 (nucleotide no. 3076 of SEQ ID NO:8). Said base is part of the 5' splice site of intron 5, and will affect primary RNA processing of the gene, i.e. RNA splicing (Sinibaldi and Mettler, 1992; see also FIG. 12).

To assess possible roles of the base mutation with respect to perturbation of normal gene splicing in the MMT-encoding gene of Mutant 8063, a detailed analysis was carried out of mutant-derived RNA in order to detect splicing intermediates. This approach was chosen because alterations in the 5' GT dinucleotide of introns may lead to accumulation of splicing intermediates (Lal et al., 1999).

To amplify fragments of interest, analysis followed the recommendations provided for use of a RT-PCR kit (OneStep RT-PCR from Qiagen, cat. no. 210212). As template was used 1 µg of total RNA from leaflets of 4-d-old seedlings of cv. Prestige and Mutant 8063, purified as described in Example 8. Using primer set 15 (Table 4), the RT-PCR reaction was designed to amplify the gene region spanning exon 3 and exon 7 of transcripts for MMT of wild-type Prestige and Mutant 8063 (FIG. 12A). Following amplification, reaction products were resolved by electrophoresis on a 1% agarose gel (FIG. 12B).

Examination of amplified products revealed only a single band from the reaction with wild-type RNA (FIG. 12B). This was excised from the gel, purified using the components of the QiaexII kit (Qiagen, cat. no. 20051), inserted into vector pCR2.1-TOPO (Invitrogen, cat. no. K4500-01), cloned, and sequenced. Analyses demonstrated the presence of a 882-bp fragment (Product 1 in FIG. 12B,C; SEQ ID NO:9), characterized by a sequence identical to that spanning bases 442-1323 of the full-length cDNA for wild-type barley MMT (SEQ ID NO:4). Based on this finding, alternative splicing is considered irrelevant for wild-type gene expression.

A RT-PCR reaction like that described in the previous paragraph, except for the application of purified template RNA from Mutant 8063, generated three specific DNA fragments—denoted Product 2, Product 3, Product 4 in FIG. 12B—each different in length from that of Product 1 amplified using wild-type RNA (FIG. 12B). Accordingly, pre-mRNA processing is obstructed by the single base mutation in the 5' splice site of intron 5 in the gene for MMT of Mutant 8063. This scenario completely abolishes the use of said 5' splice site, but activates the use of cryptic, additional splice sites.

In an effort to address the underlying molecular cause for obtaining the above-mentioned, three PCR fragments in Mutant 8063, each was prepared for DNA sequencing using the procedure as that described above in Example 8 for the PCR-derived DNA bands of cv. Prestige. The largest fragment was 1089 bp long (Product 2 in FIG. 12C; SEQ ID NO:10), and found to include all of intron 5, while Product 3 (FIG. 12C; SEQ ID NO:12) and Product 4 (FIG. 12C; SEQ ID NO:14) were 955 bp and 810 bp long, respectively, and thus shorter than the 882-bp fragment from wild-type RNA (cf. description above). DNA sequence analysis of Product 3 revealed a cryptic splice site in the middle of intron 5, while that of Product 4 was in exon 5 (FIG. 12 D).

It also was an important finding of the DNA sequence analyses to discover premature translational stop codons in Product 2 [TGA at position 3088-3090 according to the base numbering of genomic DNA from barley, cv. Prestige (SEQ ID NO:3)], Product 3 [TGA at position 3088-3090 according to the base numbering of genomic DNA from barley, cv. Prestige (SEQ ID NO:3)], and Product 4 [TGA at position 3289-3291 according to the base numbering of genomic DNA from barley, cv. Prestige (SEQ ID NO:3)], yielding 315, 315, and 289 amino acid-long translated proteins, respectively. FIG. 12C provides a graphical comparison and summary of the sequencing results of Product 1, Product 2, Product 3, and Product 4, while the illustrations in FIG. 12D and FIG. 12E provide specific data on the specific bases involved in the events of alternative splicing.

TABLE 4

Primers to detect alternative splicing of the gene encoding barley MMT.

| Primer set no. | RT-PCR product ends * | Forward primer (5'→3' DNA sequences) ** | Reverse primer (5'→3' DNA sequence) *** |
|---|---|---|---|
| 15† | 442-1323 | GTTTATGGTCTGGATATAAACCCAAG (SEQ ID NO: 65) | AAATCCAGCAACAAGATTCCGGAAA (SEQ ID NO: 67) |
| 16‡ | 246-933 | AGGATTCCAGCAAAGAAAGAAGC (SEQ ID NO: 66) | CTGCATAATTTTTGTTTGCCAGAGC (SEQ ID NO: 68) |

†For RT-PCR using RNA template of Mutant 8063.
‡For RT-PCR using RNA template of Mutant 14018.
*) Base pair numbering as that of cDNA for MMT (SEQ ID NO: 4).
**) Sequence at the 5' end of the fragment noted in the column labeled "PCR product ends".
***) Complementary sequence at the 3' end of the fragment noted in the column labeled "PCR product ends".

Example 10

Expression Plasmid Encoding Wild-Type MMT

Because of the following two observations:
(i) *E. coli* cells lack MMT and the ability to synthesize SMM (Thanbicher et al., 1998);
(ii) Plant MMT can be synthesized in *E. coli* (Tagamount et al., 2002);

heterologous expression of mutated or truncated barley MMTs in the aforementioned bacterium allows a novel way to simulate for, or confirm their lack of, enzymatic activity. As recombinant, wild-type barley MMT from *E. coli* would serve as a positive control in such experiments, a task was to design and construct an *E. coli* expression plasmid for heterologous expression of barley MMT.

To amplify relevant sequences, total RNA was first extracted from leaflets of 4-d-old seedlings of cv. Prestige (as detailed in Example 9), and 1 µg hereof used as template in a standard RT-PCR reaction, except that primer set 17 was added to the reaction mixture (Table 5). The amplified product was inserted into vector pCR2.1-TOPO (Invitrogen), yielding plasmid pCR2.1-TOPO-MMT. Following cloning of the plasmid, the entire insert was sequenced (SEQ ID NO:5), and compared with that of cv. Prestige (SEQ ID NO:4). Three PCR-induced nucleotide differences were identified in the cloned product (T1310→A, T2954→C, and G3031→A), giving the MMT amino acid substitutions Leu437→His, Tyr985→Met, and Gly1011→Ser (as determined by comparing SEQ ID NO:6 and SEQ ID NO:7). None of the amino acid changes were expected to compromise action of recombinant MMT in a way that could be of relevance in the instant application. This conclusion was based on the finding that the expressed protein was active and could be recognized by anti-MMT antibodies (cf. Example 12).

Figure 13:
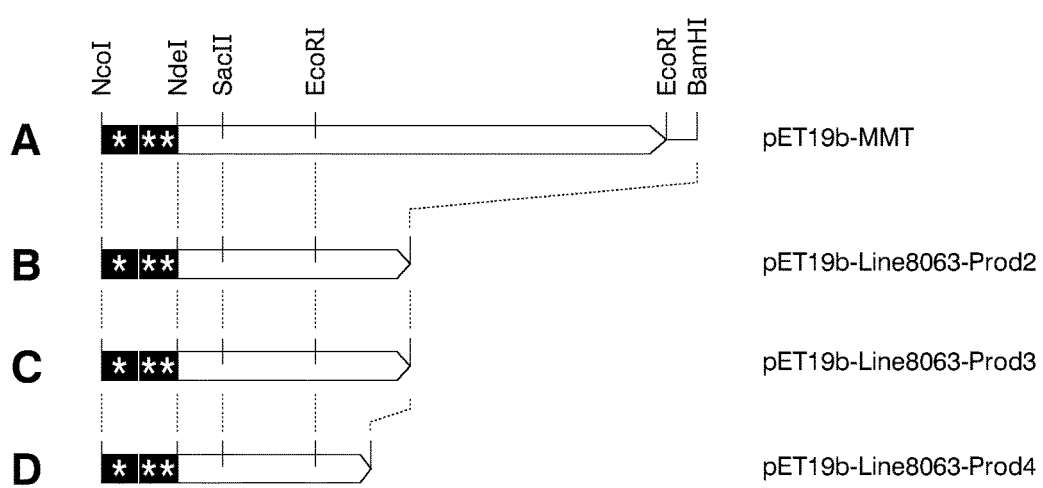
FIG. 13 shows expression plasmids for heterologous expression of aberrant MMTs of Mutant 8063, and alignment of encoded proteins. (A) Illustration of the NcoI-BamHI fragment of pET19b-MMT—including selected restriction sites—encoding wild-type MMT fused to a sequence specifying a His-tag (*; sequence MGHHHHHH-HHHH; SEQ ID NO:69) in frame with an enterokinase site (**; sequence SSGHIDDDDKH; SEQ ID NO:70). Deletion constructs are illustrated in (B), (C), and (D). (E) Alignment of the encoded MMT sequences (SEQ ID NOs: 6, 11, 13, 15 for constructs shown in A, B, C and D, respectively). A synthetic peptide corresponding to the sequence stretch marked with asterisks was used for generation of polyclonal antibodies against the barley MMT. The sequence spanning residue numbers 333 and 1084 is not shown for the wild-type enzyme (SEQ ID NO:6).

Next, pCR2.1-TOPO-MMT was cut with NdeI-EcoRI, yielding a 569-bp NdeI-EcoRI 5' fragment and a 2699-bp 3' EcoRI fragment. The 5' fragment was inserted into NdeI-EcoRI-linearized expression vector pET19b (Novagen, cat. no. 69677-3), and in the EcoRI site of the resulting plasmid was inserted the above-mentioned 2699-bp 3' fragment, thus generating expression plasmid pET19b-MMT (FIG. 13A). This expression plasmid encodes MMT linked to an N-terminal His-tag (MGHHHHHHHHHH; SEQ ID NO: 69) and an enterokinase site (SSGHIDDDDKH; SEQ ID NO:70).

result in the expression of three abnormal transcripts (cf. FIG. 12B,C), each containing a premature stop codon.

To confirm that the mutant transcripts encode nonfunctional MMTs, each corresponding open reading frame was amplified and inserted into an *E. coli* expression vector, as described below. It is notable that two of the alternatively spliced transcripts, specifically those giving Product 2 and Product 3 (FIG. 12B), encode identical proteins. Accordingly, only two expression plasmids were sufficient to determine whether abnormally spliced genes of barley Mutant 8063 encode functional MMT enzymes.

Knowing the sequence of the cryptic splice products in Mutant 8063, cf. FIG. 12D, made it possible to amplify the relevant gene parts from expression plasmid pET19b-MMT—the construction of which is detailed in Example 10. Primer set 18, as listed in Table 6, was used to amplify the 3' parts of the genes as SacII-BamHI fragments of Product 2 (SEQ ID NO:27), and Product 3 (SEQ ID NO:28). These were subsequently exchanged with the corresponding fragment of pET19b-MMT (cf. FIG. 13A), resulting in the expression plasmids pET19b-Line8063-Prod2 (FIG. 13B), and pET19b-Line8063-Prod3 (FIG. 13O). Parallel-running reactions utilized primer set 19 (Table 6), to generate expres-

TABLE 5

Primers to amplify the protein coding sequence of the barley gene for MMT.

| Primer set no. | RT-PCR product ends * | Forward primer (5'→3' DNA sequences) ** | Reverse primer (5'→3' DNA sequence) *** |
|---|---|---|---|
| 17 | 1-3267 | <u>CATATG</u>ATGGCTGCGGCGGCGGGGACGTGG (SEQ ID NO: 71) | <u>GAATTC</u>*TAGTTGCTACCATTCACCTTAGCACC* (SEQ ID NO: 72) |

*) Base pair numbering as that of cDNA for MMT (SEQ ID NO: 5), i.e excluding the sequence extensions CAT and AATTC upstream and downstream of the start and stop codon, respectively.
**) Sequence at the 5' end of the fragment noted in the column labeled "RT-PCR product ends", as defined by the primer set. NdeI site underlined; translational start codon in double underline.
***) Complementary sequence at the 3' end of the fragment noted in the column labeled "RT-PCR product ends". EcoRI site underlined; translational stop codon, including part of the EcoRI site, shown in italics.

Example 11

Expression Plasmids Encoding Truncated MMTs of Mutant 8063

The gene encoding MMT of Mutant 8063 was in Example 9 shown to contain a G→A base transition in the 5' splice site of intron 5, thereby activating two cryptic splice sites that sion plasmid pET19b-Line8063-Prod4 (FIG. 13D; with SEQ ID NO:29 listing the sequence of Product 4 for cloning), designed for synthesis of a truncated MMT corresponding to that related to Product 4 (cf. FIG. 12B).

FIG. 13E provides a detailed amino acid sequence comparison of wild-type MMT with the truncated products encoded by Mutant 8063.

TABLE 6

Primers for amplification of DNA fragments of Mutant 8063 (for plasmid constructions).

| Primer set no. | PCR product ends * | End product (SEQ ID NO:) | Primer sequence ** (5'→3' DNA sequence) |
|---|---|---|---|
| 18 | 1-27 | 27 and 28 | Forward: GG<u>CCGCGG</u>GGCTCGAGTGCTTCCGCAC (SEQ ID NO: 73) |
|  | 736-781 |  | Reverse: <u>GGATCC</u>TCAAAGAATTGCTATCTGCATAA-TTTTTGTTTGCCAGAGC (SEQ ID NO: 74) |
| 19 | 1-27 | 29 | Forward: GG<u>CCGCGG</u>GGCTCGAGTGCTTCCGCAC (SEQ ID NO: 75) |
|  | 667-703 |  | Reverse: <u>GGATCC</u><u>TTA</u>GCAGCCTTGTCCTGGCCGGCCTCCCATG (SEQ ID NO: 76) |

*) Numbers refer to nucleotide nos. in the corresponding SEQ ID NO as listed in the neighboring column.
**) Single underlining is used to mark SacII and BamHI sites of the forward and reverse primer, respectively. Double underlines indicate stop codons.

Example 12

Recombinant MMT Forms of Mutant 8063 are Inactive

To verify that MMT deletion forms of Mutant 8063 are enzymatically inactive, *E. coli* cells of strain BL21 were separately transformed with plasmids pET19b, pET19b-MMT, pET19b-Line8063-Prod3, and pET19b-Line8063-Prod4 (cf. FIG. 13), and subsequently propagated over-night in 5-mL standard Luria Broth (LB) medium, containing ampicillin. A 1.25-mL aliquot of each culture was added to 100 mL of fresh LB, and incubated at 37° C. until the cell density reached $OD_{600}$=0.6. At this point, 40 μL of 1 M IPTG was added in order to induce expression of heterologous protein. Following incubation overnight at 20° C., cells of the individual cultures were precipitated by centrifugation for 20 min at 4,000 rpm, 4° C. Each cell pellet was resuspended in 5 mL $H_2O$, then applied to several freeze-thaw cycles, and eventually incubated for 30 min at 37° C. in the presence of ~750 units/L nuclease (Sigma, cat. no. E8263-25KU), to reduce sample viscosity. After a 30-min-long centrifugation at 4,000 rpm, 4° C., to separate cell-soluble proteins (defined as those in the liquid phase) from insoluble proteins (defined as those in the pellet), the pellet was further washed by resuspending it into 2 mL of $H_2O$ containing 1 mg of lysozyme. After a 5-min incubation at ambient temperature, the sample was diluted by addition of 15 mL $H_2O$. Three similar washing-precipitation cycles were carried out before proteins of the inclusion bodies in the pellet were extracted with 1 mL of a 50-mM Tris-Cl buffer, pH 8.0, containing 7 M urea, 2 mM β-mercaptoethanol.

To assay for MMT activity, 50 μL of the samples containing cell-soluble proteins (as defined hereinabove) was transferred to 250 μL of a 25-mM K-phosphate buffer, pH 6.0, containing 0.4 mM AdoMet, 10 mM Met, 1 mM DTT, 0.1 mg/mL BSA. Following incubation for 1 h at 50° C., the samples were filtered, and 10-μL aliquots allowed to react with OPA as detailed in Example 2. Then followed analysis for SMM levels as described in said example, with the results summarized in FIG. 14A. Only the extract from cells transformed with pET19b-MMT gave rise to a chromatogram peak of the same retention time as that of the SMM standard. Accordingly, the absence of similar peaks in the chromatograms from cells transformed with pET19b-Line8063-Prod3 and pET19b-Line8063-Prod4 indicate that Mutant 8063 lacks the capacity to generate active MMT.

A separate experiment aimed at verifying that Mutant 8063 lacks the capacity to generate full-length, active MMT. 5-μL samples of cell-soluble and 10-μL samples of pellet-derived proteins of the above-mentioned *E. coli* extracts were separated by standard electrophoresis, and probed with a rabbit polyclonal anti-MMT antibody directed against a 15-residue-long peptide antigen of barley MMT [cf. FIG. 13E (sequence stretch marked with asterisks); the affinity-purified 12-mL-large preparation of polyclonal anti-MMT antibody was purchased from Invitrogen (Project No. L0402801 K; animal No. C7511), and used in standard western blot analyses at a dilution of 1:1000 (FIG. 14B,C)].

In detail, the aforementioned proteins were loaded onto a 10% SDS-polyacrylamide gel and separated by electrophoresis at 150 V for 75 min, after which the proteins were transferred to a polyvinylidene fluoride membrane (Immobilon-P, Millipore) via an electroblotting apparatus (Trans-Blot SD Semi-Dry Transfer Cell, BioRad) that was run at 2.5 mAmp per $cm^2$ (max. 25 V). Transblots were placed for 1 h at 25° C. in blocking buffer [1× phosphate-buffered saline (PBS), 1% BSA]. The blocking solution was removed and the membrane placed in a solution of the anti-MMT antibody for 1 h. Thereafter, the membrane was rinsed with 1×PBS and incubated for 1 h in a solution of goat anti-rabbit IgG alkaline phosphatase (Sigma). After the aforementioned incubation, the membrane was rinsed in 1×TBS, followed by visualization of protein bands after incubation using nitroblue tetrazolium and 5-bromo-4-chloro-3-indolyl phosphate (Sigma). The gel was finally rinsed in water to stop the phosphatase reaction.

Figure 14:
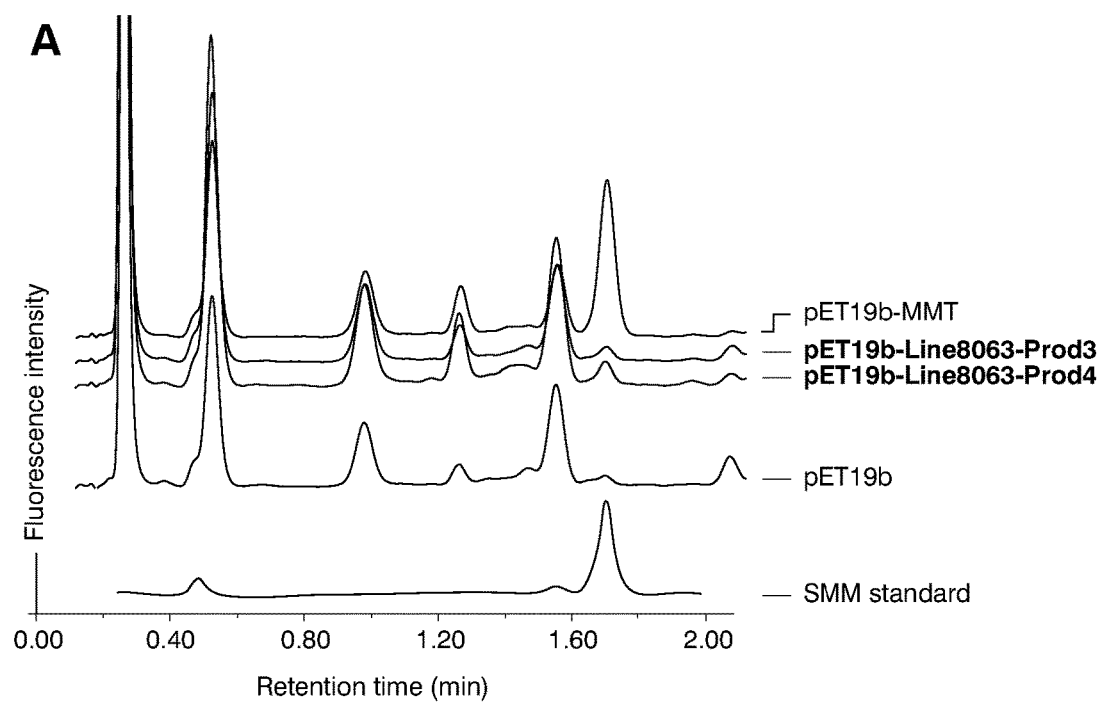
FIG. 14 shows the results of heterologous expression in *E. coli* of wild-type and mutant forms of MMT from cv. Prestige and Mutant 8063, respectively, with experimental details described in Example 12. An extract of *E. coli* cells transformed with vector pET19b, as well as an aliquot of pure SMM, served as experimental control samples. Gel areas between lanes 4 and 5 of both blots, comprising data irrelevant to the instant application, were electronically erased following scanning. (A) HPLC-profiles of pure SMM as well as extracts from *E. coli* cells transformed with the indicated plasmids. For comparative purposes, the profiles are also an integral part of FIG. 18. (B) Western blot results of size-separated proteins from soluble, cellular extracts of *E. coli* cells transformed with plasmids pET-MMT (lane 2), pET19b-Line8063-Prod3 (lane 3), pET19b-Line8063-Prod4 (lane 4), and pET19b (lane 5). Reference proteins, with the indicated masses in kDa, were separated in lane 1. (C) Western blot results of size-separated proteins from extracts of inclusion bodies of *E. coli* cells transformed with the plasmids as noted in legend to figure part B hereinabove. The primary, polyclonal antibodies used in the western analyses were raised against a synthetic 15-residue-long peptide of barley MMT, corresponding to the amino acid stretch marked with asterisks in FIG. 13.
Figure 14:
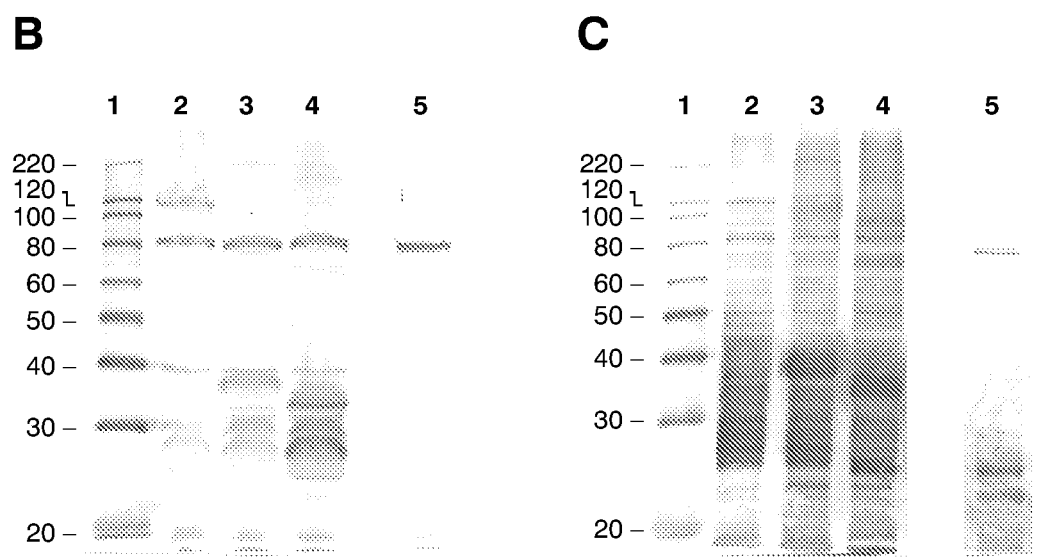

The preparation of anti-MMT antibody, as described hereinabove, was used to probe blots of cell-soluble and pellet-derived proteins of *E. coli* cells transformed with pET19b-MMT (FIG. 14B,C; lanes marked "2"), pET19b-Line8063-Prod3 (FIG. 14B,C; lanes marked "3"), pET19b-Line8063-Prod4 (FIG. 14B,C; lanes marked "4"), and pET19b (FIG. 14B,C; lanes marked "5"). Despite differences in the overall banding patterns of cell-soluble and pellet-derived proteins (with the latter generally appearing as a smear of protein bands that starts at the top of the gel and extends down to the bottom of the gel), full-length MMT was recognized as a protein band co-migrating with the 120-kDa marker protein (lanes marked "1") in extracts of cells transformed with pET19b-MMT. Inactive forms of the MMT protein of cells transformed with pET19b-Line8063-Prod3 and pET19b-Line8063-Prod4 are expected to correspond to the strongly stained bands in the blot region between 30 kDa and 40 kDa. It is notable that the stained, 80-kDa protein band is not MMT-derived as it also appears in extracts of negative control cells transformed with vector pET19b.

Based on the experimental results with heterologous expression of MMT forms, as described hereinabove, and designed to generate recombinant MMT forms of wild-type barley and Mutant 8063, it is concluded that only wild-type MMT, not the MMT forms in said mutant, is active. Accordingly, the capacity to catalyze the conversion of Met to the DMS precursor SMM is restricted to wild-type barley, as opposed to Mutant 8063.

Example 13

Monitoring Systems for Barley Mutant 8063

Figure 15:
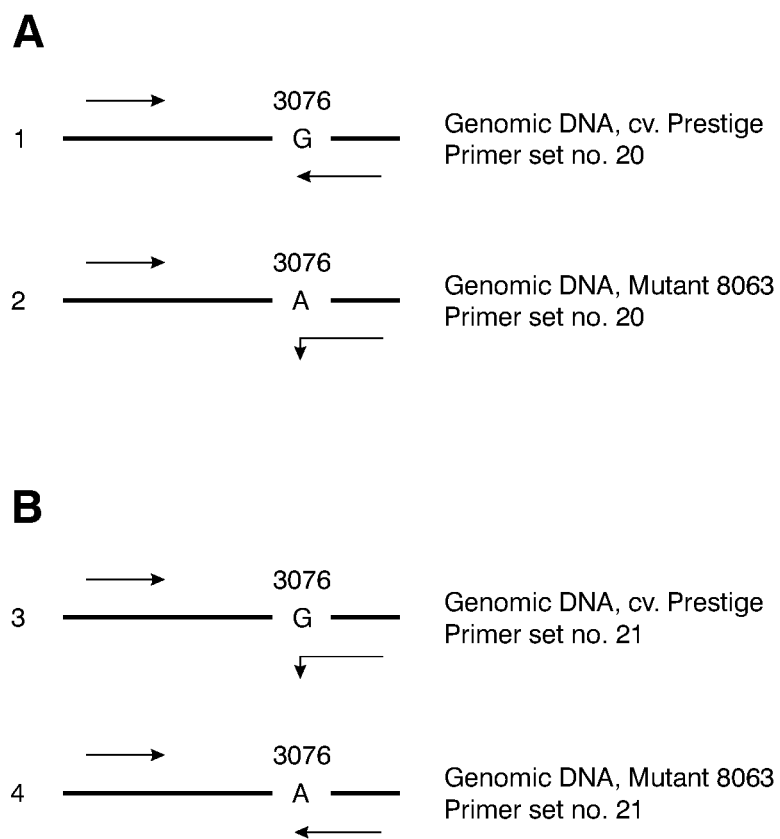
FIG. 15 shows an illustration on approaches to identify grains that are characterized by the G3076→A mutation in the gene for MMT of Mutant 8063. (A) In the hypothetical reaction 1 and reaction 2, primer set 20, cf. Table 7, yields a 271-bp PCR fragment and no fragment, respectively, as schematically shown by an ethidium bromide-stained band following agarose gel electrophoresis of the corresponding reactions (C). In hypothetical reactions 3 and 4 (B), only the latter generates a PCR fragment. Horizontal arrows indicate full sequence match to template DNA, while arrows with a sharp bend indicate a mismatch. (D) Western blot analysis with an anti-MMT antibody recognizes a 120-kDa MMT enzyme in a wild-type kernel of cv. Prestige (lane 2), but not in that of Mutant 8063. Standard proteins were separated in lane 1, with the corresponding masses in kDa indicated.
Figure 15:
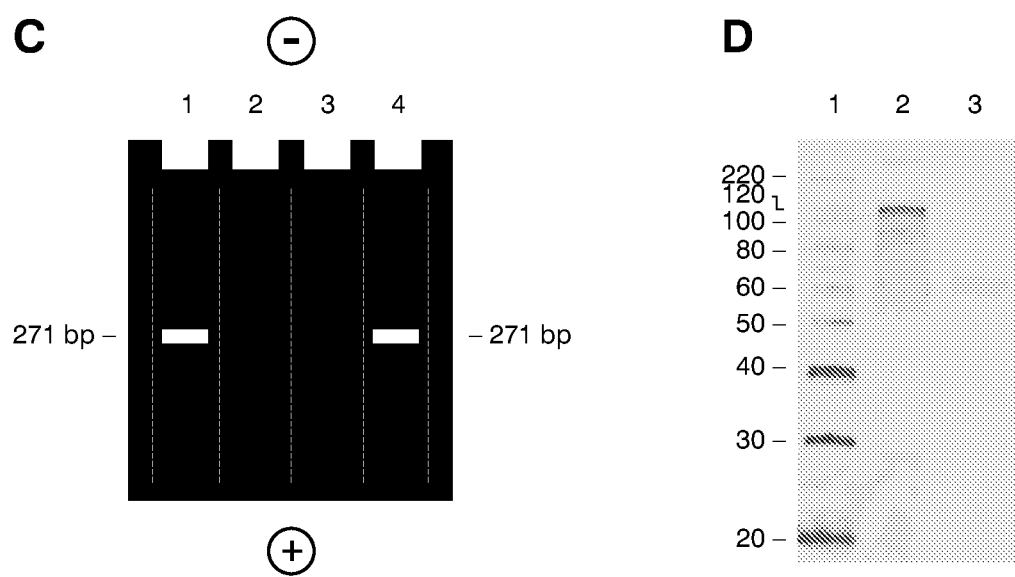

In addition to the biochemical assay for detection of barley kernels of Mutant 8063 (cf. Example 2), the present example describes a genetic method designed to identify mutant kernels or products thereof. With suitable modifications known to the skilled person, the method may also be applied to detect whether a given plant product is prepared using barley Mutant 8063. The assay is based on an analysis to detect single nucleotide polymorphism (SNP), specifically the G→A mutation at position 3076 of the gene for MTT in Mutant 8063, as illustrated in FIG. 15, and with characteristics of oligonucleotide primer sets listed in Table 7.

A PCR product of 271 bp—with the sequence given as SEQ ID NO:33—is generated when primer set no. 20 is applied in a reaction with genomic DNA of barley cv. Prestige as template, while no product is amplified when genomic DNA of Mutant 8063 serves as template—in the latter case simply because of no base pairing between the 3' end of the reverse primer and template (FIG. 19A). However, a 271-bp PCR product is obtained with primer set no. 21 in a PCR amplification with genomic DNA of Mutant 8063 (SEQ ID NO:34; FIG. 19A), as the reverse primer has full sequence match to the template. Primer set no. 22, which consists of the four above-mentioned primers listed for primer set nos. 20 and 21—two for amplification of a fragment containing the G3076→A mutation in the MMT gene of Mutant 8063, and two for the G1462→A mutation in the MMT gene of Mutant 14018 (SEQ ID NO:36, cf.

or lacks this capacity. Further molecular and biochemical tests may be employed to confirm whether a given grain is derived from Mutant 8063.

TABLE 7

Primers for SNP detection of Mutant 8063.

| Primer set no. | PCR product ends | Final product (SEQ ID NO:) | Forward primer (5'→3' DNA sequence given) **** | Reverse primer (5'→3' DNA sequence) ***** |
|---|---|---|---|---|
| 20 | 2831-3101* | 33 | CGATTCCAGCTTCCGGTTG (SEQ ID NO: 77) | CATCTAGTCACTCAAAGAATTGCTAC (SEQ ID NO: 81) |
| 21 | 2831-3101** | 34 | CGATTCCAGCTTCCGGTTG (SEQ ID NO: 78) | CATCTAGTCACTCAAAGAATTGCTAT (SEQ ID NO: 82) |
| 22 | 2831-3101** | 34 | CGATTCCAGCTTCCGGTTG (SEQ ID NO: 79) | CATCTAGTCACTCAAAGAATTGCTAT (SEQ ID NO: 83) |
|  | 1361-1483*** | 36 | GGCATCCAGATTCCATCTTCAG (SEQ ID NO: 80) | CTACGGAACAAGAGGTGCCAAT (SEQ ID NO: 84) |

*) Base pair numbering as that of the genomic wild-type sequence for MMT (SEQ ID NO: 3).
**) Base pair numbering as that of the genomic sequence for MMT of Mutant 8063 (SEQ ID NO: 8).
***) Base pair numbering as that of the genomic sequence for MMT of Mutant 14018 (SEQ ID NO: 19).
****) Sequence at the 5' end of the fragment listed in the column labelled "PCR product ends".
*****) Complementary sequence at the 3' end of the fragment noted in the column labeled "PCR product ends".

Example 17)—is designed to monitor the presence of a mutated gene for MMT that contains both of the aforementioned nucleotide mutations.

Each of the above-mentioned PCR amplifications is experimentally conducted as a 50-μL RedTaq polymerase reaction (Sigma, cat. no. D6063), consisting of 200 ng genomic DNA and 50-100 pmol of each primer of a specific primer set (Table 7). Following amplification in a standard PCR cycler (1 min at 95° C.; then 30 cycles of: 94° C., 60 sec-64° C., 30 sec-72° C., 30 sec; ending with 10 min at 72° C.), a 25-μL aliquot of the sample is applied to standard electrophoresis on a 2% agarose gel. As illustrated in FIG. 15C, PCR with genomic DNA of cv. Prestige in the presence of primer set no. 20 and primer set no. 21 yields a 271-bp DNA fragment and no fragment, respectively. And PCR with genomic DNA of Mutant 8063 the presence of primer set no. 20 and primer set no. 21 yields no fragment and a 271-bp DNA fragment, respectively. In those cases where the latter result is the outcome of a PCR with genomic DNA of a barley grain of unknown identity, there is a high likelihood that the template DNA is identical to that of Mutant 8063. Further efforts to support the conclusion include analyses to test for levels of SMM (cf. Example 2), and for MMT activity (cf. Example 4).

A separate way to verify that Mutant 8063 lacks MMT involves western blot analysis, using the technical procedure and anti-MMT antibody as detailed in Example 3. In practical terms, kernels of cv. Prestige and of Mutant 8063 were germinated at 20° C. for 4 d, followed by separate homogenization of one wild-type and one mutant kernel, each in 250 μL H$_2$O. Following centrifugation at 13,000 rpm for 10 min, 15 μL of each supernatant was mixed with 5 μL SDS loading buffer, boiled for 5 min, loaded onto a 12% SDS-polyacrylamide gel, separated by electrophoresis, electroblotted, and eventually probed with the polyclonal anti-MMT antibody (FIG. 15D). A distinct MMT protein band of 120 kDa was easily recognizable in the extract of cv. Prestige, while no immunoreactive protein of Mutant 8063 co-migrated with the 120-kDa marker protein. Accordingly, the aforementioned western blot analysis method is useful to check whether a germinating barley kernels produces MMT Example 14

The Gene Encoding MMT of Barley Mutant 14018 is Mutated in the 5' Splice Site of Intron 2

Following the discovery of extremely low levels of SMM, or nothing at all, in extracts of germinating kernels of barley Mutant 14018, the plant underwent analyses under the same experimental conditions as those detailed for Mutant 8063 in Example 9 above. However, wild-type plant material was in this case from cv. Sebastian, as it was utilized for mutagenesis with NaN$_3$ in the batch of kernels comprising Mutant 14018. Experiments to identify the mutation, which caused the null-MMT phenotype, were designed and accomplished as described herein below.

First, a comparison was performed of the distinct genomic DNA sequences for the MMT-encoding gene of cv. Sebastian (SEQ ID NO:16 for the genomic DNA sequence; SEQ ID NO:17 for the cDNA sequence; SEQ ID NO:18 for the translated cDNA sequence; in all cases with sequences identical to those of cv. Prestige as described in Example 8 herein) and Mutant 14018 (SEQ ID NO:19 for the genomic sequence, and SEQ ID NOs:20, 21, 23, 25 for cDNA sequences), with focus on the regions spanning the translational start and stop codons. A G→A base transition was identified in the sequenced gene part of Mutant 14018, specifically in a donor splice donor site immediately downstream of exon 2 at the first base of intron 2, more specifically at nucleotide no. 1462—and consequently anticipated to affect the primary RNA processing of the gene transcript (FIG. 16).

Second, using primer set 16 (Table 4), a RT-PCR reaction was designed and set up to amplify the gene region spanning exon 2 and exon 5 of the MMT-encoding gene of cv. Sebastian and Mutant 14018 (FIG. 16A). Following DNA amplification, reaction products were applied to agarose gel electrophoresis, with the result depicted in FIG. 16B. Similar to that described for Mutant 8063 in Example 9, wild-type RNA from cv. Sebastian yielded one PCR fragment, Product 5 in FIG. 16B, that in length and DNA sequence, cf. SEQ ID NO:20, was identical to that spanning bases 246 to 933 of the full-length cDNA for wild-type barley MMT (SEQ ID NO:17). This result emphasizes again that alternative splicing is not a feature of wild-type gene expression.

Third, template RNA purified from Mutant 14018 was utilized in a PCR reaction, which generated three specific fragments—denoted Product 6 (SEQ ID NO:21), Product 7 (SEQ ID NO:23), and Product 8 (SEQ ID NO:25) in FIG. 16B,C—that were different in length and sequence from the amplified product of the wild-type template. This observation suggests that the single mutation in the 5' splice site of intron 2 in the gene for MMT of Mutant 14018 obstructs pre-mRNA processing by elimination of the normal splice site, but instead activates the use of cryptic, additional splice sites. In this respect, for both Product 6 and Product 7, there was identified a cryptic splice site in intron 2, while that of Product 8 was in exon 2. A graphical comparison is provided in FIG. 16C of the aforementioned sequencing results.

In addition, DNA sequence analyses revealed premature translational stop codons in Product 6 [TAG at bases 1579-1581 according to the base numbering of genomic DNA from barley, cv. Sebastian (SEQ ID NO:16)], Product 7 [TAA at bases 1840-1842 according to the base numbering of genomic DNA from barley, cv. Sebastian (SEQ ID NO:16)], and Product 8 [TGA at bases 1916-1918 according to the base numbering of genomic DNA from barley, cv. Sebastian (SEQ ID NO:16)], yielding 186, 180, and 163 amino acid-long translated proteins, listed as SEQ ID NO:22, SEQ ID NO:24, and SEQ ID NO:26, respectively. In parallel with the results described above for Mutant 8063 (FIG. 12D,E), the illustrations in FIG. 16D,E provide specific data on the nature of specific bases involved in the alternative splicing events Example 15

Expression Plasmids for Synthesis of Truncated MMTs of Mutant 14018

The rationale and strategy for construction of expression plasmids that direct synthesis of three truncated, recombinant versions of MMT derived from Mutant 14018 were like those described in Example 11 for Mutant 8063. In short, the experimental aim was to verify that the aberrant splicing events of Mutant 14086 generate transcripts encoding inactive MMTs. Recombinant gene stretches should accordingly encode proteins whose sequences—listed in SEQ ID NO:22, SEQ ID NO:24, and SEQ ID NO:26—reflect the aberrant splicing events leading to Product 6, Product 7, and Product 8 (cf. FIG. 16B,C).

Using plasmid pET19b-MMT, cf. Example 10, as template in three standard, consecutive PCRs with primer set nos. 23, 24, and 25 (Table 8), resulted in a 394-bp amplified fragment (SEQ ID NO:30). This was digested with SacII-BamHI and ligated with the large SacII-BamHI fragment of pET19b-MMT (FIG. 17A), giving expression plasmid pET19b-Line14086-Prod6 (FIG. 17B), designed for synthesis of a truncated MMT corresponding to Product 6 as depicted in FIG. 16B.

Figure 17:
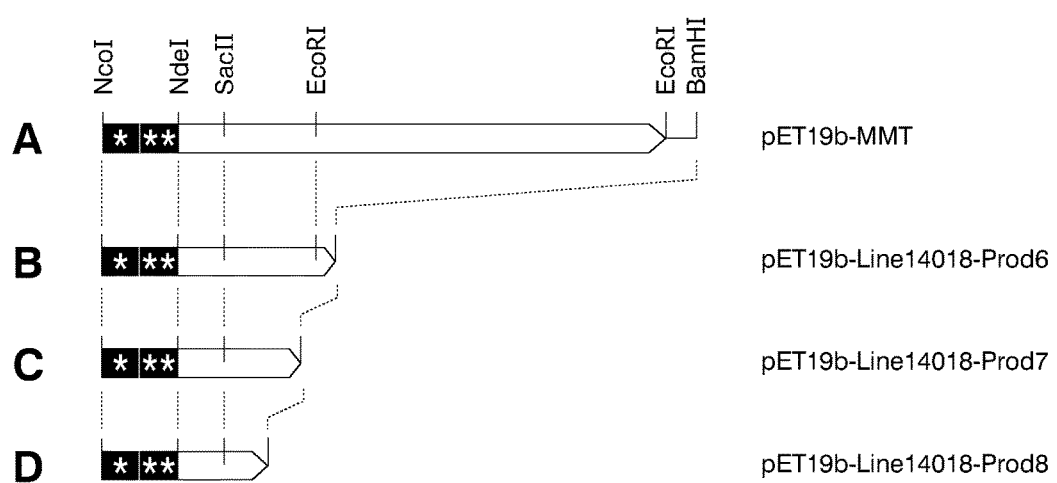
FIG. 17 shows expression plasmids for heterologous expression of aberrant MMTs of Mutant 14018, and alignment of encoded proteins. (A) Illustration of the NcoI-BamHI fragment of pET19b-MMT—including selected restriction sites—encoding wild-type MMT fused to a sequence specifying a His-tag (*; sequence MGHHHHHH-HHHH; SEQ ID NO:69) in frame with an enterokinase site (**; sequence SSGHIDDDDKH; SEQ ID NO:70). Deletion constructs are shown in (B), (C), and (D). (E) Alignment of the encoded MMT sequences (SEQ ID NOs: 18, 22, 24, 26 for constructs shown in A, B, C, and D, respectively). The sequence spanning residue number 213 to 1084 is not shown for the wild-type enzyme (SEQ ID NO:18).

Utilizing the same procedure as described hereinabove for the 394-bp fragment, but now with primer set nos. 23, 24, and 26 in three consecutive PCR amplifications (Table 8), a 376-bp fragment was generated (SEQ ID NO:31), which upon digestion with SacII-BamHI was ligated with the large SacII-BamHI fragment of pET19b-MMT (FIG. 17A), giving expression plasmid pET19b-Line14086-Prod7 (FIG. 17C). This expression plasmid is designed for synthesis of a truncated MMT corresponding to that giving Product 7 as depicted in FIG. 16B.

In a parallel running experiment—conducted in a similar way as that described above for pET19b-MMT, but with primer set nos. 27 and 28 (Table 8)—there was amplified a 325-bp fragment (SEQ ID NO:32), which upon digestion with SacII-BamHI was ligated with the large SacII-BamHI fragment of pET19b-MMT (FIG. 17A), giving expression plasmid pET19b-Line14086-Prod8 (FIG. 17D) for synthesis of a truncated MMT corresponding to Product 8 (cf. FIG. 16B).

TABLE 8

Primers for amplification of DNA fragments of Mutant 14018 (for plasmid constructions).

| Primer set no. | Primer sequence (5'→3' DNA sequence) * | | PCR product ends ** | Final product (SEQ ID NO:) |
|---|---|---|---|---|
| 23 | Forward: | GGCCGCGGGGCTCGAGTGCTTCCGCAC (SEQ ID NO: 85) | 1-27 | 30 |
|  | Reverse: | CGAGATAAGATAAATATCTACGG-AACAAGAGGTGCCAATCTTCGAAGGGCACCACTTTTCTGC (SEQ ID NO: 86) | 245-307 |  |
| 24 | Forward: | GGCCGCGGGGCTCGAGTGCTTCCGCAC (SEQ ID NO: 87) | 1-27 | 30 |
|  | Reverse: | AACCTGAGTAAATGTCTAACTTCTGCAGGTCCCATG-TTTGCAACAAACGAGATAAGATAAATATCTACGG (SEQ ID NO: 88) | 285-354 |  |
| 25 | Forward: | GGCCGCGGGGCTCGAGTGCTTCCGCAC (SEQ ID NO: 89) | 1-27 | 30 |
|  | Reverse: | GGATCCCTACTGGCAGACACCTAAAAGTTTCATATAAAGT-AACCTGAGTAAATGTCTAACTTCTGC (SEQ ID NO: 90) | 329-394 |  |

TABLE 8-continued

Primers for amplification of DNA fragments of Mutant 14018
(for plasmid constructions).

| Primer set no. | Primer sequence (5'→3' DNA sequence) * | PCR product ends ** | Final product (SEQ ID NO:) |
|---|---|---|---|
| 26 | Forward: GGCCGCGGGGCTCGAGTGCTTCCGCAC (SEQ ID NO: 91) | 1-27 | 31 |
|  | Reverse: GGATCCTTATATCCAGACCATAA-ACCTGAG-TAAATGTCTAACTTCTGC (SEQ ID NO: 92) | 329-376 |  |
| 27 | Forward: GGCCGCGGGGCTCGAGTGCTTCCGCAC (SEQ ID NO: 93) | 1-27 | 32 |
|  | Reverse: AGGTTTATCCATGCAATCTTGATAGCTCTTG-GGTTTATATCCAGACCATAAACCATTGCC-ACATCCCAGCTCTGCTACTG (SEQ ID NO: 94) | 198-277 |  |
| 28 | Forward: GGCCGCGGGGCTCGAGTGCTTCCGCAC (SEQ ID NO: 95) | 1-27 | 32 |
|  | Reverse: GGATCCTTATAGATTGGGAGACCA-TCGTCGTCTAGTGCATTCAAGTAA-AGGTTTATCCATGCAATCTTGATAGCTCTTGG (SEQ ID NO: 96) | 246-325 |  |

*) Note
that the same forward primer, with a SacII site underlined, is utilized in all reactions. For reverse primers, 5' extensions without annealing to template DNA are indicated with a wavy underline; BamHI sites are shown in italics, and complementary translational stop codons in bold type letters.
**) Numbers refer to nucleotide nos. in the corresponding SEQ ID NO listed in the neighboring column.

Example 16

Recombinant MMT Forms of Mutant 14018 are Inactive

The procedure of Example 12 was followed, Mutant 8063-derived constructs being replaced by those of Mutant 14018. E. coli bacteria were transformed with pET19b-Line14018-Prod6, pET19b-Line14018-Prod7 and pET19b-Line14018-Prod8 (FIG. 17A-D, with the corresponding amino acid alignment shown in FIG. 17E)—but the experiments excluded western blot analyses as the anti-MMT antibody described in Example 12 was raised against a sequence stretch absent in the Mutant 14018-specific part of MMT.

Figure 18:
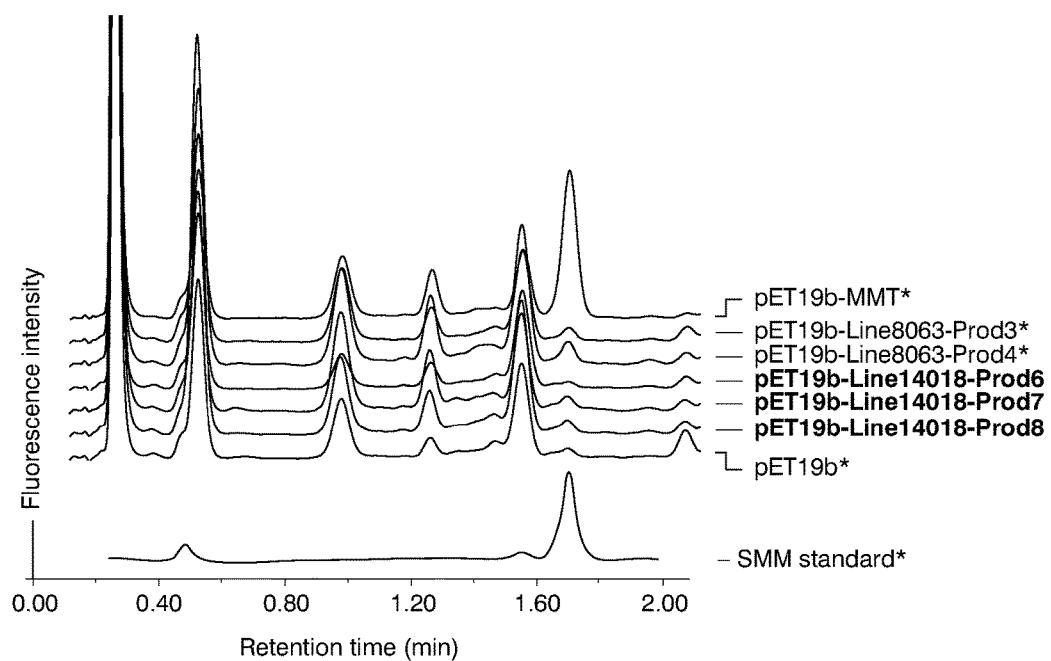
FIG. 18 shows HPLC-based experimental results of heterologous expression in *E. coli* of wild-type and mutant forms of MMT from cv. Prestige and Mutant 14018, respectively, with experimental details described in Example 15. Pure SMM and extract of *E. coli* cells transformed with vector pET19b served as experimental control samples. For comparative purposes, chromatograms marked with asterisks are also integral parts of FIG. 14A.

None of the extracts of the transformed bacteria revealed capacity to generate SMM (FIG. 18), so the same argumentation as that provided in Example 12 above provides basis for the conclusion that barley Mutant 14018 generates non-functional MMT enzymes, which lack the catalytic capability to form SMM, the DMS precursor.

Example 17

Monitoring Systems for Barley Mutant 14018

Figure 19:
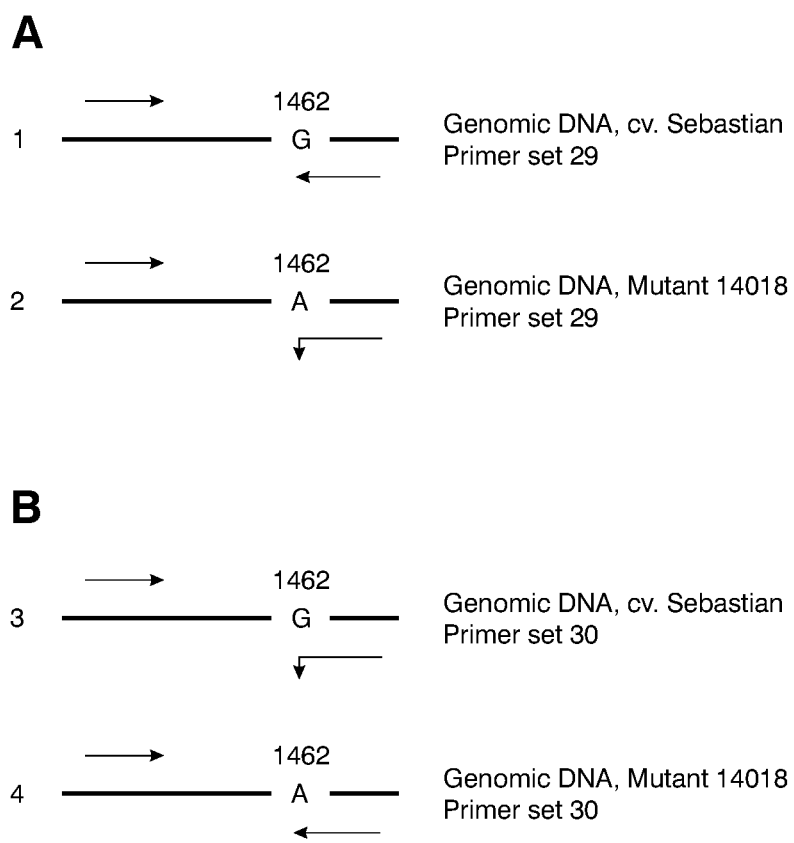
FIG. 19 shows an illustration on a genetic approach to identify grains characterized by the G1462→A mutation in the gene for MMT of Mutant 14018. (A) In the hypothetical reaction 1 and reaction 2, primer set 29, cf. Table 9, yields a 121-bp PCR fragment and no fragment, respectively, as schematically shown by an ethidium bromide-stained band following agarose gel electrophoresis of the corresponding reactions (C). In hypothetical reactions 3 and 4 (B), only the latter generates a PCR fragment (123 bp). Horizontal arrows indicate full sequence match to template DNA, while arrows with a sharp bend indicate a mismatch. (D) Western blot analysis with an anti-MMT antibody recognizes a 120-kDa MMT enzyme in a wild-type kernel of cv. Sebastian (lane 2), but not in that of Mutant 14018. Standard proteins were separated in lane 1, with the corresponding masses in kDa indicated.
Figure 19:
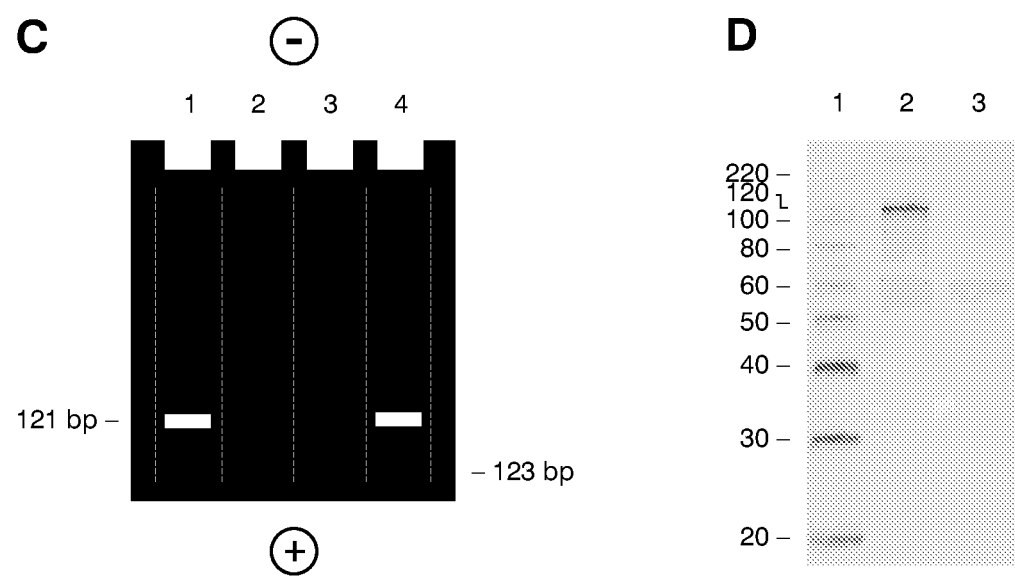

In addition to the biochemical assay for detection of barley kernels of Mutant 14018 (cf. Example 2), the present example describes a genetic method that has been designed to identify mutant kernels or plant products prepared from barley Mutant 14018. It is based on an analysis to detect single nucleotide polymorphism (SNP), specifically the G→A mutation at position 1462 of the gene for MTT in Mutant 14018, as illustrated in FIG. 19, and with characteristics of oligonucleotide primer sets listed in Table 9.

A PCR product of 121 bp—with the sequence given as SEQ ID NO:35—is generated when primer set no. 29 is used in a reaction with genomic DNA of barley cv. Sebastian as template, while no product is amplified when genomic DNA of Mutant 14018 serves as template—in the latter case simply because of no base pairing between the 3' end of the reverse primer and template (FIG. 19B). However, a 121-bp PCR product is obtained with primer set no. 30 in a PCR amplification with genomic DNA of Mutant 14018 (SEQ ID NO:36), as the reverse primer has full sequence match to the template (FIG. 19B). Primer set no. 31, which consists of the four above-mentioned primers listed for primer set nos. 29 and 30—two for amplification of a fragment containing the G1462→A mutation in the MMT gene of Mutant 14018 (i.e. SEQ ID NO:36), and two for the G3076→A mutation in the MMT gene of Mutant 8063 (i.e. SEQ ID NO:34; cf. Example 9)—is designed to monitor the presence of a mutated gene for MMT that contains both of the aforementioned nucleotide mutations.

Each of the above-mentioned PCR amplifications is experimentally conducted as a 50-μl RedTaq polymerase reaction (Sigma, cat. no. D6063), consisting of 200 ng genomic DNA and 50-100 pmol of each primer of a specific primer set (Table 7). Following amplification in a standard PCR cycler (1 min at 95° C.; then 30 cycles of: 94° C., 60 sec-64° C., 30 sec-72° C., 30 sec; ending with 10 min at 72° C.), a 25-μl aliquot of the sample is applied to standard electrophoresis on a 2% agarose gel. As illustrated in FIG. 19C, PCR with genomic DNA of cv. Sebastian in the presence of primer set no. 29 and primer set no. 30 yields a 121-bp DNA fragment and no fragment, respectively. And PCR with genomic DNA of Mutant 14018 in the presence of primer set no. 29 and primer set no. 30 yields no fragment and a 123-bp DNA fragment, respectively. In those cases where the latter result is the outcome of a PCR with genomic DNA of a barley grain of unknown identity, there is a high likelihood that the template DNA is identical to that of Mutant 14018. Further efforts to support the conclusion include analyses to test for levels of SMM (cf. Example 2), and for MMT activity (cf. Example 4).

A separate way to verify that Mutant 14018 lacks MMT involves western blot analysis, using the technical procedure and anti-MMT antibody as detailed in Example 3. In practical terms, kernels of cv. Sebastian and of Mutant 14018 were germinated at 20° C. for 4 d, followed by separate homogenization of one wild-type and one mutant kernel, each in 100 μL $H_2O$. Following centrifugation at 13,000 rpm for 10 min, 15 μL of each supernatant was mixed with 5 μL SDS loading buffer, boiled for 5 min, loaded onto a 12% SDS-polyacrylamide gel, separated by electrophoresis, electroblotted, and eventually probed with the polyclonal anti-MMT antibody (FIG. 15D). A distinct MMT protein band of 120 kDa was easily recognizable in the extract of cv. Sebastian, while no immunoreactive protein of Mutant 14018 co-migrated with the 120-kDa marker protein. Accordingly, the aforementioned western blot analysis method is useful to check whether a germinating barley kernels produces MMT or lacks this capacity. Further molecular and biochemical tests may be employed to confirm whether a given grain is derived from Mutant 14018.

American Society of Brewing Chemists, "Methods of analysis of the American Society of Brewing Chemists." ISBN 1-881696-01-4 (1992).

Bourgis, F. et al., "S-Methylmethionine plays a major role in phloem sulfur transport and is synthesized by a novel type of methyltransferase." Plant Cell 11:1485-1497, 1999.

Briggs, D. E. et al., "Malting and brewing science. Volume I Malt and sweet wort." Chapman and Hall, New York, USA. ISBN 0412165805, 1981.

Dufour, J. P., "Direct assay of S-methylmethionine using high-performance liquid chromatography and fluorescence techniques." J. Am. Soc. Brew. Chem. 44:1-6, 1986.

Durai, S. et al., "Zinc finger nucleases: custom-designed molecular scissors for genome engineering of plant and mammalian cells." Nucleic Acids Res. 33:5978-5990, 2005.

European Brewery Convention, "Analytica—EBC." ISBN 3-418-00759-7 (1998).

Hansen, M. et al., "Antisense-mediated suppression of C-hordein biosynthesis in the barley grain results in correlated changes in the transcriptome, protein profile, and amino acid composition." J. Exp. Bot. 58:3987-3995, 2007.

Hough, J. S. et al. "Malting and brewing science. Volume II Hopped wort and beer." Chapman and Hall, New York, USA. ISBN 0412165902, 1982.

TABLE 9

Primers for SNP detection of Mutant 14018.

| Primer set no. | PCR product ends | Final product (SEQ ID NO:) | Forward primer (5'→3' DNA sequence given) **** | Reverse primer (5'→3' DNA sequence) ***** |
|---|---|---|---|---|
| 29 | 1361-14818 * | 35 | GGCATCCAGATTCCATCTTCAG (SEQ ID NO: 97) | CTACGGAACAAGAGGTGCCAAC (SEQ ID NO: 101) |
| 30 | 1361-1483 ** | 36 | GGCATCCAGATTCCATCTTCAG (SEQ ID NO: 98) | CTACGGAACAAGAGGTGCCAAT (SEQ ID NO: 102) |
| 31 | 1361-1483 ** | 36 | GGCATCCAGATTCCATCTTCAG (SEQ ID NO: 99) | CTACGGAACAAGAGGTGCCAAT (SEQ ID NO: 103) |
|  | 2831-3101 *** | 34 | CGATTCCAGCTTCCGGTTG (SEQ ID NO: 100) | CATCTAGTCACTCAAAGAATTGCTAT (SEQ ID NO: 104) |

*) Base pair number ng as that of the genomic wild-type sequence for MMT (SEQ ID NO: 16).
**) Base pair number ng as that of the genomic sequence for MMT of Mutant 14018 (SEQ ID NO: 19).
***) Base pair numbering as that of the genomic sequence for MMT of Mutant 8063 (SEQ ID NO: 8).
****) Sequence at the 5' end of the fragment listed in the column labelled "PCR product ends".
*****) Complementary sequence at the 3' end of the fragment noted in the column labeled "PCR product ends".

REFERENCES CITED

Patent Documents

U.S. Pat. No. 4,683,195 to Mullis, K. B. et al.
U.S. Pat. No. 4,800,159 to Mullis, K. B. et al.
U.S. Pat. No. 5,242,694 to Reuther, H.
U.S. Pat. No. 6,660,915 to Douma, A. C. et al.
U.S. Pat. No. 7,420,105 to Breddam, K. et al.
U.S: Pat. Application Publication No. 2006/0057684 to Bisgaard-Frantzen, H. et al. AU Pat. No. 38578/93
PCT patent application WO 2005/087934 to Breddam, K. et al.

Other Publications

American Association of Cereal Chemists, "Approved methods of the American Association of Cereal Chemists." ISBN 0-913250-86-4 (1995).

Hysert, D. W. et al., "The origin and control of dimethyl sulfide and its precursor in malt." Tech. Q. MBAA 17:34-43, 1980.

Iida, S. and Terada, R., "Modification of endogenous natural genes by gene targeting in rice and other higher plants." Plant Mol. Biol. 59:205-219, 2005.

Imashuku, H., "Two new technologies for efficient and flexible wort boiling: 1. Rest before wort boiling to convert SMM to DMS; 2. Hop boiling separately from wort." 3rd World Brewing Congress, Presentation O-52, Program Book, p. 91 and attached presentation slides, 2008.

Institute of Brewing, "Institute of Brewing. Methods of analysis." ISBN 0-900489-10-3, 1997.

Kleinhofs, A. et al., "Induction and selection of specific gene mutations in Hordeum and Pisum." Mutat. Res. 51:29-35, 1978.

Ko, S. et al., "S-Methylmethionine is both a substrate and an inactivator of 1-aminocyclopropane-1-carboxylate synthase." Arch. Biochem. Biophys. 421:85-90, 2004.

Kocsic, M. G. et al., "Insertional inactivation of the methionine S-methyltransferase gene eliminates the S-methylmethionine cycle and increases the methylation ratio." Plant Physiol. 131:1808-1815, 2003.

Kumar, S. et al., "Gene targeting in plants: fingers on the move." Trends Plant Sci. 11:159-161, 2006.

Lal, S. et al., "A splice site mutant of maize activates cryptic splice sites, elicits intron inclusion and exon exclusion, and permits branch point elucidation." Plant Physiol. 121:411-418, 1999.

Maquat, L. E. and Carmichael, G. G., "Quality control of mRNA function." Cell 104:173-176, 2001.

McElroy, D. and Jacobsen, J., "What's brewing in barley biotechnology?" Bio/Technology 13:245-249, 1995.

Meilgaard, M. C., "Prediction of flavour differences between beers from their chemical composition." J. Agric. Food Chem. 30:1009-1017, 1982.

Mendell, J. T. and Dietz, H. C., "When the message goes awry: Disease-producing mutations that influence mRNA content and performance." Cell 107:411-414, 2002.

Mudd, S. H. and Datko, A. H., "The S-methylmethionine cycle in Lemna paucicostata." Plant Physiol. 93:623-630, 1990.

Nevo, E. "Origin, evolution, population genetics and resources for breeding of wild barley, Hordeum spontaneum, in the Fertile Crescent." In Shewry, P. R. (ed.): "Barley: Genetics, Biochemistry, Molecular Biology and Biotechnology," pp. 19-43. CAB International, Wallingford, UK. ISBN 0-85198-725-7, 1992. 1992.

Pimenta, M. J. et al., "Determination of S-adenosyl-L-methionine:L-methionine S-methyltransferase activity by selective adsorption of [methyl-$^3$H]S-adenosylmethionine onto activated charcoal." Anal. Biochem. 225:167-169, 1995.

Phenomenex, "HPLC application." ID No.: 15992, 2006.

Ranocha, P. et al., "The S-methylmethionine cycle in angiosperms: ubiquity, antiquity and activity." Plant J. 25:575-584, 2001.

Rasmussen, S. K. and Hatzack, F., "Identification of two low-phytate barley (Hordeum vulgare L.) grain mutants by TLC and genetic analysis." Hereditas 129:107-112, 1998.

Robbins M. P. et al., "Gene manipulation of condensed tannins in higher plants." Plant Physiol. 116:1133-1144, 1998.

Sambrook, J. and Russell, D. W., "Molecular cloning. A laboratory manual, 3rd Ed.", Cold Spring Harbor Laboratory Press, Cold Spring Harbor, N.Y., U.S.A. ISBN 0-87969-577-3, 2001.

Scheuren, H. and Sommer, K., "Vaporescence versus boiling—Expulsion of aromatic compounds during the whole wort production." 3rd World Brewing Congress, Presentation O-55, Program Book, p. 92 and attached presentation slides, 2008.

Sinibaldi, R. M. and Mettler I. J., "Intron splicing and intron-mediated enhanced expression in monocots." Prog. Nucleic Acid Res. Mol. Biol. 42:229-257, 1992.

Stahl, Y. et al., "Antisense downregulation of the barley limit dextrinase inhibitor modulates starch granule sizes distribution, starch composition and amylopectin structure". Plant J. 39:599-611, 2004.

Tagmount, A. et al., "An essential role of S-adenosyl-L-methionine:L-methionine S-methyltransferase in selenium volatilization by plants. Methylation of selenomethionine to selenium-methyl-L-selenium-methionine, the precursor of volatile selenium." Plant Phys. 130:847-856, 2002.

Thanbichler, M. et al., "S-Methylmethionine metabolism in Escherichia coli." J. Bacteriol. 181:662-665, 1998.

Tzfira, T. and White, C., "Towards targeted mutagenesis and gene replacement in plants." Trends Biotechnol. 23:567-569, 2005.

von Bothmer, R. "The wild species of Hordeum: Relationships and potential use for Improvement of cultivated barley." In Shewry, P. R. (ed.): "Barley: Genetics, Biochemistry, Molecular Biology and Biotechnology," pp. 3-18. CAB International, Wallingford, UK. ISBN 0-85198-725-7, 1992.

Wu, J. et al., "Nonsense-mediated mRNA decay (NMD) silences the accumulation of aberrant trypsin proteinase inhibitor mRNA in Nicotiana attenuata." Plant J. 51:693-706, 2007.

TABLE 10

Sequence listing.

| SEQ ID | Type | Description |
| --- | --- | --- |
| NO: 1 | Nucleic acid | Barley cDNA of cv. Haruna Nijo, spanning the start and stop codons of the gene for MMT. cDNA, open reading frame for MMT. Sequence extracted from GenBank accession no. AB028870 |
| NO: 2 | Protein | Sequence for barley MMT of cv. Haruna Nijo, translated from SEQ ID NO: 1. |
| NO: 3 | Nucleic acid | Barley gDNA of cv. Prestige, genomic sequence spanning the start and stop codons of the gene for MMT. |
| NO: 4 | Nucleic acid | Barley cDNA of cv. Prestige, spanning the start and stop codons of the gene for MMT, cDNA sequence of the open reading frame for MMT. |
| NO: 5 | Nucleic acid | Re-cloned barley cDNA of cv. Prestige; recloned cDNA of the open reading frame for MMT spanning the start and stop codons of the gene for MMT, but containing three mutations (cf. Example 10). Utilized for heterologous expression of barley MMT in E. coli. |
| NO: 6 | Protein | Sequence for barley MMT of cv. Prestige, translated from SEQ ID NO: 4. |
| NO: 7 | Protein | Sequence for MMT of barley, cv. Prestige, translated from SEQ ID NO: 5, utilized for synthesis of MMT in E. coli. |
| NO: 8 | Nucleic acid | Barley gDNA of Mutant 8063, Genomic sequence for MMT spanning the start and stop codons of the gene for MMT. |

TABLE 10-continued

Sequence listing.

| SEQ ID | Type | Description |
|---|---|---|
| NO: 9 | Nucleic acid | Sequence of amplified RT-PCR fragment of barley cv. Prestige, corresponding to Product 1 in FIG. 12B, C. |
| NO: 10 | Nucleic acid | Sequence of amplified RT-PCR fragment of barley Mutant 8063, corresponding to Product 2 in FIG. 12B, C. |
| NO: 11 | Protein | Entire translated sequence derived from mis-spliced RNA of Mutant 8063, said RNA functioning as template in the RT-PCR amplification yielding Product 2 in FIG. 12B, C. |
| NO: 12 | Nucleic acid | Sequence of amplified RT-PCR fragment of barley Mutant 8063, corresponding to Product 3 in FIG. 12B, C. |
| NO: 13 | Protein | Entire translated sequence derived from mis-spliced RNA of barley Mutant 8063, said RNA functioning as template in the RT-PCR amplification yielding Product 3 in FIG. 12B, C. |
| NO: 14 | Nucleic acid | Sequence of amplified RT-PCR fragment of barley Mutant 8063, corresponding to Product 4 in FIG. 12B, C. |
| NO: 15 | Protein | Entire translated sequence derived from mis-spliced RNA of Mutant 8063, said RNA functioning as template in the RT-PCR amplification yielding Product 4 in FIG. 12B, C. |
| NO: 16 | Nucleic acid | Barley gDNA of cv. Sebastian, Genomic sequence for MMT spanning the start and stop codons of the gene for MMT. |
| NO: 17 | Nucleic acid | Barley cDNA of cv. Sebastian, cDNA sequence of the open reading frame for MMT spanning the start and stop codons of the gene for MMT. |
| NO: 18 | Protein | Sequence for barley MMT of cv. Sebastian, translated from SEQ ID NO: 17. |
| NO: 19 | Nucleic acid | Barley gDNA of Mutant 14018, Genomic sequence for MMT spanning the start and stop codons of the gene for MMT. |
| NO: 20 | Nucleic acid | Sequence of amplified RT-PCR fragment of barley cv. Sebastian, corresponding to Product 5 in FIG. 16B, C. |
| NO: 21 | Nucleic acid | Sequence of amplified RT-PCR fragment of barley Mutant 14018, corresponding to Product 6 in FIG. 16B, C. |
| NO: 22 | Protein | Entire translated sequence derived from mis-spliced RNA of Mutant 14018, said RNA functioning as template in the RT-PCR amplification yielding Product 6 in FIG. 16B, C. |
| NO: 23 | Nucleic acid | Sequence of amplified RT-PCR fragment of barley Mutant 14018, corresponding to Product 7 in FIG. 16B, C. |
| NO: 24 | Protein | Entire translated sequence derived from mis-spliced RNA of barley Mutant 14018, said RNA functioning as template in the RT-PCR amplification yielding Product 7 in FIG. 16B, C. |
| NO: 25 | Nucleic acid | Sequence of amplified RT-PCR fragment of barley Mutant 14018, corresponding to Product 8 in FIG. 16B, C. |
| NO: 26 | Protein | Entire translated sequence derived from mis-spliced RNA of barley Mutant 14018, said RNA functioning as template in the RT-PCR amplification yielding Product 8 in FIG. 16B, C. |
| NO: 27 | Nucleic acid | SacII-BamHI fragment of Product 2 (FIG. 12B, C)-with a BamHI site introduced directly downstream of the translational stop codon-for construction of expression plasmid pET19b-Line8063-Prod2 (cf. FIG. 13B). |
| NO: 28 | Nucelic acid | SacII-BamHI fragment of Product 3 (FIG. 12B, C)-with a BamHI site introduced directly downstream of the translational stop codon-for construction of expression plasmid pET19b-Line8063-Prod3 (cf. FIG. 13C) (identical to SEQ ID NO: 27). |
| NO: 29 | Nucleic acid | SacII-BamHI fragment of Product 4 (FIG. 12B, C)-with a BamHI site introduced directly downstream of the translational stop codon-for construction of expression plasmid pET19b-Line8063-Prod4 (cf. FIG. 13D). |
| NO: 30 | Nucleic acid | SacII-BamHI fragment of Product 6 (FIG. 16B, C)-with a BamHI site introduced directly downstream of the translational stop codon-for construction of expression plasmid pET19b-Line14018-Prod6 (cf. FIG. 17B). |
| NO: 31 | Nucleic acid | SacII-BamHI fragment of Product 7 (FIG. 16B, C)-with a BamHI site introduced directly downstream of the translational stop codon-for construction of expression plasmid pET19b-Line14018-Prod7 (cf. FIG. 17C). |
| NO: 32 | Nucleic acid | SacII-BamHI fragment of Product 8 (FIG. 16B, C)-with a BamHI site introduced directly downstream of the translational stop codon-for construction of expression plasmid pET19b-Line14018-Prod8 (cf. FIG. 17D). |

TABLE 10-continued

Sequence listing.

| SEQ ID | Type | Description |
|---|---|---|
| NO: 33 | Nucleic acid | PCR fragment generated from genomic DNA of cv. Prestige, amplified using primer set no. 20 (cf. Table 7). |
| NO: 34 | Nucleic acid | PCR fragment generated from genomic DNA of Mutant 8063, amplified using primer set no. 21 (cf. Table 7). |
| NO: 35 | Nucleic acid | PCR fragment generated from genomic DNA of cv. Sebastian, amplified using primer set no. 29 (cf. Table 9). |
| NO: 36 | Nucleic acid | PCR fragment generated from genomic DNA of Mutant 14018, amplified using primer set no. 30 (cf. Table 9). |
| NO: 37 | Nucleic acid | Forward primer for amplification of the genomic sequence encoding barley MMT. |
| NO: 38 | Nucleic acid | Forward primer for amplification of the genomic sequence encoding barley MMT. |
| NO: 39 | Nucleic acid | Forward primer for amplification of the genomic sequence encoding barley MMT. |
| NO: 40 | Nucleic acid | Forward primer for amplification of the genomic sequence encoding barley MMT. |
| NO: 41 | Nucleic acid | Forward primer for amplification of the genomic sequence encoding barley MMT. |
| NO: 42 | Nucleic acid | Forward primer for amplification of the genomic sequence encoding barley MMT. |
| NO: 43 | Nucleic acid | Reverse primer for amplification of the genomic sequence encoding barley MMT. |
| NO: 44 | Nucleic acid | Reverse primer for amplification of the genomic sequence encoding barley MMT. |
| NO: 45 | Nucleic acid | Reverse primer for amplification of the genomic sequence encoding barley MMT. |
| NO: 46 | Nucleic acid | Reverse primer for amplification of the genomic sequence encoding barley MMT. |
| NO: 47 | Nucleic acid | Reverse primer for amplification of the genomic sequence encoding barley MMT. |
| NO: 48 | Nucleic acid | Reverse primer for amplification of the genomic sequence encoding barley MMT. |
| NO: 49 | Nucleic acid | Forward primer for amplification of the cDNA sequence encoding barley MMT |
| NO: 50 | Nucleic acid | Forward primer for amplification of the cDNA sequence encoding barley MMT |
| NO: 51 | Nucleic acid | Forward primer for amplification of the cDNA sequence encoding barley MMT |
| NO: 52 | Nucleic acid | Forward primer for amplification of the cDNA sequence encoding barley MMT |
| NO: 53 | Nucleic acid | Forward primer for amplification of the cDNA sequence encoding barley MMT |
| NO: 54 | Nucleic acid | Forward primer for amplification of the cDNA sequence encoding barley MMT |
| NO: 55 | Nucleic acid | Forward primer for amplification of the cDNA sequence encoding barley MMT |
| NO: 56 | Nucleic acid | Forward primer for amplification of the cDNA sequence encoding barley MMT |
| NO: 57 | Nucleic acid | Reverse primer for amplification of the cDNA sequence encoding barley MMT |
| NO: 58 | Nucleic acid | Reverse primer for amplification of the cDNA sequence encoding barley MMT |
| NO: 59 | Nucleic acid | Reverse primer for amplification of the cDNA sequence encoding barley MMT |
| NO: 60 | Nucleic acid | Reverse primer for amplification of the cDNA sequence encoding barley MMT |
| NO: 61 | Nucleic acid | Reverse primer for amplification of the cDNA sequence encoding barley MMT |
| NO: 62 | Nucleic acid | Reverse primer for amplification of the cDNA sequence encoding barley MMT |
| NO: 63 | Nucleic acid | Reverse primer for amplification of the cDNA sequence encoding barley MMT |
| NO: 64 | Nucleic acid | Reverse primer for amplification of the cDNA sequence encoding barley MMT |
| NO: 65 | Nucleic acid | Forward primer to detect alternative splicing of the gene encoding barley MMT. |
| NO: 66 | Nucleic acid | Forward primer to detect alternative splicing of the gene encoding barley MMT. |
| NO: 67 | Nucleic acid | Reverse primer to detect alternative splicing of the gene encoding barley MMT. |
| NO: 68 | Nucleic acid | Reverse primer to detect alternative splicing of the gene encoding barley MMT. |
| NO: 69 | Peptide | His-tag |
| NO: 70 | Peptide | Enterokinase site |
| NO: 71 | Nucleic acid | Forward primer to amplify the protein coding sequence of the barley gene for MMT. |

TABLE 10-continued

Sequence listing.

| SEQ ID | Type | Description |
| --- | --- | --- |
| NO: 72 | Nucleic acid | Reverse primer to amplify the protein coding sequence of the barley gene for MMT. |
| NO: 73 | Nucleic acid | Forward primer for amplification of DNA fragments of Mutant 8063 |
| NO: 74 | Nucleic acid | Reverse primer for amplification of DNA fragments of Mutant 8063 |
| NO: 75 | Nucleic acid | Forward primer for amplification of DNA fragments of Mutant 8063 |
| NO: 76 | Nucleic acid | Reverse primer for amplification of DNA fragments of Mutant 8063 |
| NO: 77 | Nucleic acid | Forward primer for SNP detection of Mutant 8063 |
| NO: 78 | Nucleic acid | Forward primer for SNP detection of Mutant 8063 |
| NO: 79 | Nucleic acid | Forward primer for SNP detection of Mutant 8063 |
| NO: 80 | Nucleic acid | Forward primer for SNP detection of Mutant 8063 |
| NO: 81 | Nucleic acid | Reverse primer for SNP detection of Mutant 8063 |
| NO: 82 | Nucleic acid | Reverse primer for SNP detection of Mutant 8063 |
| NO: 83 | Nucleic acid | Reverse primer for SNP detection of Mutant 8063 |
| NO: 84 | Nucleic acid | Reverse primer for SNP detection of Mutant 8063 |
| NO: 85 | Nucleic acid | Forward primer for amplification of DNA fragments of Mutant 14018 |
| NO: 86 | Nucleic acid | Reverse primer for amplification of DNA fragments of Mutant 14018 |
| NO: 87 | Nucleic acid | Forward primer for amplification of DNA fragments of Mutant 14018 |
| NO: 88 | Nucleic acid | Reverse primer for amplification of DNA fragments of Mutant 14018 |
| NO: 89 | Nucleic acid | Forward primer for amplification of DNA fragments of Mutant 14018 |
| NO: 90 | Nucleic acid | Reverse primer for amplification of DNA fragments of Mutant 14018 |
| NO: 91 | Nucleic acid | Forward primer for amplification of DNA fragments of Mutant 14018 |
| NO: 92 | Nucleic acid | Reverse primer for amplification of DNA fragments of Mutant 14018 |
| NO: 93 | Nucleic acid | Forward primer for amplification of DNA fragments of Mutant 14018 |
| NO: 94 | Nucleic acid | Reverse primer for amplification of DNA fragments of Mutant 14018 |
| NO: 95 | Nucleic acid | Forward primer for amplification of DNA fragments of Mutant 14018 |
| NO: 96 | Nucleic acid | Reverse primer for amplification of DNA fragments of Mutant 14018 |
| NO: 97 | Nucleic acid | Forward primer for SNP detection of Mutant 14018 |
| NO: 98 | Nucleic acid | Forward primer for SNP detection of Mutant 14018 |
| NO: 99 | Nucleic acid | Forward primer for SNP detection of Mutant 14018 |
| NO: 100 | Nucleic acid | Forward primer for SNP detection of Mutant 14018 |
| NO: 101 | Nucleic acid | Reverse primer for SNP detection of Mutant 14018 |
| NO: 102 | Nucleic acid | Reverse primer for SNP detection of Mutant 14018 |
| NO: 103 | Nucleic acid | Reverse primer for SNP detection of Mutant 14018 |
| NO: 104 | Nucleic acid | Reverse primer for SNP detection of Mutant 14018 |

The invention claimed is:

1. A barley plant, or part thereof, wherein the barley plant carries a mutation in the gene encoding methionine-S-methyltransferase (MMT) that causes a total loss of MMT function.

2. The barley plant, or part thereof, according to claim 1, wherein the mutation is within a splice site of the gene encoding MMT.

3. The barley plant, or part thereof, according to claim 1, wherein the mutation in the gene encoding MMT is a G to A mutation of base 3076 of SEQ ID NO:3 or a G to A mutation of base 1462 of SEQ ID NO:16.

4. The barley plant or a part thereof according to claim 1, wherein the mutation results in a gene encoding a truncated form of MMT comprising an N-terminal fragment of wild-type MMT and optionally additional C-terminal sequences not found in wild-type MMT, wherein said N-terminal fragment comprises at the most the 500 N terminal amino acid residues of SEQ ID NO:6.

5. The barley plant, or a part thereof, according to claim 1, wherein said plant is selected from the group consisting of plants designated "Barley, *Hordeum vulgare*: Line 8063" deposited at ATCC 13 Oct. 2008 with the designation PTA-9543, and progeny plants thereof.

6. A plant product comprising a processed barley plant or part thereof, wherein said barley plant or part thereof is the barley plant or part thereof according to claim 1.

7. The plant product according to claim 6, wherein the plant product is a malt composition comprising a processed barley plant, or part thereof, wherein said barley plant carries the mutation in the gene encoding methionine-S-methyltransferase (MMT) that causes a total loss of MMT function.

8. The malt composition according to claim 7, wherein the malt composition is milled malt.

9. The plant product according to claim 6, wherein the plant product is a wort composition prepared using the barley plant, or part thereof, wherein the barley plant carries the mutation in the gene encoding methionine-S-methyltransferase (MMT) that causes a total loss of MMT function, or using a malt composition prepared from said barley plant or part thereof, or mixtures thereof.

10. The plant product according to claim 6, wherein the plant product is selected from the group consisting of barley syrups, malt syrups, barley extracts and malt extracts.

11. A method of producing a beverage containing less than 20 ppb DMS, said method comprising the steps of:
  (i) preparing a composition comprising a barley plant or part thereof, according to claim 1; and
  (ii) processing the composition of (i) into a beverage;
thereby obtaining a beverage containing less than 20 ppb DMS.

12. A method of producing a malt composition comprising at the most 200 ppb free DMS, said method comprising the steps of:
  (i) providing kernels of a barley plant according to claim 1;
  (ii) steeping said kernels;
  (iii) germinating the steeped kernels under predetermined conditions; and
  (iv) treating germinated kernels with heat;

thereby producing a malt composition comprising at the most 200 ppb free DMS.

13. The barley plant or part thereof according to claim 1, wherein the barley plant carries:
   (i) the mutation in the gene encoding MMT, causing total loss of MMT activity; and
   (ii) a mutation in the gene encoding lipoxygenase 1, causing a total loss of lipoxygenase 1 activity.

14. The barley plant, or part thereof according to claim 13, wherein the mutation in the gene encoding MMT is a G to A mutation of base 3076 of SEQ ID NO:3 or a G to A mutation of base 1462 of SEQ ID NO:16.

15. The plant product according to claim 6 prepared from a barley plant, or part thereof, wherein the barley plant carries:
   (i) the mutation in the gene encoding MMT, causing total loss of MMT activity; and
   (ii) a mutation in the gene encoding lipoxygenase 1, causing a total loss of lipoxygenase 1 activity.

16. The plant product according to claim 15, wherein the plant product is a beverage.

17. The plant product according to claim 15, wherein the beverage is beer.

18. A beverage prepared from a barley plant according to claim 1 or a part of said plant, wherein said beverage contains a level of dimethyl sulfide (DMS) below 20 ppb.

19. The beverage according to claim 18, wherein said beverage is a malt beverage.

20. The beverage according to claim 18, wherein the beverage is beer.

21. The beverage according to claim 18, wherein the beverage contains less than 15 ppb DMS.

22. The beverage according to claim 18, wherein the beverage contains less than 20 ppb, S methyl-1-methionine (SMM).

23. The beverage according to claim 18, wherein the beverage is prepared from a barley plant, or a part thereof, wherein the mutation in the gene encoding MMT is a G to A mutation of base 3076 of SEQ ID NO:3 or a G to A mutation of base 1462 of SEQ ID NO:16.

24. The beverage according to claim 18, wherein the beverage contains no detectable DMS.

25. The beverage according to claim 18, wherein the beverage contains no detectable S-methyl-1-methionine (SMM).

26. A method of preparing a barley plant carrying a mutation in the gene encoding MMT, causing total loss of MMT activity, comprising the steps of:
   (i) mutagenizing one or more of barley plants, barley kernels, barley embryos, barley cells, or barley tissue, thereby obtaining generation M0 barley;
   (ii) propagating said generation M0 barley for at least 2 generations, thereby obtaining generation Mx barley plants, wherein x is an integer ≥2;
   (iii) obtaining one or more samples from said Mx barley plants;
   (iv) determining the level of SMM in said one or more samples;
   (v) selecting one or more plants with no detectable SMM activity;
   (vi) sequencing at least part of the MMT gene from the one or more plants of step (v); and
   (vii) selecting one or more plants carrying at least one mutation in the MMT gene;
thereby obtaining at least one barley plant carrying at least one mutation in the gene encoding MMT, wherein said barley plant has a total loss of MMT activity.

* * * * *

SEQUENCE LISTING

<160> NUMBER OF SEQ ID NOS: 104

<210> SEQ ID NO 1
<211> LENGTH: 3267
<212> TYPE: DNA
<213> ORGANISM: Barley cv. Haruna Nijo

<400> SEQUENCE: 1

```
atggctgcgg cggcggggga cgtggaggcg ttcctggcgg cgtgccaggc gtcgggcgac      60
gcggcgtacg cgccgccaa ggccgtgctg gagcggctcg aggcgccggc cacgcgcgcc     120
gaggccaggc ggctcctcgg cgccgtgcga cggcgcttcg ccgccggcgg cccggccgcg     180
gggctcgagt gcttccgcac cttccacttc cgcatccacg acgtcgtcct cgaccccac     240 ctccaaggat tccagcaaag aaagaagcta acaatgatgg agatacccag cattttcatt     300
```

```
ccagaagact ggtcattcac tttctacgag ggtctcaacc ggcatccaga ttccatcttc    360
agggataaga cagtagcaga gctgggatgt ggcaatggtt ggatatccat tgcacttgca    420
gaaaagtggt gcccttcgaa ggtttatggt ctggatataa acccaagacc tatcaagatt    480
gcatggataa acctttactt gaatgcacta gacgacgatg gtctcccaat ctatgatgcg    540
gaggggaaaa cattgcttga cagagtcgaa ttctatgaat ctgatcttct ttcttactgt    600
agagataaca agatagaact tgatcgcatt gttggatgca taccacagat tcttaacccc    660
aatccagagg caatgtcaaa gattgtaact gaaaattcaa gtgaggagtt cttgtactcc    720
ttgagcaact actgtgctct ccagggtttt gttgaggacc aatttggcct cgggttgatt    780
gctcgggctg ttgaagaagg gatatctgtg ataaagccta gtggtcttat ggtattcaac    840
atgggaggcc ggccaggaca aggtgtctgt gagcgcctat ttcttcgccg tggatttcgc    900
atcaataagc tctggcaaac aaaaattatg caggctgccg acacagacat ctccgcttta    960
gttgaaattg agaaaaatag ccggcatcgc ttcgagttct ttatggatct tgttggggat   1020
cagcctgtgt gtgcgcgcac agcatgggca tacatgaaat ctggtggccg catttcacat   1080
gctttgtctg tgtatagctg tcaacttcgc cagcccaacc aggtgaagaa aatatttgag   1140
ttccttaaag acggattcca tgaagtcagc agctccctcg atttgtcctt tgatgatgat   1200
tctgttgctg atgaaaaaat tccttttccta gcatacctag ctagtttctt gcaagagaat   1260
aagtctaatc cttgtgagcc tccagctgga tgtttaaatt tccggaatct tgttgctgga   1320
tttatgaaga gttaccacca catcccatta actcctgata tgttgttgt gttcccatcc   1380 cgtgctgttg caatcgaaaa tgctcttcgg ttgttctcac ctggacttgc aattgttgac   1440
gaacacctaa ccagacactt gcccaagcaa tggttaacat cttagcaat tgaggaaagt   1500 aaccatgcta agatacagt aactgtaatc gaagcaccac gccaatcaga tttgctgatt   1560
gagttgatca ggaaactgaa gccccaggtt gttgttactg gcatggctca gtttgaggct   1620
atcaccagtg ctgctttcgt gaacttatta agtgtaacga agatgttgg ttcccgatta   1680 ttactagata tttcagaaca tctggaattg tctagtctgc caagctcaaa tggtgtattg   1740
aaatatcttg ctgggaagac cctgccttca catgcggcta tattgtgtgg cttagttaag   1800
aatcaggttt attctgatct ggaagttgct tttgctatct ctgaagatcc aactgtttat   1860
aaggcattgt cacaaactat tgagctattg aaggacata cttctgtgat cagccagcac   1920
tattatggtt gtcttttcca tgagctgctg gcatttcaaa ttggtgaccg gcatccacaa   1980
caagagagag aacctgcaga agtgatatct aaggagatga tagggttttc aagttcagct   2040
atgtccaccc tagaaggagc tgagttttc gttcctggtt ccatggaatc cggtgtcata   2100
catatggatc tggaccgcag cttcttgcca gtaccttctg cagtaaacgc ctccattttc   2160
gaaagttttg ttcgtcagaa catcactgat tctgaaactg atgtccgttc cagcattcag   2220
cagctggtga agatagcta tggtttctca gcaggcggtg cttctgaaat tatatacggg   2280
aacacctgtc tcgcgctctt caacaagctt gttctttgct gcatgcaaga acagggcacc   2340 ttgctttttcc ccttgggaac caacgggcat tatgtcaacg cagcaaagtt tgtgaatgca   2400
accaccttga ctattccaac gaaggcagat tcaggcttca agatcgaacc aagtgctcta   2460
gccgacacac tagagaaggt gtctcagccg tgggtctata tttctggccc cacaatcaac   2520
cctactggct tcctgtacag tgacgacgat atagcagagc tgctttctgt ctgtgcgaca   2580
tacggagcca gggtggtgat agatacctcc tcctctggtc tggagttcca agccaccggc   2640
```

```
                                     -continued tgcagccagt ggaatttgga agatgtctt tctaatgtca agtcttcaaa gccctcgttc    2700
tccgttgtcc tgctcggaga gctgtccttt gagctgacca cggctgggct tgatttcggg    2760
tttctgatta tgagcgactc gtccttggtt gacacatttt acagtttccc aagcttgagt    2820
cggccacaca gcacgttgaa gtacactttc aggaagctgt tgggtcttaa gaaccagaag    2880
gatcagcatt tctctgatct catccttgag cagaaggaga cgttgaagaa tcgtgccgac    2940
cagttgatca agatgcttga gagctgcggc tgggacgctg tgggctgcca tggcggcatc    3000
tcgatgcttg caaaaccgac cgcctacatt ggcaaatcgc tcaaggtgga cggctttgag    3060
ggcaagctgg acagccacaa catgagggaa gccctcctga ggtccaccgg gctgtgcatt    3120
agcagcagcg ggtggacagg ggtgccggac tactgccgct tcagctttgc tctggagagc    3180
ggcgacttcg accgggccat ggagtgcatc gcccggttca gggagctggt ccttggtggc    3240
ggtgctaagg tgaatggtag caactag                                        3267
```

<210> SEQ ID NO 2
<211> LENGTH: 1088
<212> TYPE: PRT
<213> ORGANISM: Barley cv. Haruna Nijo

<400> SEQUENCE: 2

```
Met Ala Ala Ala Gly Asp Val Glu Ala Phe Leu Ala Ala Cys Gln
1               5                   10                  15

Ala Ser Gly Asp Ala Ala Tyr Gly Ala Lys Ala Val Leu Glu Arg
                20                  25                  30

Leu Glu Ala Pro Ala Thr Arg Ala Glu Ala Arg Arg Leu Leu Gly Ala
            35                  40                  45

Val Arg Arg Arg Phe Ala Ala Gly Gly Pro Ala Ala Gly Leu Glu Cys
        50                  55                  60

Phe Arg Thr Phe His Phe Arg Ile His Asp Val Val Leu Asp Pro His
65                  70                  75                  80

Leu Gln Gly Phe Gln Gln Arg Lys Lys Leu Thr Met Met Glu Ile Pro
                85                  90                  95

Ser Ile Phe Ile Pro Glu Asp Trp Ser Phe Thr Phe Tyr Glu Gly Leu
            100                 105                 110

Asn Arg His Pro Asp Ser Ile Phe Arg Asp Lys Thr Val Ala Glu Leu
        115                 120                 125

Gly Cys Gly Asn Gly Trp Ile Ser Ile Ala Leu Ala Glu Lys Trp Cys
    130                 135                 140

Pro Ser Lys Val Tyr Gly Leu Asp Ile Asn Pro Arg Pro Ile Lys Ile
145                 150                 155                 160

Ala Trp Ile Asn Leu Tyr Leu Asn Ala Leu Asp Asp Asp Gly Leu Pro
                165                 170                 175

Ile Tyr Asp Ala Glu Gly Lys Thr Leu Leu Asp Arg Val Glu Phe Tyr
            180                 185                 190

Glu Ser Asp Leu Leu Ser Tyr Cys Arg Asp Asn Lys Ile Glu Leu Asp
        195                 200                 205

Arg Ile Val Gly Cys Ile Pro Gln Ile Leu Asn Pro Asn Pro Glu Ala
    210                 215                 220

Met Ser Lys Ile Val Thr Glu Asn Ser Ser Glu Phe Leu Tyr Ser
225                 230                 235                 240

Leu Ser Asn Tyr Cys Ala Leu Gln Gly Phe Val Glu Asp Gln Phe Gly
                245                 250                 255

Leu Gly Leu Ile Ala Arg Ala Val Glu Glu Gly Ile Ser Val Ile Lys
```

```
                    260                 265                 270
Pro Ser Gly Leu Met Val Phe Asn Met Gly Gly Arg Pro Gly Gln Gly
                275                 280                 285

Val Cys Glu Arg Leu Phe Leu Arg Arg Gly Phe Arg Ile Asn Lys Leu
                290                 295                 300

Trp Gln Thr Lys Ile Met Gln Ala Ala Asp Thr Asp Ile Ser Ala Leu
305                 310                 315                 320

Val Glu Ile Glu Lys Asn Ser Arg His Arg Phe Glu Phe Phe Met Asp
                325                 330                 335

Leu Val Gly Asp Gln Pro Val Cys Ala Arg Thr Ala Trp Ala Tyr Met
                340                 345                 350

Lys Ser Gly Gly Arg Ile Ser His Ala Leu Ser Val Tyr Ser Cys Gln
                355                 360                 365

Leu Arg Gln Pro Asn Gln Val Lys Lys Ile Phe Glu Phe Leu Lys Asp
                370                 375                 380

Gly Phe His Glu Val Ser Ser Leu Asp Leu Ser Phe Asp Asp Asp
385                 390                 395                 400

Ser Val Ala Asp Glu Lys Ile Pro Phe Leu Ala Tyr Leu Ala Ser Phe
                405                 410                 415

Leu Gln Glu Asn Lys Ser Asn Pro Cys Glu Pro Pro Ala Gly Cys Leu
                420                 425                 430

Asn Phe Arg Asn Leu Val Ala Gly Phe Met Lys Ser Tyr His His Ile
                435                 440                 445

Pro Leu Thr Pro Asp Asn Val Val Phe Pro Ser Arg Ala Val Ala
                450                 455                 460

Ile Glu Asn Ala Leu Arg Leu Phe Ser Pro Gly Leu Ala Ile Val Asp
465                 470                 475                 480

Glu His Leu Thr Arg His Leu Pro Lys Gln Trp Leu Thr Ser Leu Ala
                485                 490                 495

Ile Glu Glu Ser Asn His Ala Lys Asp Thr Val Thr Val Ile Glu Ala
                500                 505                 510

Pro Arg Gln Ser Asp Leu Leu Ile Glu Leu Ile Arg Lys Leu Lys Pro
                515                 520                 525

Gln Val Val Val Thr Gly Met Ala Gln Phe Glu Ala Ile Thr Ser Ala
                530                 535                 540

Ala Phe Val Asn Leu Leu Ser Val Thr Lys Asp Val Gly Ser Arg Leu
545                 550                 555                 560

Leu Leu Asp Ile Ser Glu His Leu Glu Leu Ser Ser Leu Pro Ser Ser
                565                 570                 575

Asn Gly Val Leu Lys Tyr Leu Ala Gly Lys Thr Leu Pro Ser His Ala
                580                 585                 590

Ala Ile Leu Cys Gly Leu Val Lys Asn Gln Val Tyr Ser Asp Leu Glu
                595                 600                 605

Val Ala Phe Ala Ile Ser Glu Asp Pro Thr Val Tyr Lys Ala Leu Ser
                610                 615                 620

Gln Thr Ile Glu Leu Leu Glu Gly His Thr Ser Val Ile Ser Gln His
625                 630                 635                 640

Tyr Tyr Gly Cys Leu Phe His Glu Leu Leu Ala Phe Gln Ile Gly Asp
                645                 650                 655

Arg His Pro Gln Gln Glu Arg Glu Pro Ala Glu Val Ile Ser Lys Glu
                660                 665                 670

Met Ile Gly Phe Ser Ser Ser Ala Met Ser Thr Leu Glu Gly Ala Glu
                675                 680                 685
```

-continued

Phe Phe Val Pro Gly Ser Met Glu Ser Gly Val Ile His Met Asp Leu
        690             695             700

Asp Arg Ser Phe Leu Pro Val Pro Ser Ala Val Asn Ala Ser Ile Phe
705             710             715             720

Glu Ser Phe Val Arg Gln Asn Ile Thr Asp Ser Glu Thr Asp Val Arg
            725             730             735

Ser Ser Ile Gln Gln Leu Val Lys Asp Ser Tyr Gly Phe Ser Ala Gly
            740             745             750

Gly Ala Ser Glu Ile Ile Tyr Gly Asn Thr Cys Leu Ala Leu Phe Asn
            755             760             765

Lys Leu Val Leu Cys Cys Met Gln Glu Gln Gly Thr Leu Leu Phe Pro
770             775             780

Leu Gly Thr Asn Gly His Tyr Val Asn Ala Ala Lys Phe Val Asn Ala
785             790             795             800

Thr Thr Leu Thr Ile Pro Thr Lys Ala Asp Ser Gly Phe Lys Ile Glu
            805             810             815

Pro Ser Ala Leu Ala Asp Thr Leu Glu Lys Val Ser Gln Pro Trp Val
            820             825             830

Tyr Ile Ser Gly Pro Thr Ile Asn Pro Thr Gly Phe Leu Tyr Ser Asp
            835             840             845

Asp Asp Ile Ala Glu Leu Leu Ser Val Cys Ala Thr Tyr Gly Ala Arg
850             855             860

Val Val Ile Asp Thr Ser Ser Ser Gly Leu Glu Phe Gln Ala Thr Gly
865             870             875             880

Cys Ser Gln Trp Asn Leu Glu Arg Cys Leu Ser Asn Val Lys Ser Ser
            885             890             895

Lys Pro Ser Phe Ser Val Val Leu Leu Gly Glu Leu Ser Phe Glu Leu
            900             905             910

Thr Thr Ala Gly Leu Asp Phe Gly Phe Leu Ile Met Ser Asp Ser Ser
            915             920             925

Leu Val Asp Thr Phe Tyr Ser Phe Pro Ser Leu Ser Arg Pro His Ser
930             935             940

Thr Leu Lys Tyr Thr Phe Arg Lys Leu Leu Gly Leu Lys Asn Gln Lys
945             950             955             960

Asp Gln His Phe Ser Asp Leu Ile Leu Glu Gln Lys Glu Thr Leu Lys
            965             970             975

Asn Arg Ala Asp Gln Leu Ile Lys Met Leu Glu Ser Cys Gly Trp Asp
            980             985             990

Ala Val Gly Cys His Gly Gly Ile Ser Met Leu Ala Lys Pro Thr Ala
            995             1000            1005

Tyr Ile Gly Lys Ser Leu Lys Val Asp Gly Phe Glu Gly Lys Leu
   1010            1015            1020

Asp Ser His Asn Met Arg Glu Ala Leu Leu Arg Ser Thr Gly Leu
   1025            1030            1035

Cys Ile Ser Ser Ser Gly Trp Thr Gly Val Pro Asp Tyr Cys Arg
   1040            1045            1050

Phe Ser Phe Ala Leu Glu Ser Gly Asp Phe Asp Arg Ala Met Glu
   1055            1060            1065

Cys Ile Ala Arg Phe Arg Glu Leu Val Leu Gly Gly Gly Ala Lys
   1070            1075            1080

Val Asn Gly Ser Asn
   1085

<210> SEQ ID NO 3
<211> LENGTH: 6459
<212> TYPE: DNA
<213> ORGANISM: Barley cv. Prestige

<400> SEQUENCE: 3

```
atggctgcgg cggcggggga cgtggaggcg ttcctggcgg cgtgccaggc gtcgggcgac    60
gcggcgtacg cgccgccaa ggccgtgctg gagcggctcg aggcgccggc cacgcgcgcc   120
gaggccaggc ggctcctcgg cgccgtgcga cggcgcttcg ccgccggcgg cccggccgcg   180
gggctcgagt gcttccgcac cttccacttc cgcatccacg acgtcgtcct cgacccccac   240
ctccaaggtt gcccggcccc ttccctacac acccgttgtc gacccgcatc tctttcgccg   300
atctggccgt caaaagcacg cggcttggta gaaatcaagc ctgcaatcct gatccgttta   360
tggctggcca gtcgatcagt aatttggcca taactggagt ataaccttgg tctctaatct   420
ctacctgacc atataccgag ttggttttct ttcttcttgt ttccgtattt gtgtagtttt   480
ttcttttctt tcgagcatga tgttcttga attaatgcgt accagactcc agtaattcga   540
cattttgaat tttggcgagt gttcttggaa tttataacac aacgaggctt tgatcaagtg   600
gtttatgtag aggagtgttt tgttcttgt gcaccgtata caattctcta tttcccaaca   660
attttgatgg cctctaagca tcctgtagtc atgtctactg tgtaagctac agatttattc   720
atgtctatgt gtaagctgca aatggagaga aaagctatct atttggttgt tccagcttgt   780
tctttggcag aacaatcctg cccatcctat caccataagt ataaaagcac gacaaatgag   840
tggggcaagc atgctgccaa gctaatacac gacataagct acatattttg aggggcatgt   900
tatctttttt tttccttct actcagtttc ttctttggga gaacaatcct actcaaccta   960
taatcataag aataaaagca agacagatga gtgctgcaga ctattggcat atataacaac  1020
taaataggac atctgtccgc tatatcttta gttaataatt gtatatagac gcagtctttg  1080
tgctggaaaa actgcaacta atatttttct tacattatat ggaatctggg tgtgatatga  1140
cttctttgtt acgttttgtg tgcataaagc attaacttct gtctttagtt ggcgcagcgg  1200
taaaaacacc cattgcttaa tattttattt gcttccgta gcttgataaa atttcaactg  1260
cttctaggat tccagcaaag aaagaagcta acaatgatgg agatacccag cattttcatt  1320
ccagaagact ggtcattcac tttctacgag ggtctcaacc ggcatccaga ttccatcttc  1380
agggataaga cagtagcaga gctgggatgt ggcaatggtt ggatatccat tgcacttgca  1440
gaaaagtggt gcccttcgaa ggttggcacc tcttgttccg tagatattta tcttatctcg  1500
tttgttgcaa acatgggacc tgcagaagtt agacatttac tcaggttact ttatatgaaa  1560
cttttaggtg tctgccagta gtctgctggt ggtctaattt tcttggtata cctgatgccg  1620
tcgagcatat tgctttcaaa ttttgggcaa ggcattacca ccacatattg tttctacaat  1680
gctgaacaat tgctctcctt tgaaaggaag aaaaacaaga atgacatgca ccttagtagt  1740
ttaagccaca aataccagcg aatcaaatta gtttgcagtc agcttggcat taccttactt  1800
gagccttggt tgttctttg aaggtttatg gtctggatat aaacccaaga gctatcaaga  1860
ttgcatggat aaacctttac ttgaatgcac tagacgacga tggtctccca atctatgatg  1920
cggaggggaa acattgctt gacagagtcg aattctatga atctgatctt ctttcttact  1980
gtagagataa caagatagaa cttgatcgca ttgttggatg cataccacag gtacggtcag  2040
gtttttacca atttcctgtg aatggggatt atagtcgatc agaacttgat caaaatgccc  2100
ttaatatctg cctttcagat tcttaaccc aatccagagg caatgtcaaa gattgtaact  2160
```

```
gaaaattcaa gtgaggagtt cttgtactcc ttgagcaact actgtgctct ccaggtgagt    2220
tgagatctat ttaaactcaa gccattcagt ttacctgtta ctaaatggtt acccatgtca    2280
gagtctccaa atcttttct tttctcaaac agcaaagaga aagaaaact tttaagttct      2340 atcctgaaat tgactttaca atgcttgttc ataatctgct tacgaaatat gcgtttgaac    2400
atttctcttt tccttgtagg catgtggtca gacctttata taagaaaatg aagttttgt     2460 agaaataatg tatgctttgt acttatgaca tggttccacc agtataatca atttaagtct    2520
aggtagttag gaacctagga tggagagcac cgacagtgta taatatatat atgtcgatag    2580
ggggttagca gtccaaatcc acctcaagtt caacctattg cataactttt ggtcttacaa    2640
cctgtatgga caaatgtgat cagcacccca gtctttccta taaaaatgtc tgctggaata    2700
tggaattatt aacagcggta tttattttta ccctgtttaa tttttccctt tgctaaaaga   2760
atgataatcc ttatgccacg aggttacatt gtattactca agtcaatatt tgttactatg    2820
gctgattgta cgattccagc ttccggttgt taattttgtt atgtttgtga actttgctgc    2880
attcagggtt ttgttgagga ccaatttggc ctcgggttga ttgctcgggc tgttgaagaa    2940
gggatatctg tgataaagcc tagtggtctt atggtattca acatgggagg ccggccagga    3000
caaggtgtct gtgagcgcct atttctacgc cgtggatttc gcatcaataa gctctggcaa    3060
acaaaaatta tgcaggtagc aattctttga gtgactagat gttaactaat cccagtgttt    3120
ttccatgcca gcaacagcat tatatcctgg ttagaggaat atgctcttca tgttgcacac    3180
caatcttcag ctgggcctag aatttttcatc taccggctta cattttaca ttacagaacc     3240 aattttttgtt gaggatcatt accaactagt tgggtctttg caggctgctg acacagacat    3300 ctccgctta gttgaaattg agaaaaatag ccgacatcgc ttcgagttct ttatggatct      3360
tgttggggat cagcctgtgt gtgcgcgcac agcatgggca tacatgaaat ctggtggccg    3420
catttcacat gctttgtctg tgtatagctg tcaacttcgc cagcccaacc aggtaccat     3480 actctctgat tagatcttta caacaataat atagtaatgt caggaataat aataatttgg    3540
agaatttcag gtgaagaaaa tatttgagtt ccttaaagac ggattccatg aagtcagcag    3600
ctccctcgat ttgtcctttg atgatgattc tgttgctgat gaaaaaattc ctttcctagc    3660
atacctagct agtttcttgc aagagaataa gtctaatcct tgtgagcctc cagctggatg    3720 tttaaattc cggaatcttg ttgctggatt tatgaagagt taccaccaca tcccattaac     3780
tcctgatgta agacttggtg tctattgcct acaattatgt ttgcttatta gaaattcata    3840
agatcaacct atttgatgct tctcacgtat gcttcatgtg acacttcctt ttcctctggt    3900
gcaccagaat gttgttgtgt tcccatcccg tgctgttgca atcgaaaatg ctcttcggtt    3960
gttctcacct ggacttgcaa ttgttgacga acacctaacc agacacttgc ccaagcaatg    4020
gttaacatct ttagcaattg aggtactttg accgatactc ccctcttct ttctgtgttt     4080 ggaactgtgg aaaatacatg tgttctgtga agaaaaagtt atgctgacaa gaatttcgat    4140
gttattgcca ttcttctaaa tttcaggaaa gtaaccatgc taaagataca gtaactgtaa    4200
tcgaagcacc acgccaatca gatttgctga ttgagttgat caggaaactg aagcctcagg    4260
ttgttgttac tggcatggct cagtttgagg ctatcaccag tgctgctttc gtgaacttat    4320
taagtgtaac gaaagatgtt ggttcccgat tattactaga tatttcagaa catctggaat    4380
tgtctagtct gccaagctca aatggtgtat tgaaatatct tgctgggaag accctgcctt    4440
cacatgcggc tatattgtgt ggcttagtta agaatcaggt gtgtgtcaat cagcctgaac    4500
```

```
tctagttgaa ctgttgtgca tactatatag aatatcttga cttttatatg tactttagaa    4560
acactgttta aatgtactca tttcttttg cttcatttta cttgcaggtt tattctgatc     4620
tggaagttgc ttttgctatc tctgaagatc caactgttta taaggcattg tcacaaacta    4680
ttgagctatt ggaaggacat acttctgtga tcagccagca ctattatggt tgtcttttcc    4740
atgagctgct ggcatttcaa attggtgacc ggcatccaca acaagaggta aacatggctt    4800
gcctcttcca gttctccatc tcactcagtt ctgtccacaa ggtgccgaat gatctgttca    4860
agtggacact cccctcagca cgggcaagct agtccatgaa tttggattag ttccctctta    4920
gctgggtact tcgattacac cacaatgagc tcctcaacgt ggtctggttt atgtttttca    4980
tgttttccct ctaatgtttg gttgctcttt ttcagagaga acctgcagaa gtgatatcta    5040
aggagatgat agggttttca agttcagcta tgtccaccct agaaggagct gagttttcg     5100 ttcctggttc catggaatcc ggtgtcatac atatggatct ggaccgcagc ttcttgccag    5160
taccttctgc agtaaacgcc tccattttcg aaagttttgt tcgtcagaac atcactgatt    5220
ctgaaaccga tgtccgttcc agcattcagc agctggtgaa agatagctat ggtttctcag    5280
caggcggtgc ttctgaaatt atatacggga acacctgtct cgcgctcttc aacaagcttg    5340
ttctttgctg catgcaagaa cagggcacct tgcttttccc cttgggaacc aacgggcatt    5400
acgtcaacgc agcaaagttt gtgaatgcaa ccaccttgac tattccaacg aaggcagatt    5460
caggcttcaa gatcgaacca agtgctctag ccgacacact agagaaggtg tctcagccgt    5520
gggtctatat ttctggcccc acaatcaacc ctactggctt cctgtacagt gacgacgata    5580
tagcagagct gctttctgtc tgtgcgacat acggagccag ggtggtgata gatacctcct    5640
cctctggtct ggagttccaa gccaccggct gcagccagtg gaatttggaa agatgtcttt    5700
ctaatgtcaa gtcttcaaag ccctcgttct ccgttgtcct gctcggagag ctgtcctttg    5760
agctgaccac ggctgggctt gatttcgggt ttctgattat gagcgactcg tccttggttg    5820
acacatttta cagtttccca agcttgagtc ggccacacag cacgttgaag tacacgttca    5880
ggaagctgtt gggtcttaag aaccagaagg atcagcattt ctctgatctc atccttgagc    5940
agaaggagac gttgaagaat cgtgccgacc agttgatcaa ggtatgcctt tgggatatc     6000 ctgtgtttag gctctctgtt ttcttcccct gatcagctct ccgatcccct tacatcctta    6060
ggctaatttc agtacttcaa gtttgccacg catttctgac atattctttc ctcttgtttt    6120
attttcctgt gatgtgatga acagacgctt gagagctgcg gctgggacgc tgtgggctgc    6180
catggcggca tctcgatgct tgcaaaaccg accgcctaca ttggcaaatc gctcaaggtg    6240
gacggctttg agggcaagct ggacagccac aacatgaggg aagccctcct gaggtccacc    6300
gggctgtgca ttagcagcag cgggtggaca ggggtgccgg actactgccg cttcagctttt   6360 gctctggaga gcggcgactt cgaccgggcc atggagtgca tcgcccggtt cagggagctg    6420
gtccttggtg gcggtgctaa ggtgaatggt agcaactag                           6459
```

<210> SEQ ID NO 4
<211> LENGTH: 3267
<212> TYPE: DNA
<213> ORGANISM: Barley cv. Prestige

<400> SEQUENCE: 4

```
atggctgcgg cggcggggga cgtggaggcg ttcctggcgg cgtgccaggc gtcgggcgac      60
gcggcgtacg gcgccgccaa ggccgtgctg agcggctcg aggcgccggc cacgcgcgcc      120
gaggccaggc ggctcctcgg cgccgtgcga cggcgcttcg ccgccggcgg cccggccgcg     180
```

```
gggctcgagt gcttccgcac cttccacttc cgcatccacg acgtcgtcct cgaccccac      240 ctccaaggat tccagcaaag aaagaagcta acaatgatgg agatacccag cattttcatt      300
ccagaagact ggtcattcac tttctacgag ggtctcaacc ggcatccaga ttccatcttc      360
agggataaga cagtagcaga gctgggatgt ggcaatggtt ggatatccat tgcacttgca      420
gaaaagtggt gcccttcgaa ggtttatggt ctggatataa acccaagagc tatcaagatt      480
gcatggataa acctttactt gaatgcacta acgacgatg gtctcccaat ctatgatgcg       540
gaggggaaaa cattgcttga cagagtcgaa ttctatgaat ctgatcttct ttcttactgt      600
agagataaca agatagaact tgatcgcatt gttggatgca taccacagat tcttaacccc      660
aatccagagg caatgtcaaa gattgtaact gaaaattcaa gtgaggagtt cttgtactcc      720
ttgagcaact actgtgctct ccagggtttt gttgaggacc aatttggcct cgggttgatt      780
gctcgggctg ttgaagaagg gatatctgtg ataaagccta gtggtcttat ggtattcaac      840
atgggaggcc ggccaggaca aggtgtctgt gagcgcctat ttctacgccg tggatttcgc      900
atcaataagc tctggcaaac aaaaattatg caggctgctg acacagacat ctccgcttta      960
gttgaaattg agaaaaatag ccgacatcgc ttcgagttct ttatggatct tgttggggat     1020
cagcctgtgt gtgcgcgcac agcatgggca tacatgaaat ctggtggccg catttcacat     1080
gctttgtctg tgtatagctg tcaacttcgc cagcccaacc aggtgaagaa aatatttgag     1140
ttccttaaag acggattcca tgaagtcagc agctccctcg atttgtcctt tgatgatgat     1200
tctgttgctg atgaaaaaat tccttttccta gcatacctag ctagtttctt gcaagagaat    1260
aagtctaatc cttgtgagcc tccagctgga tgtttaaatt tccggaatct tgttgctgga     1320
tttatgaaga gttaccacca catcccatta actcctgata atgttgttgt gttcccatcc     1380
cgtgctgttg caatcgaaaa tgctcttcgg ttgttctcac ctggacttgc aattgttgac     1440
gaacacctaa ccagacactt gcccaagcaa tggttaacat ctttagcaat tgaggaaagt     1500
aaccatgcta aagatacagt aactgtaatc gaagcaccac gccaatcaga tttgctgatt     1560
gagttgatca ggaaactgaa gcctcaggtt gttgttactg gcatggctca gtttgaggct     1620
atcaccagtg ctgctttcgt gaacttatta agtgtaacga aagatgttgg ttcccgatta     1680
ttactagata tttcagaaca tctggaattg tctagtctgc caagctcaaa tggtgtattg     1740
aaatatcttg ctgggaagac cctgccttca catgcggcta tattgtgtgg cttagttaag     1800
aatcaggttt attctgatct ggaagttgct tttgctatct ctgaagatcc aactgtttat     1860
aaggcattgt cacaaactat tgagctattg aaggacata cttctgtgat cagccagcac     1920
tattatggtt gtcttttcca tgagctgctg gcatttcaaa ttggtgaccg gcatccacaa     1980
caagagagag aacctgcaga agtgatatct aaggagatga tagggttttc aagttcagct     2040
atgtccaccc tagaaggagc tgagttttc gttcctggtt ccatggaatc cggtgtcata     2100
catatggatc tggaccgcag cttcttgcca gtacttctg cagtaaacgc ctccattttc       2160
gaaagttttg ttcgtcagaa catcactgat tctgaaaccg atgtccgttc cagcattcag     2220
cagctggtga agatagcta tggttttctca gcaggcggtg cttctgaaat tatatacggg     2280
aacacctgtc tcgcgctctt caacaagctt gttctttgct gcatgcaaga acagggcacc     2340
ttgcttttcc ccttgggaac caacgggcat tacgtcaacg cagcaaagtt tgtgaatgca     2400
accaccttga ctattccaac gaaggcagat tcaggcttca agatcgaacc aagtgctcta     2460
gccgacacac tagagaaggt gtctcagccg tgggtctata tttctggccc cacaatcaac     2520
```

```
cctactggct tcctgtacag tgacgacgat atagcagagc tgctttctgt ctgtgcgaca   2580
tacggagcca gggtggtgat agatacctcc tcctctggtc tggagttcca agccaccggc   2640
tgcagccagt ggaatttgga aagatgtctt tctaatgtca agtcttcaaa gccctcgttc   2700
tccgttgtcc tgctcggaga gctgtccttt gagctgacca cggctgggct tgatttcggg   2760
tttctgatta tgagcgactc gtccttggtt gacacatttt acagtttccc aagcttgagt   2820
cggccacaca gcacgttgaa gtacacgttc aggaagctgt tgggtcttaa gaaccagaag   2880
gatcagcatt tctctgatct catccttgag cagaaggaga cgttgaagaa tcgtgccgac   2940
cagttgatca agacgcttga gagctgcggc tgggacgctg tgggctgcca tggcggcatc   3000
tcgatgcttg caaaaccgac cgcctacatt ggcaaatcgc tcaaggtgga cggctttgag   3060
ggcaagctgg acagccacaa catgagggaa gccctcctga ggtccaccgg gctgtgcatt   3120
agcagcagcg ggtggacagg ggtgccggac tactgccgct tcagctttgc tctggagagc   3180
ggcgacttcg accgggccat ggagtgcatc gcccggttca gggagctggt ccttggtggc   3240
ggtgctaagg tgaatggtag caactag                                      3267

<210> SEQ ID NO 5
<211> LENGTH: 3267
<212> TYPE: DNA
<213> ORGANISM: Barley cv. Prestige

<400> SEQUENCE: 5
atggctgcgg cggcggggga cgtggaggcg ttcctggcgg cgtgccaggc gtcgggcgac     60
gcggcgtacg cgccgccaa ggccgtgctg gagcggctcg aggcgccggc cacgcgtgca    120
gaggcccgtc ggctcctcgg cgccgtgcga cgtcgttttg cagcaggtgg tccagccgcg    180
gggctcgagt gcttccgcac cttccacttc cgcatccacg acgtcgtcct cgaccccac     240 ctccaaggat tccagcaaag aaagaagcta acaatgatgg agatacccag catttttcatt   300 ccagaagact ggtcattcac tttctacgag ggtctcaacc ggcatccaga ttccatcttc    360
agggataaga cagtagcaga gctgggatgt ggcaatggtt ggatatccat tgcacttgca    420
gaaaagtggt gcccttcgaa ggtttatggt ctggatataa acccaagagc tatcaagatt    480
gcatggataa accttttactt gaatgcacta gacgacgatg gtctcccaat ctatgatgcg    540 gagggggaaaa cattgcttga cagagtcgaa ttctatgaat ctgatcttct ttcttactgt    600
agggataaca agatagaact tgatcgcatt gttggatgca taccacagat tcttaacccc    660
aatccagagg caatgtcaaa gattgtaact gaaaattcaa gtgaggagtt cttgtactcc    720
ttgagcaact actgtgctct ccagggtttt gttgaggacc aatttggcct cgggttgatt    780
gctcgggctg ttgaagaagg gatatctgtg ataaagccta gtggtcttat ggtattcaac    840
atgggaggcc ggcccgggca aggtgtctgt gagcgcctat ttcttcgccg tggatttcgc    900
atcaataagc tctggcaaac aaaaattatg caggctgccg acacagacat ctccgcttta    960
gttgaaattg agaaaaatag ccggcatcgc ttcgagttct ttatggatct tgttggggat   1020
cagcctgtgt gtgcgcgcac agcatgggca tacatgaaat ctggtggccg catttcacat   1080
gctttgtctg tgtatagctg tcaacttcgc cagcccaacc aggtgaagaa aatatttgag   1140
ttccttaaag acggattcca tgaagtcagc agctccctcg atttgtcctt tgatgatgat   1200
tctgttgctg atgaaaaaat tcctttccta gcatacctag ctagtttctt gcaagagaat   1260
aagtctaatc cttgtgagcc tccagctgga tgtttaaatt tccggaatca tgttgctgga   1320
tttatgaaga gttaccacca catcccatta actcctgata atgttgttgt gttcccatcc   1380
```

```
cgtgctgttg caatcgaaaa tgctcttcgg ttgttctcac ctggacttgc aattgttgac    1440
gaacacctaa ccagacactt gcccaagcaa tggttaacat ctttagcaat tgaggaaagt    1500
aaccatgcta agatacagt aactgtaatc gaagcaccac gccaatcaga tttgctgatt    1560
gagttgatca ggaaactgaa gccccaggtt gttgttactg gcatggctca gtttgaggct    1620
atcaccagtg ctgctttcgt gaacttatta agtgtaacga agatgttgg ttcccgatta    1680 ttactagata tttcagaaca tctggaattg tctagtctgc caagctcaaa tggtgtattg    1740
aaatatcttg ctgggaagac cctgccttca catgcggcta tattgtgtgg cttagttaag    1800
aatcaggttt attctgatct ggaagttgct tttgctatct ctgaagatcc aactgtttat    1860
aaggcattgt cacaaactat tgagctattg aaggacata cttctgtgat cagccagcac    1920
tattatggtt gtcttttcca tgagctgctg gcatttcaaa ttggtgaccg gcatccacaa    1980
caagagagag aacctgcaga agtgatatct aaggagatga tagggttttc aagttcagct    2040
atgtccaccc tagaaggagc tgagtttttc gttcctggtt ccatggaatc cggtgtcata    2100
catatggatc tggaccgcag cttcttgcca gtaccttctg cagtaaacgc ctccattttc    2160
gaaagttttg ttcgtcagaa catcactgat tctgaaactg atgtccgttc cagcattcag    2220
cagctggtga agatagcta tggtttctca gcaggcggtg cttctgaaat tatatacggg    2280
aacacctgtc tcgcgctctt caacaagctt gttctttgct gcatgcaaga cagggcacc    2340 ttgctttttcc ccttgggaac caacgggcat tatgtcaacg cagcaaagtt tgtgaatgca    2400
accaccttga ctattccaac gaaggcagat tcaggcttca agatcgaacc aagtgctcta    2460
gccgacacac tagagaaggt gtctcagccg tgggtctata tttctggccc cacaatcaac    2520
cctactggct tcctgtacag tgacgacgat atagcagagc tgctttctgt ctgtgcgaca    2580
tacggagcca gggtggtgat agatacctcc tcctctggtc tggagttcca agccaccggc    2640
tgcagccagt ggaatttgga agatgtgtctt tctaatgtca agtcttcaaa gccctcgttc    2700
tccgttgtcc tgctcggaga gctgtccttt gagctgacca cggctgggct tgatttcggg    2760
tttctgatta tgagcgactc gtccttggtt gacacatttt acagtttccc aagcttgagt    2820
cggccacaca gcacgttgaa gtacactttc aggaagctgt tgggtcttaa gaaccagaag    2880
gatcagcatt tctctgatct catccttgag cagaaggaga cgttgaagaa tcgtgccgac    2940
cagttgatca agatgcttga gagctgcggc tgggacgctg tgggctgcca tggcggcatc    3000
tcgatgcttg caaaaccgac cgcctacatt agcaaatcgc tcaaggtgga cggctttgag    3060
ggcaagctgg acagccacaa catgagggaa gccctcctga gtccaccgg gctgtgcatt    3120 agcagcagcg ggtggacagg ggtgccggac tactgccgct tcagctttgc tctggagagc    3180
ggcgacttcg accgggccat ggagtgcatc gcccggttca gggagctggt ccttggtgga    3240
ggtgctaagg tgaatggtag caactag                                        3267
```

<210> SEQ ID NO 6
<211> LENGTH: 1088
<212> TYPE: PRT
<213> ORGANISM: Barley cv. Prestige

<400> SEQUENCE: 6

Met Ala Ala Ala Ala Gly Asp Val Glu Ala Phe Leu Ala Ala Cys Gln
1               5                   10                  15

Ala Ser Gly Asp Ala Ala Tyr Gly Ala Ala Lys Ala Val Leu Glu Arg
            20                  25                  30

-continued

Leu Glu Ala Pro Ala Thr Arg Ala Glu Ala Arg Arg Leu Leu Gly Ala
            35                  40                  45

Val Arg Arg Phe Ala Ala Gly Gly Pro Ala Gly Leu Glu Cys
 50                  55                  60

Phe Arg Thr Phe His Phe Arg Ile His Asp Val Val Leu Asp Pro His
 65                  70                  75                  80

Leu Gln Gly Phe Gln Gln Arg Lys Lys Leu Thr Met Met Glu Ile Pro
                85                  90                  95

Ser Ile Phe Ile Pro Glu Asp Trp Ser Phe Thr Phe Tyr Glu Gly Leu
                100                 105                 110

Asn Arg His Pro Asp Ser Ile Phe Arg Asp Lys Thr Val Ala Glu Leu
            115                 120                 125

Gly Cys Gly Asn Gly Trp Ile Ser Ile Ala Leu Ala Glu Lys Trp Cys
130                 135                 140

Pro Ser Lys Val Tyr Gly Leu Asp Ile Asn Pro Arg Ala Ile Lys Ile
145                 150                 155                 160

Ala Trp Ile Asn Leu Tyr Leu Asn Ala Leu Asp Asp Gly Leu Pro
                165                 170                 175

Ile Tyr Asp Ala Glu Gly Lys Thr Leu Leu Asp Arg Val Glu Phe Tyr
                180                 185                 190

Glu Ser Asp Leu Leu Ser Tyr Cys Arg Asp Asn Lys Ile Glu Leu Asp
            195                 200                 205

Arg Ile Val Gly Cys Ile Pro Gln Ile Leu Asn Pro Asn Pro Glu Ala
210                 215                 220

Met Ser Lys Ile Val Thr Glu Asn Ser Ser Glu Glu Phe Leu Tyr Ser
225                 230                 235                 240

Leu Ser Asn Tyr Cys Ala Leu Gln Gly Phe Val Glu Asp Gln Phe Gly
                245                 250                 255

Leu Gly Leu Ile Ala Arg Ala Val Glu Glu Gly Ile Ser Val Ile Lys
                260                 265                 270

Pro Ser Gly Leu Met Val Phe Asn Met Gly Gly Arg Pro Gly Gln Gly
            275                 280                 285

Val Cys Glu Arg Leu Phe Leu Arg Arg Gly Phe Arg Ile Asn Lys Leu
290                 295                 300

Trp Gln Thr Lys Ile Met Gln Ala Ala Asp Thr Asp Ile Ser Ala Leu
305                 310                 315                 320

Val Glu Ile Glu Lys Asn Ser Arg His Arg Phe Glu Phe Met Asp
                325                 330                 335

Leu Val Gly Asp Gln Pro Val Cys Ala Arg Thr Ala Trp Ala Tyr Met
            340                 345                 350

Lys Ser Gly Gly Arg Ile Ser His Ala Leu Ser Val Tyr Ser Cys Gln
            355                 360                 365

Leu Arg Gln Pro Asn Gln Val Lys Lys Ile Phe Glu Phe Leu Lys Asp
    370                 375                 380

Gly Phe His Glu Val Ser Ser Leu Asp Leu Ser Phe Asp Asp
385                 390                 395                 400

Ser Val Ala Asp Glu Lys Ile Pro Phe Leu Ala Tyr Leu Ala Ser Phe
                405                 410                 415

Leu Gln Glu Asn Lys Ser Asn Pro Cys Glu Pro Ala Gly Cys Leu
            420                 425                 430

Asn Phe Arg Asn Leu Val Ala Gly Phe Met Lys Ser Tyr His His Ile
            435                 440                 445

Pro Leu Thr Pro Asp Asn Val Val Val Phe Pro Ser Arg Ala Val Ala

```
            450                 455                 460
Ile Glu Asn Ala Leu Arg Leu Phe Ser Pro Gly Leu Ala Ile Val Asp
465                 470                 475                 480

Glu His Leu Thr Arg His Leu Pro Lys Gln Trp Leu Thr Ser Leu Ala
                    485                 490                 495

Ile Glu Glu Ser Asn His Ala Lys Asp Thr Val Thr Val Ile Glu Ala
                500                 505                 510

Pro Arg Gln Ser Asp Leu Leu Ile Glu Leu Ile Arg Lys Leu Lys Pro
                515                 520                 525

Gln Val Val Thr Gly Met Ala Gln Phe Glu Ala Ile Thr Ser Ala
            530                 535                 540

Ala Phe Val Asn Leu Leu Ser Val Thr Lys Asp Val Gly Ser Arg Leu
545                 550                 555                 560

Leu Leu Asp Ile Ser Glu His Leu Glu Leu Ser Ser Leu Pro Ser Ser
                565                 570                 575

Asn Gly Val Leu Lys Tyr Leu Ala Gly Lys Thr Leu Pro Ser His Ala
                580                 585                 590

Ala Ile Leu Cys Gly Leu Val Lys Asn Gln Val Tyr Ser Asp Leu Glu
                595                 600                 605

Val Ala Phe Ala Ile Ser Glu Asp Pro Thr Val Tyr Lys Ala Leu Ser
            610                 615                 620

Gln Thr Ile Glu Leu Leu Glu Gly His Thr Ser Val Ile Ser Gln His
625                 630                 635                 640

Tyr Tyr Gly Cys Leu Phe His Glu Leu Leu Ala Phe Gln Ile Gly Asp
                645                 650                 655

Arg His Pro Gln Gln Glu Arg Glu Pro Ala Glu Val Ile Ser Lys Glu
                660                 665                 670

Met Ile Gly Phe Ser Ser Ala Met Ser Thr Leu Gly Gly Ala Glu
                675                 680                 685

Phe Phe Val Pro Gly Ser Met Glu Ser Gly Val Ile His Met Asp Leu
            690                 695                 700

Asp Arg Ser Phe Leu Pro Val Pro Ser Ala Val Asn Ala Ser Ile Phe
705                 710                 715                 720

Glu Ser Phe Val Arg Gln Asn Ile Thr Asp Ser Glu Thr Asp Val Arg
                725                 730                 735

Ser Ser Ile Gln Gln Leu Val Lys Asp Ser Tyr Gly Phe Ser Ala Gly
                740                 745                 750

Gly Ala Ser Glu Ile Ile Tyr Gly Asn Thr Cys Leu Ala Leu Phe Asn
                755                 760                 765

Lys Leu Val Leu Cys Cys Met Gln Glu Gln Gly Thr Leu Leu Phe Pro
770                 775                 780

Leu Gly Thr Asn Gly His Tyr Val Asn Ala Ala Lys Phe Val Asn Ala
785                 790                 795                 800

Thr Thr Leu Thr Ile Pro Thr Lys Ala Asp Ser Gly Phe Lys Ile Glu
                805                 810                 815

Pro Ser Ala Leu Ala Asp Thr Leu Glu Lys Val Ser Gln Pro Trp Val
                820                 825                 830

Tyr Ile Ser Gly Pro Thr Ile Asn Pro Thr Gly Phe Leu Tyr Ser Asp
                835                 840                 845

Asp Asp Ile Ala Glu Leu Leu Ser Val Cys Ala Thr Tyr Gly Ala Arg
                850                 855                 860

Val Val Ile Asp Thr Ser Ser Ser Gly Leu Glu Phe Gln Ala Thr Gly
865                 870                 875                 880
```

-continued

```
Cys Ser Gln Trp Asn Leu Glu Arg Cys Leu Ser Asn Val Lys Ser Ser
                885                 890                 895

Lys Pro Ser Phe Ser Val Val Leu Leu Gly Glu Leu Ser Phe Glu Leu
            900                 905                 910

Thr Thr Ala Gly Leu Asp Phe Gly Phe Leu Ile Met Ser Asp Ser Ser
        915                 920                 925

Leu Val Asp Thr Phe Tyr Ser Phe Pro Ser Leu Ser Arg Pro His Ser
    930                 935                 940

Thr Leu Lys Tyr Thr Phe Arg Lys Leu Leu Gly Leu Lys Asn Gln Lys
945                 950                 955                 960

Asp Gln His Phe Ser Asp Leu Ile Leu Glu Gln Lys Glu Thr Leu Lys
                965                 970                 975

Asn Arg Ala Asp Gln Leu Ile Lys Thr Leu Glu Ser Cys Gly Trp Asp
            980                 985                 990

Ala Val Gly Cys His Gly Gly Ile Ser Met Leu Ala Lys Pro Thr Ala
        995                 1000                1005

Tyr Ile Gly Lys Ser Leu Lys Val Asp Gly Phe Glu Gly Lys Leu
    1010                1015                1020

Asp Ser His Asn Met Arg Glu Ala Leu Leu Arg Ser Thr Gly Leu
    1025                1030                1035

Cys Ile Ser Ser Ser Gly Trp Thr Gly Val Pro Asp Tyr Cys Arg
    1040                1045                1050

Phe Ser Phe Ala Leu Glu Ser Gly Asp Phe Asp Arg Ala Met Glu
    1055                1060                1065

Cys Ile Ala Arg Phe Arg Glu Leu Val Leu Gly Gly Ala Lys
    1070                1075                1080

Val Asn Gly Ser Asn
    1085

<210> SEQ ID NO 7
<211> LENGTH: 1088
<212> TYPE: PRT
<213> ORGANISM: Barley cv. Prestige

<400> SEQUENCE: 7

Met Ala Ala Ala Gly Asp Val Glu Ala Phe Leu Ala Ala Cys Gln
1               5                   10                  15

Ala Ser Gly Asp Ala Ala Tyr Gly Ala Ala Lys Ala Val Leu Glu Arg
            20                  25                  30

Leu Glu Ala Pro Ala Thr Arg Ala Glu Ala Arg Arg Leu Leu Gly Ala
        35                  40                  45

Val Arg Arg Arg Phe Ala Ala Gly Gly Pro Ala Ala Gly Leu Glu Cys
    50                  55                  60

Phe Arg Thr Phe His Phe Arg Ile His Asp Val Val Leu Asp Pro His
65                  70                  75                  80

Leu Gln Gly Phe Gln Gln Arg Lys Lys Leu Thr Met Met Glu Ile Pro
                85                  90                  95

Ser Ile Phe Ile Pro Glu Asp Trp Ser Phe Thr Phe Tyr Glu Gly Leu
            100                 105                 110

Asn Arg His Pro Asp Ser Ile Phe Arg Asp Lys Thr Val Ala Glu Leu
        115                 120                 125

Gly Cys Gly Asn Gly Trp Ile Ser Ile Ala Leu Ala Glu Lys Trp Cys
    130                 135                 140

Pro Ser Lys Val Tyr Gly Leu Asp Ile Asn Pro Arg Ala Ile Lys Ile
```

```
            145                 150                 155                 160
Ala Trp Ile Asn Leu Tyr Leu Asn Ala Leu Asp Asp Gly Leu Pro
                165                 170                 175
Ile Tyr Asp Ala Glu Gly Lys Thr Leu Leu Asp Arg Val Glu Phe Tyr
                180                 185                 190
Glu Ser Asp Leu Leu Ser Tyr Cys Arg Asp Asn Lys Ile Glu Leu Asp
                195                 200                 205
Arg Ile Val Gly Cys Ile Pro Gln Ile Leu Asn Pro Asn Pro Glu Ala
            210                 215                 220
Met Ser Lys Ile Val Thr Glu Asn Ser Ser Glu Glu Phe Leu Tyr Ser
225                 230                 235                 240
Leu Ser Asn Tyr Cys Ala Leu Gln Gly Phe Val Glu Asp Gln Phe Gly
                245                 250                 255
Leu Gly Leu Ile Ala Arg Ala Val Glu Glu Gly Ile Ser Val Ile Lys
                260                 265                 270
Pro Ser Gly Leu Met Val Phe Asn Met Gly Gly Arg Pro Gly Gln Gly
                275                 280                 285
Val Cys Glu Arg Leu Phe Leu Arg Arg Gly Phe Arg Ile Asn Lys Leu
            290                 295                 300
Trp Gln Thr Lys Ile Met Gln Ala Ala Asp Thr Asp Ile Ser Ala Leu
305                 310                 315                 320
Val Glu Ile Glu Lys Asn Ser Arg His Arg Phe Glu Phe Phe Met Asp
                325                 330                 335
Leu Val Gly Asp Gln Pro Val Cys Ala Arg Thr Ala Trp Ala Tyr Met
                340                 345                 350
Lys Ser Gly Gly Arg Ile Ser His Ala Leu Ser Val Tyr Ser Cys Gln
                355                 360                 365
Leu Arg Gln Pro Asn Gln Val Lys Lys Ile Phe Glu Phe Leu Lys Asp
            370                 375                 380
Gly Phe His Glu Val Ser Ser Leu Asp Leu Ser Phe Asp Asp
385                 390                 395                 400
Ser Val Ala Asp Glu Lys Ile Pro Phe Leu Ala Tyr Leu Ala Ser Phe
                405                 410                 415
Leu Gln Glu Asn Lys Ser Asn Pro Cys Glu Pro Pro Ala Gly Cys Leu
                420                 425                 430
Asn Phe Arg Asn His Val Ala Gly Phe Met Lys Ser Tyr His His Ile
            435                 440                 445
Pro Leu Thr Pro Asp Asn Val Val Phe Pro Ser Arg Ala Val Ala
450                 455                 460
Ile Glu Asn Ala Leu Arg Leu Phe Ser Pro Gly Leu Ala Ile Val Asp
465                 470                 475                 480
Glu His Leu Thr Arg His Leu Pro Lys Gln Trp Leu Thr Ser Leu Ala
                485                 490                 495
Ile Glu Glu Ser Asn His Ala Lys Asp Thr Val Thr Val Ile Glu Ala
                500                 505                 510
Pro Arg Gln Ser Asp Leu Leu Ile Glu Leu Ile Arg Lys Leu Lys Pro
            515                 520                 525
Gln Val Val Thr Gly Met Ala Gln Phe Glu Ala Ile Thr Ser Ala
                530                 535                 540
Ala Phe Val Asn Leu Leu Ser Val Thr Lys Asp Val Gly Ser Arg Leu
545                 550                 555                 560
Leu Leu Asp Ile Ser Glu His Leu Glu Leu Ser Ser Leu Pro Ser Ser
                565                 570                 575
```

```
Asn Gly Val Leu Lys Tyr Leu Ala Gly Lys Thr Leu Pro Ser His Ala
            580                 585                 590

Ala Ile Leu Cys Gly Leu Val Lys Asn Gln Val Tyr Ser Asp Leu Glu
        595                 600                 605

Val Ala Phe Ala Ile Ser Glu Asp Pro Thr Val Tyr Lys Ala Leu Ser
610                 615                 620

Gln Thr Ile Glu Leu Leu Glu Gly His Thr Ser Val Ile Ser Gln His
625                 630                 635                 640

Tyr Tyr Gly Cys Leu Phe His Glu Leu Leu Ala Phe Gln Ile Gly Asp
                645                 650                 655

Arg His Pro Gln Gln Glu Arg Glu Pro Ala Glu Val Ile Ser Lys Glu
                660                 665                 670

Met Ile Gly Phe Ser Ser Ala Met Ser Thr Leu Glu Gly Ala Glu
            675                 680                 685

Phe Phe Val Pro Gly Ser Met Glu Ser Gly Val Ile His Met Asp Leu
        690                 695                 700

Asp Arg Ser Phe Leu Pro Val Pro Ser Ala Val Asn Ala Ser Ile Phe
705                 710                 715                 720

Glu Ser Phe Val Arg Gln Asn Ile Thr Asp Ser Glu Thr Asp Val Arg
                725                 730                 735

Ser Ser Ile Gln Gln Leu Val Lys Asp Ser Tyr Gly Phe Ser Ala Gly
            740                 745                 750

Gly Ala Ser Glu Ile Ile Tyr Gly Asn Thr Cys Leu Ala Leu Phe Asn
        755                 760                 765

Lys Leu Val Leu Cys Cys Met Gln Glu Gln Gly Thr Leu Leu Phe Pro
770                 775                 780

Leu Gly Thr Asn Gly His Tyr Val Asn Ala Ala Lys Phe Val Asn Ala
785                 790                 795                 800

Thr Thr Leu Thr Ile Pro Thr Lys Ala Asp Ser Gly Phe Lys Ile Glu
                805                 810                 815

Pro Ser Ala Leu Ala Asp Thr Leu Glu Lys Val Ser Gln Pro Trp Val
            820                 825                 830

Tyr Ile Ser Gly Pro Thr Ile Asn Pro Thr Gly Phe Leu Tyr Ser Asp
        835                 840                 845

Asp Asp Ile Ala Glu Leu Leu Ser Val Cys Ala Thr Tyr Gly Ala Arg
850                 855                 860

Val Val Ile Asp Thr Ser Ser Ser Gly Leu Glu Phe Gln Ala Thr Gly
865                 870                 875                 880

Cys Ser Gln Trp Asn Leu Glu Arg Cys Leu Ser Asn Val Lys Ser Ser
                885                 890                 895

Lys Pro Ser Phe Ser Val Val Leu Leu Gly Glu Leu Ser Phe Glu Leu
            900                 905                 910

Thr Thr Ala Gly Leu Asp Phe Gly Phe Leu Ile Met Ser Asp Ser Ser
        915                 920                 925

Leu Val Asp Thr Phe Tyr Ser Phe Pro Ser Leu Ser Arg Pro His Ser
930                 935                 940

Thr Leu Lys Tyr Thr Phe Arg Lys Leu Leu Gly Leu Lys Asn Gln Lys
945                 950                 955                 960

Asp Gln His Phe Ser Asp Leu Ile Leu Glu Gln Lys Glu Thr Leu Lys
                965                 970                 975

Asn Arg Ala Asp Gln Leu Ile Lys Met Leu Glu Ser Cys Gly Trp Asp
            980                 985                 990
```

```
Ala Val Gly Cys His Gly Gly Ile Ser Met Leu Ala Lys Pro Thr Ala
        995                 1000                1005

Tyr Ile Ser Lys Ser Leu Lys Val Asp Gly Phe Glu Gly Lys Leu
    1010                1015                1020

Asp Ser His Asn Met Arg Glu Ala Leu Leu Arg Ser Thr Gly Leu
    1025                1030                1035

Cys Ile Ser Ser Ser Gly Trp Thr Gly Val Pro Asp Tyr Cys Arg
    1040                1045                1050

Phe Ser Phe Ala Leu Glu Ser Gly Asp Phe Asp Arg Ala Met Glu
    1055                1060                1065

Cys Ile Ala Arg Phe Arg Glu Leu Val Leu Gly Gly Gly Ala Lys
    1070                1075                1080

Val Asn Gly Ser Asn
    1085

<210> SEQ ID NO 8
<211> LENGTH: 6459
<212> TYPE: DNA
<213> ORGANISM: Barley, Mutant 8063

<400> SEQUENCE: 8
atggctgcgg cggcggggga cgtggaggcg ttcctggcgg cgtgccaggc gtcgggcgac      60
gcggcgtacg cgccgccaa ggccgtgctg gagcggctcg aggcgccggc cacgcgcgcc     120
gaggccaggc ggctcctcgg cgccgtgcga cggcgcttcg ccgccggcgg cccggccgcg     180
gggctcgagt gcttccgcac cttccacttc cgcatccacg acgtcgtcct cgacccccac     240
ctccaaggtt gcccggcccc ttccctacac acccgttgtc gacccgcatc tctttcgccg     300
atctggccgt caaaagcacg cggcttggta gaaatcaagc ctgcaatcct gatccgttta     360
tggctggcca gtcgatcagt aatttggcca taactggagt ataaccttgg tctctaatct     420
ctacctgacc atataccgag ttggtttttct tcttcttgt ttccgtattt gtgtagtttt     480
ttctttttctt tcgagcatga tgttctttga attaatgcgt accagactcc agtaattcga     540
cattttgaat tttggcgagt gttcttggaa tttataacac aacgaggctt tgatcaagtg     600
gtttatgtag aggagtgttt tgttcttgt gcaccgtata caattctcta tttcccaaca     660
attttgatgg cctctaagca tcctgtagtc atgtctactg tgtaagctac agattttattc     720
atgtctatgt gtaagctgca aatggagaga aaagctatct atttggttgt tccagcttgt     780
tctttggcag aacaatcctg cccatcctat caccataagt ataaaagcac gacaaatgag     840
tggggcaagc atgctgccaa gctaatacac gacataagct acatattttg agggggcatgt     900
tatcttttt tttccttct actcagtttc ttctttggga gaacaatcct actcaaccta     960
taatcataag aataaaagca agacagatga gtgctgcaga ctattggcat atataacaac    1020
taaataggac atctgtccgc tatatcttta gttaataatt gtatatagac gcagtctttg    1080
tgctggaaaa actgcaacta atatttttct tacattatat ggaatctggg tgtgatatga    1140
cttcttttgtt acgttttgtg tgcataaagc attaacttct gtctttagtt ggcgcagcgg    1200
taaaaacacc cattgcttaa tattttattt gctttccgta gcttgataaa atttcaactg    1260
cttctaggat tccagcaaag aaagaagcta acaatgatgg agatacccag cattttcatt    1320
ccagaagact ggtcattcac tttctacgag ggtctcaacc ggcatccaga ttccatcttc    1380
agggataaga cagtagcaga gctgggatgt ggcaatggtt ggatatccat tgcacttgca    1440
gaaaagtggt gcccttcgaa ggttggcacc tcttgttccg tagatattta tcttatctcg    1500
```

```
tttgttgcaa acatgggacc tgcagaagtt agacatttac tcaggttact ttatatgaaa    1560
cttttaggtg tctgccagta gtctgctggt ggtctaattt tcttggtata cctgatgccg    1620
tcgagcatat tgctttcaaa ttttgggcaa ggcattacca ccacatattg tttctacaat    1680
gctgaacaat tgctctcctt tgaaaggaag aaaaacaaga atgacatgca ccttagtagt    1740
ttaagccaca ataccagcg aatcaaatta gtttgcagtc agcttggcat taccttactt     1800
gagccttggt tgttctttg aaggtttatg gtctggatat aaacccaaga gctatcaaga     1860
ttgcatggat aaacctttac ttgaatgcac tagacgacga tggtctccca atctatgatg    1920
cggaggggaa acattgctt gacagagtcg aattctatga atctgatctt ctttcttact     1980
gtagagataa caagatagaa cttgatcgca ttgttggatg cataccacag gtacggtcag    2040
gttttttacca atttcctgtg aatgggggatt atagtcgatc agaacttgat caaaatgccc   2100
ttaatatctg cctttcagat tcttaaccccc aatccagagg caatgtcaaa gattgtaact    2160
gaaaattcaa gtgaggagtt cttgtactcc ttgagcaact actgtgctct ccaggtgagt    2220
tgagatctat ttaaactcaa gccattcagt ttacctgtta ctaaatggtt acccatgtca    2280
gagtctccaa atcttttct tttctcaaac agcaaagaga gaagaaaact tttaagttct      2340
atcctgaaat tgactttaca atgcttgttc ataatctgct tacgaaatat gcgtttgaac    2400
attttctctt tccttgtagg catgtggtca gacctttata taagaaaatg aagttttgt      2460
agaaataatg tatgctttgt acttatgaca tggttccacc agtataatca atttaagtct    2520
aggtagttag gaacctagga tggagagcac cgacagtgta taatatatat atgtcgatag    2580
gggggttagca gtccaaatcc acctcaagtt caacctattg cataactttt ggtcttacaa   2640
cctgtatgga caaatgtgat cagcaccca gtctttccta taaaaatgtc tgctggaata     2700
tggaattatt aacagcggta tttatttta ccctgtttaa ttttttcctt tgctaaaaga     2760
atgataatcc ttatgccacg aggttacatt gtattactca agtcaatatt tgttactatg    2820
gctgattgta cgattccagc ttccggttgt taattttgtt atgtttgtga actttgctgc    2880
attcagggtt tgttgagga ccaatttggc ctcgggttga ttgctcgggc tgttgaagaa     2940
gggatatctg tgataaagcc tagtggtctt atggtattca acatgggagg ccggccagga    3000
caaggtgtct gtgagcgcct atttctacgc cgtggatttc gcatcaataa gctctggcaa    3060
acaaaaatta tgcagatagc aattctttga gtgactagta gttaactaat cccagtgttt    3120
ttccatgcca gcaacagcat tatatcctgg ttagaggaat atgctcttca tgttgcacac    3180
caatcttcag ctgggcctag aattttcatc taccggctta catttttaca ttacagaacc    3240
aattttttgtt gaggatcatt accaactagt tgggtctttg caggctgctg acacagacat   3300
ctccgcttta gttgaaattg agaaaaatag ccgacatcgc ttcgagttct ttatggatct    3360
tgttggggat cagcctgtgt gtgcgcgcac agcatgggca tacatgaaat ctggtggccg    3420
catttcacat gctttgtctg tgtatagctg tcaacttcgc cagcccaacc aggtacctat    3480
actctctgat tagatcttta caacaataat atagtaatgt caggaataat aataatttgg    3540
agaatttcag gtgaagaaaa tatttgagtt ccttaaagac ggattccatg aagtcagcag    3600
ctccctcgat ttgtcctttg atgatgattc tgttgctgat gaaaaaattc ctttcctagc    3660
atacctagct agtttcttgc aagagaataa gtctaatcct tgtgagcctc cagctggatg    3720
tttaaatttc cggaatcttg ttgctggatt tatgaagagt taccaccaca tcccattaac    3780
tcctgatgta agcttggtg tctattgcct acaattatgt ttgcttatta gaaattcata     3840
agatcaacct atttgatgct tctcacgtat gcttcatgtg acacttcctt ttcctctggt    3900
```

```
gcaccagaat gttgttgtgt tcccatcccg tgctgttgca atcgaaaatg ctcttcggtt    3960
gttctcacct ggacttgcaa ttgttgacga acacctaacc agacacttgc ccaagcaatg    4020
gttaacatct ttagcaattg aggtactttg accgatactc ccctctttct ttctgtgttt    4080
ggaactgtgg aaaatacatg tgttctgtga agaaaaagtt atgctgacaa gaatttcgat    4140
gttattgcca ttcttctaaa tttcaggaaa gtaaccatgc taaagataca gtaactgtaa    4200
tcgaagcacc acgccaatca gatttgctga ttgagttgat caggaaactg aagcctcagg    4260
ttgttgttac tggcatggct cagtttgagg ctatcaccag tgctgctttc gtgaacttat    4320
taagtgtaac gaaagatgtt ggttcccgat tattactaga tatttcagaa catctggaat    4380
tgtctagtct gccaagctca aatggtgtat tgaaatatct tgctgggaag accctgcctt    4440
cacatgcggc tatattgtgt ggcttagtta agaatcaggt gtgtgtcaat cagcctgaac    4500
tctagttgaa ctgttgtgca tactatatag aatatcttga cttttatatg tactttagaa    4560
acactgttta aatgtactca tttcttttg cttcatttta cttgcaggtt tattctgatc    4620
tggaagttgc ttttgctatc tctgaagatc caactgttta taaggcattg tcacaaacta    4680
ttgagctatt ggaaggacat acttctgtga tcagccagca ctattatggt tgtcttttcc    4740
atgagctgct ggcatttcaa attggtgacc ggcatccaca acaagaggta aacatggctt    4800
gcctcttcca gttctccatc tcactcagtt ctgtccacaa ggtgccgaat gatctgttca    4860
agtggacact cccctcagca cgggcaagct agtccatgaa tttggattag ttccctctta    4920
gctgggtact tcgattacac cacaatgagc tcctcaacgt ggtctggttt atgttttca    4980 tgttttccct ctaatgtttg ttgctctttt tcagagaga acctgcagaa gtgatatcta    5040
aggagatgat agggttttca agttcagcta tgtccaccct agaaggagct gagttttcg    5100 ttcctggttc catggaatcc ggtgtcatac atatggatct ggaccgcagc ttcttgccag    5160
taccttctgc agtaaacgcc tccatttcg aaagttttgt tcgtcagaac atcactgatt    5220
ctgaaaccga tgtccgttcc agcattcagc agctggtgaa agatagctat ggtttctcag    5280
caggcggtgc ttctgaaatt atatacggga acacctgtct cgcgctcttc aacaagcttg    5340
ttctttgctg catgcaagaa cagggcacct tgcttttccc cttgggaacc aacgggcatt    5400
acgtcaacgc agcaaagttt gtgaatgcaa ccaccttgac tattccaacg aaggcagatt    5460
caggcttcaa gatcgaacca agtgctctag ccgacacact agagaaggtg tctcagccgt    5520
gggtctatat ttctggcccc acaatcaacc ctactggctt cctgtacagt gacgacgata    5580
tagcagagct gctttctgtc tgtgcgacat acggagccag ggtggtgata gatacctcct    5640
cctctggtct ggagttccaa gccaccggct gcagccagtg gaatttggaa agatgtcttt    5700
ctaatgtcaa gtcttcaaag ccctcgttct ccgttgtcct gctcggagag ctgtcctttg    5760
agctgaccac ggctgggctt gatttcgggt ttctgattat gagcgactcg tccttggttg    5820
acacatttta cagtttccca agcttgagtc ggccacacag cacgttgaag tacacgttca    5880
ggaagctgtt gggtcttaag aaccagaagg atcagcattt ctctgatctc atccttgagc    5940
agaaggagac gttgaagaat cgtgccgacc agttgatcaa ggtatgcctt ttgggatatc    6000
ctgtgtttag gctctctgtt ttcttcccct gatcagctct ccgatcccct tacatcctta    6060
ggctaatttc agtacttcaa gtttgccacg catttctgac atattctttc ctcttgtttt    6120
attttcctgt gatgtgatga acagacgctt gagagctgcg gctgggacgc tgtgggctgc    6180
catggcggca tctcgatgct tgcaaaaccg accgcctaca ttggcaaatc gctcaaggtg    6240
```

```
gacggctttg agggcaagct ggacagccac aacatgaggg aagccctcct gaggtccacc      6300
gggctgtgca ttagcagcag cgggtggaca ggggtgccgg actactgccg cttcagcttt      6360
gctctggaga gcggcgactt cgaccgggcc atggagtgca tcgcccggtt cagggagctg      6420
gtccttggtg gcggtgctaa ggtgaatggt agcaactag                             6459

<210> SEQ ID NO 9
<211> LENGTH: 882
<212> TYPE: DNA
<213> ORGANISM: Barley cv. Prestige

<400> SEQUENCE: 9
gtttatggtc tggatataaa cccaagagct atcaagattg catggataaa cctttacttg       60
aatgcactag acgacgatgg tctcccaatc tatgatgcgg aggggaaaac attgcttgac      120
agagtcgaat tctatgaatc tgatcttctt tcttactgta gagataacaa gatagaactt      180
gatcgcattg ttggatgcat accacagatt cttaaccccc atccagaggc aatgtcaaag      240
attgtaactg aaaaattcaag tgaggagttc ttgtactcct tgagcaacta ctgtgctctc      300
cagggttttg ttgaggacca atttggcctc gggttgattg ctcgggctgt tgaagaaggg      360
atatctgtga taaagcctag tggtcttatg gtattcaaca tgggaggccg gccaggacaa      420
ggtgtctgtg agcgcctatt tcttcgccgt ggatttcgca tcaataagct ctggcaaaca      480
aaaattatgc aggctgctga cacagacatc tccgctttag ttgaaattga gaaaatagc       540 cgacatcgct tcgagttctt tatggatctt gttggggatc agcctgtgtg tgcgcgcaca      600
gcatgggcat acatgaaatc tggtggccgc atttcacatg ctttgtctgt gtatagctgt      660
caacttcgcc agcccaacca ggtgaagaaa atatttgagt tccttaaaga cggattccat      720
gaagtcagca gctccctcga tttgtccttt gatgatgatt ctgttgctga tgaaaaaatt      780
cctttcctag catacctagc tagttttcttg caagagaata agtctaatcc ttgtgagcct      840
ccagctggat gtttaaattt ccggaatctt gttgctggat tt                         882

<210> SEQ ID NO 10
<211> LENGTH: 1089
<212> TYPE: DNA
<213> ORGANISM: Barley, Mutant 8063

<400> SEQUENCE: 10
gtttatggtc tggatataaa cccaagagct atcaagattg catggataaa cctttacttg       60
aatgcactag acgacgatgg tctcccaatc tatgatgcgg aggggaaaac attgcttgac      120
agagtcgaat tctatgaatc tgatcttctt tcttactgta gagataacaa gatagaactt      180
gatcgcattg ttggatgcat accacagatt cttaaccccc atccagaggc aatgtcaaag      240
attgtaactg aaaaattcaag tgaggagttc ttgtactcct tgagcaacta ctgtgctctc      300
caggttttgt tgaggaccaa tttggcctcg ggttgattgc tcgggctgtt gaagaaggga      360
tatctgtgat aaagcctagt ggtcttatgg tattcaacat gggaggccgg ccaggacaag      420
gtgtctgtga gcgcctattt ctacgccgtg gatttcgcat caataagctc tggcaaacaa      480
aaattatgca gatagcaatt cttcgagtga ctagatgtta actaatccca gtgttttcc       540 atgccagcaa cagcattgta tcctggttag aggaatatgc tcttcatgtt gcacaccaat      600
cttcatctgg acctggaatt ttcatctacc ggcttacatt tttacattac agaaccaatt      660
tttgttgagg atcattacca actagttggg tctttgcagg ctgctgacac agacatctcc      720
gctttagttg aaattgagaa aaatagccga catcgcttcg agttctttat ggatcttgtt      780
```

```
gggatcagc ctgtgtgtgc gcgcacagca tgggcataca tgaaatctgg tggccgcatt    840
tcacatgctt tgtctgtgta tagctgtcaa cttcgccagc ccaaccaggt gaagaaaata    900
tttgagttcc ttaaagacgg attccatgaa gtcagcagct ccctcgattt gtcctttgat    960
gatgattctg ttgctgatga aaaaattcct ttcctagcat acctagctag tttcttgcaa   1020
gagaataagt ctaatccttg tgagcctcca gctggatgtt taaatttccg gaatcttgtt   1080
gctggattt                                                           1089
```

<210> SEQ ID NO 11
<211> LENGTH: 315
<212> TYPE: PRT
<213> ORGANISM: Barley, Mutant 8063

<400> SEQUENCE: 11

```
Met Ala Ala Ala Gly Asp Val Glu Ala Phe Leu Ala Ala Cys Gln
 1               5                  10                  15

Ala Ser Gly Asp Ala Ala Tyr Gly Ala Lys Ala Val Leu Glu Arg
                20                  25                  30

Leu Glu Ala Pro Ala Thr Arg Ala Glu Ala Arg Arg Leu Leu Gly Ala
                35                  40                  45

Val Arg Arg Phe Ala Ala Gly Gly Pro Ala Ala Gly Leu Glu Cys
 50                  55                  60

Phe Arg Thr Phe His Phe Arg Ile His Asp Val Val Leu Asp Pro His
 65                  70                  75                  80

Leu Gln Gly Phe Gln Gln Arg Lys Lys Leu Thr Met Met Glu Ile Pro
                 85                  90                  95

Ser Ile Phe Ile Pro Glu Asp Trp Ser Phe Thr Phe Tyr Glu Gly Leu
                100                 105                 110

Asn Arg His Pro Asp Ser Ile Phe Arg Asp Lys Thr Val Ala Glu Leu
                115                 120                 125

Gly Cys Gly Asn Gly Trp Ile Ser Ile Ala Leu Ala Glu Lys Trp Cys
                130                 135                 140

Pro Ser Lys Val Tyr Gly Leu Asp Ile Asn Pro Arg Ala Ile Lys Ile
145                 150                 155                 160

Ala Trp Ile Asn Leu Tyr Leu Asn Ala Leu Asp Asp Gly Leu Pro
                165                 170                 175

Ile Tyr Asp Ala Glu Gly Lys Thr Leu Leu Asp Arg Val Glu Phe Tyr
                180                 185                 190

Glu Ser Asp Leu Leu Ser Tyr Cys Arg Asp Asn Lys Ile Glu Leu Asp
                195                 200                 205

Arg Ile Val Gly Cys Ile Pro Gln Ile Leu Asn Pro Asn Pro Glu Ala
                210                 215                 220

Met Ser Lys Ile Val Thr Glu Asn Ser Ser Glu Glu Phe Leu Tyr Ser
225                 230                 235                 240

Leu Ser Asn Tyr Cys Ala Leu Gln Gly Phe Val Glu Asp Gln Phe Gly
                245                 250                 255

Leu Gly Leu Ile Ala Arg Ala Val Glu Glu Gly Ile Ser Val Ile Lys
                260                 265                 270

Pro Ser Gly Leu Met Val Phe Asn Met Gly Gly Arg Pro Gly Gln Gly
                275                 280                 285

Val Cys Glu Arg Leu Phe Leu Arg Arg Gly Phe Arg Ile Asn Lys Leu
                290                 295                 300

Trp Gln Thr Lys Ile Met Gln Ile Ala Ile Leu
```

<210> SEQ ID NO 12
<211> LENGTH: 955
<212> TYPE: DNA
<213> ORGANISM: Barley, Mutant 8063

<400> SEQUENCE: 12

```
gtttatggtc tggatataaa cccaagagct atcaagattg catggataaa cctttacttg      60
aatgcactag acgacgatgg tctcccaatc tatgatgcgg aggggaaaac attgcttgac     120
agagtcgaat ctatgaatc tgatcttctt tcttactgta gagataacaa gatagaactt     180
gatcgcattg ttggatgcat accacagatt cttaaccca atccagaggc aatgtcaaag     240
attgtaactg aaaattcaag tgaggagttc ttgtactcct tgagcaacta ctgtgctctc     300
caggttttgt tgaggaccaa tttggcctcg ggttgattgc tcgggctgtt gaagaaggga     360
tatctgtgat aaagcctagt ggtcttatgg tattcaacat ggggccgg ccaggacaag      420
gtgtctgtga gcgccatttt ctacgccgtg gatttcgcat caataagctc tggcaaacaa     480
aaattatgca gatagcaatt cttcgagtga ctagatgtta actaatccca gtgttttcc      540
atgccagcaa cagcattgta tcctggctgc tgacacagac atctccgctt tagttgaaat     600
tgagaaaaat agccgacatc gcttcgagtt ctttatggat cttgttgggg atcagcctgt     660
gtgtgcgcgc acagcatggg catacatgaa atctggtggc cgcatttcac atgctttgtc     720
tgtgtatagc tgtcaacttc gccagcccaa ccaggtgaag aaaatatttg agttccttaa     780
agacggattc catgaagtca gcagctccct cgatttgtcc tttgatgatg attctgttgc     840
tgatgaaaaa attcctttcc tagcatacct agctagtttc ttgcaagaga ataagtctaa     900
tccttgtgag cctccagctg gatgtttaaa tttccggaat cttgttgctg gattt          955
```

<210> SEQ ID NO 13
<211> LENGTH: 315
<212> TYPE: PRT
<213> ORGANISM: Barley, Mutant 8063

<400> SEQUENCE: 13

```
Met Ala Ala Ala Gly Asp Val Glu Ala Phe Leu Ala Ala Cys Gln
1               5                   10                  15

Ala Ser Gly Asp Ala Ala Tyr Gly Ala Ala Lys Ala Val Leu Glu Arg
            20                  25                  30

Leu Glu Ala Pro Ala Thr Arg Ala Glu Ala Arg Arg Leu Leu Gly Ala
        35                  40                  45

Val Arg Arg Arg Phe Ala Ala Gly Gly Pro Ala Ala Gly Leu Glu Cys
    50                  55                  60

Phe Arg Thr Phe His Phe Arg Ile His Asp Val Leu Asp Pro His
65                  70                  75                  80

Leu Gln Gly Phe Gln Gln Arg Lys Lys Leu Thr Met Met Glu Ile Pro
                85                  90                  95

Ser Ile Phe Ile Pro Glu Asp Trp Ser Phe Thr Phe Tyr Glu Gly Leu
            100                 105                 110

Asn Arg His Pro Asp Ser Ile Phe Arg Asp Lys Thr Val Ala Glu Leu
        115                 120                 125

Gly Cys Gly Asn Gly Trp Ile Ser Ile Ala Leu Ala Glu Lys Trp Cys
    130                 135                 140

Pro Ser Lys Val Tyr Gly Leu Asp Ile Asn Pro Arg Ala Ile Lys Ile
145                 150                 155                 160
```

```
Ala Trp Ile Asn Leu Tyr Leu Asn Ala Leu Asp Asp Gly Leu Pro
            165                 170                 175

Ile Tyr Asp Ala Glu Gly Lys Thr Leu Leu Asp Arg Val Glu Phe Tyr
            180                 185                 190

Glu Ser Asp Leu Leu Ser Tyr Cys Arg Asp Asn Lys Ile Glu Leu Asp
            195                 200                 205

Arg Ile Val Gly Cys Ile Pro Gln Ile Leu Asn Pro Asn Pro Glu Ala
        210                 215                 220

Met Ser Lys Ile Val Thr Glu Asn Ser Glu Glu Phe Leu Tyr Ser
225                 230                 235                 240

Leu Ser Asn Tyr Cys Ala Leu Gln Gly Phe Val Glu Asp Gln Phe Gly
            245                 250                 255

Leu Gly Leu Ile Ala Arg Ala Val Glu Glu Gly Ile Ser Val Ile Lys
            260                 265                 270

Pro Ser Gly Leu Met Val Phe Asn Met Gly Gly Arg Pro Gly Gln Gly
            275                 280                 285

Val Cys Glu Arg Leu Phe Leu Arg Arg Gly Phe Arg Ile Asn Lys Leu
        290                 295                 300

Trp Gln Thr Lys Ile Met Gln Ile Ala Ile Leu
305                 310                 315
```

<210> SEQ ID NO 14
<211> LENGTH: 810
<212> TYPE: DNA
<213> ORGANISM: Barley, Mutant 8063

<400> SEQUENCE: 14

```
gtttatggtc tggatataaa cccaagagct atcaagattg catggataaa cctttacttg    60
aatgcactag acgacgatgg tctcccaatc tatgatgcgg aggggaaaac attgcttgac   120
agagtcgaat tctatgaatc tgatcttctt tcttactgta gagataacaa gatagaactt   180
gatcgcattg ttggatgcat accacagatt cttaaccccca atccagaggc aatgtcaaag   240
attgtaactg aaaattcaag tgaggagttc ttgtactcct tgagcaacta ctgtgctctc   300
caggttttgt tgaggaccaa tttggcctcg ggttgattgc tcgggctgtt gaagaaggga   360
tatctgtgat aaagcctagt ggtcttatgg tattcaacat gggaggccgg ccaggacaag   420
gctgctgaca cagacatctc cgctttagtt gaaattgaga aaaatagccg acatcgcttc   480
gagttcttta tggatcttgt tggggatcag cctgtgtgtg cgcgcacagc atgggcatac   540
atgaaatctg gtggccgcat ttcacatgct ttgtctgtgt atagctgtca acttcgccag   600
cccaaccagg tgaagaaaat atttgagttc cttaaagacg gattccatga agtcagcagc   660
tccctcgatt tgtcctttga tgatgattct gttgctgatg aaaaaattcc tttcctagca   720
tacctagcta gtttcttgca agagaataag tctaatcctt gtgagcctcc agctggatgt   780
ttaaatttcc ggaatcttgt tgctggattt                                    810
```

<210> SEQ ID NO 15
<211> LENGTH: 289
<212> TYPE: PRT
<213> ORGANISM: Barley, Mutant 8063

<400> SEQUENCE: 15

```
Met Ala Ala Ala Ala Gly Asp Val Glu Ala Phe Leu Ala Ala Cys Gln
1               5                   10                  15

Ala Ser Gly Asp Ala Ala Tyr Gly Ala Ala Lys Ala Val Leu Glu Arg
```

```
                    20                  25                  30
Leu Glu Ala Pro Ala Thr Arg Ala Glu Ala Arg Arg Leu Leu Gly Ala
                35                  40                  45

Val Arg Arg Arg Phe Ala Ala Gly Gly Pro Ala Gly Leu Glu Cys
        50                  55                  60

Phe Arg Thr Phe His Phe Arg Ile His Asp Val Val Leu Asp Pro His
65                  70                  75                  80

Leu Gln Gly Phe Gln Gln Arg Lys Lys Leu Thr Met Met Glu Ile Pro
                85                  90                  95

Ser Ile Phe Ile Pro Glu Asp Trp Ser Phe Thr Phe Tyr Glu Gly Leu
            100                 105                 110

Asn Arg His Pro Asp Ser Ile Phe Arg Asp Lys Thr Val Ala Glu Leu
        115                 120                 125

Gly Cys Gly Asn Gly Trp Ile Ser Ile Ala Leu Ala Glu Lys Trp Cys
    130                 135                 140

Pro Ser Lys Val Tyr Gly Leu Asp Ile Asn Pro Arg Ala Ile Lys Ile
145                 150                 155                 160

Ala Trp Ile Asn Leu Tyr Leu Asn Ala Leu Asp Asp Gly Leu Pro
                165                 170                 175

Ile Tyr Asp Ala Glu Gly Lys Thr Leu Leu Asp Arg Val Glu Phe Tyr
            180                 185                 190

Glu Ser Asp Leu Leu Ser Tyr Cys Arg Asp Asn Lys Ile Glu Leu Asp
        195                 200                 205

Arg Ile Val Gly Cys Ile Pro Gln Ile Leu Asn Pro Asn Pro Glu Ala
    210                 215                 220

Met Ser Lys Ile Val Thr Glu Asn Ser Ser Glu Glu Phe Leu Tyr Ser
225                 230                 235                 240

Leu Ser Asn Tyr Cys Ala Leu Gln Gly Phe Val Glu Asp Gln Phe Gly
                245                 250                 255

Leu Gly Leu Ile Ala Arg Ala Val Glu Glu Gly Ile Ser Val Ile Lys
            260                 265                 270

Pro Ser Gly Leu Met Val Phe Asn Met Gly Gly Arg Pro Gly Gln Gly
        275                 280                 285

Cys

<210> SEQ ID NO 16
<211> LENGTH: 6459
<212> TYPE: DNA
<213> ORGANISM: Barley cv. Sebastian

<400> SEQUENCE: 16
atggctgcgg cggcggggga cgtggaggcg ttcctggcgg cgtgccaggc gtcgggcgac    60
gcggcgtacg gcgccgccaa ggccgtgctg gagcggctcg aggcgccggc cacgcgcgcc   120
gaggccaggc ggctcctcgg cgccgtgcga cggcgcttcg ccgccggcgg cccggccgcg   180
gggctcgagt gcttccgcac cttccacttc cgcatccacg acgtcgtcct cgaccccac   240 ctccaaggtt gcccggcccc ttccctacac acccgttgtc gacccgcatc tctttcgccg   300
atctggccgt caaaagcacg cggcttggta gaaatcaagc ctgcaatcct gatccgttta   360
tggctggcca gtcgatcagt aatttggcca taactggagt ataaccttgg tctctaatct   420
ctacctgacc atataccgag ttggtttcct ttcttcttgt ttccgtattt gtgtagtttt   480
ttcttttctt tcgagcatga tgttctttga attaatgcgt accagactcc agtaattcga   540
cattttgaat tttggcgagt gttcttggaa tttataacac aacgaggctt tgatcaagtg   600
```

```
gtttatgtag aggagtgttt ttgttcttgt gcaccgtata caattctcta tttcccaaca    660
attttgatgg cctctaagca tcctgtagtc atgtctactg tgtaagctac agatttattc    720
atgtctatgt gtaagctgca aatggagaga aaagctatct atttggttgt tccagcttgt    780
tctttggcag aacaatcctg cccatcctat caccataagt ataaaagcac gacaaatgag    840
tggggcaagc atgctgccaa gctaatacac gacataagct acatattttg aggggcatgt    900 tatcttttt  tttcccttct actcagtttc ttctttggga gaacaatcct actcaaccta    960
taatcataag aataaaagca agacagatga gtgctgcaga ctattggcat atataacaac   1020
taaataggac atctgtccgc tatatcttta gttaataatt gtatatagac gcagtctttg   1080
tgctggaaaa actgcaacta aatattttct tacattatat ggaatctggg tgtgatatga   1140
cttctttgtt acgttttgtg tgcataaagc attaacttct gtctttagtt ggcgcagcgg   1200
taaaaacacc cattgcttaa tattttattt gctttccgta gcttgataaa atttcaactg   1260
cttctaggat tccagcaaag aaagaagcta acaatgatgg agatacccag cattttcatt   1320
ccagaagact ggtcattcac tttctacgag ggtctcaacc ggcatccaga ttccatcttc   1380
agggataaga cagtagcaga gctgggatgt ggcaatggtt ggatatccat tgcacttgca   1440
gaaaagtggt gcccttcgaa ggttggcacc tcttgttccg tagatattta tcttatctcg   1500
tttgttgcaa acatgggacc tgcagaagtt agacatttac tcaggttact ttatatgaaa   1560
cttttaggtg tctgccagta gtctgctggt ggtctaattt tcttggtata cctgatgccg   1620
tcgagcatat tgcttttcaaa ttttgggcaa ggcattacca ccacatattg tttctacaat   1680
gctgaacaat tgctctcctt tgaaaggaag aaaaacaaga atgacatgca ccttagtagt   1740
ttaagccaca ataccagcg  aatcaaatta gtttgcagtc agcttggcat taccttactt   1800
gagccttggt tgttcttttg aaggtttatg gtctggatat aaacccaaga gctatcaaga   1860
ttgcatggat aaacctttac ttgaatgcac tagacgacga tggtctccca atctatgatg   1920
cggaggggaa acattgctt  gacagagtcg aattctatga atctgatctt ctttcttact   1980
gtagagataa caagatagaa cttgatcgca ttgttggatg cataccacag gtacggtcag   2040 gttttacca  atttcctgtg aatggggatt atagtcgatc agaacttgat caaaatgccc   2100
ttaatatctg cctttcagat tcttaacccc aatccagagg caatgtcaaa gattgtaact   2160
gaaaattcaa gtgaggagtt cttgtactcc ttgagcaact actgtgctct ccaggtgagt   2220
tgagatctat ttaaactcaa gccattcagt ttacctgtta ctaaatggtt acccatgtca   2280
gagtctccaa atctttttct tttctcaaac agcaaagaga gaagaaaact tttaagttct   2340
atcctgaaat tgactttaca atgcttgttc ataatctgct tacgaaatat gcgtttgaac   2400
atttctcttt tccttgtagg catgtggtca gacctttata taagaaaatg aagttttgt    2460 agaaataatg tatgctttgt acttatgaca tggttccacc agtataatca atttaagtct   2520
aggtagttag gaacctagga tggagagcac cgacagtgta taatatatat atgtcgatag   2580
ggggttagca gtccaaatcc acctcaagtt caacctattg cataacttt  ggtcttacaa   2640 cctgtatgga caaatgtgat cagcaccca  gtctttccta aaaaatgtc  tgctggaata   2700 tggaattatt aacagcggta tttattttta ccctgtttaa ttttttcctt tgctaaaaga   2760
atgataatcc ttatgccacg aggttacatt gtattactca agtcaatatt tgttactatg   2820
gctgattgta cgattccagc ttccggttgt taatttgtt atgtttgtga actttgctgc    2880
attcagggtt ttgttgagga ccaatttggc ctcgggttga ttgctcgggc tgttgaagaa   2940
```

```
gggatatctg tgataaagcc tagtggtctt atggtattca acatgggagg ccggccagga    3000
caaggtgtct gtgagcgcct atttctacgc cgtggatttc gcatcaataa gctctggcaa    3060
acaaaaatta tgcaggtagc aattctttga gtgactagat gttaactaat cccagtgttt    3120
ttccatgcca gcaacagcat tatatcctgg ttagaggaat atgctcttca tgttgcacac    3180
caatcttcag ctgggcctag aattttcatc taccggctta cattttaca ttacagaacc     3240 aattttgtt gaggatcatt accaactagt tgggtctttg caggctgctg acacagacat     3300
ctccgcttta gttgaaattg agaaaaatag ccgacatcgc ttcgagttct ttatggatct    3360
tgttggggat cagcctgtgt gtgcgcgcac agcatgggca tacatgaaat ctggtggccg    3420
catttcacat gctttgtctg tgtatagctg tcaacttcgc cagcccaacc aggtacctat    3480
actctctgat tagatctta caacaataat atagtaatgt caggaataat aataatttgg     3540
agaatttcag gtgaagaaaa tatttgagtt ccttaaagac ggattccatg aagtcagcag    3600
ctccctcgat ttgtcctttg atgatgattc tgttgctgat gaaaaaattc ctttcctagc    3660
atacctagct agtttcttgc aagagaataa gtctaatcct tgtgagcctc cagctggatg    3720
tttaaatttc cggaatcttg ttgctggatt tatgaagagt taccaccaca tcccattaac    3780
tcctgatgta agacttggtg tctattgcct acaattatgt tgcttatta gaaattcata     3840 agatcaacct atttgatgct tctcacgtat gcttcatgtg acacttcctt ttcctctggt    3900
gcaccagaat gttgttgtgt tcccatcccg tgctgttgca atcgaaaatg ctcttcggtt    3960
gttctcacct ggacttgcaa ttgttgacga acacctaacc agacacttgc ccaagcaatg    4020
gttaacatct ttagcaattg aggtactttg accgatactc ccctcttcct ttctgtgttt    4080
ggaactgtgg aaaatacatg tgttctgtga agaaaaagtt atgctgacaa gaatttcgat    4140
gttattgcca ttcttctaaa tttcaggaaa gtaaccatgc taaagataca gtaactgtaa    4200
tcgaagcacc acgccaatca gatttgctga ttgagttgat caggaaactg aagcctcagg    4260
ttgttgttac tggcatggct cagtttgagg ctatcaccag tgctgctttc gtgaacttat    4320
taagtgtaac gaaagatgtt ggttcccgat tattactaga tatttcagaa catctggaat    4380
tgtctagtct gccaagctca aatggtgtat tgaaatatct tgctgggaag accctgcctt    4440
cacatgcggc tatattgtgt ggcttagtta agaatcaggt gtgtgtcaat cagcctgaac    4500
tctagttgaa ctgttgtgca tactatatag aatatcttga cttttatatg tactttagaa    4560
acactgttta aatgtactca tttctttttg cttcatttta cttgcaggtt tattctgatc    4620
tggaagttgc ttttgctatc tctgaagatc caactgttta taaggcattg tcacaaacta    4680
ttgagctatt ggaaggacat acttctgtga tcagccagca ctattatggt tgtcttttcc    4740
atgagctgct ggcatttcaa attggtgacc ggcatccaca acaagaggta acatggcttt    4800
gcctcttcca gttctccatc tcactcagtt ctgtccacaa ggtgccgaat gatctgttca    4860
agtggacact ccctcagca cgggcaagct agtccatgaa tttggattag ttccctctta    4920
gctgggtact tcgattacac cacaatgagc tcctcaacgt ggtctggttt atgttttca     4980 tgttttccct ctaatgtttg gttgctcttt tcagagaga acctgcagaa gtgatatcta     5040
aggagatgat agggttttca agttcagcta tgtccaccct agaaggagct gagttttcg     5100 ttcctggttc catggaatcc ggtgtcatac atatggatct ggaccgcagc ttcttgccag    5160
taccttctgc agtaaacgcc tccatttcg aaagttttgt tcgtcagaac atcactgatt     5220
ctgaaaccga tgtccgttcc agcattcagc agctggtgaa agatagctat ggtttctcag    5280
caggcggtgc ttctgaaatt atatacggga acacctgtct cgcgctcttc aacaagcttg    5340
```

```
ttctttgctg catgcaagaa cagggcacct tgcttttccc cttgggaacc aacgggcatt    5400
acgtcaacgc agcaaagttt gtgaatgcaa ccaccttgac tattccaacg aaggcagatt    5460
caggcttcaa gatcgaacca agtgctctag ccgacacact agagaaggtg tctcagccgt    5520
gggtctatat ttctggcccc acaatcaacc ctactggctt cctgtacagt gacgacgata    5580
tagcagagct gctttctgtc tgtgcgacat acggagccag ggtggtgata gatacctcct    5640
cctctggtct ggagttccaa gccaccggct gcagccagtg gaatttggaa agatgtcttt    5700
ctaatgtcaa gtcttcaaag ccctcgttct ccgttgtcct gctcggagag ctgtcctttg    5760
agctgaccac ggctgggctt gatttcgggt ttctgattat gagcgactcg tccttggttg    5820
acacatttta cagtttccca agcttgagtc ggccacacag cacgttgaag tacacgttca    5880
ggaagctgtt gggtcttaag aaccagaagg atcagcattt ctctgatctc atccttgagc    5940
agaaggagac gttgaagaat cgtgccgacc agttgatcaa ggtatgcctt ttgggatatc    6000
ctgtgtttag gctctctgtt ttcttcccct gatcagctct ccgatcccct tacatcctta    6060
ggctaatttc agtacttcaa gtttgccacg catttctgac atattctttc ctcttgtttt    6120
attttcctgt gatgtgatga acagacgctt gagagctgcg gctgggacgc tgtgggctgc    6180
catggcggca tctcgatgct tgcaaaaccg accgcctaca ttggcaaatc gctcaaggtg    6240
gacggctttg agggcaagct ggacagccac aacatgaggg aagccctcct gaggtccacc    6300
gggctgtgca ttagcagcag cgggtggaca ggggtgccgg actactgccg cttcagcttt    6360
gctctggaga gcggcgactt cgaccgggcc atggagtgca tcgcccggtt cagggagctg    6420
gtccttggtg gcggtgctaa ggtgaatggt agcaactag                          6459
```

<210> SEQ ID NO 17
<211> LENGTH: 3267
<212> TYPE: DNA
<213> ORGANISM: Barley cv. Sebastian

<400> SEQUENCE: 17

```
atggctgcgg cggcggggga cgtggaggcg ttcctggcgg cgtgccaggc gtcgggcgac      60
gcggcgtacg gcgccgccaa ggccgtgctg gagcggctcg aggcgccggc cacgcgcgcc     120
gaggccaggc ggctcctcgg cgccgtgcga cggcgcttcg ccgccggcgg cccggccgcg     180
gggctcgagt gcttccgcac cttccacttc cgcatccacg acgtcgtcct cgaccccac      240 ctccaaggat tccagcaaag aaagaagcta acaatgatgg agatacccag cattttcatt     300
ccagaagact ggtcattcac tttctacgag gtctcaacc ggcatccaga ttccatcttc      360
agggataaga cagtagcaga gctgggatgt ggcaatggtt ggatatccat tgcacttgca     420
gaaaagtggt gcccttcgaa ggtttatggt ctggatataa acccaagagc tatcaagatt     480
gcatggataa accttactt gaatgcacta gacgacgatg gtctcccaat ctatgatgcg     540 gagggggaaaa cattgcttga cagagtcgaa ttctatgaat ctgatcttct ttcttactgt     600
agagataaca agatagaact tgatcgcatt gttggatgca taccacagat tcttaacccc     660
aatccagagg caatgtcaaa gattgtaact gaaaattcaa gtgaggagtt cttgtactcc     720
ttgagcaact actgtgctct ccagggtttt gttgaggacc aatttggcct cgggttgatt     780
gctcgggctg ttgaagaagg gatatctgtg ataaagccta gtggtcttat ggtattcaac     840
atgggaggcc ggccaggaca aggtgtctgt gagcgcctat ttctacgccg tggatttcgc     900
atcaataagc tctggcaaac aaaaattatg caggctgctg acacagacat ctccgcttta     960
```

-continued

| | |
|---|---|
| gttgaaattg agaaaaatag ccgacatcgc ttcgagttct ttatggatct tgttggggat | 1020 |
| cagcctgtgt gtgcgcgcac agcatgggca tacatgaaat ctggtggccg catttcacat | 1080 |
| gctttgtctg tgtatagctg tcaacttcgc cagcccaacc aggtgaagaa aatatttgag | 1140 |
| ttccttaaag acggattcca tgaagtcagc agctccctcg atttgtcctt tgatgatgat | 1200 |
| tctgttgctg atgaaaaaat tcctttccta gcatacctag ctagtttctt gcaagagaat | 1260 |
| aagtctaatc cttgtgagcc tccagctgga tgtttaaatt tccggaatct tgttgctgga | 1320 |
| tttatgaaga gttaccacca catcccatta actcctgata atgttgttgt gttcccatcc | 1380 |
| cgtgctgttg caatcgaaaa tgctcttcgg ttgttctcac ctggacttgc aattgttgac | 1440 |
| gaacacctaa ccagacactt gcccaagcaa tggttaacat ctttagcaat tgaggaaagt | 1500 |
| aaccatgcta agatacagt aactgtaatc gaagcaccac gccaatcaga tttgctgatt | 1560 |
| gagttgatca ggaaactgaa gcctcaggtt gttgttactg gcatggctca gtttgaggct | 1620 |
| atcaccagtg ctgctttcgt gaacttatta agtgtaacga agatgttgg ttcccgatta | 1680 |
| ttactagata tttcagaaca tctggaattg tctagtctgc caagctcaaa tggtgtattg | 1740 |
| aaatatcttg ctgggaagac cctgccttca catgcggcta tattgtgtgg cttagttaag | 1800 |
| aatcaggttt attctgatct ggaagttgct tttgctatct ctgaagatcc aactgtttat | 1860 |
| aaggcattgt cacaaactat tgagctattg aaggacata cttctgtgat cagccagcac | 1920 |
| tattatggtt gtcttttcca tgagctgctg gcatttcaaa ttggtgaccg gcatccacaa | 1980 |
| caagagagag aacctgcaga agtgatatct aaggagatga tagggttttc aagttcagct | 2040 |
| atgtccaccc tagaaggagc tgagttttc gttcctggtt ccatggaatc cggtgtcata | 2100 |
| catatggatc tggaccgcag cttcttgcca gtaccttctg cagtaaacgc ctccattttc | 2160 |
| gaaagttttg ttcgtcagaa catcactgat tctgaaaccg atgtccgttc cagcattcag | 2220 |
| cagctggtga agatagcta tggtttctca gcaggcggtg cttctgaaat tatatacggg | 2280 |
| aacacctgtc tcgcgctctt caacaagctt gttctttgct gcatgcaaga acagggcacc | 2340 |
| ttgcttttcc ccttgggaac caacgggcat tacgtcaacg cagcaaagtt tgtgaatgca | 2400 |
| accaccttga ctattccaac gaaggcagat tcaggcttca agatcgaacc aagtgctcta | 2460 |
| gccgacacac tagagaaggt gtctcagccg tgggtctata tttctggccc cacaatcaac | 2520 |
| cctactggct tcctgtacag tgacgacgat atagcagagc tgctttctgt ctgtgcgaca | 2580 |
| tacggagcca gggtggtgat agatacctcc tcctctggtc tggagttcca agccaccggc | 2640 |
| tgcagccagt ggaatttgga aagatgtctt tctaatgtca agtcttcaaa gccctcgttc | 2700 |
| tccgttgtcc tgctcggaga gctgtccttt gagctgacca cggctgggct tgatttcggg | 2760 |
| tttctgatta tgagcgactc gtccttggtt gacacatttt acagtttccc aagcttgagt | 2820 |
| cggccacaca gcacgttgaa gtacacgttc aggaagctgt tgggtcttaa gaaccagaag | 2880 |
| gatcagcatt tctctgatct catccttgag cagaaggaga cgttgaagaa tcgtgccgac | 2940 |
| cagttgatca agacgcttga gagctgcggc tgggacgctg tgggctgcca tggcggcatc | 3000 |
| tcgatgcttg caaaaccgac cgcctacatt ggcaaatcgc tcaaggtgga cggctttgag | 3060 |
| ggcaagctgg acagcacaa catgagggaa gccctcctga gtccaccgg gctgtgcatt | 3120 |
| agcagcagcg ggtggacagg ggtgccggac tactgccgct tcagctttgc tctggagagc | 3180 |
| ggcgacttcg accgggccat ggagtgcatc gcccggttca gggagctggt ccttggtggc | 3240 |
| ggtgctaagg tgaatggtag caactag | 3267 |

-continued

```
<210> SEQ ID NO 18
<211> LENGTH: 1088
<212> TYPE: PRT
<213> ORGANISM: Barley cv. Sebastian

<400> SEQUENCE: 18
```

Met Ala Ala Ala Gly Asp Val Glu Ala Phe Leu Ala Ala Cys Gln
1               5                   10                  15

Ala Ser Gly Asp Ala Ala Tyr Gly Ala Ala Lys Ala Val Leu Glu Arg
            20                  25                  30

Leu Glu Ala Pro Ala Thr Arg Ala Glu Ala Arg Arg Leu Leu Gly Ala
        35                  40                  45

Val Arg Arg Phe Ala Ala Gly Gly Pro Ala Ala Gly Leu Glu Cys
    50                  55                  60

Phe Arg Thr Phe His Phe Arg Ile His Asp Val Val Leu Asp Pro His
65                  70                  75                  80

Leu Gln Gly Phe Gln Gln Arg Lys Lys Leu Thr Met Met Glu Ile Pro
                85                  90                  95

Ser Ile Phe Ile Pro Glu Asp Trp Ser Phe Thr Phe Tyr Glu Gly Leu
            100                 105                 110

Asn Arg His Pro Asp Ser Ile Phe Arg Asp Lys Thr Val Ala Glu Leu
        115                 120                 125

Gly Cys Gly Asn Gly Trp Ile Ser Ile Ala Leu Ala Glu Lys Trp Cys
    130                 135                 140

Pro Ser Lys Val Tyr Gly Leu Asp Ile Asn Pro Arg Pro Ile Lys Ile
145                 150                 155                 160

Ala Trp Ile Asn Leu Tyr Leu Asn Ala Leu Asp Asp Asp Gly Leu Pro
                165                 170                 175

Ile Tyr Asp Ala Glu Gly Lys Thr Leu Leu Asp Arg Val Glu Phe Tyr
            180                 185                 190

Glu Ser Asp Leu Leu Ser Tyr Cys Arg Asp Asn Lys Ile Glu Leu Asp
        195                 200                 205

Arg Ile Val Gly Cys Ile Pro Gln Ile Leu Asn Pro Asn Pro Glu Ala
    210                 215                 220

Met Ser Lys Ile Val Thr Glu Asn Ser Ser Glu Glu Phe Leu Tyr Ser
225                 230                 235                 240

Leu Ser Asn Tyr Cys Ala Leu Gln Gly Phe Val Glu Asp Gln Phe Gly
                245                 250                 255

Leu Gly Leu Ile Ala Arg Ala Val Glu Glu Gly Ile Ser Val Ile Lys
            260                 265                 270

Pro Ser Gly Leu Met Val Phe Asn Met Gly Gly Arg Pro Gly Gln Gly
        275                 280                 285

Val Cys Glu Arg Leu Phe Leu Arg Arg Gly Phe Arg Ile Asn Lys Leu
    290                 295                 300

Trp Gln Thr Lys Ile Met Gln Ala Ala Asp Thr Asp Ile Ser Ala Leu
305                 310                 315                 320

Val Glu Ile Glu Lys Asn Ser Arg His Arg Phe Glu Phe Phe Met Asp
                325                 330                 335

Leu Val Gly Asp Gln Pro Val Cys Ala Arg Thr Ala Trp Ala Tyr Met
            340                 345                 350

Lys Ser Gly Gly Arg Ile Ser His Ala Leu Ser Val Tyr Ser Cys Gln
        355                 360                 365

Leu Arg Gln Pro Asn Gln Val Lys Ile Phe Glu Phe Leu Lys Asp
    370                 375                 380

```
Gly Phe His Glu Val Ser Ser Leu Asp Leu Ser Phe Asp Asp Asp
385                 390                 395                 400

Ser Val Ala Asp Glu Lys Ile Pro Phe Leu Ala Tyr Leu Ala Ser Phe
            405                 410                 415

Leu Gln Glu Asn Lys Ser Asn Pro Cys Glu Pro Pro Ala Gly Cys Leu
        420                 425                 430

Asn Phe Arg Asn Leu Val Ala Gly Phe Met Lys Ser Tyr His His Ile
    435                 440                 445

Pro Leu Thr Pro Asp Asn Val Val Phe Pro Ser Arg Ala Val Ala
450                 455                 460

Ile Glu Asn Ala Leu Arg Leu Phe Ser Pro Gly Leu Ala Ile Val Asp
465                 470                 475                 480

Glu His Leu Thr Arg His Leu Pro Lys Gln Trp Leu Thr Ser Leu Ala
                485                 490                 495

Ile Glu Glu Ser Asn His Ala Lys Asp Thr Val Thr Val Ile Glu Ala
                500                 505                 510

Pro Arg Gln Ser Asp Leu Leu Ile Glu Leu Ile Arg Lys Leu Lys Pro
            515                 520                 525

Gln Val Val Thr Gly Met Ala Gln Phe Glu Ala Ile Thr Ser Ala
530                 535                 540

Ala Phe Val Asn Leu Leu Ser Val Thr Lys Asp Val Gly Ser Arg Leu
545                 550                 555                 560

Leu Leu Asp Ile Ser Glu His Leu Glu Leu Ser Ser Leu Pro Ser Ser
                565                 570                 575

Asn Gly Val Leu Lys Tyr Leu Ala Gly Lys Thr Leu Pro Ser His Ala
            580                 585                 590

Ala Ile Leu Cys Gly Leu Val Lys Asn Gln Val Tyr Ser Asp Leu Glu
            595                 600                 605

Val Ala Phe Ala Ile Ser Glu Asp Pro Thr Val Tyr Lys Ala Leu Ser
610                 615                 620

Gln Thr Ile Glu Leu Leu Glu Gly His Thr Ser Val Ile Ser Gln His
625                 630                 635                 640

Tyr Tyr Gly Cys Leu Phe His Glu Leu Leu Ala Phe Gln Ile Gly Asp
                645                 650                 655

Arg His Pro Gln Gln Glu Arg Glu Pro Ala Glu Val Ile Ser Lys Glu
            660                 665                 670

Met Ile Gly Phe Ser Ser Ala Met Ser Thr Leu Glu Gly Ala Glu
            675                 680                 685

Phe Phe Val Pro Gly Ser Met Glu Ser Gly Val Ile His Met Asp Leu
690                 695                 700

Asp Arg Ser Phe Leu Pro Val Pro Ser Ala Val Asn Ala Ser Ile Phe
705                 710                 715                 720

Glu Ser Phe Val Arg Gln Asn Ile Thr Asp Ser Glu Thr Asp Val Arg
                725                 730                 735

Ser Ser Ile Gln Gln Leu Val Lys Asp Ser Tyr Gly Phe Ser Ala Gly
            740                 745                 750

Gly Ala Ser Glu Ile Ile Tyr Gly Asn Thr Cys Leu Ala Leu Phe Asn
            755                 760                 765

Lys Leu Val Leu Cys Cys Met Gln Glu Gln Gly Thr Leu Leu Phe Pro
    770                 775                 780

Leu Gly Thr Asn Gly His Tyr Val Asn Ala Ala Lys Phe Val Asn Ala
785                 790                 795                 800

Thr Thr Leu Thr Ile Pro Thr Lys Ala Asp Ser Gly Phe Lys Ile Glu
```

```
              805                 810                 815
Pro Ser Ala Leu Ala Asp Thr Leu Glu Lys Val Ser Gln Pro Trp Val
            820                 825                 830

Tyr Ile Ser Gly Pro Thr Ile Asn Pro Thr Gly Phe Leu Tyr Ser Asp
            835                 840                 845

Asp Asp Ile Ala Glu Leu Leu Ser Val Cys Ala Thr Tyr Gly Ala Arg
850                 855                 860

Val Val Ile Asp Thr Ser Ser Gly Leu Glu Phe Gln Ala Thr Gly
865                 870                 875                 880

Cys Ser Gln Trp Asn Leu Glu Arg Cys Leu Ser Asn Val Lys Ser Ser
                885                 890                 895

Lys Pro Ser Phe Ser Val Leu Leu Gly Glu Leu Ser Phe Glu Leu
                900                 905                 910

Thr Thr Ala Gly Leu Asp Phe Gly Phe Leu Ile Met Ser Asp Ser Ser
                915                 920                 925

Leu Val Asp Thr Phe Tyr Ser Phe Pro Ser Leu Ser Arg Pro His Ser
            930                 935                 940

Thr Leu Lys Tyr Thr Phe Arg Lys Leu Leu Gly Leu Lys Asn Gln Lys
945                 950                 955                 960

Asp Gln His Phe Ser Asp Leu Ile Leu Glu Gln Lys Glu Thr Leu Lys
                965                 970                 975

Asn Arg Ala Asp Gln Leu Ile Lys Met Leu Glu Ser Cys Gly Trp Asp
            980                 985                 990

Ala Val Gly Cys His Gly Gly Ile Ser Met Leu Ala Lys Pro Thr Ala
                995                1000                1005

Tyr Ile Gly Lys Ser Leu Lys Val Asp Gly Phe Glu Gly Lys Leu
   1010                1015                1020

Asp Ser His Asn Met Arg Glu Ala Leu Leu Arg Ser Thr Gly Leu
   1025                1030                1035

Cys Ile Ser Ser Ser Gly Trp Thr Gly Val Pro Asp Tyr Cys Arg
   1040                1045                1050

Phe Ser Phe Ala Leu Glu Ser Gly Asp Phe Asp Arg Ala Met Glu
   1055                1060                1065

Cys Ile Ala Arg Phe Arg Glu Leu Val Leu Gly Gly Gly Ala Lys
   1070                1075                1080

Val Asn Gly Ser Asn
   1085

<210> SEQ ID NO 19
<211> LENGTH: 6459
<212> TYPE: DNA
<213> ORGANISM: Barley, Mutant 14018

<400> SEQUENCE: 19
atggctgcgg cggcggggga cgtggaggcg ttcctggcgg cgtgccaggc gtcgggcgac      60
gcggcgtacg gcgccgccaa ggccgtgctg gagcggctcg aggcgccggc cacgcgcgcc     120
gaggccaggc ggctcctcgg cgccgtgcga cggcgcttcg ccgccggcgg cccggccgcg     180
gggctcgagt gcttccgcac cttccacttc cgcatccacg acgtcgtcct cgaccccccac    240 ctccaaggtt gcccggcccc ttccctacac acccgttgtc gacccgcatc tctttcgccg     300
atctggccgt caaaagcacg cggcttggta gaaatcaagc ctgcaatcct gatccgttta     360
tggctggcca gtcgatcagt aatttggcca taactggagt ataaccttgg tctctaatct     420
ctacctgacc atataccgag ttggttttct ttcttcttgt ttccgtattt gtgtagtttt     480
```

```
ttctttcctt tcgagcatga tgttctttga attaatgcgt accagactcc agtaattcga    540
cattttgaat tttggcgagt gttcttggaa tttataacac aacgaggctt tgatcaagtg    600
gtttatgtag aggagtgttt ttgttcttgt gcaccgtata caattctcta tttcccaaca    660
attttgatgg cctctaagca tcctgtagtc atgtctactg tgtaagctac agatttattc    720
atgtctatgt gtaagctgca aatggagaga aaagctatct atttggttgt tccagcttgt    780
tctttggcag aacaatcctg cccatcctat caccataagt ataaaagcac gacaaatgag    840
tggggcaagc atgctgccaa gctaatacac gacataagct acatattttg aggggcatgt    900
tatctttttt tttcccttct actcagtttc ttctttggga gaacaatcct actcaaccta    960
taatcataag aataaaagca agacagatga gtgctgcaga ctattggcat atataacaac   1020
taaataggac atctgtccgc tatatcttta gttaataatt gtatatagac gcagtctttg   1080
tgctggaaaa actgcaacta atatttttct tacattatat ggaatctggg tgtgatatga   1140
cttctttgtt acgttttgtg tgcataaagc attaacttct gtctttagtt ggcgcagcgg   1200
taaaaacacc cattgcttaa tattttattt gctttccgta gcttgataaa atttcaactg   1260
cttctaggat tccagcaaag aaagaagcta acaatgatgg agatacccag cattttcatt   1320
ccagaagact ggtcattcac tttctacgag ggtctcaacc ggcatccaga ttccatcttc   1380
agggataaga cagtagcaga gctgggatgt ggcaatggtt ggatatccat tgcacttgca   1440
gaaaagtggt gcccttcgaa gattggcacc tcttgttccg tagatattta tcttatctcg   1500
tttgttgcaa acatgggacc tgcagaagtt agacatttac tcaggttact ttatatgaaa   1560
cttttaggtg tctgccagta gtctgctggt ggtctaattt tcttggtata cctgatgccg   1620
tcgagcatat tgcttccaaa ttttgggcaa ggcattacca ccacatattg tttctacaat   1680
gctgaacaat tgctctcctt tgaaaggaag aaaaacaaga atgacatgca ccttagtagt   1740
ttaagccaca ataccagcg aatcaaatta gtttgcagtc agcttggcat taccttactt    1800
gagccttggt tgttcttttg aaggtttatg gtctggatat aaacccaaga gctatcaaga   1860
ttgcatggat aaacctttac ttgaatgcac tagacgacga tggtctccca atctatgatg   1920 cggagggaa acattgctt gacagagtcg aattctatga atctgatctt ctttcttact    1980
gtagagataa caagatagaa cttgatcgca ttgttggatg cataccacag gtacggtcag   2040 gttttacca atttcctgtg aatggggatt atagtcgatc agaacttgat caaaatgccc    2100
ttaatatctg cctttcagat tcttaacccc aatccagagg caatgtcaaa gattgtaact   2160
gaaaattcaa gtgaggagtt cttgtactcc ttgagcaact actgtgctct ccaggtgagt   2220
tgagatctat ttaaactcaa gccattcagt ttacctgtta ctaaatggtt acccatgtca   2280
gagtctccaa atcttttcct tttctcaaac agcaaagaga gaagaaaact tttaagttct   2340
atcctgaaat tgactttaca atgcttgttc ataatctgct tacgaaatat gcgtttgaac   2400
atttctcttt tccttgtagg catgtggtca gacctttata taagaaatg aagttttgt    2460 agaaataatg tatgctttgt acttatgaca tggttccacc agtataatca atttaagtct   2520
aggtagttag gaacctagga tggagagcac cgacagtgta taatatatat atgtcgatag   2580
ggggttagca gtccaaatcc acctcaagtt caacctattg cataactttt ggtcttacaa   2640
cctgtatgga caaatgtgat cagcaccca gtctttccta taaaaatgtc tgctggaata    2700
tggaattatt aacagcggta tttatttta ccctgtttaa ttttttcctt tgctaaaaga    2760
atgataatcc ttatgccacg aggttacatt gtattactca agtcaatatt tgttactatg   2820
```

```
gctgattgta cgattccagc ttccggttgt taattttgtt atgtttgtga actttgctgc    2880
attcagggtt ttgttgagga ccaatttggc ctcgggttga ttgctcgggc tgttgaagaa    2940
gggatatctg tgataaagcc tagtggtctt atggtattca acatgggagg ccggccagga    3000
caaggtgtct gtgagcgcct atttctacgc cgtggatttc gcatcaataa gctctggcaa    3060
acaaaaatta tgcaggtagc aattctttga gtgactagat gttaactaat cccagtgttt    3120
ttccatgcca gcaacagcat tatatcctgg ttagaggaat atgctcttca tgttgcacac    3180
caatcttcag ctgggcctag aattttcatc taccggctta cattttaca ttacagaacc     3240
aattttgtt gaggatcatt accaactagt tgggtctttg caggctgctg acacagacat     3300
ctccgcttta gttgaaattg agaaaaatag ccgacatcgc ttcgagttct ttatggatct    3360
tgttggggat cagcctgtgt gtgcgcgcac agcatgggca tacatgaaat ctggtggccg    3420
catttcacat gctttgtctg tgtatagctg tcaacttcgc cagcccaacc aggtacctat    3480
actctctgat tagatcttta caacaataat atagtaatgt caggaataat aataatttgg    3540
agaatttcag gtgaagaaaa tatttgagtt ccttaaagac ggattccatg aagtcagcag    3600
ctccctcgat ttgtcctttg atgatgattc tgttgctgat gaaaaaattc cttttcctagc   3660
atacctagct agtttcttgc aagagaataa gtctaatcct tgtgagcctc cagctggatg    3720
tttaaatttc cggaatcttg ttgctggatt tatgaagagt taccaccaca tcccattaac    3780
tcctgatgta agacttggtg tctattgcct acaattatgt ttgcttatta gaaattcata    3840
agatcaacct atttgatgct tctcacgtat gcttcatgtg acacttcctt ttcctctggt    3900
gcaccagaat gttgttgtgt tcccatcccg tgctgttgca atcgaaaatg ctcttcggtt    3960
gttctcacct ggacttgcaa ttgttgacga acacctaacc agacacttgc ccaagcaatg    4020
gttaacatct ttagcaattg aggtactttg accgatactc ccctctttct ttctgtgttt    4080
ggaactgtgg aaaatacatg tgttctgtga agaaaaagtt atgctgacaa gaatttcgat    4140
gttattgcca ttcttctaaa tttcaggaaa gtaaccatgc taaagataca gtaactgtaa    4200
tcgaagcacc acgccaatca gatttgctga ttgagttgat caggaaactg aagcctcagg    4260
ttgttgttac tggcatggct cagtttgagg ctatacccag tgctgctttc gtgaacttat    4320
taagtgtaac gaaagatgtt ggttcccgat tattactaga tatttcagaa catctggaat    4380
tgtctagtct gccaagctca aatggtgtat tgaaatatct tgctgggaag accctgcctt    4440
cacatgcggc tatattgtgt ggcttagtta agaatcaggt gtgtgtcaat cagcctgaac    4500
tctagttgaa ctgttgtgca tactatatag aaatatcttga cttttatatg tactttagaa   4560
acactgttta aatgtactca tttctttttg cttcatttta cttgcaggtt tattctgatc    4620
tggaagttgc ttttgctatc tctgaagatc caactgttta taaggcattg tcacaaacta    4680
ttgagctatt ggaaggacat acttctgtga tcagccagca ctattatggt tgtcttttcc    4740
atgagctgct ggcatttcaa attggtgacc ggcatccaca acaagaggta aacatggctt    4800
gcctcttcca gttctccatc tcactcagtt ctgtccacaa ggtgccgaat gatctgttca    4860
agtggacact cccctcagca cgggcaagct agtccatgaa tttggattag ttccctctta    4920
gctgggtact tcgattacac cacaatgagc tcctcaacgt ggtctggttt atgttttca    4980
tgttttccct ctaatgtttg gttgctcttt ttcagagaga acctgcagaa gtgatatcta    5040
aggagatgat agggttttca agttcagcta tgtccaccct agaaggagct gagttttcg    5100
ttcctggttc catggaatcc ggtgtcatac atatggatct ggaccgcagc ttcttgccag    5160
taccttctgc agtaaacgcc tccattttcg aaagttttgt tcgtcagaac atcactgatt    5220
```

```
ctgaaaccga tgtccgttcc agcattcagc agctggtgaa agatagctat ggtttctcag    5280
caggcggtgc ttctgaaatt atatacggga acacctgtct cgcgctcttc aacaagcttg    5340
ttctttgctg catgcaagaa cagggcacct tgcttttccc cttgggaacc aacgggcatt    5400
acgtcaacga agcaaagttt gtgaatgcaa ccaccttgac tattccaacg aaggcagatt    5460
caggcttcaa gatcgaacca agtgctctag ccgacacact agagaaggtg tctcagccgt    5520
gggtctatat ttctggcccc acaatcaacc ctactggctt cctgtacagt gacgacgata    5580
tagcagagct gctttctgtc tgtgcgacat acggagccag ggtggtgata gatacctcct    5640
cctctggtct ggagttccaa gccaccggct gcagccagtg gaatttggaa agatgtcttt    5700
ctaatgtcaa gtcttcaaag ccctcgttct ccgttgtcct gctcggagag ctgtcctttg    5760
agctgaccac ggctgggctt gatttcgggt ttctgattat gagcgactcg tccttggttg    5820
acacatttta cagtttccca agcttgagtc ggccacacag cacgttgaag tacacgttca    5880
ggaagctgtt gggtcttaag aaccagaagg atcagcattt ctctgatctc atccttgagc    5940
agaaggagac gttgaagaat cgtgccgacc agttgatcaa ggtatgcctt ttgggatatc    6000
ctgtgtttag gctctctgtt ttcttcccct gatcagctct ccgatcccct tacatcctta    6060
ggctaatttc agtacttcaa gtttgccacg catttctgac atattctttc ctcttgtttt    6120
attttcctgt gatgtgatga acagacgctt gagagctgcg gctgggacgc tgtgggctgc    6180
catggcggca tctcgatgct tgcaaaaccg accgcctaca ttggcaaatc gctcaaggtg    6240
gacggctttg agggcaagct ggacagccac aacatgaggg aagccctcct gaggtccacc    6300
gggctgtgca ttagcagcag cgggtggaca ggggtgccgg actactgccg cttcagcttt    6360
gctctggaga gcggcgactt cgaccgggcc atggagtgca tcgcccggtt cagggagctg    6420
gtccttggtg gcggtgctaa ggtgaatggt agcaactag                           6459
```

<210> SEQ ID NO 20
<211> LENGTH: 688
<212> TYPE: DNA
<213> ORGANISM: Barley cv. Sebastian

<400> SEQUENCE: 20

```
aggattccag caaagaaaga agctaacaat gatggagata cccagcattt tcattccaga     60
agactggtca ttcactttct acgagggtct caaccggcat ccagattcca tcttcaggga    120
taagacagta gcagagctgg gatgtggcaa tggttggata tccattgcac ttgcagaaaa    180
gtggtgccct tcgaaggttt atggtctgga tataaaccca agagctatca agattgcatg    240
gataaacctt tacttgaatg cactagacga cgatggtctc ccaatctatg atgcggaggg    300
gaaaacattg cttgacagag tcgaattcta tgaatctgat cttctttctt actgtagaga    360
taacaagata gaacttgatc gcattgttgg atgcatacca cagattctta accccaatcc    420
agaggcaatg tcaaagattg taactgaaaa ttcaagtgag gagttcttgt actccttgag    480
caactactgt gctctccagg gttttgttga ggaccaattt ggcctcgggt tgattgctcg    540
ggctgttgaa gaagggatat ctgtgataaa gcctagtggt cttatggtat tcaacatggg    600
aggccggcca ggacaaggtg tctgtgagcg cctatttctt cgccgtggat ttcgcatcaa    660
taagctctgg caaacaaaaa ttatgcag                                      688
```

<210> SEQ ID NO 21
<211> LENGTH: 1050
<212> TYPE: DNA

<213> ORGANISM: Barley, Mutant 14018

<400> SEQUENCE: 21

```
aggattccag caaagaaaga agctaacaat gatggagata cccagcattt tcattccaga      60
agactggtca ttcactttct acgagggtct caaccggcat ccagattcca tcttcaggga     120
taagacagta gcagagctgg gatgtggcaa tggttggata tccattgcac ttgcagaaaa     180
gtggtgccct tcgaagattg gcacctcttg ttccgtagat atttatctta tctcgtttgt     240
tgcaaacatg ggacctgcag aagttagaca tttactcagg ttactttata tgaaactttt     300
aggtgtctgc cagtagtctg ctggtggtct aattttcttg gtatacctga tgccgtcgag     360
catattgctt tcaaattttg ggcaaggcat taccaccaca tattgtttct acaatgctga     420
acaattgctc tcctttgaaa ggaagaaaaa caagaatgac atgcacctta gtagtttaag     480
ccacaaatac cagcgaatca aattagtttg cagtcagctt ggcattacct tacttgagcc     540
ttggttgttc ttttgaaggt ttatggtctg gatataaacc caagagctat caagattgca     600
tggataaacc tttacttgaa tgcactagac gacgatggtc tcccaatcta tgatgcggag     660
gggaaaacat tgcttgacag agtcgaattc tatgaatctg atcttctttc ttactgtaga     720
gataacaaga tagaacttga tcgcattgtt ggatgcatac cacagattct taaccccaat     780
ccagaggcaa tgtcaaagat tgtaactgaa aattcaagtg aggagttctt gtactccttg     840
agcaactact gtgctctcca gggttttgtt gaggaccaat ttggcctcgg gttgattgct     900
cgggctgttg aagaagggat atctgtgata aagcctagtg gtcttatggt attcaacatg     960
ggaggccggc caggacaagg tgtctgtgag cgcctatttc ttcgccgtgg atttcgcatc    1020
aataagctct ggcaaacaaa aattatgcag                                    1050
```

<210> SEQ ID NO 22
<211> LENGTH: 186
<212> TYPE: PRT
<213> ORGANISM: Barley, Mutant 14018

<400> SEQUENCE: 22

```
Met Ala Ala Ala Ala Gly Asp Val Glu Ala Phe Leu Ala Ala Cys Gln
1               5                   10                  15

Ala Ser Gly Asp Ala Ala Tyr Gly Ala Ala Lys Ala Val Leu Glu Arg
            20                  25                  30

Leu Glu Ala Pro Ala Thr Arg Ala Glu Ala Arg Arg Leu Leu Gly Ala
        35                  40                  45

Val Arg Arg Arg Phe Ala Ala Gly Gly Pro Ala Gly Leu Glu Cys
    50                  55                  60

Phe Arg Thr Phe His Phe Arg Ile His Asp Val Val Leu Asp Pro His
65                  70                  75                  80

Leu Gln Gly Phe Gln Gln Arg Lys Lys Leu Thr Met Met Glu Ile Pro
                85                  90                  95

Ser Ile Phe Ile Pro Glu Asp Trp Ser Phe Thr Phe Tyr Glu Gly Leu
            100                 105                 110

Asn Arg His Pro Asp Ser Ile Phe Arg Asp Lys Thr Val Ala Glu Leu
        115                 120                 125

Gly Cys Gly Asn Gly Trp Ile Ser Ile Ala Leu Ala Glu Lys Trp Cys
    130                 135                 140

Pro Ser Lys Ile Gly Thr Ser Cys Ser Val Asp Ile Tyr Leu Ile Ser
145                 150                 155                 160

Phe Val Ala Asn Met Gly Pro Ala Glu Val Arg His Leu Leu Arg Leu
```

Leu Tyr Met Lys Leu Leu Gly Val Cys Gln
           180                 185

<210> SEQ ID NO 23
<211> LENGTH: 771
<212> TYPE: DNA
<213> ORGANISM: Barley, Mutant 14018

<400> SEQUENCE: 23

```
aggattccag caaagaaaga agctaacaat gatggagata cccagcattt tcattccaga      60
agactggtca ttcactttct acgagggtct caaccggcat ccagattcca tcttcaggga    120
taagacagta gcagagctgg gatgtggcaa tggttggata tccattgcac ttgcagaaaa    180
gtggtgccct tcgaagattg gcacctcttg ttccgtagat atttatctta tctcgtttgt    240
tgcaaacatg ggacctgcag aagttagaca tttactcagg tttatggtct ggatataaac    300
ccaagagcta tcaagattgc atggataaac ctttacttga atgcactaga cgacgatggt    360
ctcccaatct atgatgcgga ggggaaaaca ttgcttgaca gagtcgaatt ctatgaatct    420
gatcttcttt cttactgtag agataacaag atagaacttg atcgcattgt tggatgcata    480
ccacagattc ttaaccccaa tccagaggca atgtcaaaga ttgtaactga aaattcaagt    540
gaggagttct tgtactcctt gagcaactac tgtgctctcc agggttttgt tgaggaccaa    600
tttggcctcg ggttgattgc tcgggctgtt gaagaaggga tatctgtgat aaagcctagt    660
ggtcttatgg tattcaacat gggaggccgg ccaggacaag gtgtctgtga gcgcctattt    720
cttcgccgtg gatttcgcat caataagctc tggcaaacaa aaattatgca g             771
```

<210> SEQ ID NO 24
<211> LENGTH: 180
<212> TYPE: PRT
<213> ORGANISM: Barley, Mutant 14018

<400> SEQUENCE: 24

Met Ala Ala Ala Ala Gly Asp Val Glu Ala Phe Leu Ala Ala Cys Gln
1               5                   10                  15

Ala Ser Gly Asp Ala Ala Tyr Gly Ala Ala Lys Ala Val Leu Glu Arg
            20                  25                  30

Leu Glu Ala Pro Ala Thr Arg Ala Glu Ala Arg Arg Leu Leu Gly Ala
        35                  40                  45

Val Arg Arg Arg Phe Ala Ala Gly Gly Pro Ala Gly Leu Glu Cys
    50                  55                  60

Phe Arg Thr Phe His Phe Arg Ile His Asp Val Val Leu Asp Pro His
65                  70                  75                  80

Leu Gln Gly Phe Gln Gln Arg Lys Lys Leu Thr Met Met Glu Ile Pro
                85                  90                  95

Ser Ile Phe Ile Pro Glu Asp Trp Ser Phe Thr Phe Tyr Glu Gly Leu
            100                 105                 110

Asn Arg His Pro Asp Ser Ile Phe Arg Asp Lys Thr Val Ala Glu Leu
        115                 120                 125

Gly Cys Gly Asn Gly Trp Ile Ser Ile Ala Leu Ala Glu Lys Trp Cys
    130                 135                 140

Pro Ser Lys Ile Gly Thr Ser Cys Ser Val Asp Ile Tyr Leu Ile Ser
145                 150                 155                 160

Phe Val Ala Asn Met Gly Pro Ala Glu Val Arg His Leu Leu Arg Phe
                165                 170                 175

Met Val Trp Ile
            180

<210> SEQ ID NO 25
<211> LENGTH: 644
<212> TYPE: DNA
<213> ORGANISM: Barley, Mutant 14018

<400> SEQUENCE: 25
aggattccag caaagaaaga agctaacaat gatggagata cccagcattt tcattccaga      60
agactggtca ttcactttct acgagggtct caaccggcat ccagattcca tcttcaggga    120
taagacagta gcagagctgg gatgtggcaa tggtttatgg tctggatata aacccaagag    180
ctatcaagat tgcatggata aacctttact tgaatgcact agacgacgat ggtctcccaa    240
tctatgatgc ggaggggaaa acattgcttg acagagtcga attctatgaa tctgatcttc    300
tttcttactg tagagataac aagatagaac ttgatcgcat tgttggatgc ataccacaga    360
ttcttaaccc caatccagag gcaatgtcaa agattgtaac tgaaaattca agtgaggagt    420
tcttgtactc cttgagcaac tactgtgctc tccagggttt tgttgaggac caatttggcc    480
tcgggttgat tgctcgggct gttgaagaag ggatatctgt gataaagcct agtggtctta    540
tggtattcaa catgggaggc cggccaggac aaggtgtctg tgagcgccta tttcttcgcc    600
gtggatttcg catcaataag ctctggcaaa caaaaattat gcag                     644

<210> SEQ ID NO 26
<211> LENGTH: 163
<212> TYPE: PRT
<213> ORGANISM: Barley, Mutant 14018

<400> SEQUENCE: 26

Met Ala Ala Ala Gly Asp Val Glu Ala Phe Leu Ala Ala Cys Gln
1               5                   10                  15

Ala Ser Gly Asp Ala Ala Tyr Gly Ala Ala Lys Ala Val Leu Glu Arg
            20                  25                  30

Leu Glu Ala Pro Ala Thr Arg Ala Glu Ala Arg Arg Leu Leu Gly Ala
        35                  40                  45

Val Arg Arg Arg Phe Ala Ala Gly Gly Pro Ala Ala Gly Leu Glu Cys
    50                  55                  60

Phe Arg Thr Phe His Phe Arg Ile His Asp Val Val Leu Asp Pro His
65                  70                  75                  80

Leu Gln Gly Phe Gln Gln Arg Lys Lys Leu Thr Met Met Glu Ile Pro
                85                  90                  95

Ser Ile Phe Ile Pro Glu Asp Trp Ser Phe Thr Phe Tyr Glu Gly Leu
            100                 105                 110

Asn Arg His Pro Asp Ser Ile Phe Arg Asp Lys Thr Val Ala Glu Leu
        115                 120                 125

Gly Cys Gly Asn Gly Leu Trp Ser Gly Tyr Lys Pro Lys Ser Tyr Gln
    130                 135                 140

Asp Cys Met Asp Lys Pro Leu Leu Glu Cys Thr Arg Arg Trp Ser
145                 150                 155                 160

Pro Asn Leu

<210> SEQ ID NO 27
<211> LENGTH: 781
<212> TYPE: DNA
<213> ORGANISM: Artificial

```
<220> FEATURE:
<223> OTHER INFORMATION: SacII BamHI fragment of Product 2

<400> SEQUENCE: 27
ggccgcgggg ctcgagtgct tccgcacctt ccacttccgc atccacgacg tcgtcctcga      60
cccccacctc aaggattcc agcaaagaaa gaagctaaca atgatggaga tacccagcat     120
tttcattcca gaagactggt cattcacttt ctacgagggt ctcaaccggc atccagattc    180
catcttcagg gataagacag tagcagagct gggatgtggc aatggttgga tatccattgc    240
acttgcagaa aagtggtgcc cttcgaaggt ttatggtctg gatataaacc caagagctat    300
caagattgca tggataaacc tttacttgaa tgcactagac gacgatggtc tcccaatcta    360
tgatgcggag gggaaaacat tgcttgacag agtcgaattc tatgaatctg atcttctttc    420
ttactgtaga gataacaaga tagaacttga tcgcattgtt ggatgcatac cacagattct    480 taacccccaat ccagaggcaa tgtcaaagat tgtaactgaa aattcaagtg aggagttctt   540
gtactccttg agcaactact gtgctctcca gggttttgtt gaggaccaat ttggcctcgg    600
gttgattgct cgggctgttg aagaagggat atctgtgata aagcctagtg gtcttatggt    660
attcaacatg ggaggccggc caggacaagg tgtctgtgag cgcctatttc tacgccgtgg    720
atttcgcatc aataagctct ggcaaacaaa aattatgcag atagcaattc tttgaggatc    780
c                                                                    781

<210> SEQ ID NO 28
<211> LENGTH: 781
<212> TYPE: DNA
<213> ORGANISM: Artificial
<220> FEATURE:
<223> OTHER INFORMATION: SacII BamHI fragment of Product 3

<400> SEQUENCE: 28
ggccgcgggg ctcgagtgct tccgcacctt ccacttccgc atccacgacg tcgtcctcga      60
cccccacctc aaggattcc agcaaagaaa gaagctaaca atgatggaga tacccagcat     120
tttcattcca gaagactggt cattcacttt ctacgagggt ctcaaccggc atccagattc    180
catcttcagg gataagacag tagcagagct gggatgtggc aatggttgga tatccattgc    240
acttgcagaa aagtggtgcc cttcgaaggt ttatggtctg gatataaacc caagagctat    300
caagattgca tggataaacc tttacttgaa tgcactagac gacgatggtc tcccaatcta    360
tgatgcggag gggaaaacat tgcttgacag agtcgaattc tatgaatctg atcttctttc    420
ttactgtaga gataacaaga tagaacttga tcgcattgtt ggatgcatac cacagattct    480 taacccccaat ccagaggcaa tgtcaaagat tgtaactgaa aattcaagtg aggagttctt   540
gtactccttg agcaactact gtgctctcca gggttttgtt gaggaccaat ttggcctcgg    600
gttgattgct cgggctgttg aagaagggat atctgtgata aagcctagtg gtcttatggt    660
attcaacatg ggaggccggc caggacaagg tgtctgtgag cgcctatttc tacgccgtgg    720
atttcgcatc aataagctct ggcaaacaaa aattatgcag atagcaattc tttgaggatc    780
c                                                                    781

<210> SEQ ID NO 29
<211> LENGTH: 703
<212> TYPE: DNA
<213> ORGANISM: Artificial
<220> FEATURE:
<223> OTHER INFORMATION: SacII BamHI fragment of Product 4
```

<400> SEQUENCE: 29

```
ggccgcgggg ctcgagtgct tccgcacctt ccacttccgc atccacgacg tcgtcctcga      60
cccccacctc caaggattcc agcaaagaaa gaagctaaca atgatggaga tacccagcat     120
tttcattcca gaagactggt cattcacttt ctacgagggt ctcaaccggc atccagattc     180
catcttcagg gataagacag tagcagagct gggatgtggc aatggttgga tatccattgc    240
acttgcagaa aagtggtgcc cttcgaaggt ttatggtctg gatataaacc caagagctat     300
caagattgca tggataaacc tttacttgaa tgcactagac gacgatggtc tcccaatcta     360
tgatgcggag gggaaaacat tgcttgacag agtcgaattc tatgaatctg atcttctttc    420
ttactgtaga gataacaaga tagaacttga tcgcattgtt ggatgcatac cacagattct    480
taacccaat ccagaggcaa tgtcaaagat tgtaactgaa aattcaagtg aggagttctt     540
gtactccttg agcaactact gtgctctcca gggttttgtt gaggaccaat ttggcctcgg    600
gttgattgct cgggctgttg aagaagggat atctgtgata aagcctagtg gtcttatggt    660
attcaacatg ggaggccggc caggacaagg ctgctaagga tcc                      703
```

<210> SEQ ID NO 30
<211> LENGTH: 394
<212> TYPE: DNA
<213> ORGANISM: Artificial
<220> FEATURE:
<223> OTHER INFORMATION: SacII BamHI fragment of Product 6

<400> SEQUENCE: 30

```
ggccgcgggg ctcgagtgct tccgcacctt ccacttccgc atccacgacg tcgtcctcga      60
cccccacctc caaggattcc agcaaagaaa gaagctaaca atgatggaga tacccagcat     120
tttcattcca gaagactggt cattcacttt ctacgagggt ctcaaccggc atccagattc     180
catcttcagg gataagacag tagcagagct gggatgtggc aatggttgga tatccattgc    240
acttgcagaa aagtggtgcc cttcgaagat tggcacctct tgttccgtag atatttatct    300
tatctcgttt gttgcaaaca tgggacctgc agaagttaga catttactca ggttacttta    360
tatgaaactt ttaggtgtct gccagtaggg atcc                                394
```

<210> SEQ ID NO 31
<211> LENGTH: 376
<212> TYPE: DNA
<213> ORGANISM: Artificial
<220> FEATURE:
<223> OTHER INFORMATION: SacII BamHI fragment of Product 7

<400> SEQUENCE: 31

```
ggccgcgggg ctcgagtgct tccgcacctt ccacttccgc atccacgacg tcgtcctcga      60
cccccacctc caaggattcc agcaaagaaa gaagctaaca atgatggaga tacccagcat     120
tttcattcca gaagactggt cattcacttt ctacgagggt ctcaaccggc atccagattc     180
catcttcagg gataagacag tagcagagct gggatgtggc aatggttgga tatccattgc    240
acttgcagaa aagtggtgcc cttcgaagat tggcacctct tgttccgtag atatttatct    300
tatctcgttt gttgcaaaca tgggacctgc agaagttaga catttactca ggtttatggt    360
ctggatataa ggatcc                                                    376
```

<210> SEQ ID NO 32
<211> LENGTH: 325
<212> TYPE: DNA
<213> ORGANISM: Artificial

```
<220> FEATURE:
<223> OTHER INFORMATION: SacII BamHI fragment of Product 8

<400> SEQUENCE: 32
ggccgcgggg ctcgagtgct tccgcacctt ccacttccgc atccacgacg tcgtcctcga      60
cccccacctc caaggattcc agcaaagaaa gaagctaaca atgatggaga tacccagcat     120
tttcattcca gaagactggt cattcacttt ctacgagggt ctcaaccggc atccagattc     180
catcttcagg gataagacag tagcagagct gggatgtggc aatggtttat ggtctggata     240
taaacccaag agctatcaag attgcatgga taaaccttta cttgaatgca ctagacgacg     300
atggtctccc aatctataag gatcc                                            325

<210> SEQ ID NO 33
<211> LENGTH: 271
<212> TYPE: DNA
<213> ORGANISM: Barley cv. Prestige

<400> SEQUENCE: 33
cgattccagc ttccggttgt taattttgtt atgtttgtga actttgctgc attcagggtt      60
ttgttgagga ccaatttggc ctcgggttga ttgctcgggc tgttgaagaa gggatatctg     120
tgataaagcc tagtggtctt atggtattca acatgggagg ccggccagga caaggtgtct     180
gtgagcgcct atttctacgc cgtggatttc gcatcaataa gctctggcaa acaaaaatta     240
tgcaggtagc aattctttga gtgactagat g                                     271

<210> SEQ ID NO 34
<211> LENGTH: 271
<212> TYPE: DNA
<213> ORGANISM: Barley Mutant 8063

<400> SEQUENCE: 34
cgattccagc ttccggttgt taattttgtt atgtttgtga actttgctgc attcagggtt      60
ttgttgagga ccaatttggc ctcgggttga ttgctcgggc tgttgaagaa gggatatctg     120
tgataaagcc tagtggtctt atggtattca acatgggagg ccggccagga caaggtgtct     180
gtgagcgcct atttctacgc cgtggatttc gcatcaataa gctctggcaa acaaaaatta     240
tgcagatagc aattctttga gtgactagat g                                     271

<210> SEQ ID NO 35
<211> LENGTH: 121
<212> TYPE: DNA
<213> ORGANISM: Barley cv. Sebastian

<400> SEQUENCE: 35
ggcatccaga ttccatcttc agggataaga cagtagcaga gctgggatgt ggcaatggtt      60
ggatatccat tgcacttgca gaaaagtggt gcccttcgaa ggttggcacc tcttgttccg     120
t                                                                     121

<210> SEQ ID NO 36
<211> LENGTH: 123
<212> TYPE: DNA
<213> ORGANISM: Barley Mutant 14018

<400> SEQUENCE: 36
ggcatccaga ttccatcttc agggataaga cagtagcaga gctgggatgt ggcaatggtt      60
ggatatccat tgcacttgca gaaaagtggt gcccttcgaa gattggcacc tcttgttccg     120
``` tag                                                           123

<210> SEQ ID NO 37
<211> LENGTH: 25
<212> TYPE: DNA
<213> ORGANISM: Artificial
<220> FEATURE:
<223> OTHER INFORMATION: PCR primer

<400> SEQUENCE: 37
atggctgcgg cggcggggga cgtgg                                    25

<210> SEQ ID NO 38
<211> LENGTH: 23
<212> TYPE: DNA
<213> ORGANISM: Artificial
<220> FEATURE:
<223> OTHER INFORMATION: PCR primer

<400> SEQUENCE: 38
aggattccag caaagaaaga agc                                      23

<210> SEQ ID NO 39
<211> LENGTH: 24
<212> TYPE: DNA
<213> ORGANISM: Artificial
<220> FEATURE:
<223> OTHER INFORMATION: PCR primer

<400> SEQUENCE: 39
gattcttaac cccaatccag aggc                                     24

<210> SEQ ID NO 40
<211> LENGTH: 25
<212> TYPE: DNA
<213> ORGANISM: Artificial
<220> FEATURE:
<223> OTHER INFORMATION: PCR primer

<400> SEQUENCE: 40
gggttttgtt gaggaccaat ttggc                                    25

<210> SEQ ID NO 41
<211> LENGTH: 21
<212> TYPE: DNA
<213> ORGANISM: Artificial
<220> FEATURE:
<223> OTHER INFORMATION: PCR primer

<400> SEQUENCE: 41
tgctgctttc gtgaacttat t                                        21

<210> SEQ ID NO 42
<211> LENGTH: 26
<212> TYPE: DNA
<213> ORGANISM: Artificial
<220> FEATURE:
<223> OTHER INFORMATION: PCR primer

<400> SEQUENCE: 42
catatggatc tggaccgcag cttctt                                   26

<210> SEQ ID NO 43
<211> LENGTH: 25
<212> TYPE: DNA
<213> ORGANISM: Artificial

```
<220> FEATURE:
<223> OTHER INFORMATION: PCR primer

<400> SEQUENCE: 43
ccttcgaagg gcaccacttt tctgc                                   25

<210> SEQ ID NO 44
<211> LENGTH: 25
<212> TYPE: DNA
<213> ORGANISM: Artificial
<220> FEATURE:
<223> OTHER INFORMATION: PCR primer

<400> SEQUENCE: 44
ctggagagca cagtagttgc tcaag                                   25

<210> SEQ ID NO 45
<211> LENGTH: 25
<212> TYPE: DNA
<213> ORGANISM: Artificial
<220> FEATURE:
<223> OTHER INFORMATION: PCR primer

<400> SEQUENCE: 45
ctgcataatt tttgtttgcc agagc                                   25

<210> SEQ ID NO 46
<211> LENGTH: 24
<212> TYPE: DNA
<213> ORGANISM: Artificial
<220> FEATURE:
<223> OTHER INFORMATION: PCR primer

<400> SEQUENCE: 46
tacaccattt gagcttggca gact                                    24

<210> SEQ ID NO 47
<211> LENGTH: 24
<212> TYPE: DNA
<213> ORGANISM: Artificial
<220> FEATURE:
<223> OTHER INFORMATION: PCR primer

<400> SEQUENCE: 47
aaaatggagg cgtttactgc agaa                                    24

<210> SEQ ID NO 48
<211> LENGTH: 27
<212> TYPE: DNA
<213> ORGANISM: Artificial
<220> FEATURE:
<223> OTHER INFORMATION: PCR primer

<400> SEQUENCE: 48
ctagttgcta ccattcacct tagcacc                                 27

<210> SEQ ID NO 49
<211> LENGTH: 25
<212> TYPE: DNA
<213> ORGANISM: Artificial
<220> FEATURE:
<223> OTHER INFORMATION: PCR primer

<400> SEQUENCE: 49
atggctgcgg cggcggggga cgtgg                                   25
```

<210> SEQ ID NO 50
<211> LENGTH: 25
<212> TYPE: DNA
<213> ORGANISM: Artificial
<220> FEATURE:
<223> OTHER INFORMATION: PCR primer

<400> SEQUENCE: 50
atggctgcgg cggcggggga cgtgg                                    25

<210> SEQ ID NO 51
<211> LENGTH: 25
<212> TYPE: DNA
<213> ORGANISM: Artificial
<220> FEATURE:
<223> OTHER INFORMATION: PCR primer

<400> SEQUENCE: 51
atggctgcgg cggcggggga cgtgg                                    25

<210> SEQ ID NO 52
<211> LENGTH: 25
<212> TYPE: DNA
<213> ORGANISM: Artificial
<220> FEATURE:
<223> OTHER INFORMATION: PCR primer

<400> SEQUENCE: 52
atggctgcgg cggcggggga cgtgg                                    25

<210> SEQ ID NO 53
<211> LENGTH: 25
<212> TYPE: DNA
<213> ORGANISM: Artificial
<220> FEATURE:
<223> OTHER INFORMATION: PCR primer

<400> SEQUENCE: 53
atggctgcgg cggcggggga cgtgg                                    25

<210> SEQ ID NO 54
<211> LENGTH: 25
<212> TYPE: DNA
<213> ORGANISM: Artificial
<220> FEATURE:
<223> OTHER INFORMATION: PCR primer

<400> SEQUENCE: 54
ggctcctcgg cgccgtgcga cggcg                                    25

<210> SEQ ID NO 55
<211> LENGTH: 25
<212> TYPE: DNA
<213> ORGANISM: Artificial
<220> FEATURE:
<223> OTHER INFORMATION: PCR primer

<400> SEQUENCE: 55
ggctcctcgg cgccgtgcga cggcg                                    25

<210> SEQ ID NO 56
<211> LENGTH: 25
<212> TYPE: DNA
<213> ORGANISM: Artificial
<220> FEATURE:
<223> OTHER INFORMATION: PCR primer

```
<400> SEQUENCE: 56
ggctcctcgg cgccgtgcga cggcg                                    25

<210> SEQ ID NO 57
<211> LENGTH: 20
<212> TYPE: DNA
<213> ORGANISM: Artificial
<220> FEATURE:
<223> OTHER INFORMATION: PCR primer

<400> SEQUENCE: 57
gtacgccgcg tcgcccgacg                                          20

<210> SEQ ID NO 58
<211> LENGTH: 20
<212> TYPE: DNA
<213> ORGANISM: Artificial
<220> FEATURE:
<223> OTHER INFORMATION: PCR primer

<400> SEQUENCE: 58
ccgccggcgg cgaagcgccg                                          20

<210> SEQ ID NO 59
<211> LENGTH: 20
<212> TYPE: DNA
<213> ORGANISM: Artificial
<220> FEATURE:
<223> OTHER INFORMATION: PCR primer

<400> SEQUENCE: 59
gtgcggaagc actcgagccc                                          20

<210> SEQ ID NO 60
<211> LENGTH: 20
<212> TYPE: DNA
<213> ORGANISM: Artificial
<220> FEATURE:
<223> OTHER INFORMATION: PCR primer

<400> SEQUENCE: 60
cgtggatgcg gaagtggaag                                          20

<210> SEQ ID NO 61
<211> LENGTH: 26
<212> TYPE: DNA
<213> ORGANISM: Artificial
<220> FEATURE:
<223> OTHER INFORMATION: PCR primer

<400> SEQUENCE: 61
cttggaggtg ggggtcgagg acgacg                                   26

<210> SEQ ID NO 62
<211> LENGTH: 20
<212> TYPE: DNA
<213> ORGANISM: Artificial
<220> FEATURE:
<223> OTHER INFORMATION: PCR primer

<400> SEQUENCE: 62
gtgcggaagc actcgagccc                                          20

<210> SEQ ID NO 63
```

```
<211> LENGTH: 20
<212> TYPE: DNA
<213> ORGANISM: Artificial
<220> FEATURE:
<223> OTHER INFORMATION: PCR primer

<400> SEQUENCE: 63
cgtggatgcg gaagtggaag                                              20

<210> SEQ ID NO 64
<211> LENGTH: 26
<212> TYPE: DNA
<213> ORGANISM: Artificial
<220> FEATURE:
<223> OTHER INFORMATION: PCR primer

<400> SEQUENCE: 64
cttggaggtg ggggtcgagg acgacg                                       26

<210> SEQ ID NO 65
<211> LENGTH: 26
<212> TYPE: DNA
<213> ORGANISM: Artificial
<220> FEATURE:
<223> OTHER INFORMATION: PCR primer

<400> SEQUENCE: 65
gtttatggtc tggatataaa cccaag                                       26

<210> SEQ ID NO 66
<211> LENGTH: 23
<212> TYPE: DNA
<213> ORGANISM: Artificial
<220> FEATURE:
<223> OTHER INFORMATION: PCR primer

<400> SEQUENCE: 66
aggattccag caaagaaaga agc                                          23

<210> SEQ ID NO 67
<211> LENGTH: 25
<212> TYPE: DNA
<213> ORGANISM: Artificial
<220> FEATURE:
<223> OTHER INFORMATION: PCR primer

<400> SEQUENCE: 67
aaatccagca acaagattcc ggaaa                                        25

<210> SEQ ID NO 68
<211> LENGTH: 25
<212> TYPE: DNA
<213> ORGANISM: Artificial
<220> FEATURE:
<223> OTHER INFORMATION: PCR primer

<400> SEQUENCE: 68
ctgcataatt tttgtttgcc agagc                                        25

<210> SEQ ID NO 69
<211> LENGTH: 12
<212> TYPE: PRT
<213> ORGANISM: Artificial
<220> FEATURE:
<223> OTHER INFORMATION: His Tag

<400> SEQUENCE: 69
```

```
Met Gly His His His His His His His His His
1               5                   10
```

<210> SEQ ID NO 70
<211> LENGTH: 11
<212> TYPE: PRT
<213> ORGANISM: Artificial
<220> FEATURE:
<223> OTHER INFORMATION: Enterokinase site

<400> SEQUENCE: 70

```
Ser Ser Gly His Ile Asp Asp Asp Asp Lys His
1               5                   10
```

<210> SEQ ID NO 71
<211> LENGTH: 31
<212> TYPE: DNA
<213> ORGANISM: Artificial
<220> FEATURE:
<223> OTHER INFORMATION: PCR primer

<400> SEQUENCE: 71
catatgatgg ctgcggcggc gggggacgtg g                              31

<210> SEQ ID NO 72
<211> LENGTH: 32
<212> TYPE: DNA
<213> ORGANISM: Artificial
<220> FEATURE:
<223> OTHER INFORMATION: PCR primer

<400> SEQUENCE: 72
gaattctagt tgctaccatt caccttagca cc                             32

<210> SEQ ID NO 73
<211> LENGTH: 27
<212> TYPE: DNA
<213> ORGANISM: Artificial
<220> FEATURE:
<223> OTHER INFORMATION: PCR primer

<400> SEQUENCE: 73
ggccgcgggg ctcgagtgct tccgcac                                   27

<210> SEQ ID NO 74
<211> LENGTH: 46
<212> TYPE: DNA
<213> ORGANISM: Artificial
<220> FEATURE:
<223> OTHER INFORMATION: PCR primer

<400> SEQUENCE: 74
ggatcctcaa agaattgcta tctgcataat ttttgtttgc cagagc              46

<210> SEQ ID NO 75
<211> LENGTH: 27
<212> TYPE: DNA
<213> ORGANISM: Artificial
<220> FEATURE:
<223> OTHER INFORMATION: PCR primer

<400> SEQUENCE: 75
ggccgcgggg ctcgagtgct tccgcac                                   27

<210> SEQ ID NO 76

```
<211> LENGTH: 37
<212> TYPE: DNA
<213> ORGANISM: Artificial
<220> FEATURE:
<223> OTHER INFORMATION: PCR primer

<400> SEQUENCE: 76
ggatccttag cagccttgtc ctggccggcc tcccatg                              37

<210> SEQ ID NO 77
<211> LENGTH: 19
<212> TYPE: DNA
<213> ORGANISM: Artificial
<220> FEATURE:
<223> OTHER INFORMATION: PCR primer

<400> SEQUENCE: 77
cgattccagc ttccggttg                                                 19

<210> SEQ ID NO 78
<211> LENGTH: 19
<212> TYPE: DNA
<213> ORGANISM: Artificial
<220> FEATURE:
<223> OTHER INFORMATION: PCR primer

<400> SEQUENCE: 78
cgattccagc ttccggttg                                                 19

<210> SEQ ID NO 79
<211> LENGTH: 19
<212> TYPE: DNA
<213> ORGANISM: Artificial
<220> FEATURE:
<223> OTHER INFORMATION: PCR primer

<400> SEQUENCE: 79
cgattccagc ttccggttg                                                 19

<210> SEQ ID NO 80
<211> LENGTH: 22
<212> TYPE: DNA
<213> ORGANISM: Artificial
<220> FEATURE:
<223> OTHER INFORMATION: PCR primer

<400> SEQUENCE: 80
ggcatccaga ttccatcttc ag                                             22

<210> SEQ ID NO 81
<211> LENGTH: 26
<212> TYPE: DNA
<213> ORGANISM: Artificial
<220> FEATURE:
<223> OTHER INFORMATION: PCR primer

<400> SEQUENCE: 81
catctagtca ctcaaagaat tgctac                                         26

<210> SEQ ID NO 82
<211> LENGTH: 26
<212> TYPE: DNA
<213> ORGANISM: Artificial
<220> FEATURE:
<223> OTHER INFORMATION: PCR primer

<400> SEQUENCE: 82
```
catctagtca ctcaaagaat tgctat 26

<210> SEQ ID NO 83
<211> LENGTH: 26
<212> TYPE: DNA
<213> ORGANISM: Artificial
<220> FEATURE:
<223> OTHER INFORMATION: PCR primer

<400> SEQUENCE: 83
catctagtca ctcaaagaat tgctat 26

<210> SEQ ID NO 84
<211> LENGTH: 22
<212> TYPE: DNA
<213> ORGANISM: Artificial
<220> FEATURE:
<223> OTHER INFORMATION: PCR primer

<400> SEQUENCE: 84
ctacggaaca agaggtgcca at 22

<210> SEQ ID NO 85
<211> LENGTH: 27
<212> TYPE: DNA
<213> ORGANISM: Artificial
<220> FEATURE:
<223> OTHER INFORMATION: PCR primer

<400> SEQUENCE: 85
ggccgcgggg ctcgagtgct tccgcac 27

<210> SEQ ID NO 86
<211> LENGTH: 63
<212> TYPE: DNA
<213> ORGANISM: Artificial
<220> FEATURE:
<223> OTHER INFORMATION: PCR primer

<400> SEQUENCE: 86
cgagataaga taaatatcta cggaacaaga ggtgccaatc ttcgaagggc accactttc 60 tgc 63

<210> SEQ ID NO 87
<211> LENGTH: 27
<212> TYPE: DNA
<213> ORGANISM: Artificial
<220> FEATURE:
<223> OTHER INFORMATION: PCR primer

<400> SEQUENCE: 87
ggccgcgggg ctcgagtgct tccgcac 27

<210> SEQ ID NO 88
<211> LENGTH: 70
<212> TYPE: DNA
<213> ORGANISM: Artificial
<220> FEATURE:
<223> OTHER INFORMATION: PCR primer

<400> SEQUENCE: 88
aacctgagta aatgtctaac ttctgcaggt cccatgtttg caacaaacga gataagataa 60
atatctacgg 70

<210> SEQ ID NO 89
<211> LENGTH: 27
<212> TYPE: DNA
<213> ORGANISM: Artificial
<220> FEATURE:
<223> OTHER INFORMATION: PCR primer

<400> SEQUENCE: 89
ggccgcgggg ctcgagtgct tccgcac                                         27

<210> SEQ ID NO 90
<211> LENGTH: 66
<212> TYPE: DNA
<213> ORGANISM: Artificial
<220> FEATURE:
<223> OTHER INFORMATION: PCR primer

<400> SEQUENCE: 90
ggatccctac tggcagacac ctaaaagttt catataaagt aacctgagta aatgtctaac     60
ttctgc                                                                66

<210> SEQ ID NO 91
<211> LENGTH: 27
<212> TYPE: DNA
<213> ORGANISM: Artificial
<220> FEATURE:
<223> OTHER INFORMATION: PCR primer

<400> SEQUENCE: 91
ggccgcgggg ctcgagtgct tccgcac                                         27

<210> SEQ ID NO 92
<211> LENGTH: 48
<212> TYPE: DNA
<213> ORGANISM: Artificial
<220> FEATURE:
<223> OTHER INFORMATION: PCR primer

<400> SEQUENCE: 92
ggatccttat atccagacca taaacctgag taaatgtcta acttctgc                  48

<210> SEQ ID NO 93
<211> LENGTH: 27
<212> TYPE: DNA
<213> ORGANISM: Artificial
<220> FEATURE:
<223> OTHER INFORMATION: PCR primer

<400> SEQUENCE: 93
ggccgcgggg ctcgagtgct tccgcac                                         27

<210> SEQ ID NO 94
<211> LENGTH: 80
<212> TYPE: DNA
<213> ORGANISM: Artificial
<220> FEATURE:
<223> OTHER INFORMATION: PCR primer

<400> SEQUENCE: 94
aggtttatcc atgcaatctt gatagctctt gggtttatat ccagaccata aaccattgcc     60
acatcccagc tctgctactg                                                 80

<210> SEQ ID NO 95
<211> LENGTH: 27

```
<212> TYPE: DNA
<213> ORGANISM: Artificial
<220> FEATURE:
<223> OTHER INFORMATION: PCR primer

<400> SEQUENCE: 95
ggccgcgggg ctcgagtgct tccgcac                                             27

<210> SEQ ID NO 96
<211> LENGTH: 80
<212> TYPE: DNA
<213> ORGANISM: Artificial
<220> FEATURE:
<223> OTHER INFORMATION: PCR primer

<400> SEQUENCE: 96
ggatccttat agattgggag accatcgtcg tctagtgcat tcaagtaaag gtttatccat         60
gcaatcttga tagctcttgg                                                     80

<210> SEQ ID NO 97
<211> LENGTH: 22
<212> TYPE: DNA
<213> ORGANISM: Artificial
<220> FEATURE:
<223> OTHER INFORMATION: PCR primer

<400> SEQUENCE: 97
ggcatccaga ttccatcttc ag                                                  22

<210> SEQ ID NO 98
<211> LENGTH: 22
<212> TYPE: DNA
<213> ORGANISM: Artificial
<220> FEATURE:
<223> OTHER INFORMATION: PCR primer

<400> SEQUENCE: 98
ggcatccaga ttccatcttc ag                                                  22

<210> SEQ ID NO 99
<211> LENGTH: 22
<212> TYPE: DNA
<213> ORGANISM: Artificial
<220> FEATURE:
<223> OTHER INFORMATION: PCR primer

<400> SEQUENCE: 99
ggcatccaga ttccatcttc ag                                                  22

<210> SEQ ID NO 100
<211> LENGTH: 19
<212> TYPE: DNA
<213> ORGANISM: Artificial
<220> FEATURE:
<223> OTHER INFORMATION: PCR primer

<400> SEQUENCE: 100
cgattccagc ttccggttg                                                      19

<210> SEQ ID NO 101
<211> LENGTH: 22
<212> TYPE: DNA
<213> ORGANISM: Artificial
<220> FEATURE:
<223> OTHER INFORMATION: PCR primer
```

```
<400> SEQUENCE: 101
ctacggaaca agaggtgcca ac                                              22

<210> SEQ ID NO 102
<211> LENGTH: 22
<212> TYPE: DNA
<213> ORGANISM: Artificial
<220> FEATURE:
<223> OTHER INFORMATION: PCR primer

<400> SEQUENCE: 102
ctacggaaca agaggtgcca at                                              22

<210> SEQ ID NO 103
<211> LENGTH: 22
<212> TYPE: DNA
<213> ORGANISM: Artificial
<220> FEATURE:
<223> OTHER INFORMATION: PCR primer

<400> SEQUENCE: 103
ctacggaaca agaggtgcca at                                              22

<210> SEQ ID NO 104
<211> LENGTH: 26
<212> TYPE: DNA
<213> ORGANISM: Artificial
<220> FEATURE:
<223> OTHER INFORMATION: PCR primer

<400> SEQUENCE: 104
catctagtca ctcaaagaat tgctat                                          26
```